US007754856B2

(12) United States Patent
Uno et al.

(10) Patent No.: US 7,754,856 B2
(45) Date of Patent: Jul. 13, 2010

(54) HUMAN SODIUM-DEPENDENT BILE ACID TRANSPORTER PROTEINS

(75) Inventors: Yumiko Uno, Tsukuba (JP); Atsushi Nakanishi, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1146 days.

(21) Appl. No.: 10/501,566

(22) PCT Filed: Jan. 16, 2003

(86) PCT No.: PCT/JP03/00311

§ 371 (c)(1),
(2), (4) Date: Jul. 15, 2004

(87) PCT Pub. No.: WO03/062274

PCT Pub. Date: Jul. 31, 2003

(65) Prior Publication Data

US 2006/0234924 A1 Oct. 19, 2006

(30) Foreign Application Priority Data

Jan. 18, 2002 (JP) ............................ 2002-010840
Jan. 24, 2002 (JP) ............................ 2002-015995
Feb. 1, 2002 (JP) ............................ 2002-025662
Feb. 1, 2002 (JP) ............................ 2002-025706
Feb. 6, 2002 (JP) ............................ 2002-030015
Feb. 8, 2002 (JP) ............................ 2002-033111
Feb. 21, 2002 (JP) ............................ 2002-045058
Feb. 22, 2002 (JP) ............................ 2002-046951

(51) Int. Cl.
*C07K 14/435* (2006.01)
*C12N 1/21* (2006.01)

(52) U.S. Cl. .................. 530/350; 435/69.1; 435/252.3; 536/23.5

(58) Field of Classification Search ....................... None
See application file for complete search history.

(56) References Cited

U.S. PATENT DOCUMENTS 5,589,358 A * 12/1996 Dawson ..................... 435/69.1
2002/0119523 A1 8/2002 Curtis
2002/0164327 A1 11/2002 Silanes et al.
2002/0164627 A1 * 11/2002 Wilganowski et al. ......... 435/6
2003/0027232 A1 2/2003 Davis et al.
2003/0064369 A1 4/2003 Taupier, Jr. et al.

FOREIGN PATENT DOCUMENTS

EP 1 225 182 7/2002
GB 2 372 993 9/2002
WO WO 95/17905 7/1995
WO WO 02/00722 A2 1/2002
WO WO 02/04520 A2 1/2002
WO 02/10216 2/2002
WO WO 02/12340 A2 2/2002
WO WO 02/33087 A2 4/2002
WO WO 02/44210 A2 6/2002
WO 02/072774 9/2002
WO WO 02/077237 A2 10/2002
WO WO 02/101045 A2 12/2002

OTHER PUBLICATIONS

Wells, J.A. (1990). Additivity of mutational effects in proteins. Biochemistry. 29(37):8509-8517.*

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*

Skolnick et al. (2000). From genes to protein structure and function: novel applications of computational approaches in the genomic era. Trends in Biotechnology. 18:34-39.*

J. Kawai, et al., "Functional annotation of a full-length mouse cDNA collection", Nature, (2001), pp. 685-686, vol. 409.

J. Orlowski, et al., "Molecular Cloning of Putative Members of the Na/H Exchanger Gene Family", The Journal of Biological Chemistry, (1992), pp. 9331-9339, vol. 267, No. 13.

M. Halleck, et al., "Differential expression of putative transbilayer amphipath transporters", Physiological Genomics, (1999), pp. 139-150, vol. 1, No. 3.

M. Wong, et al., "Identification of a Mutation in the Ileal Sodium-dependent Bile Acid Transporter Gene That Abolishes Transport Activity", The Journal of Biological Chemistry, (1995), pp. 27228-27234, vol. 270, No. 45.

P. Carninci, et al., "High-efficiency full-length cDNA cloning", Gen Bank #BAB31203, (Jul. 10, 2000).

International Search Report for PCT/JP03/00311 dated May 13, 2003.

Saeki et al., "Characterization, cDNA Cloning, and Functional Expression of Mouse Ileal Sodium-Dependent Bile Acid Transporter", *J. Biochem*., 125:846-851 (1999).

Wong et al., "Expression Cloning and Characterization of the Hamster Ileal Sodium-Dependent Bile Acid Transporter", *The Journal of Biological Chemistry*, 269(2):1340-1347 (1994).

Oelkers et al., Primary Bile Acid Malabsorption Caused by Mutations in the Ileal Sodium-Dependent Bile Acid Transporter Gene (SLC10A2), *J. Clin. Invest*., 99(8):1880-1887 (1997).

"Large scale genome analysis technology and gene function analysis in the post-sequence era", edited by Ryouei Hayashizaki, First Edition, published by Nakayama Shoten, pp. 2-22 (2001); Record of prior art search results - Notice of Reasons for Rejection including concise explanation of the relevance in English, Partial English Translation.

* cited by examiner

*Primary Examiner*—Christine J Saoud
*Assistant Examiner*—Jon M Lockard
(74) *Attorney, Agent, or Firm*—Sughrue Mion, PLLC

(57) ABSTRACT

A novel sodium-dependent bile acid transporter protein, an $Na^{+}/H^{+}$ exchange transporter protein, a P-type ATPase protein and a vanilloid receptor protein, and polynucleotides encoding these proteins are useful in screening preventives/remedies for hyperlipemia, arteriosclerosis, genital diseases or digestive diseases; respiratory diseases, renal diseases or digestive diseases; pancreatic diseases, central nerve diseases, digestive diseases or respiratory diseases; inflammatory diseases, rheumatoid diseases or diabetic neurosis; etc.

4 Claims, 33 Drawing Sheets

FIG. 1

```
1    M N D P N S C V D N A T V C S G A S C - - - V V P E S N F N N I L S V V L S T V ISBT
1    M R A - - N C - S S S S A C P A N S S E E E L P V G L E V H G N L E L V F T V V TCH230

38   L T I L L A L V M F S M G C N V E I K K F L G H I K R P W G I C V G F L C Q F G ISBT
38   S T V M M G L L M F S L G C S V E I R K L W S H I R R P W G I A V G L L C Q F G TCH230
                                                                             *
78   I M P L T G F I L S V A F D I L P L Q A V V V L I I G C C P G G T A S N I L A Y ISBT
78   L M P F T A Y L L A I S F S L K P V Q A I A V L I M G C C P G G T I S N I F T P TCH230

118  W V D G D M D L S V S M T T C S T L L A L G M M P L C L L I Y T K M W V D S G S ISBT
118  W V D G D M D L S I S M T T C S T V A A L G M M P L C I Y L Y T W S W S L Q Q N TCH230

158  I V I P Y D N I G T S L V A L V V P V S I G M F V N H K W P Q K A K I I L K I G ISBT
158  L T I P Y Q N I G I T L V C L T I P V A F G V Y V N Y R W P K Q S K I I L K I G TCH230

198  S I A G A I L I V L I A V V G G I L Y Q S A W I I A P K L W I I G T I F P V A G ISBT
198  A V V G G V L L L V V A V A G V V L A K G S W N S D I T L L T I S F I F P L I G TCH230

238  Y S L G F L L A R I A G L P W Y R C R T V A F E T G M Q N T Q L C S T I V Q L S ISBT
238  H V T G F L L A L F T H Q S W Q R C R T I S L E T G A Q N I Q M C I T M L Q L S TCH230

278  F T P E E L N V V F T F P L I Y S I F Q L A F A A I F L G F Y V A Y K K C - - - ISBT
278  F T A E H L V Q M L S F P L A Y G L F Q L I D G F L I V A A Y Q T Y K R R L K N TCH230

315  - H G K N K A - - - E I P E S K E N G T E P E S S F Y - - - K A N G G F Q P D E ISBT
318  K H G K K N S G C T E V C H T R K S T S S R E T N A F L E V N E E G A I T P G P TCH230

348  - - - - - - - - - - - - - - - - - - - K                                         ISBT
358  P G P M D C H R A L E P V G H I T S C E                                         TCH230
```

FIG. 6

```
                                  TM1
TCH234     MALQMFVTYSPWNCL-------LLLVALECSEASSDLNESANSTAQYASNAWFAAASSEH---------G 54
ratNHE4    MGEAMLRAFSSWKWL-------LLLMVLTGLEASSYVNESSSPGGQQTPDARFAASSSDH---------D 54
humanNHE2  MEE-----LGNWRSLRAPLPPMLLLLLLQVAGPVGALAETLLNAPRAMGTSSSPPSPASVVAPGTTLFEE 65

                           TM2                               TM3
TCH234     EGISVFELDYDYVQIPYEVTLWILLASLAKIGFHLYHRLPGLMPESCLLILVGALVGGIIFGTDHKSPPV 124
ratNHE4    ERISVFELDYDYVQIPYEVTLWILLASLAKIGFHLYHRLPHLMPESCLLIIVGALVGSIIFGTHHKSPPV 124
humanNHE2  SRLPVFTLDYPHVQIPFEITLWILLASLAKIGFHLYHKLPTIVPESCLLIMVGLLLGGIIFGVDEKSPPA 135

              A      TM4                          TM5
TCH234     MDSSIYFLYLLPPIVLEGGYFMPTRPFFENIGSILWWAVLGALINALGIGLSLYLICQVKAFGLGDVNLL 194
ratNHE4    MDSSIYFLYLLPPIVLESGYFMPTRPFFENIGSILWWAGLGALINAFGIGLSLYFICQIKAFGLGDINLL 194
humanNHE2  MKTDVFFLYLLPPIVLDAGYFMPTRPFFENIGTIFWYAVVGTLWNSIGIGVSLFGICQIEAFGLSDITLL 205

              TM6                                        TM7
TCH234     QNLLFGSLISAVDPVAVLAVFEEARVNEQLYMMIFGEALLNDGITVVLYNMLIAFTKMHKFEDIETVDII 264
ratNHE4    QNLLFGSLISAVDPVAVLAVFEEARVNEQLYMMIFGEALLNDGISVVLYNILIAFTKMHKFEDIEAVDII 264
humanNHE2  QNLLFGSLISAVDPVAVLAVFENIHVNEQLYILVFGESLLNDAVTVVLYNLFKSFCQMK---TIETIDVF 272

              TM8                                   TM9
TCH234     AGCARFIVVGLGGVLFGIVFGFISAFITRFTQNISAIEPLIVFMFSYLSYLAAETLYLSGILAITACAVT 334
ratNHE4    AGCARFVIVGCGGVFFGIIFGFISAFITRFTQNISAIEPLIVFMFSYLSYLAAETLYLSGILAITACAVT 334
humanNHE2  AGIANFFVVGIGGVLIGIFLGFIAAFTTRFTHNIRVIEPLFVFLYSYLSYITAEMFHLSGIMAITACAMT 342

                                          TM10                         TM11
TCH234     MKKYVEENVSQTSYTTIKYFMKMLSSVSETLIFIFMGVSTVGKNHEWNWAFICFTLAFCQIWRAISVFAL 404
ratNHE4    MKKYVEENVSQTSYTTIKYFMKMLSSVSETLIFIFMGVSTVGKNHEWNWAFVCFTLAFCQIWRAISVFTL 404
humanNHE2  MNKYVEENVSQKSYTTIKYFMKMLSSVSETLIFIFMGVSTVGKNHEWNWAFVCFTLAFCLMWRALGVFVL 412

                                          TM12                     TM13
TCH234     FYISNQFRTFPFSIKDQCIIFYSGVRGAGSFSLAFLLPLSLFPRKKMFVTATLVVIYFTVFIQGITVGPL 474
ratNHE4    FYVSNQFRTFPFSIKDQLIIFYSGVRGAGSFSLAFLLPLTLFPRKKLFVTATLVVTYFTVFFQGITIGPL 474
humanNHE2  TQVINRFRTIPLTFKDQFIIAYGGLRGAICFALVFLLPAAVFPRKKLFITAAIVVIFFTVFILGITIRPL 482

TCH234     VRYLDVKKTNKKE-SINEELHIRLMDHLKAGIEDVCGHWSHYQVRDKFKKFDHRYLRKILIRKNLPKSSI 543
ratNHE4    VRYLDVRKTNKKE-SINEELHIRLMDHLKAGIEDVCGQWSHYQVRDKFKKFDHRYLRKILIRRNQPKSSI 543
humanNHE2  VEFLDVKRSNKKQQAVSEEIYCRLFDHVKTGIEDVCGHWGHNFWRDKFKKFDDKYLRKLLIRENQPKSSI 552

TCH234     VSLYKKLEMKQAIEMVETGILSSTAFSIPHQAQRIQGIKRLSPEDVESIRDILTSNMYQVRQRTLSYNKY 613
ratNHE4    VSLYKKLEMKQAIEMAETGLLSSVASPTPYQSERIQGIKRLSPEDVESMRDILTRNMYQVRQRTLSYNKY 613
humanNHE2  VSLYKKLEIKHAIEMAETGMISTVPTFASLNDCREEKIRKVTSSETDEIRELLSRNLYQIRQRTLSYNRH 622

TCH234     NLKPQTSEKQAKEILIRRQNTLRESMRKGHSLPWGKPAGTKNIRYLSYPYNGNPQSAG-RDTRAAGFSDDD 682
ratNHE4    NLKPQTSEKQAKEILIRRQNTLRESLRKGQSLPWVKPAGTKNFRYLSFPYSNPQPAR-RGARAA----ES 678
humanNHE2  SLTADTSERQAKEILIRRRHSLRESIRKDSSLNREHRASTSTSRYLSLPKNTKLPEKLQKRRTISIADGN 692

TCH234     SSDRGSPSIQFSAGSRIGSLQKQEAQEIIPMKSLHRGRKAFSFGYQRNTSQEEYLG-------------G 739
ratNHE4    TGNE---------QCWL---------------LH----------------------FH--------------- 690
humanNHE2  SSDSDADAGTT-----VLNLQPR-RRRFLPEQFSKKSPQSYKMEWKNEVDVDSGRDMPSTPPTPHSREKG 756

TCH234     VRRVALRPKPIFHAVDEEGESGGE-SEGKASLVEVRSRWTRDHGHSRDHHRSHSPLLQKK         798
ratNHE4    ----------LCRAM------------------VEKIWGPG------GQETQPRLICRNLN        717
humanNHE2  TQTSGQLQQPLLSKDQSGSGREDSLTEGIPPKPPPRLVWRRSEPGSRKARFGSEK-------P      812
```

FIG. 8A

```
1    M S R A T S V G D Q L E A P A - - - - - - - - - - - - - - - - - - - - - R I I Y L N Q S H L N K F C D N R I S T A K Y S  mATP8A2
1    M P T M R R T V S E I R S K A E G Y E K T D D V S E K T S L A D Q E E V R T I F I N Q P Q L T K F C N N H V S T A K Y N  ATP8A1
1    M S R A T S V G D Q L E A P A - - - - - - - - - - - - - - - - - - - - - R T I Y L N Q P H L N K F R D N Q I S T A K Y S  TCH212

                                   TM1                                        TM2
40   V L T F L P R F L Y E Q I R R A A N A F F L F I A L L Q Q I P D V S P T G R Y T T L V P L V I I L T I A G I K E I I E D  mATP8A2
61   I I T F L P R F L Y S Q F R R A A N S F F L F I A L L Q Q I P D V S P T G R Y T T L V P L L F I L A V A A I K E I I E D  ATP8A1
40   V L T F L P R F L Y E Q I R R A A N A F F L F I A L L Q Q I P D V S P T G R Y T T L V P L I I I L T I A G I K E I V E D  TCH212

100  F K R H K A D N A V N K K K T I V L R N G M W H T I M W K E V A V G D I V K V L N G Q Y L P A D M V L F S S S E P Q G M  mATP8A2
121  I K R H K A D N A V N K K Q T Q V L R N G A W E I V H W E K V A V G E I V K V T N G E H L P A D L I S L S S S E P Q A M  ATP8A1
100  F K R H K A D N A V N K K K T I V L R N G M W H T I M W K E V A V G D I V K V V N G Q Y L P A D V V L L S S S E P Q A M  TCH212

160  C Y V E T A N L D G E T N L K I R Q G L S H T T D M Q T R D V L M K L S G R I E C E G P N R H L Y D F T G N L H L D G K  mATP8A2
181  C Y I E T S N L D G E T N L K I R Q G L P A T S D I K D V D S L M R I S G R I E C E S P N R H L Y D F V G N I R L D G H  ATP8A1
160  C Y V E T A N L D G E T N L K I R Q G L S H T A D M Q T R E V L M K L S G T I E C E G P N R H L Y D F T G N L N L D G K  TCH212

220  S S V A L G P D Q I L L R G T Q L R N T Q W V F G V V V Y T G H D S K L M Q N S T K A P L K R S N V E K V T N V Q I L V  mATP8A2
241  G T V P L G A D Q I L L R G A Q L R N T Q W V H G I V V Y T G H D T K L M Q N S T S P P L K L S N V E R I T N V Q I L I  ATP8A1
220  S L V A L G P D Q I L L R G T Q L R N T Q W V F G I V V Y T G H D T K L M Q N S T K A P L K R S N V E K V T N V Q I L V  TCH212

                 TM3                                                                 TM4
280  L F G I L L V M A L V S S V G A L F W N G S H G G K S W Y I K K M D T N S D N F G Y N L L T F I I L Y N N L I P I S L L  mATP8A2
301  L F C I L I A M S L V C S V G S A I W N R R H S G K D W Y L N L N Y G G A S N F G L N F L T F I I L F N N L I P I S L L  ATP8A1
280  L F G I L L V M A L V S S A G A L Y W N R S H G E K N W Y I K K M D T T S D N F G Y N L L T F I I L Y N N L I P I S L L  TCH212

340  V T L E V V K Y T Q A L F I N W D M D M Y Y I E N D T P A M A R T S N L N E E L G Q V K Y L F S D K T G T L T C N I M N  mATP8A2
361  V T L E V V K F T Q A Y F I N W D L D M H Y E P T D T A A M A R T S N L N E E L G Q V K Y I F S D K T G T L T C N V M Q  ATP8A1
340  V T L E V V K Y T Q A L F I N W D T D M Y Y I G N D T P A M A R T S N L N E E L G Q V K Y L F S D K T G T L T C N I M N  TCH212
```

FIG. 8B

```
400 FKKCSIAGVTYGHFPELAREQSSDDF-C----RMTSCTNDSCDFNDPRLLKNIEDQHPTA mATP8A2
421 FKKCTIAGVAYGHVPE------PEDYGCSPDEWQNSQFGDEKTFSDSSLLENLQNNHPTA ATP8A1
400 FKKCSIAGVTYGHFPELAREPSSDDF-C----RMPPPCSDSCDFDDPRLLKNIEDRHPTA TCH212

455 PCIQEFLTLLAVCHTVVPEKDGDEIIYQASSPDEAALVKGAKKLGFVFTGRTPYSVIIEA mATP8A2
475 PIICEFLTMMAVCHTAVPEREGDKIIYQAASPDEGALVRAAKQLNFVFTGRTPDSVIIDS ATP8A1
455 PCIQEFLTLLAVCHTVVPEKDGDNIIYQASSPDEAALVKGAKKLGFVFTARTPFSVIIEA TCH212

515 MGQEQTFGILNVLEFSSDRKRMSVIVRLPSGQLRLYCKGADNVIFERLSKDSKYMEETLC mATP8A2
535 LGQEERYELLNVLEFTSARKRMSVIVRTPSGKLRLYCKGADTVIYDRLAETSKYKEITLK ATP8A1
515 MGQEQTFGILNVLEFSSDRKRMSVIVRTPSGRLRLYCKGADNVIFERLSKDSKYMEETLC TCH212

575 HLEYFATEGLRTLCVAYADLSENEYEEWLKVYQEASIILKDRAQRLEECYEIIEKNLLLL mATP8A2
595 HLEQFATEGLRTLCFAVAEISESDFQEWRAVYQRASTSVQNRLLKLEESYELIEKNLQLL ATP8A1
575 HLEYFATEGLRTLCVAYADLSENEYEEWLKVYQEASTILKDRAQRLEECYEIIEKNLLLL TCH212

635 GATAIEDRLQAGVPETIATLLKAEIKIWVLTGDKQETAINIGYSCRLVSQNMALILLKED mATP8A2
655 GATAIEDKLQDQVPETIETLMKADIKIWILTGDKQETAINIGHSCKLLKKNMGMIVINEG ATP8A1
635 GATAIEDRLQAGVPETIATLLKAEIKIWVLTGDKQETAINIGYSCRLVSQNMALILLKED TCH212

695 SLDATRAAITQHCTDLGNLLGKENDVALIIDGHTLKYALSFEVRRSFLDLALSCKAVICC mATP8A2
715 SLDGTRETLSRHCTTLGDALRKENDFALIIDGKTLKYALTFGVRQYFLDLALSCKAVICC ATP8A1
695 SLDATRAAITQHCTDLGNLLGKENDVALIIDGHTLKYALSFEVRRSFLDLALSCKAVICC TCH212

755 RVSPLQKSEIVDVVKKRVKAITLAIGDGANDVGMIQTAHVGVGISGNEGMQATNNSDYAI mATP8A2
775 RVSPLQKSEVVEMVKKQVKVVTLAIGDGANDVSMIQTAHVGVGISGNEGLQAANSSDYSI ATP8A1
755 RVSPLQKSEIVDVVKKRVKAITLAIGDGANDVGMIQTAHVGVGISGNEGMQATNNSDYAI TCH212
```

FIG. 8C

```
815  AQFSYLEKLLLVHGAWSYNRVTKCILYCFYKNVVLYIIELWFAFVNGFSGQILFERWCIG mATP8A2
835  AQFKYLKNLLMIHGAWNYNRVSKCILYCFYKNIVLYIIEIWFAFVNGFSGQILFERWCIG ATP8A1
815  AQFSYLEKLLLVHGAWSYNRVTKCILYCFYKNVVLYIIELWFAFVNGFSGQILFERWCIG TCH212

875  LYNVIFTALPPFTLGIFERSCTQESMLRFPQLYRITQNAEGFNTKVFWGHCINALVHSLI mATP8A2
895  LYNVMFTAMPPLTLGIFERSCRKENMLKYPELYKTSQNALDFNTKVFWVHCLNGLFHSVI ATP8A1
875  LYNVIFTALPPFTLGIFERSCTQESMLRFPQLYKITQNGEGFNTKVFWGHCINALVHSLI TCH212

935  LFWVPMKALEHDTPVTSGHATDYLFVGNIVYTYVVVTVCLKAGLETTAWTKFSHLAVWGS mATP8A2
955  LFWFPLKALQYGTAFGNGKTSDYLLLGNFVYTFVVITVCLKAGLETSYWTWFSHIAIWGS ATP8A1
935  LFWFPMKALEHDTVLTSGHATDYLFVGNIVYTYVVVTVCLKAGLETTAWTKFSHLAVWGS TCH212

995  MLIWLVFFGVYSTIWPTIPIAPDMKGQATMVLSSAYFWLGLFLVPTACLIEDVAWRAAKH mATP8A2
1015 IALWVVFFGIYSSLWPAIPMAPDMSGEAAMLFSSGVFWMGLLFIPVASLLLDVVYKVIKR ATP8A1
995  MLTWLVFFGIYSTIWPTIPIAPDMRGQATMVLSSAHFWLGLFLVPTACLIEDVAWRAAKH TCH212

1055 TCKKTLLEEVQELETKSRVMGKAMLRDSNGKRMNERDRLIKRLSRKTPPTLFRTGSIQQC mATP8A2
1075 TAFKTLVDEVQELEAKSQDPGAVVL----GKSLTERAQLLKNVFKKNHVNLYRSESLQQN ATP8A1
1055 TCKKTLLEEVQELETKSRVLGKAVLRDSNGKRLNERDRLIKRLGRKTPPTLFRGSSLQQG TCH212

1115 VSHGYAFSQEEHGAVTQEEIVRAYDTTKENSRKK mATP8A2
1131 LLHGYAFSQDENGIVSQSEVIRAYDTTKQRPDEW ATP8A1
1115 VPHGYAFSQEEHGAVSQEEVIRAYDTTKKKSRKK TCH212
```

```
1   M K K W S S T D L G A A A D P L Q K D T C P D P L D G D P N S R P P P A K P Q L S T A K S R T R hVR1
1   M K A H P K E M V P L M G K R V A A P S - - - - - - G N P A V L P E K R P A E I T P T K K S A H TCH200

49  L F - - - - - - - - G K G D S E E A F P V D C P H E E G E L D S C P T I T V S P V I T I Q R P G hVR1
43  F F L E I E G F E P N P T V A K T S P P V F S K P M D S N I R Q C I S G N C D D M D S P Q S P Q TCH200

89  D G P T G A R L L S Q D S V A A S T E K T L R L Y D R R - - - S I F E A V A Q N N C Q D L E S L hVR1
91  D D V T E T P S N P N S P S A Q L A K E E Q R R K K R R L K K R I F A A V S E G C V E E L V E L TCH200

134 L L F L Q K - - S K K H L T D - - - - - - N E F K D P E T G K T C L L K A M L N L H D G Q N T T hVR1
139 L V E L Q E L C R R R H D E D V P D F L M H K L T A S D T G K T C L M K A L L N I N P N T K E I TCH200
                                                                                  A1
174 I P L L L E I A R Q T D S L K E L V N A S Y T D S Y Y K G Q T A L H I A I E R R N M A L V T L L hVR1
187 V R I L L A F A E E N D I L G R F I N A E Y T E E A Y E G Q T A L N I A I E R R Q G D I A A L L TCH200
                                                                                  A2
222 V E N G A D V Q A A A H G D F F K K T K G R P G F Y F G E L P L S L A A C T N Q L G I V K F L L hVR1
235 I A A G A D V N A H A K G A F F N P K Y Q H E G F Y F G E T P L A L A A C T N Q P E I V Q L L M TCH200

270 Q N S W Q T A D I S A R D S V G N T V L H A L V E V A D N T A D N T K F V T S M Y N E I L I L G hVR1
283 E H - - E Q T D I T S R D S R G N N I L H A L V T V A E D F K T Q N D F V K R M Y D M I L L R S TCH200
                                                      A3
318 A K L H P T L K L E E L T N K K G M M P L A L A A G T G K I G V L A Y I L Q R E I Q E P E C R H hVR1
329 G N W E - - - - L E T T R N N D G L T P L Q L A A K M G K A E I L K Y I L S R E I K E K R L R S TCH200

366 L S R K F T E W A Y G P V H S S L Y D L S C I D T C E K N S V L E V I A Y S S S E T P N R H D M hVR1
373 L S R K F T D W A Y G P V S S S L Y D L T N V D T T D N S V L E I T V Y N T N I D - N R H E M TCH200
                                                    TM1
414 L L V E P L N R L L Q D K W D R F V K R I F Y F N F L V Y C L Y M I I F T M A A Y Y R P V D G L hVR1
420 L T L E P L H T L L H M K W K K F A K H M F F L S F C F Y F F Y N I T L T L S Y Y R P R E E - TCH200
                                                                      TM2
462 P P F K M E K T G D Y F R V T G E I - - L S V L G G V Y F F F - - - - - - - - - R G I Q Y F L Q R hVR1
467 - - - - - E A I P H P L A L T H K M G W L Q L L G R M F V L I W A M C I S V K E G I A I F L I R TCH200
                                                    TM3
500 R P S M K T L F V D S Y S E M L F F L Q S L F M L A T V V L Y F S H L K E Y V A S M V F S L A L hVR1
510 P S D L Q S I L S D A W F H F V F F I Q A V L V I L S V F L Y L F A Y K E Y L A C L V L A M A L TCH200
          TM4                                                  TM5
548 G W T N M L Y Y T R G F Q Q M G I Y A V M I E K M I L R D L C R F M F V Y I V F L F G F S T A V hVR1
558 G W A N M L Y Y T R G F Q S M G M Y S V M I Q K V I L H D V L K F L F V Y I V F L L G F G V A L TCH200

596 V T L I E D G K N D S L P S E S T S H R W R G P A C R P P D S S Y N S L Y S T C L E L F K F T I hVR1
606 A S L I E K C P K D N - - - - - - - - - - - - - K D C - - - S S Y G S F S D A V L E L F K L T I TCH200
                                                     TM6
644 G M G D L E F T E N Y D F K A V F I I L L L A Y V I L T Y I L L L N M L I A L M G E T V N K I A hVR1
638 G L G D L N I Q Q N S K Y P I L F L F L L I T Y V I L T F V L L L N M L I A L M G E T V E N V S TCH200

692 Q E S K N I W K L Q R A I T I L D T E K S F L K C M R K A F R S G K L L Q V G Y T P D G K D D Y hVR1
686 K E S E R I W R L Q R A R T I L E F E K M L P E W L R S R F R M G E L C K V A - - - - - E D D F TCH200

740 R W C F R V D E V N W T T W N T N V G I I N E D P G N C E G V K R T L S F S L R S S R V S G R H hVR1
729 R L C L R I N E V K W T E W K T H V S F L N E D P G P - - - V R R T A D F N - - - - - - - - - - - TCH200

788 W K N F A L V P L L R E A S A R D R Q S A Q P E E V Y L R Q F S G S L K P E D A E V F K S P A A hVR1
764 - - - - - - - - - - - - K I Q D S S R N N S K T T - - - L N A F - - - - - - E E V E E F - - - P E TCH200

836 S G E K                                                                                          hVR1
789 T S V                                                                                            TCH200
```

FIG. 13

```
1   M R A N C S S S S A C P A N S S E E E L P V G L E V H G N L E L V F T V V S T V hTCH230
1   M S T D C A G N S T C P V N S T E E D P P V G M E G H A N L K L L F T V L S A V mTCH230

41  M M G L L M F S L G C S V E I R K L W S H I R R P W G I A V G L L C Q F G L M P hTCH230
41  M V G L V M F S F G C S V E S Q K L W L H L R R P W G I A V G L L S Q F G L M P mTCH230

81  F T A Y L L A I S F S L K P V Q A I A V L I M G C C P G G T I S N I F T F W V D hTCH230
81  L T A Y L L A I G F G L K P F Q A I A V L M M G S C P G G T I S N V L T F W V D mTCH230

121 G D M D L S I S M T T C S T V A A L G M M P L C I Y L Y T W S W S L Q Q N L T I hTCH230
121 G D M D L S I S M T T C S T V A A L G M M P L C L Y I Y T R S W T L T Q N L V I mTCH230

161 P Y Q N I G I T L V C L T I P V A F G V Y V N Y R W P K Q S K I I L K I G A V V hTCH230
161 P Y Q S I G I T L V S L V V P V A S G V Y V N Y R W P K Q A T V I L K V G A I L mTCH230

201 G G V L L L V V A V A G V V L A K G S W N S D I T L L T I S F I F P L I G H V T hTCH230
201 G G M L L L V V A V T G M V L A K G - W N T D V T L L V I S C I F P L V G H V T mTCH230

241 G F L L A L F T H Q S W Q R C R T I S L E T G A Q N I Q M C I T M L Q L S F T A hTCH230
240 G F L L A F L T H Q S W Q R C R T I S I E T G A Q N I Q L C I A M L Q L S F S A mTCH230

281 E H L V Q M L S F P L A Y G L F Q L I D G F L I V A A Y Q T Y K R R L K N K H G hTCH230
280 E Y L V Q L L N F A L A Y G L F Q V L H G L L I V A A Y Q A Y K R R Q K S K C R mTCH230

321 K K N S G C T E V C H T R K S T S S R E T N A F L E V N E E G A I T P G P P G P hTCH230
320 R Q H P D C P D V C Y E K Q P - - - R E T S A F L D K G D E A A V T L G P V Q P mTCH230

361 M D C H R A L E P V G H I T S C E                                                 hTCH230
357 E Q H H R A A E L T S H I P S C E                                                 mTCH230
```

HUMAN SODIUM-DEPENDENT BILE ACID TRANSPORTER PROTEINS

This application is the National Phase filing of International Patent Application No. PCT/JP03/00311, filed Jan. 16, 2003.

TECHNICAL FIELD

The present invention provides a novel sodium-dependent bile acid transporter protein, an $Na^+/H^+$ exchange transporter protein, a P-type ATPase protein, a vanilloid receptor protein, polynucleotides encoding these proteins, antisense polynucleotides to the polynucleotides, antibodies to these proteins, compounds that promote or inhibit the activities of the proteins, a method of screening compounds that promote or inhibit the activities of the proteins, compounds obtained by the screening method, and the like.

BACKGROUND ART

Bile acid is synthesized in the liver and secreted into a small intestine, and plays an important role in promoting absorption of lipids, lipid-soluble vitamins and cholesterols in the small intestine. Bile acid is re-absorbed efficiently through the small intestine (ileum), returned via a portal vein to the liver and excreted again into bile (enterohepatic circulation). The cholesterol pool size in the body is subject to feedback regulation not only by cholesterol in a meal but also by bile acid in enterohepatic circulation, and thus hypercholesterolemia therapy is conducted by suppression of re-absorption of bile acid into intestines by using a bile acid adsorbent (anion exchange resin).

The sodium-dependent bile acid transporter is considered to contribute to transport of bile acid. In humans, two isoforms of sodium-dependent bile acid transporter have been identified, and NTCP ($Na^+$/taurocholate cotransporting polypeptide) is expressed mainly in the liver (J. Clin. Invest., 93, 1326-1331, 1994), while ISBT (ileal sodium/bile salt cotransporter) is expressed mainly in the ileum/kidney (J. Biol. Chem., 270, 27228-27234, 1995). With respect to ISBT, direct relationship between a gene mutation accompanied by amino acid substitution and insufficient absorption of bile acid is suggested (J. Clin. Invest., 99, 1880-1887, 1997).

A $Na^+/H^+$ exchange transporter (NHE) is a typical cation antiporter, which couples in animal cells with $Na^+$ inflow to discharge $H^+$. NHE is divided into 2 major regions, that is, an amino terminal (N) region containing about 500 amino acids comprising a 10- to 13-times transmembrane region and a carboxyl terminal (C) region comprising about 300 amino acids, and its whole structure is common among isoforms. It is known that the former is an ion transport region comprising an amyloride-binding site, and the latter functions as an activity regulatory region.

As isoforms of NHE in humans, 6 kinds of isoforms i.e. NHE1 to NHE3 and NHE5 to NHE7 are reported. NHE1 is distributed broadly in tissues, and involved in regulation of intracellular pH and cell volume. The activity of NHE1 is promoted by a growth factor or simulation with high osmotic pressure, resulting in an increase in intracellular pH. NHE3 is expressed in the kidney and small intestine, and plays an important role in absorption of $Na^+$. It is thus known that the respective isoforms are different in their expression distribution, regulatory mechanism, and the effect of inhibitor.

NHE1 is considered as one factor increasing intracellular $Na^+$ levels after ischemia and participating in causing myocardial difficulties. It is also reported that the activity of NHE1 in patients with hypertension is significantly higher than in healthy persons. In mice spontaneously developing epilepsy, it is confirmed that the disease is caused by a mutation in NHE (Cell, 91, 139-148, 1997).

P-type ATPase is a membrane enzyme participating in transport of various substrates by utilizing energy upon hydrolysis of ATP. The P-type ATPase is divided into 3 classes, depending on its substrate. Type-1 utilizes heavy metals such as $Cu^{2+}$ ion and $Cd^{2+}$ ion as the substrate, possesses an N-terminal characteristic structure involved in binding to heavy metals, and has an 8-times transmembrane structure. Wilson's disease is a disease accompanying an abnormality in $Cu^{2+}$-ATPase participating in excretion of copper in the liver. Type-2 utilizes alkali metals ($K^+$ ion, $Na^+$ ion), alkaline earth metals ($Ca^{2+}$ ion) or proton ($H^+$) as the substrate. In particular, $H^+$, $K^+$-ATPase (proton pump) in stomach acid-secreting cells is a target of chemicals such as proton pump inhibitors (omeplazole, lansoprazole etc.) that are therapeutic products for stomach ulcer/duodenum ulcer/reflux esophagitis. Further, $Na^+$, $K^+$-ATPase (sodium pump) is a target of chemicals such as cardiac glycosides used for cardiac diseases, and its activity is inhibited by ouabain. Type-3 is the latest determined type, and utilizes aminophospholipids as the substrate. It is also called aminophospholipid translocase (flippase), and reversely transfer phospholipids selectively from outer to inner layers by using energy generated upon hydrolysis of ATP. It is estimated that uneven distribution of lipids on the biomembrane is thereby maintained. No significant difference in structure is recognized between type-2 and type-3, both of which have a 10-times transmembrane structure (Biochemistry, 34, 15607-15613, 1995; Science, 272, 1495-1497, 1996).

Up to now, 17 isoforms of P-type ATPase of type-3 have been identified in mammals. Among them, FIC1 is expressed in tissues such as the pancreas, small intestine, liver etc., and the relationship between an alteration in its gene and hereditary cholestasis is reported (Nature Genet., 18, 219-224, 1998).

The P-type ATPase of type 3 is considered to play an important role in transport of aminophospholipids and in uneven distribution of lipids on the biomembrane, but the detailed functions and structure of each isoform and the relationship thereof with the disease are not so revealed.

As a pain receptor, a vanilloid receptor subtype 1 (VR1) is a non-selective cation channel with high $Ca^{2+}$ permeability having outward rectification. It is known that VR1 has a 6-times transmembrane region, possesses an H5 region regarded as forming a pore between fifth and sixth transmembrane sites, and has 3 ankyrin repeat domains at the N-terminal thereof. In addition to VR1 (Biochemical and Biophysical Research Communications, 281, 1183, 2001), VRL (vanilloid receptor-like protein) 1 and VRL2 in humans have been cloned up to now, and have about 40% homology with VR1 respectively (Physiol Genomics 4, 165-174, 2001).

Capsaicin has a vanillyl group and is thus called vanilloid, and is an extraneous ligand of vanilloid receptor. No intrinsic ligand has been revealed. Single electric current measurement revealed that VR1 is activated electrophysiologically directly by capsaicin. Further, VR1 is a receptor of multi-stimuli, which is activated not only by chemical stimulation with capsaicin or the like but also by heat stimulation regarded pain stimulation (at a temperature of higher than 43° C. that is a threshold temperature at which pain is induced in humans) and acid stimulation (tissues are acidified in inflammations and ischemia).

VR1 is activated by stimuli (for example capsaicin, heat, proton) causing pain in the living body, and in a morbid state, these stimuli are considered to occur not singly but simultaneously. Receptiveness of every pain in the living body is not elucidated by only VR1, and the presence of other homologues and cofactors is also estimated. In the previously reported VR family, there are various expression sites and stimulation receptivity, and these are considered to function depending on one another, to transmit pain stimulation.

The sodium-dependent bile acid transporter is considered to play an important role in transport of bile acid in the liver and small intestine, but its detailed mechanism and the relationship thereof with the disease are not so revealed. Full elucidation of the substrate specificity of the sodium-dependent bile acid transporter and its role in bile acid metabolism leads to development of therapeutic products for diseases associated with bile acid metabolism.

As described above, NHE is involved in many morbid states, and elucidation of the mechanism of activation and regulation of each isoform of NHE leads to development of therapeutic products.

Elucidation of detailed functions of P-type ATPase of type 3 leads to development of therapeutic products for diseases such as metabolic diseases, central nerve diseases, genital diseases and cancers associated with P-type ATPase of type 3.

The above-mentioned capsaicin is used as an analgesic for relieving pains in diabetic neurosis and articular rheumatism, and thus elucidation of the structure, function and mutual relationship of VR family is considered to lead to development of therapeutic products for pains as a whole.

DISCLOSURE OF INVENTION

The present inventors made extensive study for solving the problem described above, and as a result they found a novel sodium-dependent bile acid transporter protein. The inventors found that the protein has 44% homology at the amino acid level with human ISBT, and its substrate is estrone sulfate and dehydroepiandrosterone sulfate, and as a result of further examination, they completed the present invention.

The present inventors made extensive study for solving the problem described above, and as a result they found a novel $Na^+/H^+$ exchange transporter protein. The amino acid residues at the N-terminal side of the protein consisting of 707 residues were identical with those of the amino acid sequence of TRICH-21 described in WO 02/04520. For inhibiting the protein, it is anticipated that for example, cation ($Na^+$, $K^+$)/$H^+$ exchange transport is inhibited, or transcription of the protein is inhibited to reduce the expression level. For activating the protein, it is anticipated that for example, cation ($Na^+$, $K^+$)/$H^+$ exchange transport is promoted, a promoter for the protein is activated, or its mRNA is stabilized to promote the expression level. As a result of further examination on the basis of these findings, the present inventors arrived at the present invention.

The present inventors made extensive study for solving the problem described above, and as a result they found a novel P-type ATPase. This protein has 67% homology at the amino acid level with P-type ATPase of type 3 i.e. P-type ATPase 8A1 (ATP8A1) (Biochem. Biophys. Res. Commun., 257, 333-339, 1999) and 95% homology with mouse P-type ATPase 8A2 (ATP8A2) (Physiol. Genomics (Online), 1, 139-150, 1999), and can function as P-type ATPase of type 3. For inhibiting the protein, it is anticipated that for example, transport of aminophospholipids is inhibited, or transcription of the protein is inhibited to reduce the expression level. For activating the protein, it is anticipated that for example, transport of aminophospholipids is promoted, a promoter for the protein is activated, or its mRNA is stabilized to promote the expression level. As a result of further examination on the basis of these findings, the present inventors arrived at the present invention.

The present inventors made extensive study for solving the problem described above, and as a result they found a novel vanilloid receptor. This protein has 43% homology at the amino acid level with human vanilloid receptor subtype 1 and can function as a vanilloid receptor. For inhibiting the protein, it is anticipated that for example, cation permeation is inhibited, or transcription of the protein is inhibited to reduce the expression level. For activating the protein, it is anticipated that for example, cation permeation is promoted, a promoter for the protein is activated, or its mRNA is stabilized to promote the expression level. As a result of further examination on the basis of these findings, the present inventors arrived at the present invention.

That is, the present invention provides:

(1) A protein comprising the same or substantially the same amino acid sequence as an amino acid sequence represented by SEQ ID NO: 1, SEQ ID NO: 14 or SEQ ID NO: 104, or a salt thereof.

(2) A protein consisting of an amino acid sequence represented by SEQ ID NO: 1 or SEQ ID NO: 14, or a salt thereof.

(3) A protein consisting of an amino acid sequence represented by SEQ ID NO: 104, or a salt thereof (4) A partial peptide of the protein according to the above-mentioned (1), or a salt thereof (5) A polynucleotide comprising a polynucleotide encoding the protein according to the above-mentioned (1) or the partial peptide according to the above-mentioned (4).

(6) The polynucleotide according to the above-mentioned (5), which is DNA.

(7) A DNA consisting of a base sequence represented by SEQ ID NO: 2, SEQ ID NO: 11, SEQ ID NO: 12, SEQ ID NO: 14, SEQ ID NO: 105 or SEQ ID NO: 112.

(8) A recombinant vector comprising the polynucleotide according to the above-mentioned (5).

(9) A transformant transformed with the recombinant vector according to the above-mentioned (8).

(10) A method of manufacturing the protein or its salt according to the above-mentioned (1) or the partial peptide or its salt according to the above-mentioned (4), which comprises culturing the transformant according to the above-mentioned (9), forming and accumulating the protein according to the above-mentioned (1) or the partial peptide according to the above-mentioned (4), and recovering it.

(11) A medicine comprising the protein according to the above-mentioned (1) or the partial peptide according to the above-mentioned (4).

(12) A medicine comprising the polynucleotide according to the above-mentioned (5).

(13) An antibody to the protein according to the above-mentioned (1), the partial peptide according to the above-mentioned (4), or a salt of the protein or partial peptide.

(14) A medicine comprising the antibody according to the above-mentioned (13).

(15) A diagnostic agent comprising the antibody according to the above-mentioned (13).

(16) A polynucleotide comprising a base sequence complementary or substantially complementary to the base sequence of the polynucleotide according to the above-mentioned (5) or a part of the base sequence.

(17) A medicine comprising the polynucleotide according to the above-mentioned (16).

(18) A method of screening a compound or its salt that promotes or inhibits the activity of the protein or its salt according to the above-mentioned (1) or the partial peptide or its salt according to the above-mentioned (4), which comprises using the protein or its salt according to the above-mentioned (1) or the partial peptide or its salt according to the above-mentioned (4).

(19) The screening method according to the above-mentioned (18), wherein the activity of the protein or its salt according to the above-mentioned (1) or the partial peptide or its salt according to the above-mentioned (4) is the substrate transport activity of the protein.

(19a) The screening method according to the above-mentioned (19), wherein the substrate is a steroid hormone or a metabolite thereof or bile acid.

(19b) The screening method according to the above-mentioned (19a), wherein the substrate is a steroid hormone or a metabolite thereof.

(19c) The screening method according to the above-mentioned (19b), wherein the steroid hormone or a metabolite thereof is estrogen, progestogen, androgen, mineral corticoid or glucocorticoid or a sulfate conjugate or glucuronide conjugate thereof.

(19d) The screening method according to the above-mentioned (19b), wherein the steroid hormone or a metabolite is estrogen, androgen or a sulfate conjugate.

(19e) The screening method according to the above-mentioned (19a), wherein the substrate is estrogen, dehydroepiandrosterone or a sulfate conjugate thereof.

(20) A kit for screening a compound or its salt that promotes or inhibits the activity of the protein or its salt according to the above-mentioned (1) or the partial peptide or its salt according to the above-mentioned (4), which comprises the protein or its salt according to the above-mentioned (1) or the partial peptide or its salt according to the above-mentioned (4).

(21) A compound or its salt that promotes or inhibits the activity of the protein or its salt according to the above-mentioned (1) or the partial peptide or its salt according to the above-mentioned (4), which is obtained by using the screening method according to the above-mentioned (18) or the screening kit according to the above-mentioned (19).

(22) A medicine comprising the compound or its salt according to the above-mentioned (21).

(23) A method of screening a compound or its salt that promotes or inhibits the expression of a gene for the protein according to the above-mentioned (1), which comprises using the polynucleotide according to the above-mentioned (5).

(24) A kit for screening a compound or its salt that promotes or inhibits the expression of a gene for the protein according to the above-mentioned (1), which comprises the polynucleotide according to the above-mentioned (5).

(25) A compound or its salt that promotes or inhibits the expression of a gene for the protein according to the above-mentioned (1), which is obtained by the screening method according to the above-mentioned (23) or the screening kit according to the above-mentioned (24).

(26) A medicine comprising the compound or its salt according to the above-mentioned (25).

(27) The medicine according to the above-mentioned (11), (12), (14), (17), (22) or (26), which is a prophylactic/therapeutic agent for hyperlipemia, arteriosclerosis, genital diseases or digestive diseases.

(28) A prophylactic/therapeutic method for hyperlipemia, arteriosclerosis, genital diseases or digestive diseases, which comprises administering an effective amount of the compound or its salt according to the above-mentioned (21) or (25) into a mammal.

(29) Use of the compound or its salt according to the above-mentioned (21) or (25) in producing a prophylactic/therapeutic agent for hyperlipemia, arteriosclerosis, genital diseases or digestive diseases.

(30) A protein or its salt comprising an amino acid sequence identical or substantially identical with an amino acid sequence represented by SEQ ID NO: 18.

(31) A protein consisting of an amino acid sequence represented by SEQ ID NO: 18, or a salt thereof.

(32) A partial peptide of the protein according to the above-mentioned (30), or a salt thereof.

(33) A polynucleotide comprising a polynucleotide encoding the protein according to the above-mentioned (30) or the partial peptide according to the above-mentioned (32).

(34) The polynucleotide according to the above-mentioned (33), which is DNA.

(35) A DNA consisting of a base sequence represented by SEQ ID NO: 19 or SEQ ID NO: 41.

(36) A recombinant vector comprising the polynucleotide according to the above-mentioned (33).

(37) A transformant transformed with the recombinant vector according to the above-mentioned (36).

(38) A method of manufacturing the protein or its salt according to the above-mentioned

(30) or the partial peptide or its salt according to the above-mentioned (32), which comprises culturing the transformant according to the above-mentioned (37), forming and accumulating the protein according to the above-mentioned (30) or the partial peptide according to the above-mentioned (32), and recovering it.

(39) A medicine comprising the protein according to the above-mentioned (30) or the partial peptide according to the above-mentioned (32).

(40) A medicine comprising the polynucleotide according to the above-mentioned (33).

(41) An antibody to the protein according to the above-mentioned (30), the partial peptide according to the above-mentioned (32), or a salt of the protein or partial peptide.

(42) A medicine comprising the antibody according to the above-mentioned (41).

(43) A diagnostic agent comprising the antibody according to the above-mentioned (41).

(44) A polynucleotide comprising a base sequence complementary or substantially complementary to the base sequence of the polynucleotide according to the above-mentioned (33) or a part of the base sequence.

(45) A medicine comprising the polynucleotide according to the above-mentioned (44).

(46) A method of screening a compound or its salt that promotes or inhibits the activity of the protein or its salt according to the above-mentioned (30) or the partial peptide or its salt according to the above-mentioned (32), which comprises using the protein or its salt according to the above-mentioned (30) or the partial peptide or its salt according to the above-mentioned (32).

(47) A kit for screening a compound or its salt that promotes or inhibits the activity of the protein or its salt according to the above-mentioned (30) or the partial peptide or its salt according to the above-mentioned (32), which comprises the protein or its salt according to the above-mentioned (30) or the partial peptide or its salt according to the above-mentioned (32).

(48) A compound or its salt that promotes or inhibits the activity of the protein or its salt according to the above-mentioned (30) or the partial peptide or its salt according to the above-mentioned (32), which is obtained by using the screening method according to the above-mentioned (46) or the screening kit according to the above-mentioned (47).

(49) A medicine comprising the compound or its salt according to the above-mentioned (48).

(50) A method of screening a compound or its salt that promotes or inhibits the expression of a gene for the protein according to the above-mentioned (30), which comprises using the polynucleotide according to the above-mentioned (33).

(51) A kit for screening a compound or its salt that promotes or inhibits the expression of a gene for the protein according to the above-mentioned (30), which comprises the polynucleotide according to the above-mentioned (33).

(52) A compound or its salt that promotes or inhibits the expression of a gene for the protein according to the above-mentioned (30), which is obtained by the screening method according to the above-mentioned (50) or the screening kit according to the above-mentioned (51).

(53) A medicine comprising the compound or its salt according to the above-mentioned (52).

(54) The medicine according to the above-mentioned (39), (40), (42), (45), (49) or (53), which is a prophylactic/therapeutic agent for respiratory diseases, renal diseases or digestive diseases.

(55) A prophylactic/therapeutic method for respiratory diseases, renal diseases or digestive diseases, which comprises administering an effective amount of the compound or its salt according to the above-mentioned (48) or (52) into a mammal.

(56) Use of the compound or its salt according to the above-mentioned (48) or (52) in producing a prophylactic/therapeutic agent for respiratory diseases, renal diseases or digestive diseases.

(57) A protein comprising an amino acid sequence identical or substantially identical with an amino acid sequence represented by SEQ ID NO: 42, or its salt.

(58) A protein consisting of an amino acid sequence represented by SEQ ID NO: 42, or a salt thereof.

(59) A partial peptide of the protein according to the above-mentioned (57), or a salt thereof

(60) A polynucleotide comprising a polynucleotide encoding the protein according to the above-mentioned (57) or the partial peptide according to the above-mentioned (59).

(61) The polynucleotide according to the above-mentioned (60), which is DNA.

(62) A DNA consisting of a base sequence represented by SEQ ID NO: 43, SEQ ID NO: 60, SEQ ID NO: 61 or SEQ ID NO: 62.

(63) A recombinant vector comprising the polynucleotide according to the above-mentioned (60).

(64) A transformant transformed with the recombinant vector according to the above-mentioned (63).

(65) A method of manufacturing the protein or its salt according to the above-mentioned (57) or the partial peptide or its salt according to the above-mentioned (59), which comprises culturing the transformant according to the above-mentioned (64), forming and accumulating the protein according to the above-mentioned (57) or the partial peptide according to the above-mentioned (59), and recovering it.

(66) A medicine comprising the protein according to the above-mentioned (57) or the partial peptide according to the above-mentioned (59).

(67) A medicine comprising the polynucleotide according to the above-mentioned (60).

(68) An antibody to the protein according to the above-mentioned (57), the partial peptide according to the above-mentioned (59), or a salt of the protein or partial peptide.

(69) A medicine comprising the antibody according to the above-mentioned (68).

(70) A diagnostic agent comprising the antibody according to the above-mentioned (68).

(71) A polynucleotide comprising a base sequence complementary or substantially complementary to the base sequence of the polynucleotide according to the above-mentioned (60) or a part of the base sequence.

(72) A medicine comprising the polynucleotide according to the above-mentioned (71).

(73) A method of screening a compound or its salt that promotes or inhibits the activity of the protein or its salt according to the above-mentioned (57) or the partial peptide or its salt according to the above-mentioned (59), which comprises using the protein or its salt according to the above-mentioned (57) or the partial peptide or its salt according to the above-mentioned (59).

(74) A kit for screening a compound or its salt that promotes or inhibits the activity of the protein or its salt according to the above-mentioned (57) or the partial peptide or its salt according to the above-mentioned (59), which comprises the protein or its salt according to the above-mentioned (57) or the partial peptide or its salt according to the above-mentioned (59).

(75) A compound or its salt that promotes or inhibits the activity of the protein or its salt according to the above-mentioned (57) or the partial peptide or its salt according to the above-mentioned (59), which is obtained by using the screening method according to the above-mentioned (73) or the screening kit according to the above-mentioned (74).

(76) A medicine comprising the compound or its salt according to the above-mentioned (75).

(77) A method of screening a compound or its salt that promotes or inhibits the expression of a gene for the protein according to the above-mentioned (57), which comprises using the polynucleotide according to the above-mentioned (60).

(78) A kit for screening a compound or its salt that promotes or inhibits the expression of a gene for the protein according to the above-mentioned (57), which comprises the polynucleotide according to the above-mentioned (60).

(79) A compound or its salt that promotes or inhibits the expression of a gene for the protein according to the above-mentioned (57), which is obtained by the screening method according to the above-mentioned (77) or the screening kit according to the above-mentioned (78).

(80) A medicine comprising the compound or its salt according to the above-mentioned (79).

(81) The medicine according to the above-mentioned (66), (67), (69), (72), (76) or (80), which is a prophylactic/therapeutic agent for pancreatic diseases, central nerve diseases, digestive diseases or respiratory diseases.

(82) A prophylactic/therapeutic method for pancreatic diseases, central nerve diseases, digestive diseases or respiratory diseases, which comprises administering an effective amount of the compound or its salt according to the above-mentioned (75) or (79) into a mammal.

(83) Use of the compound or its salt according to the above-mentioned (75) or (79) in producing a prophylactic/therapeutic agent for pancreatic diseases, central nerve diseases, digestive diseases or respiratory diseases.

(84) A protein or its salt comprising an amino acid sequence identical or substantially identical with an amino acid sequence represented by SEQ ID NO: 66.

(85) A protein consisting of an amino acid sequence represented by SEQ ID NO: 66, or a salt thereof.

(86) A partial peptide of the protein according to the above-mentioned (84), or a salt thereof.

(87) A polynucleotide comprising a polynucleotide encoding the protein according to the above-mentioned (84) or the partial peptide according to the above-mentioned (86).

(88) The polynucleotide according to the above-mentioned (87), which is DNA.

(89) A DNA consisting of a base sequence represented by SEQ ID NO: 67 or SEQ ID NO: 103.

(90) A recombinant vector comprising the polynucleotide according to the above-mentioned (86).

(91) A transformant transformed with the recombinant vector according to the above-mentioned (90).

(92) A method of manufacturing the protein or its salt according to the above-mentioned (84) or the partial peptide or its salt according to the above-mentioned (86), which comprises culturing the transformant according to the above-mentioned (91), forming and accumulating the protein according to the above-mentioned (84) or the partial peptide according to the above-mentioned (86), and recovering it.

(93) A medicine comprising the protein according to the above-mentioned (84) or the partial peptide according to the above-mentioned (86).

(94) A medicine comprising the polynucleotide according to the above-mentioned (87).

(95) An antibody to the protein according to the above-mentioned (84), the partial peptide according to the above-mentioned (86), or a salt of the protein or partial peptide.

(96) A medicine comprising the antibody according to the above-mentioned (95).

(97) A diagnostic agent comprising the antibody according to the above-mentioned (95).

(98) A polynucleotide comprising a base sequence complementary or substantially complementary to the base sequence of the polynucleotide according to the above-mentioned (87) or a part of the base sequence.

(99) A medicine comprising the polynucleotide according to the above-mentioned (98).

(100) A method of screening a compound or its salt that promotes or inhibits the activity of the protein or its salt according to the above-mentioned (84) or the partial peptide or its salt according to the above-mentioned (86), which comprises using the protein or its salt according to the above-mentioned (84) or the partial peptide or its salt according to the above-mentioned (86).

(101) A kit for screening a compound or its salt that promotes or inhibits the activity of the protein or its salt according to the above-mentioned (84) or the partial peptide or its salt according to the above-mentioned (86), which comprises the protein or its salt according to the above-mentioned (84) or the partial peptide or its salt according to the above-mentioned (86).

(102) A compound or its salt that promotes or inhibits the activity of the protein or its salt according to the above-mentioned (84) or the partial peptide or its salt according to the above-mentioned (86), which is obtained by using the screening method according to the above-mentioned (100) or the screening kit according to the above-mentioned (101).

(103) A medicine comprising the compound or its salt according to the above-mentioned (102).

(104) A method of screening a compound or its salt that promotes or inhibits the expression of a gene for the protein according to the above-mentioned (84), which comprises using the polynucleotide according to the above-mentioned (87).

(105) A kit for screening a compound or its salt that promotes or inhibits the expression of a gene for the protein according to the above-mentioned (84), which comprises the polynucleotide according to the above-mentioned (87).

(106) A compound or its salt that promotes or inhibits the expression of a gene for the protein according to the above-mentioned (84), which is obtained by the screening method according to the above-mentioned (104) or the screening kit according to the above-mentioned (105).

(107) A medicine comprising the compound or its salt according to the above-mentioned (106).

(108) A method of determining a ligand to the protein or its salt according to the above-mentioned (84) or the partial peptide or its salt according to the above-mentioned (86), which comprises using the protein or its salt.

(109) A method of screening a compound or its salt that alters the binding property between a ligand and the protein or its salt according to the above-mentioned (84) or the partial peptide or its salt according to the above-mentioned (86), which comprises using the protein, the partial peptide or its salt.

(110) A kit for screening a compound or its salt that alters the binding property between a ligand and the protein or its salt according to the above-mentioned (84) or the partial peptide or its salt according to the above-mentioned (86), which comprises the protein, the partial peptide or its salt.

(111) A compound or its salt that alters the binding property between a ligand and the protein or its salt according to the above-mentioned (84) or the partial peptide or its salt according to the above-mentioned (86), which is obtained by the screening method according to the above-mentioned (109) or the screening kit according to the above-mentioned (110).

(112) A medicine comprising the compound or its salt according to the above-mentioned (111).

(113) A medicine according to the above-mentioned (93), the above-mentioned (94), the above-mentioned (96), the above-mentioned (99), the above-mentioned (103), the above-mentioned (107) or the above-mentioned (112), which is a prophylactic/therapeutic agent for inflammatory diseases, rheumatoid diseases or diabetic neurosis.

(114) A prophylactic/therapeutic method for inflammatory diseases, rheumatoid diseases or diabetic neurosis, which comprises administering an effective amount of the compound or its salt according to the above-mentioned (102), (106) or (111) into a mammal.

(115) Use of the compound or its salt according to the above-mentioned (102), (106) or (111) in producing a prophylactic/therapeutic agent for inflammatory diseases, rheumatoid diseases or diabetic neurosis.

BRIEF DESCRIPTION OF DRAWINGS

FIG. 1 shows comparison in amino acid sequence between human TCH230 (SEQ ID NO:1)) and ileum sodium-dependent bile acid transporter (ISBT (SEQ ID NO:173)). In FIG. 1, TCH230 shows an amino acid sequence of human TCH230 (SEQ ID NO:1); ISBT (SEQ ID NO:173) shows an amino acid sequence of ileum sodium-dependent bile acid transporter (ISBT (SEQ ID NO:173)); * shows the position of amino acid substitution (Ile→Val) derived from single nucleotide polymorphisms (SNPs). The symbol represented by opened square shows coincident amino acids between human TCH230 (SEQ ID NO:1) and ISBT (SEQ ID NO:173).

FIG. 6 shows comparisons in amino acid sequence among human TC14234 (SEQ ID NO: 18), rat NHE4 (SEQ ID NO:174) and human NHE2 (SEQ ID NO:175). In FIG. 6, TCH23 shows an amino acid sequence of human TCH234 (SEQ ID NO:18); rat NHE4 (SEQ ID NO:174) shows an amino acid sequence of rat NHE4 (SEQ ID NO:174); human NHE2 (SEQ ID NO:175) shows an amino acid sequence of human NHE2 (SEQ ID NO:175); the symbol "A" shows an amyloid-binding site; and TM1 to TM13 show a transmembrane region respectively. The symbol represented by opened square shows coincident amino acids with those in human TCH234 (SEQ ID NO:18).

FIG. 8A shows comparisons in amino acid sequence among human TCH212 (SEQ ID NO:42), ATP8A1 (SEQ ID NO:176) and mATP8A2 (SEQ ID NO:177). In FIG. 8A, TCH212 shows an amino acid sequence of human TCH212 (SEQ ID NO:42); ATP8A1 (SEQ ID NO:176) shows an amino acid sequence of P-type ATPase 8A1; and mATP8A2 (SEQ ID NO:177) shows an amino acid sequence of mouse P-type ATPase 8A2. The symbol represented by opened square shows amino acids coincident with those in human TCH212 (SEQ ID NO:42). TM1 to 10 show a transmembrane region, respectively (continued to FIG. 8B).

FIG. 8B shows comparisons in amino acid sequence among human TCH212 (SEQ ID NO:42), ATP8A1 (SEQ ID NO:176) and mATP8A2 (SEQ ID NO:177). In FIG. 8B, TCH212 shows an amino acid sequence of human TCH212 (SEQ ID NO:42); ATP8A1 (SEQ ID NO:176) shows an amino acid sequence of P-type ATPase 8A1; and mATP8A2 (SEQ ID NO:177) shows an amino acid sequence of mouse P-type ATPase 8A2. The symbol represented by opened square shows coincident amino acids with those in human TCH212 (SEQ ID NO:42). TM1 to 10 show a transmembrane region, respectively (continued from FIG. 8A to FIG. 8C).

FIG. 8C shows comparison in amino acid sequence among human TCH212 (SEQ ID NO:42), ATP8A1 (SEQ ID NO:176) and mATP8A2 (SEQ ID NO:177). In FIG. 8C, TCH212 shows an amino acid sequence of human TCH212 (SEQ ID NO:42); ATP8A1 (SEQ ID NO:176) shows an amino acid sequence of P-type ATPase 8A1; and mATP8A2 (SEQ ID NO:177) shows an amino acid sequence of mouse P-type ATPase 8A2. The symbol represented by opened square shows coincident amino acids with those in human TCH212 (SEQ ID NO:42). TM1 to 10 show a transmembrane region, respectively (continued from FIG. 8B).

FIG. 11 shows comparison in amino acid sequence between human TCH200 (SEQ ID NO:66) and human VR1 (SEQ ID NO:178). In FIG. 11, TCH200 (SEQ ID NO:66) shows an amino acid sequence of human TCH200 (SEQ ID NO:66); and hVR1 shows an amino acid sequence of humanVR1 (SEQ ID NO:178). TM1 to 6 show a transmembrane region, respectively. A1 to 3h show Ankyrin repeat sequence. The symbol represented by opened square shows coincident amino acids between two sequences.

FIG. 13 shows comparison in amino acid sequence between mouse TCH230 (SEQ ID NO: 112) and human TCH230 (SEQ ID NO: 1). In FIG. 13, hTCH230 shows an amino acid sequence of human TCH230 (SEQ ID NO:1); and mTCH230 shows an amino acid sequence of mouse TCH230 (SEQ ID NO:112). The symbol represented by opened square shows coincident amino acids between two sequences.

In FIG. 17, the cell having vector pcDNA3.1(+) introduced into it is represented as Mock, and human TCH230 (SEQ ID NO:1)-expressing CHO cell is expressed as TCH230, and the cells incorporating [6,7-$^3$H(N)]-estrone sulfate with NaCl buffer are represented as Mock/NaCl and TCH230/NaCl respectively, and the cells incorporating [6,7-$^3$H(N)]-estrone sulfate with NMDG buffer are expressed as Mock/NMDG and TCH230/NMDG respectively.

In FIG. 18, the cell having vector pcDNA3.1(+) introduced into it is represented as Mock, and human TCH230 (SEQ ID NO:1)-expressing CHO cell is represented as TCH230, and the cells incorporating [1,2,6,7-$^3$H(N)]-DHEA-S with NaCl buffer are represented as Mock/NaCl and TCH230/NaCl respectively, and the cells incorporating [1,2,6,7-$^3$H(N)]-DHEA-S with NMDG buffer are represented as Mock/NMDG and TCH230/NMDG respectively.

BEST MODE FOR CARRYING OUT THE INVENTION

Figure 2:
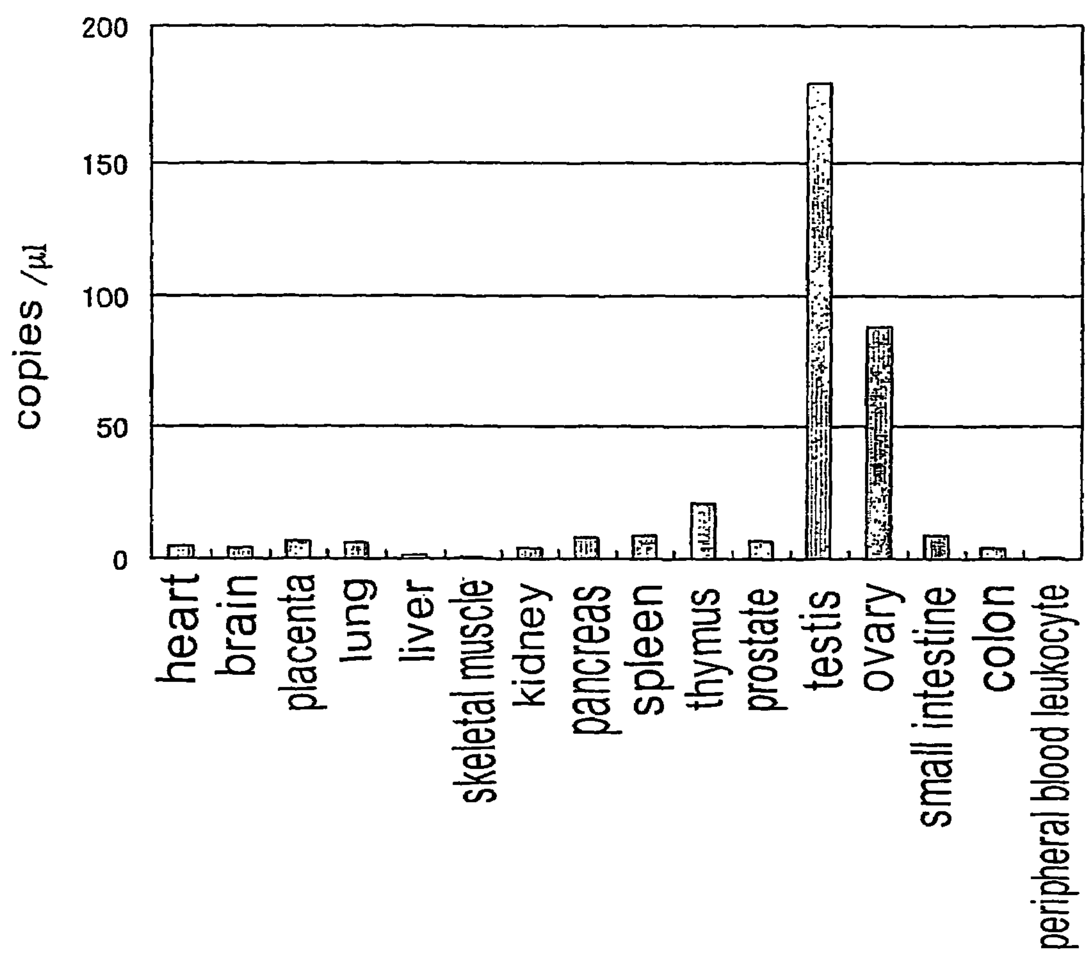
FIG. 2 shows the expression level of human TCH230 (SEQ ID NO:1) gene product in each tissue. The expression level is represented in terms of copy number per μl of cDNA solution.
Figure 3:
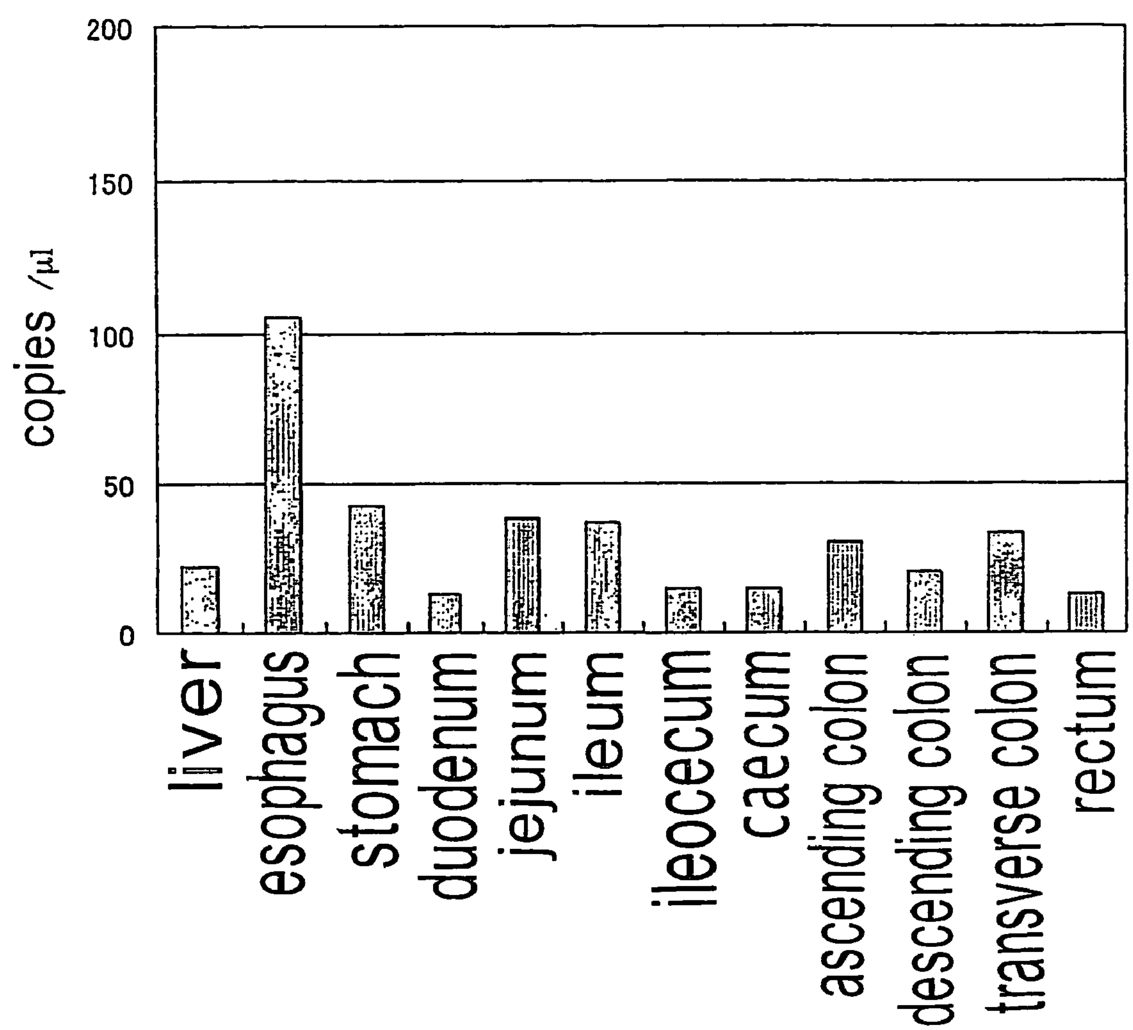
FIG. 3 shows the expression level of human TCH230 (SEQ ID NO:1) gene product in each tissue. The expression level is represented in terms of copy number per μl of cDNA solution.
Figure 4:
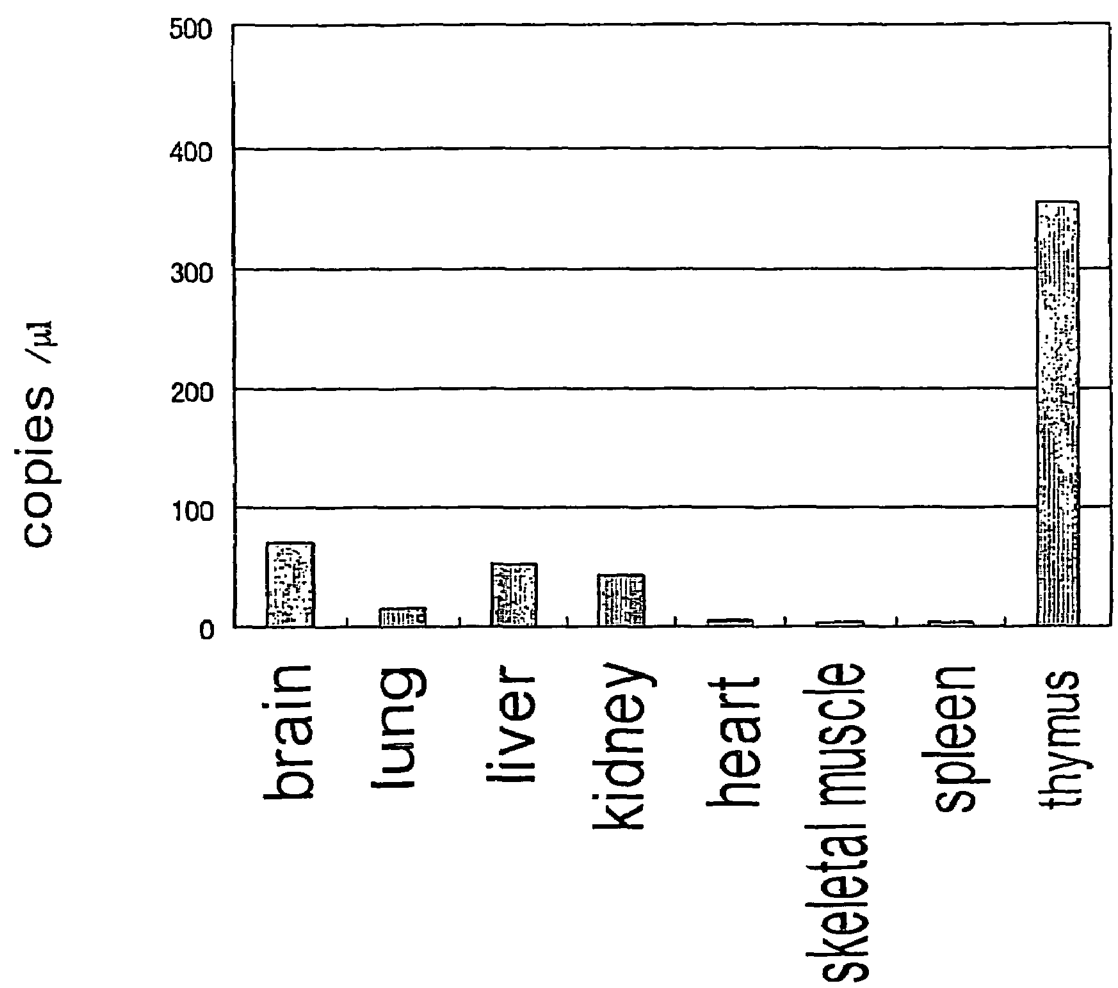
FIG. 4 shows the expression level of human TCH230 (SEQ ID NO:1) gene product in each tissue. The expression level is represented in terms of copy number per μl of cDNA solution.
Figure 5:
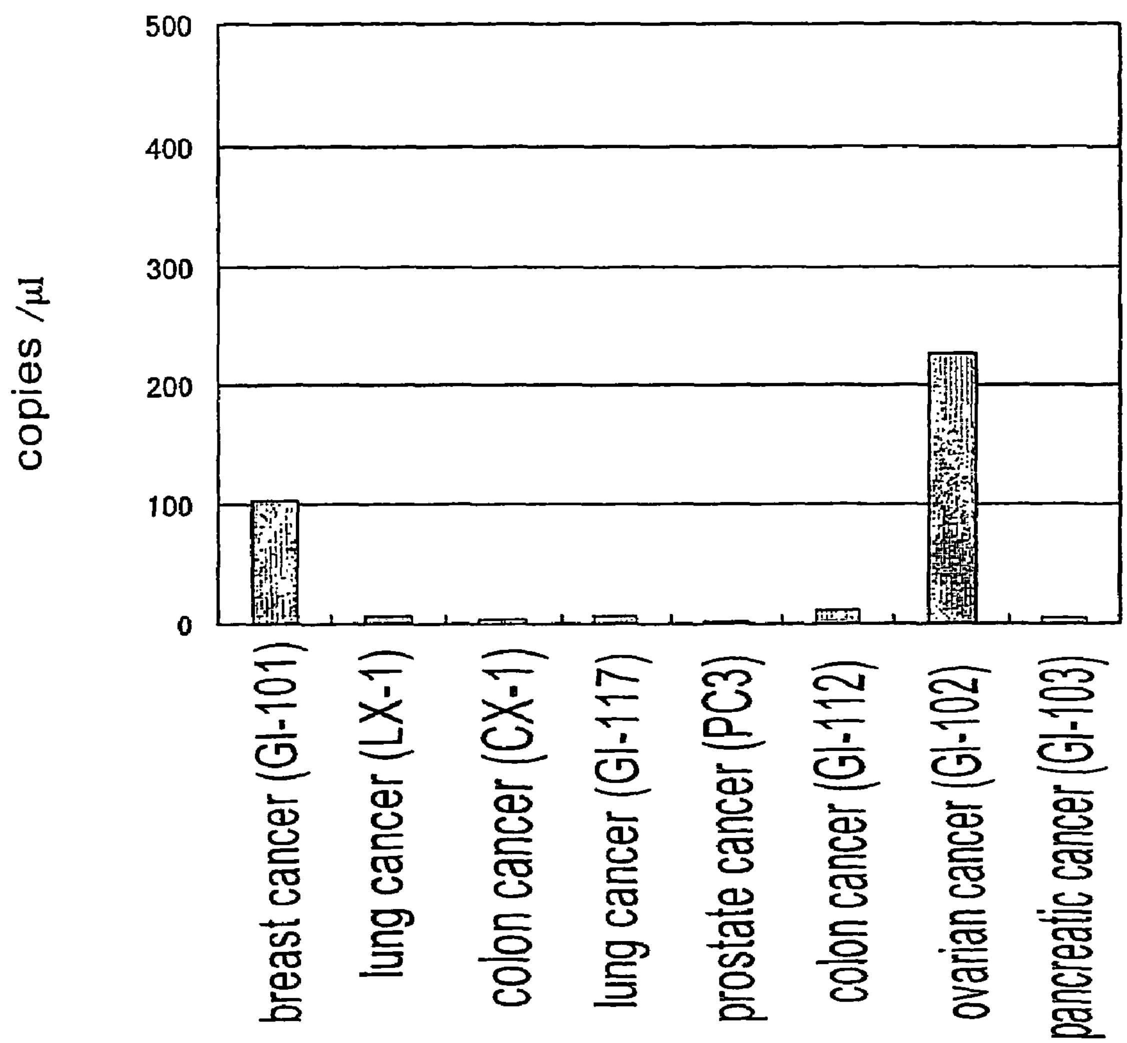
FIG. 5 shows the expression level of human TCH230 (SEQ ID NO:1) gene product in each tissue. The expression level is represented in terms of copy number per μl of cDNA solution.

A protein comprising the same or substantially the same amino acid sequence as an amino acid sequence represented by SEQ ID NO: 1, 14, 104, 18, 42 or 66 (hereinafter, sometimes referred as to the protein of the present invention) may be any protein derived from any cells (e.g., liver cells, splenocytes, nerve cells, glial cells, β cells of pancreas, bone marrow cells, mesangial cells, Langerhans' cells, epidermic cells, epithelial cells, goblet cells, endothelial cells, smooth muscular cells, fibroblasts, fibrocytes, myocytes, fat cells, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells, hepatocytes or interstitial cells, the corresponding precursor cells, stem cells, cancer cells, etc.), or any tissues where such cells are present, e.g., brain or any region of the brain (e.g., olfactory bulb, amygdaloid nucleus, basal ganglia, hippocampus, thalamus, hypothalamus, cerebral cortex, medulla oblongata and cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc. from human and non-human mammals (e.g., guinea pigs, rats, mice, chickens, rabbits, swine, sheep, bovine, monkeys, etc.), or the protein may also be a synthetic protein.

Substantially the same amino acid sequence as the amino acid sequence represented by SEQ ID NO: 1 includes an amino acid sequence having at least about 50% homology, preferably at least about 70% homology, more preferably at least about 80% homology, still more preferably at least about 90% homology, further more preferably at least about 95% homology to the amino acid sequence represented by SEQ ID NO: 1.

Preferable examples of the protein comprising substantially the same amino acid sequence as that represented by SEQ ID NO: 1 include a protein comprising substantially the same amino acid sequence as that represented by SEQ ID NO: 1 and having an activity substantially equivalent to that of a protein having the amino acid sequence represented by SEQ ID NO: 1, etc.

Substantially the same amino acid sequence as that represented by SEQ ID NO: 14 includes an amino acid sequence having at least about 50% homology, preferably at least about 70% homology, more preferably at least about 80% homology, still more preferably at least about 90% homology, further more preferably at least about 95% homology to the amino acid sequence represented by SEQ ID NO: 14.

Preferable examples of the protein comprising substantially the same amino acid sequence as that represented by SEQ ID NO: 14 include a protein comprising substantially the same amino acid sequence as that represented by SEQ ID NO: 14 and having an activity substantially equivalent to a protein having the amino acid sequence represented by SEQ ID NO: 14, etc.

Substantially the same amino acid sequence as that represented by SEQ ID NO: 104 includes an amino acid sequence having at least about 75% homology, preferably at least about 80% homology, more preferably at least about 90% homology, still more preferably at least about 95% homology to the amino acid sequence represented by SEQ ID NO: 104.

Preferable examples of the protein comprising substantially the same amino acid sequence as that represented by SEQ ID NO: 104 include a protein comprising substantially the same amino acid sequence as that represented by SEQ ID NO: 104 and having an activity substantially equivalent to that of a protein having the amino acid sequence represented by SEQ ID NO: 104, etc.

The substantially equivalent activity includes, for example, substrate transport.

The substrate includes, for example, steroid hormone, bile acid etc.

The steroid hormone includes, for example, estrogen, progestogen, androgen, mineral corticoid, glucocorticoid, steroid chemicals or metabolites thereof (e.g., sulfate conjugates, glucuronide conjugates etc.) etc.

The estrogen includes, for example, estrone, estradiol, estriol, estetrol etc.

The progestogen includes, for example, progesterone, pregnanediol etc.

The androgen includes, for example, dehydroepiandrosterone, testosterone, androstanedione, 5α-dihydrotestosterone, androsterone etc.

The mineral corticoid includes, for example, aldosterone etc.

The glucocorticoid includes, for example, cortisol, cortisone, corticosterone, dehydrocorticosterone etc.

The steroid chemicals include, for example, dexamethasone, betamethasone, prednisolone, triamcinolone, fluorocortisone, clomiphene, tamoxifen, danazol etc.

The bile acid includes, for example, taurocholic acid, glicocholic acid, cholic acid, lithocholic acid, deoxycholic acid, taurodeoxycholic acid, tauroursodeoxycholic acid, chenodeoxycholic acid, glicochenodeoxycholic acid, glicodeoxycholic acid etc.

The terms "substantially equivalent" mean that the activity is inherently (e.g. physiologically or pharmacologically) equivalent. Therefore, although it is preferred that the above-mentioned substrate transport be equivalent (e.g., about 0.01- to 100-fold, preferably about 0.1- to 10-fold, more preferably about 0.5- to 2-fold), quantitative factors such as a level of the activity, a molecular weight of the protein, etc. may differ.

The activities such as substrate transport or the like can be determined according to a publicly known method, for example, by a method described in Am. J. Physiol., 274, G157-169, 1998, or its modified method.

Substantially the same amino acid sequence as that represented by SEQ ID NO: 18 includes an amino acid sequence having at least about 90% homology, preferably at least about 95% homology, more preferably at least about 97% homology, much more preferably at least about 99% homology to the amino acid sequence represented by SEQ ID NO: 18.

Preferable examples of the protein comprising substantially the same amino acid sequence as that represented by SEQ ID NO: 18 include a protein comprising substantially the same amino acid sequence as that represented by SEQ ID NO: 18 and having an activity substantially equivalent to a protein having the amino acid sequence represented by SEQ ID NO: 18, etc.

The substantially equivalent activity includes, for example, a cation (preferably monovalent cation such as $Na^+$, $K^+$, etc.)/$H^+$ exchange transport activity. The terms "substantially equivalent" mean that the activity is inherently (e.g. physiologically or pharmacologically) equivalent. Therefore, although it is preferred that the cation (preferably monovalent cation such as $Na^+$, $K^+$, etc.)/$H^+$ exchange transport activity be equivalent (e.g., about 0.01- to 100-fold, preferably about 0.1- to 10-fold, more preferably about 0.5- to 2-fold), quantitative factors such as a level of the activity, a molecular weight of the protein, etc. may differ.

The activities such as the cation (preferably monovalent cation such as $Na^+$, $K^+$, etc.)/$H^+$ exchange transport activity or the like can be determined according to a publicly known method, for example, by a method described in J. Biol. Chem., 274, 3978-3987, 1998, or its modified method.

Substantially the same amino acid sequence as that represented by SEQ ID NO: 42 includes an amino acid sequence having at least about 96% homology, preferably at least about 97% homology, more preferably at least about 98% homology, much more preferably at least about 99% homology to the amino acid sequence represented by SEQ ID NO: 42.

Preferable examples of the protein comprising substantially the same amino acid sequence as that represented by SEQ ID NO: 42 include a protein comprising substantially the same amino acid sequence as that represented by SEQ ID NO: 42 and having an activity substantially equivalent to that of a protein having the amino acid sequence represented by SEQ ID NO: 42, etc.

The substantially equivalent activity includes, for example, transport of aminophospholipid. The terms "substantially equivalent" mean that the activity is inherently (e.g. physiologically or pharmacologically) equivalent. Therefore, although it is preferred that the transport of aminophospholipid be equivalent (e.g., about 0.01- to 100-fold, preferably about 0.1- to 10-fold, more preferably about 0.5- to 2-fold), quantitative factors such as a level of the activity, a molecular weight of the protein, etc. may differ.

The activities such as the transport of aminophospholipid or the like can be determined according to a publicly known method, for example, by a method described in J. Biol. Chem., 275, 23378-23386, 1998, or its modified method.

Substantially the same amino acid sequence as that represented by SEQ ID NO: 66 includes an amino acid sequence having at least about 45% homology, preferably at least about 50% homology, more preferably at least about 70% homology, still more preferably at least about 80% homology, further more preferably at least about 90% homology, further still more preferably at least about 95% homology to the amino acid sequence represented by SEQ ID NO: 66.

Preferable examples of the protein comprising substantially the same amino acid sequence as that represented by SEQ ID NO: 66 include a protein comprising substantially the same amino acid sequence as that represented by SEQ ID NO: 66 and having an activity substantially equivalent to that of a protein having the amino acid sequence represented by SEQ ID NO: 66, etc.

The substantially equivalent activity includes, for example, a cation (e.g., $Ca^{+2}$ etc.) channel activity. The terms "substantially equivalent" mean that the activity is inherently (e.g. physiologically or pharmacologically) equivalent. Therefore, although it is preferred that the cation channel activity be equivalent (e.g., about 0.01- to 100-fold, preferably about 0.1- to 10-fold, more preferably about 0.5- to 2-fold), quantitative factors such as a level of the activity, a molecular weight of the protein, etc. may differ.

The activities such as the cation channel activity or the like can be determined according to a publicly known method, for example, by a method described in Nature, 389, 816, 1997, or its modified method.

The protein of the present invention includes, for example, (1) (i) amino acid sequences represented by SEQ ID NO: 1, SEQ ID NO: 14 or SEQ ID NO: 104, wherein at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably approximately 1 to 10, and most preferably several (1 to 5) amino acids) are deleted, (ii) amino acid sequences represented by SEQ ID NO: 1, SEQ ID NO: 14 or SEQ ID NO: 104, to which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably approximately 1 to 10, and most preferably several (1 to 5) amino acids) are added, (iii) amino acid sequences represented by SEQ ID NO: 1, SEQ ID NO: 14 or SEQ ID NO: 104, into which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably approximately 1 to 10, and most preferably several (1 to 5) amino acids) are inserted, (iv) amino acid sequences represented by SEQ ID NO: 1, SEQ ID NO: 14 or SEQ ID NO: 104, wherein at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably approximately 1 to 10, and most preferably several (1 to 5) amino acids) are substituted by other amino acids or (v) muteins comprising a combination of the amino acid sequences described in the above, (2) (i) an amino acid sequence represented by SEQ ID NO: 18, from which at least 1 or 2 amino acids (for example approximately 1 to 90 amino acids, preferably approximately 1 to 50 amino acids, more preferably approximately 1 to 30 amino acids, still more preferably approximately 1 to 10 amino acids, further more preferably several (1 to 5) amino acids) are deleted, (ii) an amino acid sequence represented by SEQ ID NO: 18, to which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are added, (iii) an amino acid sequence represented by SEQ ID NO: 18, into which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are inserted, (iv) an amino acid sequence represented by SEQ ID NO: 18, wherein at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are substituted by other amino acids or (v) muteins comprising a combination of the amino acid sequences described in the above, (3) (i) an amino acid sequence represented by SEQ ID NO: 42, from which at least 1 or 2 amino acids (for example approximately 1 to 50 amino acids, preferably approximately 1 to 30 amino acids, more preferably approximately 1 to 10 amino acids, and most preferably several (1 to 5) amino acids) are deleted, (ii) an amino acid sequence represented by SEQ ID NO: 42, to which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are added, (iii) an amino acid sequence represented by SEQ ID NO: 42, into which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are inserted, (iv) an amino acid sequence represented by SEQ ID NO: 42, wherein at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are substituted by other amino acids or (v) muteins comprising a combination of the amino acid sequences described in the above, and (4) (i) an amino acid sequence represented by SEQ ID NO: 66, from which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are deleted, (ii) an amino acid sequence represented by SEQ ID NO: 66, to which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are added, (iii) an amino acid sequence represented by SEQ ID NO: 66, into which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are inserted, (iv) an amino acid sequence represented by SEQ ID NO: 66, wherein at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are substituted by other amino acids or (v) muteins comprising a combination of the amino acid sequences described in the above.

When the amino acid sequence has undergone insertion, deletion or substitution as described above, the position of the insertion, deletion or substitution is not particularly limited.

The proteins in the present specification are represented in accordance with the conventional way of describing peptides, that is, the N-terminus (amino terminus) at the left hand and the C-terminus (carboxyl terminus) at the right hand. In the proteins of the present invention including the protein comprising the amino acid sequence represented by SEQ ID NO: 1, the C-terminus is usually in the form of a carboxyl group (—COOH) or a carboxylate ($—COO^-$) but may be in the form of an amide ($—CONH_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; and a pivaloyloxymethyl group or the like.

Where the protein of the present invention has a carboxyl group (or a carboxylate) at a position other than the C-terminus, it may be amidated or esterified and such an amide or ester is also included within the protein of the present invention. As the ester group herein, the same esters as those described with respect to the above C-terminal are used.

Furthermore, examples of the protein of the present invention include variants of the above proteins, wherein the N-terminal amino group residue (e.g. methionine residue) of the protein supra is protected with a protecting group (for example, a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins having sugar chains bound thereto.

Specific examples of the protein of the present invention include proteins comprising amino acid sequences represented by SEQ ID NO: 1, SEQ ID NO: 14, SEQ ID NO: 104, SEQ ID NO: 18, SEQ ID NO: 42 or SEQ ID NO: 66.

Partial peptides of the protein of the present invention may be any peptides insofar as they are partial peptides of the protein of the present invention and preferably have properties identical with those of the protein of the present invention.

For example, peptides having at least 5, preferably at least 10, more preferably at least 20, still more preferably at least 50, further more preferably at least 70, further still more preferably at least 100 and most preferably at least 200 amino acids in the amino acid sequence which constitutes the protein of the present invention are used.

The partial peptide of the present invention may contain an amino acid sequence, wherein at least 1 or 2 amino acids (for example approximately 1 to 20 amino acids, preferably approximately 1 to 10 amino acids, more preferably several (1 to 5) amino acids) are deleted, to which at least 1 or 2 amino acids (for example approximately 1 to 20 amino acids, preferably approximately 1 to 10 amino acids, more preferably several (1 to 5) amino acids) are added, into which at least 1 or 2 amino acids (for example approximately 1 to 20 amino acids, preferably approximately 1 to 10 amino acids, more preferably approximately several (1 to 5) amino acids) are inserted, or in which at least 1 or 2 amino acids (for example approximately 1 to 20 amino acids, preferably approximately 1 to 10 amino acids, more preferably approximately several (1 to 5) amino acids) are substituted by other amino acids.

The partial peptide of the present invention includes, for example, a peptide having an amino acid sequence in e.g. positions 1 to 28, 99 to 129, 180 to 193 or 246 to 286 in the amino acid sequence represented by SEQ ID NO: 1 or SEQ ID NO: 14, a peptide having an amino acid sequence in e.g. positions 40 to 60 or 330 to 350 in the amino acid sequence represented by SEQ ID NO: 18, a peptide having an amino acid sequence in e.g. positions 301 to 322, 941 to 952 or 1012 to 1028 in the amino acid sequence represented by SEQ ID NO: 42, a peptide having an amino acid sequence in e.g. positions 460 to 485 or 610 to 630 in the amino acid sequence represented by SEQ ID NO: 66, and a peptide having an amino acid sequence in e.g. positions 1 to 28, 99 to 129, 180 to 193 or 245 to 285 in the amino acid sequence represented by SEQ ID NO: 104.

In the partial peptide of the present invention, the C-terminus is usually in the form of a carboxyl group (—COOH) or a carboxylate ($—COO^-$) but may be in the form of an amide ($—CONH_2$) or an ester (—COOR) as described above with respect to the protein of the present invention.

Like the protein of the present invention, the partial peptide of the present invention includes those having a carboxyl group (or a carboxylate) at a position other than the C-terminus, those wherein an amino group of the N-terminal amino acid residue (e.g., methionine residue) is protected with a protecting group, those wherein the N-terminal region is cleaved in vivo and a glutamine reissue thus formed is pyroglutaminated, those wherein a substituent on the side chain of an amino acid in the molecule is protected with a suitable protecting group, or conjugated proteins such as glycoproteins having sugar chains bound thereto.

The partial peptide of the present invention can also be used as an antigen for preparing an antibody. For the purpose of preparing the antibody of the present invention, mention can be made of, for example, a peptide having an amino acid sequence in e.g. positions 1 to 28, 99 to 129, 180 to 193 or 246 to 286 in the amino acid sequence represented by SEQ ID NO: 1 or SEQ ID NO: 14, a peptide having an amino acid sequence in e.g. positions 40 to 60 or 330 to 350 in the amino acid sequence represented by SEQ ID NO: 18, a peptide having an amino acid sequence in e.g. positions 301 to 322, 941 to 952 or 1012 to 1028 in the amino acid sequence represented by SEQ ID NO: 42, a peptide having an amino acid sequence in e.g. positions 460 to 485 or 610 to 630 in the amino acid sequence represented by SEQ ID NO: 66, and a peptide having an amino acid sequence in e.g. positions 1 to 28, 99 to 129, 180 to 193 or 245 to 285 in the amino acid sequence represented by SEQ ID NO: 104.

As salts of the protein or partial peptide of the present invention, use is made of salts with physiologically acceptable acids (e.g., inorganic acids or organic acids) or bases (e.g., alkali metal salts), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The protein or partial peptide of the present invention or salts thereof may be manufactured from the human and other warm-blooded animal cells or tissues described above by a publicly known protein purification method, or by culturing a transformant that comprises the DNA encoding the protein of the present invention. Furthermore, the protein or partial peptide or salts thereof may also be manufactured by the peptide synthesis method, which will be described below.

Where the protein or its salts are manufactured from human and other mammalian tissues or cells, human or other mammalian tissues or cells are homogenized, then extracted with an acid or the like, and the extract is isolated and purified by a combination of chromatography techniques such as reverse phase chromatography, ion exchange chromatography, and the like.

To synthesize the protein of the present invention, its partial peptide, or salts or amides thereof according to the present invention, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective protein according to various condensation methods publicly known in the art. At the end of the reaction, the protein is excised from the resin and at the same time, the protecting groups are removed. Then, intramolecular disulfide bond-forming reaction is performed in a highly diluted solution to obtain the objective protein or the partial peptide, or amides thereof.

For condensation of the protected amino acids described above, a variety of activation reagents for protein synthesis may be used, and carbodiimides are particularly preferable. Examples of such carbodiimides include DCC, N,N'-diisopropylcarbodiimide, N-ethyl-N'-(3-dimethylaminopropyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be appropriately chosen from solvents known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse effect on the subsequent reaction.

Examples of the protecting groups used to protect the amino groups of the starting materials include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting materials include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol, which is activated by ligand. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the protein or partial peptide, for example, the α-carboxyl group of the carboxy terminal amino acid is first protected by amidation, and the peptide (protein) chain is then extended from the amino group side to a desired length. Thereafter, a protein or partial peptide in which only the protecting group of the N-terminal α-amino group in the peptide chain has been eliminated from the protein and a protein or partial peptide in which only the protecting group of the C-terminal carboxyl group has been eliminated are prepared. The two proteins or peptides are condensed in a mixture of the solvents described above. The details of the condensation reaction are the same as described above. After the protected protein or peptide obtained by the condensation is purified, all the protecting groups are eliminated by the method described above to give the desired crude protein or peptide. This crude protein or peptide is purified by various known purification means. Lyophilization of the major fraction gives the amide of the desired protein or peptide.

To prepare the esterified protein or peptide, for example, the α-carboxyl group of the carboxy terminal amino acid is condensed with a desired alcohol to prepare the amino acid ester, which is followed by procedure similar to the preparation of the amidated protein or peptide above to give the ester form of the desired protein or peptide.

The partial peptide of the present invention or its salts can be manufactured by publicly known methods for peptide synthesis, or by cleaving the protein of the present invention with an appropriate peptidase. For the methods for peptide synthesis, for example, either solid phase synthesis or liquid phase synthesis may be used. That is, the partial peptide or amino acids that can construct the partial peptide of the present invention are condensed with the remaining part. Where the product contains protecting groups, these protecting groups are removed to give the desired peptide. Publicly known methods for condensation and elimination of the protecting groups are described in (a) to (e) below.

(a) M. Bodanszky & M. A. Ondetti: Peptide Synthesis, Interscience Publishers, New York (1966)

(b) Schroeder & Luebke: The Peptide, Academic Press, New York (1965)

(c) Nobuo Izumiya, et al.: Peptide Gosei-no-Kiso to Jikken (Basics and experiments of peptide synthesis), published by Maruzen Co. (1975)

(d) Haruaki Yajima & Shunpei Sakakibara: Seikagaku Jikken Koza (Biochemical Experiment) 1, Tanpakushitsu no Kagaku (Chemistry of Proteins) IV, 205 (1977)

(e) Haruaki Yajima, ed.: Zoku lyakuhin no Kaihatsu (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the partial peptide obtained by the above methods is in a free form, the peptide can be converted into an appropriate salt form by a publicly known method; when the partial peptide is obtained in a salt form, it can be converted into a free form by a publicly known method.

The polynucleotide encoding the protein of the present invention may be any polynucleotide so long as it comprises the base sequence encoding the protein of the present invention described above. The polynucleotide is preferably DNA. The DNA may also be any of genomic DNA, genomic cDNA library, cDNA derived from the cells or tissues described above, cDNA library derived from the cells or tissues described above, and synthetic DNA.

The vector to be used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

The DNA encoding the protein of the present invention may be for example (1) DNA comprising the base sequence represented by SEQ ID NO: 2 or SEQ ID NO: 11, or DNA hybridizing under high stringent conditions with the base sequence represented by SEQ ID NO: 2 or SEQ ID NO: 11 and encoding a protein having properties substantially equivalent to those of a protein comprising the amino acid sequence represented by SEQ ID NO: 1, (2) DNA comprising the base sequence represented by SEQ ID NO: 13 or SEQ ID NO: 12, or DNA hybridizing under high stringent conditions with the base sequence represented by SEQ ID NO: 13 or SEQ ID NO: 12 and encoding a protein having properties substantially equivalent to those of a protein comprising the amino acid sequence represented by SEQ ID NO: 14, (3) DNA comprising the base sequence represented by SEQ ID NO: 105 or SEQ ID NO: 112, or DNA hybridizing under high stringent conditions with the base sequence represented by SEQ ID NO: 105 or SEQ ID NO: 112 and encoding a protein having properties substantially equivalent to those of a protein comprising the amino acid sequence represented by SEQ ID NO: 104, (4) DNA comprising the base sequence represented by SEQ ID NO: 19 or SEQ ID NO: 41, or DNA hybridizing under high stringent conditions with the base sequence represented by SEQ ID NO: 19 or SEQ ID NO: 41 and encoding a protein having properties substantially equivalent to those of a protein comprising the amino acid sequence represented by SEQ ID NO: 18, (5) DNA comprising the base sequence represented by SEQ ID NO: 43, SEQ ID NO: 60, SEQ ID NO: 61 or SEQ ID NO: 62, or DNA hybridizing under high stringent conditions with the base sequence represented by SEQ ID NO: 43, SEQ ID NO: 60, SEQ ID NO: 61 or SEQ ID NO: 62 and encoding a protein having properties substantially equivalent to those of a protein comprising the amino acid sequence represented by SEQ ID NO: 42, or (6) DNA comprising the base sequence represented by SEQ ID NO: 67 or SEQ ID NO: 103, or DNA hybridizing under high stringent conditions with the base sequence represented by SEQ ID NO: 67 or SEQ ID NO: 103 and encoding a protein having properties substantially equivalent to those of a protein comprising the amino acid sequence represented by SEQ ID NO: 66.

As the DNA hybridizing under high stringent conditions with the base sequence represented by SEQ ID NO: 2 or SEQ ID NO: 11, there may be employed e.g. DNA comprising a base sequence having at least about 50% homology, preferably at least about 60% homology, more preferably at least about 70% homology, still more preferably at least about 80% homology, further more preferably at least about 90% homology to the base sequence represented by SEQ ID NO: 2 or SEQ ID NO: 11.

As the DNA hybridizing under high stringent conditions with the base sequence represented by SEQ ID NO: 13 or SEQ ID NO: 12, there may be employed e.g. DNA comprising a base sequence having at least about 50% homology, preferably at least about 60% homology, more preferably at least about 70% homology, still more preferably at least about 80% homology, further more preferably at least about 90% homology to the base sequence represented by SEQ ID NO: 13 or SEQ ID NO: 12.

As the DNA hybridizing under high stringent conditions with the base sequence represented by SEQ ID NO: 105 or SEQ ID NO: 112, there may be employed e.g. DNA comprising a base sequence having at least about 75% homology, preferably at least about 80% homology, more preferably at least about 90% homology, still more preferably at least about 95% homology to the base sequence represented by SEQ ID NO: 105 or SEQ ID NO: 112.

As the DNA hybridizing under high stringent conditions with the base sequence represented by SEQ ID NO: 19 or SEQ ID NO: 41, there may be employed e.g. DNA comprising a base sequence having at least about 90% homology, preferably at least about 95% homology, more preferably at least about 97% homology, still more preferably at least about 99% homology to the base sequence represented by SEQ ID NO: 19 or SEQ ID NO: 41.

As the DNA hybridizing under high stringent conditions with the base sequence represented by SEQ ID NO: 43, SEQ ID NO: 60, SEQ ID NO: 61 or SEQ ID NO: 62, there may be employed e.g. DNA comprising a base sequence having at least about 96% homology, preferably at least about 97% homology, more preferably at least about 98% homology, still more preferably at least about 99% homology to the base sequence represented by SEQ ID NO: 43, SEQ ID NO: 60, SEQ ID NO: 61 or SEQ ID NO: 62.

As the DNA hybridizing under high stringent conditions with the base sequence represented by SEQ ID NO: 67 or SEQ ID NO: 103, there may be employed e.g. DNA comprising a base sequence having at least about 45% homology, preferably at least about 50% homology, more preferably at least about 70% homology, still more preferably at least about 80% homology, further more preferably at least about 90% homology still further more preferably at least about 95% homology to the base sequence represented by SEQ ID NO: 67 or SEQ ID NO: 103.

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration of about 19 mM at a temperature of about 65° C. are most preferred.

More specifically, as the DNA encoding a protein comprising the amino acid sequence represented by SEQ ID NO: 1, there may be employed, e.g. DNA comprising the base sequence represented by SEQ ID NO: 2 or SEQ ID NO: 11; as the DNA encoding a protein comprising the amino acid sequence represented by SEQ ID NO: 14, there may be employed, e.g. DNA comprising the base sequence represented by SEQ ID NO: 13 or SEQ ID NO: 12; as the DNA encoding a protein comprising the amino acid sequence represented by SEQ ID NO: 104, there may be employed, e.g. DNA comprising the base sequence represented by SEQ ID NO: 105 or SEQ ID NO: 112; as the DNA encoding a protein comprising the amino acid sequence represented by SEQ ID NO: 18, there may be employed, e.g. DNA comprising the base sequence represented by SEQ ID NO: 19 or SEQ ID NO: 41; as the DNA encoding a protein comprising the amino acid sequence represented by SEQ ID NO: 42, there may be employed, e.g. DNA comprising the base sequence represented by SEQ ID NO: 43, SEQ ID NO: 60, SEQ ID NO: 61 or SEQ ID NO: 62; and as the DNA encoding a protein comprising the amino acid sequence represented by SEQ ID NO: 66, there may be employed, e.g. DNA comprising the base sequence represented by SEQ ID NO: 67 or SEQ ID NO: 103.

The polynucleotide encoding the partial peptide of the present invention may be any polynucleotide so long as it comprises a base sequence encoding the partial peptide of the present invention described above. The polynucleotide is preferably DNA. The DNA may also be any of genomic DNA, genomic DNA library, cDNA derived from the cells and tissues described above, cDNA library derived from the cells and tissues described above and synthetic DNA.

As the DNA encoding the partial peptide of the present invention, there may be employed, for example, DNA having a part of DNA having the base sequence represented by SEQ ID NO: 2, SEQ ID NO: 11, SEQ ID NO: 12, SEQ ID NO: 13, SEQ ID NO: 19, SEQ ID NO: 41, SEQ ID NO: 43, SEQ ID NO: 60, SEQ ID NO: 61, SEQ ID NO: 62, SEQ ID NO: 67, SEQ ID NO: 103, SEQ ID NO: 105 or SEQ ID NO: 112, or DNA comprising a base sequence hybridizing under stringent conditions with the base sequence represented by SEQ ID NO: 2, SEQ ID NO: 11, SEQ ID NO: 12, SEQ ID NO: 13, SEQ ID NO: 19, SEQ ID NO: 41, SEQ ID NO: 43, SEQ ID NO: 60, SEQ ID NO: 61, SEQ ID NO: 62, SEQ ID NO: 67, SEQ ID NO: 103, SEQ ID NO: 105 or SEQ ID NO: 112 and comprising a part of DNA encoding a protein having an activity substantially equivalent to that of the protein of the present invention.

The DNA hybridizable with the base sequence represented by SEQ ID NO: 2, SEQ ID NO: 11, SEQ ID NO: 12, SEQ ID NO: 13, SEQ ID NO: 19, SEQ ID NO: 41, SEQ ID NO: 43, SEQ ID NO: 60, SEQ ID NO: 61, SEQ ID NO: 62, SEQ ID NO: 67, SEQ ID NO: 103, SEQ ID NO: 105 or SEQ ID NO: 112 has the same meaning as described above.

As the hybridization method and high stringent conditions, those described above are used.

For cloning of the DNA that completely encodes the protein of the present invention or its partial peptide (hereinafter sometimes merely referred to as the protein of the present invention), the DNA may be amplified by PCR using synthetic DNA primers comprising a part of the base sequence encoding the protein of the present invention, or the DNA inserted into an appropriate vector can be selected by hybridization with a labeled DNA fragment or synthetic DNA that encodes a part or entire region of the protein of the present invention. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

Conversion of the base sequence of the DNA can be effected by publicly known methods such as the ODA-LA PCR method, the gapped duplex method or the Kunkel method or its modification using a publicly known kit available as Mutan™-G or Mutan™-K (both manufactured by Takara Shuzo Co., Ltd.).

The cloned DNA encoding the protein can be used as it is, depending upon purpose or if desired after digestion with a restriction enzyme or after addition of a linker thereto. The DNA may have ATG as a translation initiation codon at the 5' end thereof and may further have TAA, TGA or TAG as a translation termination codon at the 3' end thereof. These translation initiation and termination codons may also be added by using an appropriate synthetic DNA adapter.

The expression vector for the protein of the present invention can be manufactured, for example, by (a) excising the desired DNA fragment from the DNA encoding the protein of the present invention, and then (b) ligating the DNA fragment to an appropriate expression vector downstream from a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRx promoter, SV40 promoter, LTR promoter, CMV promoter, HSV-TK promoter, etc.

Among them, CMV (cytomegalovirus) promoter or SRα promoter is preferably used. Where the host is bacteria of the genus *Escherichia*, preferred examples of the promoter include trp promoter, lac promoter, recA promoter, λPL promoter, lpp promoter, T7 promoter etc. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin prompter and P10 promoter.

In addition to the foregoing examples, the expression vector may further optionally contain an enhancer, a splicing signal, a polyA addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker in dhfr gene-deficient Chinese hamster's cells, selection can also be made on thymidine free media.

If necessary and desired, a signal sequence that matches with a host is added to the N-terminus of the protein of the present invention. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector comprising the DNA encoding the protein of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the bacteria belonging to the genus *Bacillus* include *Bacillus subtilis* MI114 (Gene, 24, 255 (1983)), 207-21 (Journal of Biochemistry, 95, 87 (1984)), etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cells (Sf cells), MG1 cells derived from mid-intestine of *Trichoplusia ni*, HIGH FIVE™ (BTI-Tn-5B1-4) cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. are used. Examples of the Sf cell which can be used are Sf9 cells (ATCC CRL1711) and Sf21 cells (both cells are described in Vaughn, J. L. et al., In Vivo, 13, 213-217 (1977).

As the insect, for example, a larva of *Bombyx mori* can be used (Maeda, et al., Nature, 315, 592 (1985)).

Examples of animal cells include monkey cells COS-7, Vero, Chinese hamster cells CHO (hereinafter referred to as CHO cells), dhfr gene deficient Chinese hamster cells CHO (hereinafter simply referred to as CHO($dhfr^-$) cell), mouse L cells, mouse AtT-20, mouse myeloma cells, rat GH3, human FL cells, etc.

Bacteria belonging to the genus *Escherichia* can be transformed, for example, by the method described in Proc. Natl. Acad. Sci. U.S.A., 69, 2110 (1972) or Gene, 17, 107 (1982).

Bacteria belonging to the genus *Bacillus* can be transformed, for example, by the method described in Molecular & General Genetics, 168, 111 (1979).

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55 (1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995), published by Shujunsha, or Virology, 52, 456 (1973).

Thus, the transformant transformed with the expression vector comprising the DNA encoding the protein can be obtained.

Where the host is bacteria belonging to the genus *Escherichia* or the genus *Bacillus*, the transformant can be appropriately incubated in a liquid medium which contains materials required for growth of the transformant such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431-433, Cold Spring Harbor Laboratory, New York, 1972). If necessary and desired, a chemical such as 3β-indolylacrylic acid can be added to the medium to activate the promoter efficiently.

Where the bacteria belonging to the genus *Escherichia* are used as the host, the transformant is usually cultivated at about 15° C. to about 43° C. for about 3 hours to about 24 hours. If necessary and desired, the culture may be aerated or agitated.

Where the bacteria belonging to the genus *Bacillus* are used as the host, the transformant is cultivated generally at about 30° C. to about 40° C. for about 6 hours to about 24 hours. If necessary and desired, the culture can be aerated or agitated.

Where yeast is used as the host, the transformant is cultivated, for example, in Burkholder's minimal medium (Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A., 81, 5330 (1984)). Preferably, pH of the medium is adjusted to about 5 to about 8. In general, the transformant is cultivated at about 20° C. to about 35° C. for about 24 hours to about 72 hours. If necessary and desired, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (1950)), etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the protein of the present invention can be produced in the cell, in the cell membrane or out of the cell of the transformant.

The protein of the present invention can be separated and purified from the culture described above by the following procedures.

When the protein of the present invention is extracted from the culture or cells after cultivation, the transformants or cells are collected by a publicly known method and suspended in an appropriate buffer. The transformants or cells are then disrupted by publicly known methods such as ultrasonication, a treatment with lysozyme and/or freeze-thaw cycling, followed by centrifugation, filtration, etc. Thus, the crude extract of the protein of the present invention can be obtained. The buffer used for the procedures may contain a protein modifier such as urea or guanidine hydrochloride, or a surfactant such as TRITON X-100™ (Polyoxyethylene (10) Octylphenyl Ether), etc. When the protein is secreted in the culture, the supernatant after completion of the cultivation can be separated from the transformants or cells to collect the supernatant by a publicly known method.

The protein contained in the supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the protein thus obtained is in a free form, it can be converted into the salt by publicly known methods or modifications thereof. On the other hand, when the protein is obtained in the form of a salt, it can be converted into the free form or in the form of a different salt by publicly known methods or modifications thereof.

The protein produced by the recombinant can be treated, prior to or after the purification, with an appropriate protein-modifying enzyme so that the protein can be appropriately modified to partially remove a polypeptide. Examples of the protein-modifying enzyme include trypsin, chymotrypsin, arginyl endopeptidase, protein kinase, glycosidase or the like.

The activity of the thus produced protein of the present invention or salts thereof can be determined by a test binding to a labeled ligand, by an enzyme immunoassay using a specific antibody, or the like.

Antibodies to the protein of the present invention, its partial peptides, or salts thereof may be any of polyclonal antibodies and monoclonal antibodies as long as they are capable of recognizing the protein of the present invention, its partial peptides, or salts thereof.

The antibodies to the protein of the present invention, its partial peptides, or salts thereof (hereinafter sometimes collectively referred to as the protein of the present invention) may be manufactured by publicly known methods for manufacturing antibodies or antisera, using as antigens the protein of the present invention.

[Preparation of Monoclonal Antibody]

(a) Preparation of Monoclonal Antibody-Producing Cells

The protein of the present invention is administered to mammals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once in every two to six weeks and 2 to 10 times in total. Examples of the applicable warm-blooded animals are monkeys, rabbits, dogs, guinea pigs, mice, rats, sheep, goats and chickens, with mice and rats being preferred.

In the preparation of monoclonal antibody-producing cells, warm-blooded animals, e.g., mice, immunized with an antigen wherein the antibody titer is noted is selected, then the spleen or lymph node is collected after 2 to 5 days from the final immunization and antibody-producing cells contained therein are fused with myeloma cells from an animal of the same or different species to give monoclonal antibody-producing hybridomas. Measurement of the antibody titer in antisera may be made, for example, by reacting a labeled form of the protein, which will be described later, with the antiserum followed by assaying the binding activity of the labeling agent bound to the antibody. The fusion may be operated, for example, by the known Koehler and Milstein method (Nature, 256, 495, 1975). Examples of the fusion accelerator are polyethylene glycol (PEG), Sendai virus, etc., among which PEG is preferably employed.

Examples of the myeloma cells are warm-blooded animal myeloma cells such as NS-1, P3U1, SP2/0, AP-1 etc., among which P3U1 is particularly preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at about 20 to about 40° C., preferably at about 30 to about 37° C. for about 1 to about 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the protein etc. as an antigen directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the protein labeled with a radioactive substance or an enzyme and detecting the monoclonal antibody bound to the solid phase.

The monoclonal antibody can be selected by publicly known methods or by modifications of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at about 37° C., for 5 days to 3 weeks, preferably 1 to 2 weeks. The cultivation can be conducted normally in 5% $CO_2$. The antibody titer of the culture supernatant of hybridomas can be determined as in the assay for the antibody titer in antisera described above.

(b) Purification of Monoclonal Antibody

Separation and purification of a monoclonal antibody can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G, etc. and dissociating the binding to obtain the antibody].

[Preparation of Polyclonal Antibody]

The polyclonal antibody of the present invention can be manufactured by publicly known methods or modifications thereof. For example, an immunogen (antigen such as the protein) itself or a complex prepared from an immunogen and a carrier protein is used to immunize a warm-blooded animal a manner similar to the method described above for the manufacture of monoclonal antibodies. The product containing the antibody to the protein of the present invention is collected from the immunized animal followed by separation and purification of the antibody.

In the complex of an immunogen and a carrier protein used to immunize a warm-blooded animal, the type of carrier protein and the mixing ratio of a carrier to hapten may be any type and in any ratio, as long as the antibody is efficiently produced to the hapten immunized by crosslinking to the carrier. For example, bovine serum albumin, bovine thyroglobulins, hemocyanin, etc. is coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide-activated ester, activated ester reagents containing thiol group or dithiopyridyl group, etc. are used for the coupling.

The condensation product is administered to warm-blooded animals either solely or together with carriers or diluents to the site in which the antibody can be produce by the administration. In order to potentiate the antibody productivity upon the administration, complete Freund's adjuvant or incomplete Freund's adjuvant may be administered. The administration is usually made once approximately in every 2 to 6 weeks and about 3 to about 10 times in total.

The polyclonal antibody can be collected from the blood, ascites, etc., preferably from the blood of warm-blooded animals immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as applied to the separation and purification of monoclonal antibodies described hereinabove.

The antisense polynucleotide having a complementary or substantially complementary base sequence, or a part of thereof, to the DNA encoding the protein or partial peptide of the present invention (which in the following description of the antisense polynucleotide, is referred to sometimes as the DNA of the present invention) can be any antisense polynucleotide so long as it possesses a complementary or substantially complementary base sequence, or a part thereof, to that of the DNA of the present invention and capable of suppressing expression of the DNA. The antisense polynucleotide is preferably antisense DNA.

The base sequence substantially complementary to the DNA of the present invention includes, for example, a base sequence having at least about 70% homology, preferably at least about 80% homology, more preferably at least about 90% homology and most preferably at least about 95% homology, to the full-length base sequence or partial base sequence of the base sequence complementary to the DNA of the present invention (i.e., complementary strand to the DNA of the present invention). The base sequence substantially complementary to the DNA of the present invention is particularly an antisense polynucleotide having at least about 70% homology, preferably at least about 80% homology, more preferably at least about 90% homology and most preferably at least about 95% homology to the complementary strand of the base sequence encoding the N-terminal site of the protein of the present invention (e.g., the base sequence around the initiation codon), in the entire base sequence of the complementary strand to the DNA of the present invention.

Specifically, the base sequence substantially complementary to the DNA of the present invention is an antisense polynucleotide having a complementary or substantially complementary base sequence, or a part thereof, to the base sequence of DNA having the base sequence represented by SEQ ID NO: 2, SEQ ID NO: 11, SEQ ID NO: 12, SEQ ID NO: 13, SEQ ID NO: 19, SEQ ID NO: 41, SEQ ID NO: 43, SEQ ID NO: 60, SEQ ID NO: 61, SEQ ID NO: 62, SEQ ID NO: 67, SEQ ID NO: 103, SEQ ID NO: 105 or SEQ ID NO: 112, preferably an antisense polynucleotide having a complementary or substantially complementary base sequence, or a part thereof, to the base sequence of DNA having the base sequence represented by SEQ ID NO: 2, SEQ ID NO: 11, SEQ ID NO: 12, SEQ ID NO: 13, SEQ ID NO: 19, SEQ ID NO: 41, SEQ ID NO: 43, SEQ ID NO: 60, SEQ ID NO: 61, SEQ ID NO: 62, SEQ ID NO: 67, SEQ ID NO: 103, SEQ ID NO: 105 or SEQ ID NO: 112.

The antisense polynucleotide is composed of usually about 10 to 40 bases, preferably about 15 to 30 bases.

For preventing degradation by hydrolases such as nuclease etc., phosphoric acid residues (phosphates) of nucleotides constituting the antisense DNA may be substituted by chemically modified phosphoric acid residues such as phosphorothioate, methylphosphonate, phosphorodithionate etc. These antisense polynucleotides can be manufactured by a publicly known DNA synthesizer and the like.

According to the present invention, antisense polynucleotides (nucleic acids) which can inhibit the replication or expression of the gene for the protein of the present invention and which correspond to the gene can be designed and synthesized based on the base sequence information of the cloned or determined DNA encoding the protein. Such antisense polynucleotide is capable of hybridizing with RNA of the protein gene of the present invention to inhibit the synthesis or function of said RNA or capable of modulating or controlling the expression of the protein gene of the invention via interaction with the protein-associated RNA of the invention. Polynucleotides complementary to the selected sequences of the protein-RNA of the invention, and polynucleotides specifically hybridizable with the protein-associated RNA of the invention, are useful in modulating or controlling the expression of the protein gene of the invention in vivo and in vitro, and useful for the treatment or diagnosis of diseases. The term “corresponding” is used to mean homologous to or complementary to a particular sequence of the nucleotide, base sequence or nucleic acid including the gene. The term “corresponding” between nucleotides, base sequences or nucleic acids and proteins usually refer to amino acids of a protein under the order derived from the sequence of nucleotides (nucleic acids) or their complements. In the protein genes, the 5' end hairpin loop, 5' end 6-base-pair repeats, 5' end untranslated region, polypeptide translation initiation codon, protein coding region, ORF translation termination codon, 3' end untranslated region, 3' end palindrome region, and 3' end hairpin loop, may be selected as preferred target regions, though any other region may be selected as a target in the protein genes.

The relationship between the targeted nucleic acids and the polynucleotides complementary to at least a part of the target, or the relationship between the target and the polynucleotides hybridizable with the target, can be denoted to be “antisense”. Examples of the antisense polynucleotides include polydeoxynucleotides containing 2-deoxy-D-ribose, polynucleotides containing D-ribose, any other type of polynucleotides which are N-glycosides of a purine or pyrimidine base, or other polymers containing non-nucleotide backbones (e.g., protein nucleic acids and synthetic sequence-specific nucleic acid polymers commercially available) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., α anomeric nucleic acids, etc.), and the like. Herein the terms “nucleoside”, “nucleotide” and “nucleic acid” are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide of the present invention is RNA, DNA or a modified nucleic acid (RNA, DNA). Specific examples of the modified nucleic acid include, but are not limited to, sulfur and thiophosphate derivatives of nucleic acids and those resistant to degradation of polynucleoside amides or oligonucleoside amides. The antisense polynucleotides of the present invention can be modified preferably based on the following design, that is, by increasing the intracellular stability of the antisense polynucleotide, increasing the cellular permeability of the antisense polynucleotide, increasing the affinity of the polynucleotide to the targeted sense strand to a higher level, or minimizing the toxicity, if any, of the antisense polynucleotide. Many of such modifications are reported for example in Pharm. Tech. Japan, Vol. 8, p. 247 or 395, 1992, Antisense Research and Applications, CRC Press, 1993, etc.

The antisense polynucleotide of the present invention may contain altered or modified sugars, bases or linkages. The antisense polynucleotide may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense polynucleotide can be examined using the transformant of the present invention, the gene expression system of the present invention in vivo and in vitro, or the translation system of the protein of the present invention in vivo and in vitro.

Hereinafter, the protein of the present invention, its partial peptides, or salts thereof (hereinafter sometimes referred to as the protein of the present invention), the DNA encoding the protein of the present invention or its partial peptides (hereinafter sometimes referred to as the DNA of the present invention), the antibodies to the protein of the present invention, its partial peptides, or salts thereof (hereinafter sometimes referred to as the antibodies of the present invention) and the antisense polynucleotide of the DNA of the present invention (hereinafter sometimes referred to as the antisense polynucleotide of the present invention) are specifically described for the use or applications.

The protein comprising an amino acid sequence identical or substantially identical with the amino acid sequence represented by SEQ ID NO: 1, SEQ ID NO: 14 or SEQ ID NO: 104 is sometimes referred to "protein A of the present invention"; the protein comprising an amino acid sequence identical or substantially identical with the amino acid sequence represented by SEQ ID NO: 18 is sometimes referred to "protein B of the present invention"; the protein comprising an amino acid sequence identical or substantially identical with the amino acid sequence represented by SEQ ID NO: 42 is sometimes referred to "protein C of the present invention"; and the protein comprising an amino acid sequence identical or substantially identical with the amino acid sequence represented by SEQ ID NO: 66 is sometimes referred to "protein D of the present invention".

[1] Prophylactic and/or Therapeutic Agents for Diseases Associated with the Protein of the Present Invention The protein A of the present invention contributes to transport of a substrate, and plays an important role in metabolism of the substrate, etc. Hereinafter, the substrate of the protein A of the present invention is referred to sometimes as "substrate A".

The substrate A includes, for example, steroid hormone, bile acid etc.

The steroid hormone includes, for example, estrogen, progestogen, androgen, mineral corticoid, glucocorticoid, steroid chemicals or metabolites thereof (e.g., sulfate conjugates, glucuronide conjugates etc.) etc. In particular, steroid hormone or metabolites thereof are preferable. Estrogen or androgen or metabolites thereof (preferably sulfate conjugates etc.) are more preferable. Estrone, dehydroepiandrosterone or sulfate conjugates thereof are most preferable.

The estrogen includes, for example, estrone, estradiol, estriol, estetrol etc.

The progestogen includes, for example, progesterone, pregnanediol etc.

The androgen includes, for example, dehydroepiandrosterone, testosterone, androstanedione, 5α-dihydrotestosterone, androsterone etc.

The mineral corticoid includes, for example, aldosterone etc.

The glucocorticoid includes, for example, cortisol, cortisone, corticosterone, dehydrocorticosterone etc.

The steroid chemicals include, for example, dexamethasone, betamethasone, prednisolone, triamcinolone, fluorocortisone, clomiphene, tamoxifen, danazol etc.

The bile acid includes, for example, taurocholic acid, glicocholic acid, cholic acid, lithocholic acid, deoxycholic acid, taurodeoxycholic acid, tauroursodeoxycholic acid, chenodeoxycholic acid, glicochenodeoxycholic acid, glicodeoxycholic acid etc.

Accordingly, when DNA encoding the protein A of the present invention is abnormal or deficient or when the amount of the protein A of the invention expressed is reduced, there occur various diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc.

Accordingly, the protein A of the invention and the DNA encoding it can be used as safe medicines such as prophylactic/therapeutic agents for diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc.

For example, when there is a patient who cannot sufficiently or normally exhibit an activity of transporting substrate A because of a decrease or deficiency in the protein A of the present invention in the living body, (i) DNA encoding the protein A of the invention is administered into the patient to express the protein A of the invention in the living body, (ii) the DNA is inserted into target cells to express the protein A of the invention and the cells are transplanted to the patient, or (iii) the protein A of the invention is administered into the patient, whereby the role of the protein of the invention can be exhibited sufficiently or normally in the patient.

The protein B of the present invention has a cation (preferably monovalent cation such as $Na^+$, $K^+$, etc.)/$H^+$ exchange transport activity, and plays an important role in regulation of intracellular pH, regulation of cell volume, and re-absorption of $Na^+$ into the kidney and small intestine.

Accordingly, when DNA encoding the protein B of the present invention is abnormal or deficient or when the amount of the protein B of the invention expressed is reduced, there occur various diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc. Preferably, there occur many diseases such as respiratory diseases, renal diseases, digestive diseases etc.

Accordingly, the protein B of the present invention and DNA encoding the same can be used as safe medicines such as prophylactic/therapeutic agents for renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc. The protein B of the present invention and DNA encoding the same are preferably prophylactic/therapeutic agents for respiratory diseases, renal diseases, digestive diseases etc.

For example, when there is a patient who cannot sufficiently or normally exhibit a cation (preferably monovalent cation such as $Na^+$, $K^+$ etc.)/$H^+$ exchange transport activity because of a decrease or deficiency in the protein B of the present invention in the living body, (i) DNA encoding the protein B of the invention is administered into the patient to express the protein B of the invention in the living body, (ii) the DNA is inserted into target cells to express the protein B of the invention and the cells are transplanted to the patient, or (iii) the protein B of the invention is administered into the patient, whereby the role of the protein B of the invention can be exhibited sufficiently or normally in the patient.

The protein C of the present invention has an activity of transporting aminophospholipids, to contribute to transport of aminophospholipids, and simultaneously plays an important role in distributing lipids on a biomembrane.

Accordingly, when DNA encoding the protein C of the invention is abnormal or deficient or when the amount of the protein C of the invention expressed is reduced, there occur various diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc.

Accordingly, the protein C of the invention and the DNA encoding it can be used as safe medicines such as prophylactic/therapeutic agents for pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc. preferably pancreatic diseases, central nerve diseases, digestive diseases, respiratory diseases etc.

For example, when there is a patient who cannot sufficiently or normally exhibit an activity of transporting aminophospholipids because of a decrease or deficiency in the protein C of the present invention in the living body, (i) DNA encoding the protein C of the invention is administered into the patient to express the protein C of the invention in the living body, (ii) the DNA is inserted into target cells to express the protein C of the invention and the cells are transplanted to the patient, or (iii) the protein C of the invention is administered into the patient, whereby the role of the protein of the invention can be exhibited sufficiently or normally in the patient.

The protein D of the present invention has a cation channel activity, and plays an important role in recognition of stimuli such as pain. The protein D can also function as temperature-sensitive cation channel.

Accordingly, when DNA encoding the protein D of the invention is abnormal or deficient or when the amount of the protein D of the invention expressed is reduced, there occur various diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

Accordingly, the protein D of the invention and the DNA encoding it can be used as safe medicines such as prophylactic/therapeutic agents for inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc. The protein D of the invention and the DNA encoding it are preferably prophylactic/therapeutic agents for inflammatory diseases, rheumatoid diseases, diabetic neurosis etc.

For example, when there is a patient who cannot sufficiently or normally exhibit a cation channel activity because of a decrease or deficiency in the protein D of the present invention in the living body, (i) DNA encoding the protein D of the invention is administered into the patient to express the protein D of the invention in the living body, (ii) the DNA is inserted into target cells to express the protein D of the invention and the cells are transplanted to the patient, or (iii) the protein D of the invention is administered into the patient, whereby the role of the protein of the invention can be exhibited sufficiently or normally in the patient.

Where the DNA of the present invention is used as the prophylactic/therapeutic agents described above, the DNA itself is administered directly to human or other warm-blooded animal; alternatively, the DNA is inserted into an appropriate vector such as retrovirus vector, adenovirus vector, adenovirus-associated virus vector, etc. and then administered to human or other warm-blooded animal in a conventional manner. The DNA of the present invention may also be administered as an intact DNA, or prepared into medicines together with physiologically acceptable carriers such as adjuvants to assist its uptake, which are administered by gene gun or through a catheter such as a hydrogel catheter.

Where the protein of the present invention is used as the aforesaid prophylactic/therapeutic agents, the protein is advantageously used on a purified level of at least 90%, preferably at least 95%, more preferably at least 98% and most preferably at least 99%.

The protein of the present invention can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing the protein of the present invention with a physiologically acceptable known carrier, a flavoring agent, an excipient, a vehicle, an antiseptic agent, a stabilizer, a binder, etc. in a unit dosage form required in a generally accepted manner that is applied to making medicines. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose or saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredient in a vehicle such as water for injection, with a naturally occurring vegetable oil such as sesame oil, coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., POLYSORBATE 80™ (Polyoxyethylene (20) Sorbitan Monooleate) and HCO-50), etc. Examples of the oily medium include sesame oil, soybean oil, etc., which may also be used in combination with a dissolution aid such as benzyl benzoate, benzyl alcohol, etc. The protein of the present invention may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The vector in which the DNA of the present invention is inserted may also be prepared into medicines in a manner similar to the procedures above, and such preparations are generally used parenterally.

Since the thus obtained medicine is safe and low toxic, and can be administered to, for example, warm-blooded animals (e.g., human, rat, mouse, guinea pig, rabbit, chicken, sheep, swine, bovine, horse, cat, dog, monkey, chimpanzee etc.).

The dose of the protein A of the present invention may vary depending on target disease, subject to be administered, route for administration, etc. When the protein A of the present invention is orally administered for example for the purpose of treatment of hyperlipemia, the protein is administered to adult (as 60 kg) generally in a daily dose of approximately 0.1 mg to 100 mg, preferably approximately 1.0 mg to 50 mg, more preferably approximately 1.0 to 20 mg. When the protein is parenterally administered, a single dose of the protein of the present invention may vary depending on subject to be administered, target disease, etc. When the protein A of the present invention is administered to adult (as 60 kg body weight), it is convenient to administer the protein A by injection to the affected area, generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

The dose of the protein B of the present invention may vary depending on target disease, subject to be administered, route for administration, etc. When the protein B of the present invention is orally administered for example for the purpose of treatment of renal insufficiency, the protein is administered to adult (as 60 kg) generally in a daily dose of approximately 0.1 mg to 100 mg, preferably approximately 1.0 mg to 50 mg, more preferably approximately 1.0 to 20 mg. When the protein is parenterally administered, a single dose of the protein may vary depending on subject to be administered, target disease, etc. When the protein B of the present invention is administered to adult (as 60 kg body weight) for the purpose of treatment of renal insufficiency, it is convenient to administer the protein by injection to the affected area, generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

The dose of the protein C of the present invention may vary depending on target disease, subject to be administered, route for administration, etc. When the protein C of the present invention is orally administered for example for the purpose of treatment of diabetes, the protein of the present invention is administered to adult (as 60 kg) generally in a daily dose of approximately 0.1 mg to 100 mg, preferably approximately 1.0 mg to 50 mg, more preferably approximately 1.0 to 20 mg. When the protein is parenterally administered, a single dose of the protein may vary depending on subject to be administered, target disease, etc. When the protein C of the present invention is administered to adult (as 60 kg body weight) for the purpose of treatment of diabetes, it is convenient to administer the protein by injection to the affected area, generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

The dose of the protein D of the present invention may vary depending on target disease, subject to be administered, route for administration, etc. When the protein D of the present invention is orally administered for example for the purpose of treatment of chronic articular rheumatism, the protein is administered to adult (as 60 kg) generally in a daily dose of approximately 0.1 mg to 100 mg, preferably approximately 1.0 mg to 50 mg, more preferably approximately 1.0 to 20 mg.

When the protein is parenterally administered, a single dose may vary depending on subject to be administered, target disease, etc. When the protein D of the present invention is administered to adult (as 60 kg body weight) for the purpose of treatment of chronic articular rheumatism, it is convenient to administer the protein by injection to the affected area, generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

[2] Screening of a Candidate Drug for Diseases

The protein of the present invention is useful as a reagent for screening a compound or its salt that promotes or inhibits the activity of the protein of the present invention.

The present invention provides (1) a method of screening a compound or a salt thereof (also referred to hereinafter as a promoter and inhibitor) that promotes or inhibits the activity (e.g., an activity of transporting substrate A etc.) of the protein A of the invention, which comprises using the protein A of the present invention. More specifically, the present invention provides, for example, (2) a method of screening a promoter or an inhibitor, which comprises comparing (i) the substrate A transport activity of a cell having an ability to produce the protein A of the present invention with (ii) the substrate A transport activity of a mixture of a test compound and a cell having an ability to produce the protein A of the present invention.

Specifically, the amount of the substrate A in a labeled form incorporated into the cell is measured and compared between (i) and (ii) in the screening method described above.

As the labeling agent, use is made of, for example, radioisotopes (for example, [$^{3}$H], [$^{125}$I], [$^{14}$C], [$^{32}$P], [$^{33}$P], [$^{35}$S], etc.), fluorescent substances (for example, cyanine fluorescent dyes (e.g., Cy2, Cy3, Cy5, Cy5.5, Cy7 (Amersham Bioscience) etc), fluorescein etc.), luminescent substances (for example, luminol etc.), enzymes (for example, peroxidase etc.) or lanthanide elements.

As the labeled substrate A, use is made of, for example, [6,7-$^{3}$H(N)]-estrone sulfate or [1,2,6,7-$^{3}$H(N)]-dehydroepiandrosterone sulfate.

Examples of the test compounds include peptides, proteins, non-peptide compounds, synthetic compounds, fermentation products, cell extracts, plant extracts, animal tissue extracts, etc. and these compounds may be novel compounds or publicly known compounds.

To perform the screening method described above, a protein preparation is prepared by suspending cells having an ability to produce the protein A of the present invention, in a buffer appropriate for screening. A buffer such as a phosphate buffer or a borate buffer having a pH value of about 4 to 10 (preferably pH of about 6 to 8) can be used so long as it does not inhibit the activity of the protein A of the present invention.

As the cells having an ability to produce the protein A of the present invention, for example a host (transformant) transformed with a vector comprising the DNA encoding the protein A of the present invention described above is used. As the host, animal cells such as CHO cells are preferably used. In the screening, for example a transformant expressing the protein A of the present invention on a cell membrane by culturing it by the method described above is preferably used.

The substrate A transport activity can be measured according to known methods, for example a method described in Am. J. Physiol., 274, G157-169, 1998 or a modification thereto.

For example, a compound or a salt thereof that promotes the substrate A transport activity in (ii) above by about at least 20%, preferably at least 30%, more preferably about at least 50% as compared with the activity in (i) above can be selected as a compound or a salt thereof that promotes the activity of the protein A of the present invention.

For example, a compound or a salt thereof that inhibits the substrate A transport activity in (ii) above by about at least 20%, preferably at least 30%, more preferably about at least 50% as compared with the activity in (i) above can be selected as a compound or a salt thereof that inhibits (or suppresses) the activity of the protein A of the present invention.

Specifically, the screening method is as follows:

First, the cells are cultured in a multi-well plate etc. In screening, the medium is exchanged with a fresh buffer or a suitable buffer not toxic to the cells, and a given amount (5,000 cpm to 500,000 cpm) of a labeled form of the protein A is added to the cells, and at the same time, $10^{-10}$ to $10^{-7}$ M of a test compound is co-present. The reaction is carried out at 0° C. to 50° C., preferably about 4° C. to 37° C. for 20 minutes to 24 hours, preferably 30 minutes to 3 hours. After completion of the reaction, the medium or buffer is removed, and the cells are washed with an appropriate volume of a buffer (for example, PBS etc.), and then the residual radioactivity of the labeled substrate A incorporated into the cells is measured by means of a liquid scintillation counter. Assuming that the count in the absence of a test compound as an antagonizing compound is 100%, a test compound by which the count is reduced to e.g. 50% or less can be selected as a candidate compound capable of competitive inhibition.

Alternatively, after a gene for secretory alkaline phosphatase, luciferase or the like is inserted into a region downstream from a promoter of the protein A gene of the present invention and the gene is expressed in the cells described above, a compound or a salt thereof that promotes or inhibits the expression of the protein A of the present invention (that is, a compound or a salt thereof that promotes or inhibits the activity of the protein A of the present invention) can be screened by examining whether a test compound when brought into contact with the cells activates or inhibits the enzyme activity.

The present invention provides (1') a method of screening a compound or a salt thereof (also referred to hereinafter as a promoter and inhibitor) that promotes or inhibits the activity [for example, cation (preferably monovalent cation such as $Na^+$, $K^+$ etc.)/$H^+$ exchange transport activity] of the protein B of the invention, which comprises using the protein B of the present invention. More specifically, the present invention provides, for example:

(2') a method of screening a promoter or an inhibitor, which comprises comparing (i') the cation (preferably monovalent cation such as $Na^+$, $K^+$ etc.)/$H^+$ exchange transport activity of a cell having an ability to produce the protein B of the present invention with (ii') the cation (preferably monovalent cation such as $Na^+$, $K^+$ etc.)/$H^+$ exchange transport activity of a mixture of a test compound and a cell having an ability to produce the protein B of the present invention.

Specifically, the screening method comprises, for example, measuring the cation (preferably monovalent cation such as $Na^+$, $K^+$ etc.)/$H^+$ exchange transport activity as an indicator by a fluorescent dye and comparing the cation (preferably monovalent cation such as $Na^+$, $K^+$ etc.)/$H^+$ exchange transport activity in (i') above, with that in (ii').

Examples of the test compounds include peptides, proteins, non-peptide compounds, synthetic compounds, fermentation products, cell extracts, plant extracts, animal tissue extracts, etc. and these compounds may be novel compounds or publicly known compounds.

To perform the screening method described above, a protein preparation is prepared by suspending cells having an ability to produce the protein B of the present invention, in a buffer appropriate for screening. A buffer such as a phosphate buffer or a borate buffer having a pH value of about 4 to 10 (preferably pH of about 6 to 8) can be used so long as it does not inhibit the cation (preferably monovalent cation such as $Na^+$, $K^+$, etc.)/$H^+$ exchange transport activity of the protein B of the present invention.

As the cells having an ability to produce the protein B of the present invention, for example a host (transformant) transformed with a vector comprising the DNA encoding the protein of the present invention described above is used. As the host, animal cells such as CHO cells are preferably used. In the screening, for example a transformant expressing the protein B of the present invention on a cell membrane by culturing it by the method described above is preferably used.

The cation (preferably monovalent cation such as $Na^+$, $K^+$, etc.)/$H^+$ exchange transport activity of the protein B of the present invention can be measured according to known methods, for example a method described in J. Biol. Chem. 274, 3978-3987, 1998 or a modification thereto.

For example, a test compound that promotes the cation (preferably monovalent cation such as $Na^+$, $K^+$, etc.)/$H^+$ exchange transport activity in (ii') above by about at least 20%, preferably at least 30%, more preferably about at least 50% as compared with the activity in (i') above can be selected as a compound or a salt thereof that promotes the activity of the protein B of the present invention.

For example, a test compound that inhibits (or suppresses) the cation (preferably monovalent cation such as $Na^+$, $K^+$, etc.)/$H^+$ exchange transport activity in (ii') above by about at least 20%, preferably at least 30%, more preferably about at least 50% as compared with the activity in (i') above can be selected as a compound or a salt thereof that inhibits the activity of the protein B of the present invention.

Alternatively, after a gene for secretory alkaline phosphatase, luciferase or the like is inserted into a region downstream from a promoter of the protein B gene of the present invention and the gene is expressed in the cells described above, a compound or a salt thereof that promotes or inhibits the expression of the protein B of the present invention (that is, a compound or a salt thereof that promotes or inhibits the activity of the protein B of the present invention) can be screened by examining whether a test compound when brought into contact with the cells activates or inhibits the enzyme activity.

The present invention provides (1") a method of screening a compound or a salt thereof (also referred to hereinafter as a promoter and inhibitor) that promotes or inhibits the activity (for example, aminophospholipid transport etc.) of the protein C of the invention, which comprises using the protein C of the present invention. More specifically, the present invention provides, for example:

(2") a method of screening a promoter or an inhibitor, which comprises comparing (i") the aminophospholipid transport activity of a cell having an ability to produce the protein C of the present invention with (ii") the aminophospholipid transport activity of a mixture of a test compound and a cell having an ability to produce the protein C of the present invention.

Specifically, the screening method comprises, for example, measuring aminophospholipid transport as an indicator by a radioisotope-labeled substrate or a fluorescent dye and comparing the aminophospholipid transport in (i") with that in (ii").

Examples of the test compounds include peptides, proteins, non-peptide compounds, synthetic compounds, fermentation products, cell extracts, plant extracts, animal tissue extracts, etc. and these compounds may be novel compounds or publicly known compounds.

To perform the screening method described above, a protein preparation is prepared by suspending cells having an ability to produce the protein C of the present invention, in a buffer appropriate for screening. A buffer such as a phosphate buffer or a borate buffer having a pH value of about 4 to 10 (preferably pH of about 6 to 8) can be used so long as it does not inhibit the aminophospholipid transport activity of the protein C of the present invention.

As the cells having an ability to produce the protein C of the present invention, for example a host (transformant) transformed with a vector comprising the DNA encoding the protein C of the present invention described above is used. As the host, animal cells such as CHO cells are preferably used. In the screening, for example a transformant expressing the protein C of the present invention on a cell membrane by culturing it by the method described above is preferably used.

The aminophospholipid transport activity of the protein C of the present invention can be measured according to known methods, for example a method described in J. Biol. Chem., 275, 23378-23386, 1998 or a modification thereto.

For example, a test compound that promotes the aminophospholipid transport activity in (ii') above by about at least 20%, preferably at least 30%, more preferably about at least 50% compared with the activity in (i') above can be selected as a compound or a salt thereof that promotes the activity of the protein C of the present invention.

For example, a test compound that inhibits (or suppresses) the aminophospholipid transport activity in (ii') above by about at least 20%, preferably at least 30%, more preferably about at least 50% compared with the activity (i') above can be selected as a compound or a salt thereof that inhibits the activity of the protein C of the present invention.

Alternatively, after a gene for secretory alkaline phosphatase, luciferase or the like is inserted into a region downstream from a promoter of the protein C gene of the present invention and the gene is expressed in the cells described above, a compound or a salt thereof that promotes or inhibits the expression of the protein C of the present invention (that is, a compound or a salt thereof that promotes or inhibits the activity of the protein C of the present invention) can be screened by examining whether a test compound when brought into contact with the cells activates or inhibits the enzyme activity.

The present invention provides (1"') a method of screening a compound or a salt thereof (also referred to hereinafter as a promoter and inhibitor) that promotes or inhibits the activity (for example, cation channel activity) of the protein D of the invention, which comprises using the protein D of the present invention. More specifically, the present invention provides, for example:

(2"') a method of screening a promoter or an inhibitor, which comprises comparing (i"') the cation channel activity of a cell having an ability to produce the protein D of the present invention with (ii"') the cation channel activity of a mixture of a test compound and a cell having an ability to produce the protein D of the present invention.

Specifically, the screening method comprises, for example, measuring the cation channel activity as an indicator by a patch clamp method and comparing the cation channel activity in (i''') with that in (ii''').

Examples of the test compounds include peptides, proteins, non-peptide compounds, synthetic compounds, fermentation products, cell extracts, plant extracts, animal tissue extracts, etc. and these compounds may be novel compounds or publicly known compounds.

To perform the screening method described above, a protein preparation is prepared by suspending cells having an ability to produce the protein D of the present invention, in a buffer appropriate for screening. A buffer such as a phosphate buffer or a borate buffer having a pH value of about 4 to 10 (preferably pH of about 6 to 8) can be used so long as it does not inhibit the cation channel activity of the protein D of the present invention.

As the cells having an ability to produce the protein of the present invention, for example a host (transformant) transformed with a vector comprising the DNA encoding the protein of the present invention described above is used. As the host, animal cells such as CHO cells are preferably used. In the screening, for example a transformant expressing the protein of the present invention on a cell membrane by culturing it by the method described above is preferably used.

The cation channel activity of the protein D of the present invention can be measured according to known methods, for example a method described in Nature, 389, 816, 1997 or a modification thereto.

For example, a test compound that promotes the cation channel activity in (ii''') above by about at least 20%, preferably at least 30%, more preferably about at least 50% as compared with the activity in (i''') above can be selected as a compound or a salt thereof that promotes the activity of the protein D of the present invention.

For example, a test compound that inhibits (or suppresses) the cation channel activity in (ii''') above by about at least 20%, preferably at least 30%, more preferably about at least 50% as compared with the activity in (i''') above can be selected as a compound or a salt thereof that inhibits the activity of the protein D of the present invention.

Alternatively, after a gene for secretory alkaline phosphatase, luciferase or the like is inserted into a region downstream from a promoter of the protein D gene of the present invention and the gene is expressed in the cells described above, a compound or a salt thereof that promotes or inhibits the expression of the protein D of the present invention (that is, a compound or a salt thereof that promotes or inhibits the activity of the protein D of the present invention) can be screened by examining whether a test compound when brought into contact with the cells activates or inhibits the enzyme activity.

Using the protein D of the present invention, or using the ligand binding assay system of the expression system constructed using a recombinant of the protein D of the present invention, compounds (e.g., peptides, proteins, non-peptide compounds, synthetic compounds, fermentation products, etc.) or salt forms thereof that alter the binding property between the protein D of the present invention and its ligand (hereinafter referred to as the ligand of the present invention) can be efficiently screened.

Specifically, the case (i) where the ligand of the present invention is brought into contact with the protein D of the present invention is compared with the case (ii) where the ligand of the present invention and a test compound are brought into contact with the protein D of the present invention. In this comparison, for example the amount of the ligand of the present invention bound to the protein D of the present invention is measured.

Specifically, the screening method of the present invention includes, for example:

(a) a method of screening a compound or its salt that alters the binding property between the ligand of the present invention and the protein D of the present invention, which comprises measuring and comparing the amount of the ligand of the invention bound to the protein D of the invention in the case where the ligand of the invention is brought into contact with the protein D of the invention, with that in the case where the ligand of the invention and a test compound are brought into contact with the protein D of the invention, (b) a method of screening a compound or its salt that alters the binding property between the ligand of the present invention and the protein D of the present invention, which comprises measuring and comparing the amount of the ligand of the invention bound to cells containing the protein D of the invention or a membrane fraction of the cells in the case where the ligand of the invention is brought into contact with the cells or the cell membrane fraction, with that in the case where the ligand of the invention and a test compound are brought into contact with the cells or the cell membrane fraction, (c) the screening method according to the above-mentioned (b), wherein the protein D of the present invention is the protein D of the present invention which was expressed on a cell membrane by culturing a transformant comprising DNA encoding the protein D of the present invention, and (d) the screening method according to the above-mentioned (a) to (c), wherein the ligand of the present invention is a labeled ligand.

The protein D of the present invention is preferably the one in membrane fractions from organs in humans or warm-blooded animals. However, acquisition of human-derived organs is extremely difficult, and thus the protein D used in screening is preferably the one expressed in a large amount by a transformant.

For producing the protein D of the present invention, the above-described process for producing the protein D of the resent invention is used.

When cells containing the protein D of the present invention or a membrane fraction of the cells is used in the screening method described above, a preparation method described later may be followed.

Where cells containing the protein D of the present invention are used, the cells may be fixed using glutaraldehyde, formalin, etc. The fixation can be made by a publicly known method.

The cells containing the protein D of the present invention are host cells that have expressed the protein D of the present invention, and the host cells include *Escherichia coli, Bacillus subtilis*, yeast, insect cells, animal cells, and the like. The method of producing the cells is the same as described above.

The cell membrane fraction refers to a fraction abundant in cell membrane obtained by cell disruption and subsequent fractionation by a publicly known method. Useful cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the protein D expressed and membrane components such as cell-derived phospholipids and membrane proteins.

The amount of the protein D of the invention in the cells containing the protein D and in the membrane fraction of the cells is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To carry out the screening method described above, for example a fraction of the protein D of the present invention and the ligand of the present invention (for example, the labeled ligand of the present invention) are used. The fraction of the protein D of the present invention is preferably a fraction of the naturally occurring protein D of the present invention or the recombinant protein D of the present invention having an activity equivalent to that of the natural protein. Herein, the equivalent activity is intended to mean a ligand binding activity etc. As the labeled ligand, use can be made of ligands labeled for example with radioisotopes (for example, [$^3$H], [$^{125}$I], [$^{14}$C], [$^{32}$P], [$^{33}$P], [$^{35}$S], etc.), fluorescent substances (for example, cyanine fluorescent dyes (e.g., Cy2, Cy3, Cy5, Cy5.5, Cy7 (Amersham Bioscience) etc), fluorescein etc.), luminescent substances (for example, luminol etc.), enzymes (for example, peroxidase etc.) or lanthanide elements.

Specifically, to screen the compounds or salts thereof that alter the binding property between the ligand of the present invention and the protein D of the present invention, first, the receptor standard is prepared by suspending cells or cell membrane fraction containing the protein D of the present invention in a buffer appropriate for the screening. For the buffer, any buffer that does not interfere with the binding of the ligand to the protein is usable and examples of such a buffer are phosphate buffer, Tris-hydrochloride buffer, etc., having a pH value of 4 to 10 (preferably a pH value of 6 to 8). To minimize a non-specific binding, a surfactant such as CHAPS, TWEEN-80™ (Polyoxyethylene (20) Sorbitan Monooleate) (Kao-Atlas Co.), digitonin, deoxycholate, etc. may be added to the buffer. To inhibit degradation of the protein D of the present invention by proteases, protease inhibitors such as PMSF, leupeptin, E-64 (manufactured by Peptide Research Laboratory, Co.), and pepstatin may be added. A predetermined amount (5,000 to 500,000 cpm) of the labeled ligand of the present invention is added to 0.01 to 10 ml solution of the protein in the coexistence of $10^{-10}$ to $10^{-7}$ M test compound. To examine non-specific binding (NSB), a reaction tube containing the unlabeled ligand of the present invention in large excess is also prepared. The reaction is carried out at approximately 0 to 50° C., preferably about 4 to 37° C. for about 20 minutes to about 24 hours, preferably about 30 minutes to about 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. Assuming that the count ($B_0$-NSB) obtained by subtracting the amount of non-specific binding (NSB) from the count obtained in the absence of any competitive substance ($B_0$) is 100%, the test compound by which the amount of specific binding (B-NSB) is reduced for example to 50% or less can be selected as a candidate substance having a potential of competitive inhibition.

The compounds or salts thereof obtained by using the screening method of the present invention are the compounds or salts thereof that alter the binding property between the protein D of the present invention and the ligand of the present invention.

The polynucleotide encoding the protein of the present invention is useful as a reagent for screening a compound or its salt that promotes or inhibits the expression of the protein gene of the present invention.

The present invention provides (3) a method of screening a compound or a salt thereof (also referred to hereinafter the promoter and inhibitor) that promotes or inhibits the expression of the gene for the protein of the invention, which comprises using a polynucleotide encoding the protein of the present invention. More specifically, the present invention provides, for example:

(4) a method of screening the promoter and inhibitor, which comprises comparing the case (iii) where cells having an ability to produce the protein of the present invention are cultured, with the case (iv) where a mixture of a test compound and cells having an ability to produce the protein of the present invention is cultured.

The screening method comprises, for example, measuring and comparing the expression level of the gene for the protein of the present invention (specifically, the amount of the protein of the present invention or the amount of mRNA encoding the protein) in the case (iii), with that in the case (iv).

Examples of the test compounds include peptides, proteins, non-peptide compounds, synthetic compounds, fermentation products, cell extracts, plant extracts, animal tissue extracts etc. and these compounds may be novel compounds or publicly known compounds.

To perform the screening method described above, a protein preparation is prepared by suspending cells having an ability to produce the protein of the present invention in a buffer appropriate for screening. A buffer such as a phosphate buffer or a borate buffer having a pH value of about 4 to 10 (preferably pH of about 6 to 8) can be used so long as it does not inhibit expression of the protein of the present invention.

As the cells having an ability to produce the protein of the present invention, for example a host (transformant) transformed with a vector comprising the DNA encoding the protein of the present invention described above is used. As the host, animal cells such as CHO cells are preferably used. In the screening, for example a transformant expressing the protein of the present invention on a cell membrane by culturing it by the method described above is preferably used.

In measuring the amount of the protein of the present invention, the protein present in a cellular extract or the like can be measured according to known methods, for example by Western analysis, ELISA or the like, or a modification thereof, with antibodies recognizing the protein of the present invention.

The expression level of the protein gene of the present invention can be measured by known methods, for example Northern blotting, reverse transcription-polymerase chain reaction (RT-PCR), a real-time PCR analysis system (TaqMan polymerase chain reaction, Applied Biosystems) or by a modification thereof.

For example, a test compound by which the expression level of the protein gene of the present invention in the case (iv) is promoted by at least about 20%, preferably at least about 30%, more preferably at least about 50%, as compared with the expression level in the case (iii), can be selected as a compound or its salt that promotes the expression level of the protein gene of the present invention.

For example, a test compound by which the expression level of the protein gene of the present invention in the case (iv) is inhibited by at least about 20%, preferably at least about 30%, more preferably at least about 50%, as compared with the expression level in the case (iii), can be selected as a compound or its salt that inhibits the expression level of the protein gene of the present invention.

The antibody of the present invention is useful as a reagent for screening a compound or a salt thereof that promotes or inhibits the expression of the protein of the present invention.

The present invention provides (5) a method of screening a compound or a salt thereof (also referred to hereinafter as the promoter and inhibitor) that promotes or inhibits the expression of the protein of the present invention, which comprises using the antibody of the present invention. More specifically, the present invention provides, for example:

(6) a method of screening the promoter or inhibitor, which comprises comparing the case (v) where cells having an ability to produce the protein of the present invention are cultured, with the case (vi) where a mixture of a test compound and cells having an ability to produce the protein of the present invention is cultured.

The screening method comprises, for example, the measurement (e.g., detection of the expression of the protein of the present invention, quantification of the expressed protein of the present invention, etc.) of the expression level of the protein of the present invention (specifically, the amount of the protein of the present invention) by the antibody of the present invention and comparing the amount of the expressed protein in the case (v) with that in the case (vi).

Examples of the test compounds include peptides, proteins, non-peptide compounds, synthetic compounds, fermentation products, cell extracts, plant extracts, animal tissue extracts, etc. and these compounds may be novel compounds or publicly known compounds.

To perform the screening method described above, a protein preparation is prepared by suspending cells having an ability to produce the protein of the present invention in a buffer appropriate for screening. A buffer such as a phosphate buffer or a borate buffer having a pH value of about 4 to 10 (preferably pH of about 6 to 8) can be used so long as it does not inhibit the activity of the protein of the present invention.

As the cells having an ability to produce the protein of the present invention, for example a host (transformant) transformed with a vector comprising the DNA encoding the protein of the present invention described above is used. As the host, animal cells such as CHO cells are preferably used. In the screening, for example a transformant expressing the protein of the present invention on a cell membrane by culturing it by the method described above is preferably used.

The amount of the protein of the present invention can determined by measuring the protein present in a cell extract with the antibody of the invention recognizing the protein by publicly known methods, for example, Western analysis, ELISA, or a modification of the known methods.

For example, a test compound by which the expression of the protein of the invention in the case (vi) is promoted by at least about 20%, preferably at least about 30%, more preferably at least about 50%, as compared with the expression in the case (v) can be selected as a compound or its salt that promotes the expression of the protein of the present invention.

For example, a test compound by which the expression of the protein of the invention in the case (vi) is inhibited by at least about 20%, preferably at least about 30%, more preferably at least about 50%, as compared with the expression in the case (v) can be selected as a compound or its salt that inhibits the expression of the protein of the present invention.

The screening kit of the present invention comprises the protein of the present invention or its partial peptide or salts thereof, a cell having an ability to produce the protein or partial peptide of the present invention, the ligand of the present invention, the antibody of the present invention, etc.

The compounds or salts thereof, which are obtainable using the screening method or screening kit of the present invention, are compounds (or salts thereof) selected from, e.g., peptides, proteins, non-peptide compounds, synthetic compounds, fermentation products, cell extracts, plant extracts, animal tissue extracts, blood plasma, and the like, and these compounds or salts thereof are compounds or their salts promoting or inhibiting the activity of the protein of the present invention, compounds or their salts promoting or inhibiting the expression of the protein gene of the present invention, compounds or their salts promoting or inhibiting the expression of the protein of the present invention, compounds or their salts altering the binding property between the protein A of the present invention and the ligand of the present invention, etc.

For salts of these compounds, the same salts as those given for the protein of the present invention above may be used.

The compound or its salt promoting the activity of the protein A of the present invention, the compound or its salt promoting the expression of the protein A gene of the present invention, and the compound or its salt promoting the expression of the protein A of the present invention are useful as safe and low toxic drugs such as prophylactic/therapeutic agents for diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc.

The compound or its salt inhibiting the activity of the protein A of the present invention, the compound or its salt inhibiting the expression of the protein A gene of the present invention, and the compound or its salt inhibiting the expression of the protein A of the present invention are useful as safe and low toxic drugs such as prophylactic/therapeutic agents for diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc.

The compound or its salt promoting the activity of the protein B of the present invention, the compound or its salt promoting the expression of the protein B gene of the present invention, and the compound or its salt promoting the expression of the protein B of the present invention are useful as safe and low toxic drugs such as prophylactic/therapeutic agents for diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.), preferably respiratory diseases, renal diseases, digestive diseases etc.

The compound or its salt inhibiting the activity of the protein B of the present invention, the compound or its salt inhibiting the expression of the protein B gene of the present invention, and the compound or its salt inhibiting the expression of the protein B of the present invention are useful as safe and low toxic drugs such as prophylactic/therapeutic agents for diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.), preferably respiratory diseases, renal diseases, digestive diseases etc.

The compound or its salt promoting the activity of the protein C of the present invention, the compound or its salt promoting the expression of the protein C gene of the present invention, and the compound or its salt promoting the expression of the protein C of the present invention are useful as safe and low toxic drugs such as prophylactic/therapeutic agents for diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc.

The compound or its salt inhibiting the activity of the protein C of the present invention, the compound or its salt inhibiting the expression of the protein C gene of the present invention, and the compound or its salt inhibiting the expression of the protein C of the present invention are useful as safe and low toxic drugs such as prophylactic/therapeutic agents for diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive puhnonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc.

The compound or its salt promoting the activity of the protein D of the present invention, the compound or its salt promoting the expression of the protein D gene of the present invention, and the compound or its salt promoting the expression of the protein D of the present invention are useful as safe and low toxic drugs such as prophylactic/therapeutic agents for diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

The compound or its salt inhibiting the activity of the protein D of the present invention, the compound or its salt inhibiting the expression of the protein D gene of the present invention, and the compound or its salt inhibiting the expression of the protein D of the present invention are useful as safe and low toxic drugs such as prophylactic/therapeutic agents for diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

The compound or its salt altering the binding property between the protein D of the present invention and the ligand of the present invention is useful as a safe and low toxic drug such as a prophylactic/therapeutic agent for diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

When the compounds obtainable using the screening method or screening kit of the present invention are used as the prophylactic/therapeutic agents described above, the compounds can be formulated by the conventional methods. The compounds may be prepared for example in the form of tablets, capsules, elixirs, microcapsules, sterile solutions, suspensions, etc.

Since the thus obtained medicine is safe and low toxic, and can be administered to, for example, humans or warm-blooded animals (e.g., mouse, rat, rabbit, sheep, swine, bovine, horse, chicken, cat, dog, monkey, chimpanzee etc.).

The dose of the above compound or its salt may vary depending on its action, target disease, subject to be administered, route for administration, etc. When the compound or its salt that promotes the activity or expression of the protein A of the present invention is orally administered for example for the purpose of treatment of hyperlipemia, the compound or its salt is administered to adult (as 60 kg) generally in a daily dose of approximately 0.1 mg to 100 mg, preferably approximately 1.0 mg to 50 mg, more preferably approximately 1.0 to 20 mg. When the compound or its salt is parenterally administered, a single dose of the compound or its salt may vary depending on subject to be administered, target disease, etc. When the compound or its salt is administered in the form of an injection to adult (as 60 kg body weight) for the purpose of treatment of hyperlipemia, it is convenient to administer the compound or its salt by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

The dose of the compound or its salt may vary depending on its action, target disease, subject to be administered, route for administration, etc. When the compound or its salt that promotes the activity or expression of the protein B of the present invention is orally administered for example for the purpose of treatment of renal insufficiency, the compound or its salt is administered to adult (as 60 kg) generally in a daily dose of approximately 0.1 mg to 100 mg, preferably approximately 1.0 mg to 50 mg, more preferably approximately 1.0 to 20 mg. When the compound or its salt is parenterally administered, a single dose of the compound or its salt may vary depending on subject to be administered, target disease, etc. When the compound or its salt is administered in the form of an injection to adult (as 60 kg body weight) for the purpose of treatment of renal insufficiency, it is convenient to administer the compound or its salt by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

The dose of the compound or its salt may vary depending on its action, target disease, subject to be administered, route for administration, etc. When the compound or its salt that promotes the activity or expression of the protein C of the present invention is orally administered for example for the purpose of treatment of diabetes, the compound or its salt is administered to adult (as 60 kg) generally in a daily dose of approximately 0.1 mg to 100 mg, preferably approximately 1.0 mg to 50 mg, more preferably approximately 1.0 to 20 mg. When the compound or its salt is parenterally administered, a single dose of the compound or its salt may vary depending on subject to be administered, target disease, etc. When the compound or its salt is administered in the form of an injection to adult (as 60 kg body weight) for the purpose of treatment of diabetes, it is convenient to administer the compound or its salt by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

The dose of the compound or its salt may vary depending on its action, target disease, subject to be administered, route for administration, etc. When the compound or its salt that promotes the activity or expression of the protein D of the present invention, or the compound or its salt that alters the binding property between the protein D of the present invention and the ligand of the present invention is orally administered for example for the purpose of treatment of chronic articular rheumatism, the compound or its salt is administered to adult (as 60 kg) generally in a daily dose of approximately 0.1 mg to 100 mg, preferably approximately 1.0 mg to 50 mg, more preferably approximately 1.0 to 20 mg. When the compound or its salt is parehterally administered, a single dose of the compound or its salt may vary depending on subject to be administered, target disease, etc. When the compound or its salt is administered in the form of an injection to adult (as 60 kg body weight) for the purpose of treatment of chronic articular rheumatism, it is convenient to administer the compound or its salt by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

[3] Quantification of the Protein of the Present Invention, its Partial Peptide, or its Salt The antibody of the present invention is capable of specifically recognizing the protein of the present invention and can thus be used for quantification of the protein of the present invention in a test sample fluid, in particular, for quantification by the sandwich immunoassay.

That is, the present invention provides:

(i) a method for quantification of the protein of the present invention in a test sample fluid, which comprises competitively reacting the antibody of the present invention, a test sample fluid and a labeled form of the protein of the present invention, and measuring the ratio of the labeled protein of the present invention bound to the antibody; and (ii) a method for quantification of the protein of the present invention in a test sample fluid, which comprises reacting the test sample fluid simultaneously or continuously with the antibody of the present invention immobilized on a carrier and a labeled form of the antibody of the present invention, and then measuring the activity of the labeling agent on the insoluble carrier.

In the quantification method in the above-mentioned (ii), it is desirable that one antibody is an antibody recognizing the N-terminal region of the protein of the present invention, and the other antibody is an antibody reacting with the C-terminal region of the protein of the present invention.

The monoclonal antibody to the protein of the present invention (hereinafter sometimes referred to as the monoclonal antibody of the present invention) may be used to quantify the protein of the present invention. Besides, the protein of the present invention may also be detected by means of tissue staining. For these purposes, the antibody molecule per se may be used or $F(ab')_2$, Fab' or Fab fractions of the antibody molecule may be used as well.

There is no particular limitation to the method of quantifying the protein of the present invention using the antibody of the present invention; any method may be used so far as it relates to a method in which the amount of antibody, antigen or antibody-antigen complex can be detected by a chemical or a physical means, depending on or corresponding to the amount of antigen (e.g., the amount of the protein) in a test sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be later described, is particularly preferred.

Examples of the labeling agent used in the assay method using the labeling substance are radioisotopes (for example, [$^{125}$I], [$^{131}$I], [$^{3}$I], [$^{14}$C] etc.), fluorescent substances [for example, cyanine fluorescent dyes (e.g., Cy2, Cy3, Cy5, Cy5.5, Cy7 (Amersham Bioscience) etc), fluorescamine, fluorescein isothiocyanate etc.], enzymes (for example, β-galactosidase, β-glucosidase, alkaline phosphatase, peroxidase, malate dehydrogenase etc), luminescent substances (for example, luminol, a luminol derivative, luciferin, lucigenin etc.), biotin, and lanthanide elements. Furthermore, the biotin-avidin system may also be used for binding of an antibody or antigen to a labeling agent.

For immobilization of antigen or antibody, physical adsorption may be used. Chemical binding methods conventionally used for insolubilization or immobilization of proteins or enzymes may also be used. For the carrier, for example, insoluble polysaccharides such as agarose, dextran, cellulose, etc.; synthetic resin such as polystyrene, polyacrylamide, silicon, etc., and glass or the like. are used.

In the sandwich method, the immobilized monoclonal antibody of the present invention is reacted with a test fluid (primary reaction), then with the labeled monoclonal antibody of the present invention (secondary reaction), and the activity of the label on the immobilizing carrier is measured, whereby the amount of the protein of the present invention in the test fluid can be quantified. The order of the primary and secondary reactions may be reversed, and the reactions may be performed simultaneously or with an interval. The methods of labeling and immobilization can be performed by the methods described above. In the immunoassay by the sandwich method, the antibody used for immobilized or labeled antibodies is not necessarily one species, but a mixture of two or more species of antibody may be used to increase the measurement sensitivity.

In the method for assaying the protein of the present invention by the sandwich method according to the present invention, preferred monoclonal antibodies of the present invention used for the primary and the secondary reactions are antibodies whose binding sites to the protein of the present invention are different from one another. Thus, the antibodies used in the primary and the secondary reactions are those wherein, when the antibody used in the secondary reaction recognizes the C-terminal region of the protein of the present invention, the antibody recognizing the site other than the C-terminal region, e.g., recognizing the N-terminal region, is preferably used in the primary reaction.

The monoclonal antibody of the present invention may be used in an assay system other than the sandwich method, such as a competitive method, an immunometric method, nephrometry, etc.

In the competitive method, an antigen in a test sample fluid and a labeled antigen are competitively reacted with an antibody, then the unreacted labeled antigen (F) and the labeled antigen bound to the antibody (B) are separated (B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody described above is used, and a solid phase method in which an immobilized antibody is used as the first antibody or a soluble antibody is used as the first antibody while an immobilized antibody is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase, and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, laser nephrometry utilizing laser scattering can be suitably used.

In applying each of those immunoassays to the quantification method of the present invention, any special conditions or operations are not required to set forth. The assay system for the protein of the present invention may be constructed in addition to conditions or operations conventionally used for each of the methods, taking the technical consideration by one skilled in the art into account. For the details of such conventional technical means, a variety of reviews, reference books, etc. may be referred to (for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); etc.)

As described above, the protein of the present invention can be quantified with high sensitivity, using the antibody of the present invention.

When a reduction in the concentration of the protein A of the present invention is detected by quantifying the concentration of the protein A of the invention with the antibody of the present invention, it can be diagnosed that there highly likely occur diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc. On the other hand, when an increase in the concentration of the protein A of the present invention is detected, it can be diagnosed that there highly likely occur diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc.

When a reduction in the concentration of the protein B of the present invention is detected by quantifying the concentration of the protein B of the invention with the antibody of the present invention, it can be diagnosed that there highly likely occur diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.), preferably respiratory diseases, renal diseases, digestive diseases etc. On the other hand, when an increase in the concentration of the protein B of the present invention is detected, it can be diagnosed that there highly likely occur diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc., preferably respiratory diseases, renal diseases, digestive diseases etc.

When a reduction in the concentration of the protein C of the present invention is detected by quantifying the concentration of the protein D of the invention with the antibody of the present invention, it can be diagnosed that there highly likely occur diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc. On the other hand, when an increase in the concentration of the protein C of the present invention is detected, it can be diagnosed that there highly likely occur diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc.

When a reduction in the concentration of the protein D of the present invention is detected by quantifying the concentration of the protein D of the invention with the antibody of the present invention, it can be diagnosed that there highly likely occur diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases and diabetic neurosis. On the other hand, when an increase in the concentration of the protein D of the present invention is detected, it can be diagnosed that there highly likely occur diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

The antibodies of the present invention can also be used for specifically detecting the protein of the present invention present in test samples such as body fluids or tissues. The antibodies may also be used for preparation of antibody columns for purification of the protein of the present invention, for detection of the protein of the present invention in each fraction upon purification, and for analysis of the behavior of the protein of the present invention in the test cells.

[4] Gene Diagnostic Agent

By using the DNA of the present invention as a probe, an abnormality (gene abnormality) of the DNA or mRNA encoding the protein of the present invention or its partial peptide in human or non-human warm-blooded animals (e.g., rat, mouse, guinea pig, rabbit, chicken, sheep, swine, bovine, horse, cat, dog, monkey, chimpanzee etc.) can be detected. Therefore, the DNA of the present invention is useful as a gene diagnostic agent for the damage against the DNA or mRNA, its mutation, or its decreased expression, or increased expression or over-expression of the DNA or mRNA.

The gene diagnosis described above using the DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)).

For example, when the increased expression of the protein A gene of the present invention is detected by Northern hybridization, it can be diagnosed that there highly likely occur diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc. On the other hand, when a reduction in the expression is detected or when a mutation in the DNA is detected by PCR-SSCP, it can be diagnosed that there highly likely occur diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc.

For example, when the increased expression of the protein B gene of the present invention is detected by Northern hybridization, it can be diagnosed that there highly likely occur diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc., preferably respiratory diseases, renal diseases, digestive diseases etc. On the other hand, a reduction in the expression is detected or when a mutation in the DNA is detected by PCR-SSCP, it can be diagnosed that there highly likely occur diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc., preferably respiratory diseases, renal diseases, digestive diseases etc.

For example, when the increased expression of the protein C gene of the present invention is detected by Northern hybridization, it can be diagnosed that there highly likely occur diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc. On the other hand, a reduction in the expression is detected or when a mutation in the DNA is detected by PCR-SSCP, it can be diagnosed that there highly likely occur diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc.

For example, when the increased expression of the protein D gene of the present invention is detected by Northern hybridization, it can be diagnosed that there highly likely occur diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc. On the other hand, a reduction in the expression is detected or when a mutation in the DNA is detected by PCR-SSCP, it can be diagnosed that there highly likely occur diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

[5] Medicine Comprising the Antisense Polynucleotide

The antisense polynucleotide of the present invention that binds complementarily to the DNA encoding the protein A of the present invention to inhibit expression of the DNA is low-toxic and can suppress the functions and activity of the protein or DNA in the body, and can thus be used as a medicine such as a prophylactic/therapeutic agent for diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc, preferably hyperlipemia, arteriosclerosis, genital diseases, digestive diseases etc.

The antisense polynucleotide of the present invention that binds complementarily to the DNA encoding the protein B of the present invention to inhibit expression of the DNA is low-toxic and can suppress the functions and activity of the protein or DNA in the body, and can thus be used as a medicine such as a prophylactic/therapeutic agent for diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc., preferably respiratory diseases, renal diseases, digestive diseases etc.

The antisense polynucleotide of the present invention that binds complementarily to the DNA encoding the protein C of the present invention to inhibit expression of the DNA is low-toxic and can suppress the functions and activity of the protein or DNA in the body, and can thus be used as a medicine such as a prophylactic/therapeutic agent for diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc.

The antisense polynucleotide of the present invention that binds complementarily to the DNA encoding the protein D of the present invention to inhibit expression of the DNA is low-toxic and can suppress the functions and activity of the protein or DNA in the body, and can thus be used as a medicine such as a prophylactic/therapeutic agent for diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

When the antisense polynucleotide is used as the aforesaid prophylactic/therapeutic agent, it can be formed into a medicine and administered in publicly known methods.

For example, when the antisense polynucleotide is used, the antisense polynucleotide itself, or the antisense polynucleotide inserted into an appropriate vector such as retrovirus vector, adenovirus vector, adenovirus-associated virus vector, etc., is administered orally or parenterally to human or other warm-blooded animal (e.g., rat, rabbit, sheep, swine, bovine, cat, dog, monkey, etc.) in a conventional manner. The antisense polynucleotide may also be administered as it is, or prepared into medicines together with physiologically acceptable carriers such as adjuvants to assist its uptake, and such preparations are administered by gene gun or through a catheter like a hydrogel catheter.

The dose of the antisense polynucleotide may vary depending upon target disease, subject to be administered, route for administration, etc. When the antisense nucleotide is administered topically to a specific digestive organ for the purpose of treatment of hyperlipemia, the antisense polynucleotide is administered to adult (60 kg body weight) usually in a daily dose of approximately 0.1 to 100 mg.

In addition, the antisense polynucleotide may also be employed as an oligonucleotide probe for diagnosis to examine the presence of the DNA of the present invention in tissues or cells, or the states of its expression.

Further, the present invention provides:

(i) double-stranded RNA comprising a part of RNA encoding the protein of the present invention and RNA complementary thereto, (ii) a medicine comprising the double-stranded RNA, (iii) ribozyme comprising a part of RNA encoding the protein of the present invention, (iv) a medicine comprising the ribozyme, and (v) an expression vector comprising a gene (DNA) encoding the ribozyme.

The double-stranded RNA or the ribozyme, similar to the antisense polynucleotide described above, can destroy RNA transcribed from the DNA of the present invention, or suppress the functions thereof.

The double-stranded RNA or ribozyme which can suppress the functions of the protein A of the present invention or the DNA encoding it can be used as a prophylactic/therapeutic agent for diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc.

The double-stranded RNA or ribozyme which can suppress the functions of the protein B of the present invention or the DNA encoding it can be used as a prophylactic/therapeutic agent for diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc., preferably respiratory diseases, renal diseases, digestive diseases etc.

The double-stranded RNA or ribozyme which can suppress the functions of the protein C of the present invention or the DNA encoding it can be used as a prophylactic/therapeutic agent for diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc.

The double-stranded RNA or ribozyme which can suppress the functions of the protein D of the present invention or the DNA encoding it can be used as a prophylactic/therapeutic agent for diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

According to known methods (for example, Nature, vol. 411, p. 494, 2001), the double-stranded RNA can be produced by designing it on the basis of the sequence of the polynucleotide of the present invention.

According to known methods (for example, TRENDS in Molecular Medicine, vol. 7, p. 221, 2001), the ribozyme can be produced by designing it on the basis of the sequence of the polynucleotide of the present invention. For example, the ribozyme can be produced by partially replacing a known ribozyme sequence by a part of RNA encoding the protein of the present invention. The part of RNA encoding the protein of the present invention includes a sequence adjacent to a consensus sequence NUX (N represents any base, and X represents a base other than G) which can be cleaved with a known ribozyme.

When the double-stranded RNA or the ribozyme is to be used as the aforesaid prophylactic/therapeutic agent, it can be formed into a medicine and administered in the same manner as for the antisense polynucleotide. The expression vector in (v) above is used as the aforesaid prophylactic/therapeutic agent in the same manner as in known gene therapy methods.

[6] Creation of an Animal Having the DNA of the Present Invention

The present invention provides a non-human mammal having the DNA encoding the protein of the present invention, which is exogenous (hereinafter simply referred to as the exogenous DNA of the present invention) or its mutant DNA (sometimes simply referred to as the exogenous mutant DNA of the present invention).

Thus, the present invention provides:

(1) a non-human mammal having the exogenous DNA of the present invention or its mutant DNA;

(2) the mammal according to (1), wherein the non-human mammal is a rodent;

(3) the mammal according to (2), wherein the rodent is mouse or rat; and (4) a recombinant vector comprising the exogenous DNA of the present invention or its mutant DNA and capable of expression in a mammal.

The non-human mammal having the exogenous DNA of the present invention or its mutant DNA (hereinafter simply referred to as the DNA transgenic animal of the present invention) can be created by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase) by standard means such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell or the like, by the DNA transfection methods, and utilize the transformant for cell culture, tissue culture, etc. In addition, these cells may be fused with the above-described germinal cell by a publicly known cell fusion method to create the transgenic animal of the present invention.

Examples of the non-human mammal that can be used include bovine, swine, sheep, goat, rabbits, dogs, cats, guinea pigs, hamsters, mice, rats and the like. Above all, preferred are rodents, especially mice (e.g., C57BL/6 strain, DBA2 strain, etc. for a pure line and for a cross line, $B6C3F_1$ strain, $BDF_1$ strain, $B6D2F_1$ strain, BALB/c strain, ICR strain, etc.) or rats (Wistar, SD, etc.) and the like, since they are relatively short in ontogeny and life cycle from a standpoint of creating model disease animals, and are easy in breeding.

"Mammals" in a recombinant vector that can be expressed in mammals include human etc. in addition to the aforesaid non-human mammals.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean the DNA that expresses the abnormal protein of the present invention and exemplified by such a DNA that expresses a protein suppressing the functions of the normal protein of the present invention, or the like.

The exogenous DNA of the present invention may be any one of those derived from a mammal of the same species as, or a different species from, the mammal as the target animal. In transfecting the DNA of the present invention to the target animal, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level can be prepared by microinjecting a DNA construct (e.g., vector, etc.) ligated with the human DNA of the present invention into a fertilized egg of the target mammal, e.g., a fertilized egg of mouse, downstream the various promoters capable of expressing the DNA derived from various mammals (e.g., rabbits, dogs, cats, guinea pigs, hamsters, rats, mice, etc.) having the DNA of the present invention highly homologous to the human DNA.

As expression vectors for the protein of the present invention, there are *Escherichia coli*-derived plasmids, *Bacillus subtilis*-derived plasmids, yeast-derived plasmids, bacteriophages such as λ phage, etc., retroviruses such as Moloney leukemia virus, etc., animal viruses such as vaccinia virus, baculovirus, etc. Of these vectors, *Escherichia coli*-derived plasmids, *Bacillus subtilis*-derived plasmids, yeast-derived plasmids, etc. are preferably used.

Examples of these promoters for regulating the DNA expression include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na, K-ATPase), neurofilament light chain, metallothioneins I and IIA, metalloproteinase 1 tissue inhibitor, MHC class I antigen (H-2L), H-ras, renin, dopamine β-hydroxylase, thyroid peroxidase (TPO), polypeptide chain elongation factor 1α(EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human peptide elongation factor 1α (EF-1α) promoters, human and chicken β actin promoters etc., which can achieve high expression in the whole body, are preferred.

It is preferred that the vectors described above have a sequence for terminating the transcription of the desired messenger RNA in the DNA transgenic animal (generally called a terminator); for example, a sequence of each DNA derived from viruses and various mammals. SV40 terminator of the simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5, upstream of the promoter region, or between the promoter region and the translational region, or at the 3' downstream of the translational region, depending upon purposes.

The normal translational region of the protein of the present invention can be prepared as the whole or a part of genomic DNA from DNA derived from liver, kidney, thyroid cells, fibroblasts etc. derived from humans or mammals (for example, rabbit, dog, cat, guinea pig, hamster, rat, mouse etc.) and a wide variety of commercial DNA libraries, or from complementary DNA as a starting material prepared by a known method from RNA derived from liver, kidney, thyroid cells, fibroblasts etc. As the extraneous abnormal DNA, a translational region can be prepared by point mutation of the normal translational region of the polypeptide obtained from the above cells or tissues.

The translational region can be prepared, as a DNA construct capable of being expressed in the transgenic animal, by a conventional DNA engineering technique, in which the DNA is ligated downstream the aforesaid promoter and if desired, upstream the translation termination site.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal, in which the normal exogenous DNA of the present invention has been transfected can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells of the target mammal. The fact that the exogenous DNA of the present invention is excessively present in the germinal cells of the prepared animal after transfection means that all of the offspring of the animal prepared have the exogenous DNA of the present invention excessively in all of the germinal cells and somatic cells thereof. The offspring of the animal of this kind that inherits the exogenous DNA of the present invention excessively have the DNA of the present invention in all of the germinal cells and somatic cells thereof.

By obtaining a homozygotic animal having the transfected DNA in both of homologous chromosomes and mating a male and female of the animal, all offspring can be passaged to excessively retain the DNA.

In a non-human mammal bearing the normal DNA of the present invention, the normal DNA of the present invention is expressed to a high level, and may eventually develop the hyperfunction of the protein of the present invention by promoting the functions of endogenous normal DNA. Therefore, the animal can be utilized as a pathologic model animal for such a disease. Specifically, using the normal DNA transgenic animal of the present invention, it becomes possible to elucidate the hyperfunction of the protein of the present invention and to clarify the pathological mechanism of the disease associated with the protein of the present invention and to determine how to treat these diseases.

Furthermore, since a mammal transfected with the exogenous normal DNA of the present invention exhibits an increasing symptom of the librated protein of the present invention, the animal is usable for screening of therapeutic agents agent for the disease associated with the protein of the present invention.

On the other hand, non-human mammal having the exogenous abnormal DNA of the present invention can be passaged under normal breeding conditions as the DNA-bearing animal by confirming the stable retaining of the exogenous DNA via crossing. In addition, the objective exogenous DNA can be utilized as a starting material by inserting the objective exogenous DNA into the plasmid described above. The DNA construct with a promoter can be prepared using conventional DNA engineering techniques. The transfection of the abnormal DNA of the present invention at the fertilized egg cell stage is preserved to be present in all of the germinal and somatic cells of the mammals to be targeted. The fact that the abnormal DNA of the present invention is present in the germinal cells of the animal after DNA transfection means that all of the offspring of the prepared animal have the abnormal DNA of the present invention in all of the germinal and somatic cells. The offspring of such an animal that inherits the exogenous DNA of the present invention has the abnormal DNA of the present invention in all the germinal and somatic cells. A homozygous animal having the introduced DNA on both of homologous chromosomes can be acquired and then by mating these male and female animals, all the offspring can be bred to have the DNA.

Since the non-human mammal having the abnormal DNA of the present invention expresses the abnormal DNA of the present invention at a high level, the animal may cause the function inactive type inadaptability of the protein of the present invention by inhibiting the functions of the endogenous normal DNA, and can be utilized as its disease model animal. For example, using the abnormal DNA-transferred animal of the present invention, it is possible to elucidate the mechanism of the function inactive type inadaptability of the protein of the present invention and to study a method for treatment of this disease.

In its specific applicability, the transgenic animal of the present invention expressing the abnormal DNA of the present invention to a high level is also expected to serve as a model for the elucidation of the mechanism of the functional inhibition (dominant negative effect) of a normal protein by the abnormal protein of the present invention in the function inactive type inadaptability of the protein of the present invention.

A mammal bearing the abnormal exogenous DNA of the present invention is also expected to serve for screening a candidate drug for the treatment of the function inactive type inadaptability of the protein of the present invention, since the protein of the present invention is increased in such an animal in its free form.

Other potential applicability of the two kinds of the transgenic animals described above includes:

(i) use as a cell source for tissue culture;

(ii) elucidation of the association with a peptide that is specifically expressed or activated by the protein of the present invention, through direct analysis of DNA or RNA in tissue of the DNA transgenic animal of the present invention or by analysis of the peptide tissue expressed by the DNA;

(iii) research in the function of cells derived from tissues that are cultured usually only with difficulty, using cells of tissue bearing the DNA cultured by a standard tissue culture technique;

(iv) screening for a drug that enhances the functions of cells using the cells described in (iii) above; and, (v) isolation and purification of the variant protein of the present invention and preparation of an antibody thereto.

Furthermore, clinical conditions of a disease associated with the protein of the present invention, including the function inactive type inadaptability of the protein of the present invention can be determined using the DNA transgenic animal of the present invention. Also, pathological findings on each organ in a disease model associated with the protein of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve as identification of cells capable of producing the protein of the present invention, and as studies on association with apoptosis, differentiation or propagation or on the mechanism of signal transduction in these properties to inspect any abnormality therein. Thus, the DNA transgenic animal of the present invention can provide an effective research material for the protein of the present invention and for elucidating the function and effect thereof.

To develop pharmaceuticals for the treatment of diseases associated with the protein of the present invention, including the function inactive type inadaptability of the protein of the present invention, using the DNA transgenic animal of the present invention, an effective and rapid method for screening the pharmaceuticals for the treatment of diseases can be provided by using the method for inspection and the method for quantification, etc. described above. It is also possible to investigate and develop a method for DNA therapy for the treatment of diseases associated with the protein of the present invention, using the DNA transgenic animal of the present invention or a vector capable of expressing the exogenous DNA of the present invention.

[7] Knockout Animal

The present invention provides a non-human mammal embryonic stem cell bearing the DNA of the present invention inactivated and a non-human mammal deficient in expressing the DNA of the present invention.

Thus, the present invention provides:

(1) a non-human mammal embryonic stem cell in which the DNA of the present invention is inactivated;

(2) the embryonic stem cell according to (1), wherein the DNA is inactivated by introducing a reporter gene (e.g., β-galactosidase gene derived from *Escherichia coli*);

(3) the embryonic stem cell according to (1), which is resistant to neomycin;

(4) the embryonic stem cell according to (1), wherein the non-human mammal is a rodent;

(5) an embryonic stem cell according to (4), wherein the rodent is mouse;

(6) a non-human mammal deficient in expressing the DNA of the present invention, wherein the DNA of the present invention is inactivated;

(7) the non-human mammal according to (6), wherein the DNA is inactivated by inserting a reporter gene (e.g., β-galactosidase derived from *Escherichia coli*) therein and the reporter gene is capable of being expressed under the control of a promoter for the DNA of the present invention;

(8) the non-human mammal according to (6), which is a rodent;

(9) the non-human mammal according to (8), wherein the rodent is mouse; and

(10) a method for screening a compound or its salt that promotes or inhibits the promoter activity for the DNA of the present invention, which comprises administering a test compound to the animal of (7) and detecting expression of the reporter gene.

The non-human mammalian embryonic stem cell, in which the DNA of the present invention is inactivated, refers to a non-human mammalian embryonic stem cell that suppresses the ability of the non-human mammalian to express the DNA by artificially mutating the DNA of the present invention possessed in the non-human mammal, or the DNA has no substantial ability to express the protein of the present invention (hereinafter sometimes referred to as the knockout DNA of the present invention) by substantially inactivating the activities of the protein of the present invention encoded by the DNA (hereinafter merely referred to as ES cell).

As the non-human mammalian, the same examples as described above apply.

Techniques for artificially mutating the DNA of the present invention include deletion of a part or all of the DNA sequence and insertion of, or substitution with, other DNA, e.g., by genetic engineering. By these variations, the knockout DNA of the present invention may be prepared, for example, by shifting the reading frame of a codon or by disrupting the function of a promoter or exon.

Specifically, the non-human mammalian embryonic stem cell, in which the DNA of the present invention is inactivated (hereinafter merely referred to as the ES cell with the DNA of the present invention inactivated or the knockout ES cell of the present invention), can be obtained by, for example, isolating the DNA of the present invention possessed by the target non-human mammal, inserting a DNA strand (hereinafter simply referred to as targeting vector) having a DNA sequence constructed so as to eventually destroy the gene by inserting into its exon site a chemical resistant gene such as a neomycin resistant gene or a hygromycin resistant gene, or a reporter gene such as lacZ (β-galactosidase gene) or cat (chloramphenicol acetyltransferase gene), etc. thereby destroying the functions of exon, or by inserting into the intron site between exons a DNA sequence which terminates gene transcription (e.g., polyA-added signal, etc.) thereby disabling the synthesis of complete messenger RNA, into a chromosome of the animal cells by, e.g., homologous recombination. The thus obtained ES cells are analyzed by the Southern hybridization using as a probe a DNA sequence on or near the DNA of the present invention, or by PCR using as primers a DNA sequence on the targeting vector and another DNA sequence near the DNA of the present invention which is not included in the targeting vector, and the knockout ES cell of the present invention is selected.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum collection per C57BL/6 mouse or C57BL/6 has been improved by crossing with DBA/2, may be preferably used, instead of obtaining a pure line of ES cells with the clear immunological genetic background. The $BDF_1$ mouse is advantageous in that when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes of 3.5 days after fertilization are commonly used. A large number of early stage embryos may be acquired more efficiently, by collecting the embryos of the 8-cell stage and using the same after culturing until the blastocyte stage.

Although the ES cells used may be of either sex, male ES cells are generally more convenient for generation of a germ cell line chimera and are therefore preferred. It is desirable to identify sexes as soon as possible also in order to save painstaking culture time.

As an example of the method for sex identification of the ES cell, mention may be made of a method in which a gene in the sex-determining region on the Y-chromosome is amplified by PCR and detected. When this method is used, ES cells (about 50 cells) corresponding to almost 1 colony are sufficient, whereas karyotype analysis hitherto required about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and about 90% air) in the presence of LIF (1-10000 U/ml) on appropriate feeder cells such as STO fibroblasts, treated with a trypsin/EDTA solution (normally about 0.001 to about 0.5% trypsin/about 0.1 to 5 mM EDTA, preferably about 0.1% trypsin/about 1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

By allowing ES cells to reach a high density in mono-layers or to form cell aggregates in suspension under appropriate conditions, it is possible to differentiate them to various cell types, for example, parietal and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention, are useful for studying the functions of the protein of the present invention or the protein of the present invention in vitro cytologically or molecular biologically.

The non-human mammal deficient in expression of the DNA of the present invention can be identified from a normal animal by measuring the amount of mRNA in the subject animal by a publicly known method, and indirectly comparing the levels of expression.

As the non-human mammal, the same examples supra apply.

With respect to the non-human mammal deficient in expression of the DNA of the present invention, the DNA of the present invention can be made knockout by transfecting a targeting vector, prepared as described above, to mouse embryonic stem cells or mouse oocytes thereof, and conducting homologous recombination in which a targeting vector DNA sequence, wherein the DNA of the present invention is inactivated by the transfection, is replaced with the DNA of the present invention on a chromosome of a mouse embryonic stem cell or mouse oocyte.

The cells with the DNA of the present invention in which the DNA of the present invention is rendered knockout can be identified by the Southern hybridization analysis using as a probe a DNA sequence on or near the DNA of the present invention, or by PCR analysis using as primers a DNA sequence on the targeting vector and another DNA sequence which is not included in the DNA of the present invention derived from mouse, which is used as the targeting vector. When non-human mammalian embryonic stem cells are used, the cell line wherein the DNA of the present invention is inactivated is cloned by homologous recombination; the resulting cloned cell line is injected to, e.g., a non-human mammalian embryo or blastocyte, at an appropriate stage such as the 8-cell stage. The resulting chimeric embryos are transplanted to the uterus of the pseudo-pregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, in which all tissues are composed of cells having an artificially mutated locus of the DNA of the present invention, can be selected from a series of offspring obtained by crossing between such a chimeric animal and a normal animal, e.g., by coat color identification, etc. The individuals thus obtained are normally deficient in heterozygous expression of the protein of the present invention. The individuals deficient in homozygous expression of the protein of the present invention can be obtained from offspring of the intercross between the heterozygotes.

When an oocyte is used, a DNA solution may be injected, e.g., to the prenucleus by microinjection thereby obtaining a transgenic non-human mammal having a targeting vector introduced into its chromosome. From such transgenic non-human mammals, those having a mutation at the locus of the DNA of the present invention can be obtained by selection based on homologous recombination.

As described above, individuals wherein the DNA of the present invention is rendered knockout permit passage rearing under ordinary rearing conditions, after it is confirmed that in the animal individuals obtained by their crossing, the DNA has been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention fails to express, lacks various biological activities induced by the protein of the present invention, such an animal can be a disease model suspected of inactivated biological activities of the protein of the present invention and thus, offers an effective study to investigate causes for and therapy for these diseases.

[7a] Method for Screening of Compounds Having Therapeutic/Prophylactic Effects for Diseases Caused by Deficiency, Damages, etc. of the DNA of the Present Invention The non-human mammal deficient in expression of the DNA of the present invention can be used to screen compounds having therapeutic/prophylactic effects for diseases caused by deficiency, damages, etc. of the DNA of the present invention.

That is, the present invention provides a method for screening of a compound or its salt having therapeutic/prophylactic effects for diseases caused by deficiency, damages, etc. of the DNA of the present invention, which comprises administering a test compound to the non-human mammal deficient in expression of the DNA of the present invention, and observing and measuring a change having occurred in the animal.

As the non-human mammal deficient in expression of the DNA of the present invention used for the screening method, the same examples as given hereinabove apply.

Examples of the test compounds include peptides, proteins, non-peptide compounds, synthetic compounds, fermentation products, cell extracts, plant extracts, animal tissue extracts, blood plasma, etc. and these compounds may be novel compounds or publicly known compounds.

Specifically, the non-human mammal deficient in the expression of the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be tested with a test compound, for example, oral administration, intravenous injection, etc. are applied and the treatment is appropriately selected depending upon conditions of the test animal, properties of the test compound, etc. Furthermore, the amount of a test compound administered can be appropriately selected depending on administration route, nature of the test compound, or the like.

For example, when a compound having a therapeutic effect on hyperlipemia is screened, a test compound is administered into a non-human mammalian animal deficient in expressing DNA encoding the protein A of the present invention, raised with common feed or cholesterol-containing common feed, and then the amount of total bile acid in feces or total serum cholesterol in the animal is measured with time.

For example, when a compound having a prophylactic/therapeutic effect on renal insufficiency is screened, a test compound is administered into a non-human mammalian animal deficient in expressing DNA encoding the protein B of the present invention, and then the amount of blood creatine or urine protein in the animal is measured with time.

For example, when a compound having a therapeutic effect on diabetics is screened, a non-human mammalian animal deficient in expressing DNA encoding the protein C of the present invention is subjected to a sugar loading treatment, a test compound is administered before or after the sugar loading treatment, and blood sugar level, body weight change, etc. of the animal are measured with time.

For example, when a compound having a prophylactic/therapeutic effect on chronic articular rheumatism is screened, a test compound is administered into a non-human mammalian animal deficient in expressing DNA encoding the protein D of the present invention, and then the volume of a swelling in a joint in the animal is measured with time, or the damage in the joint is evaluated by X-ray, MRI. histological techniques etc.

The compound obtained by the above screening is a compound selected from the test compounds described above, and has therapeutic/prophylactic effects on diseases caused by deficiency, damages, etc. of the protein of the present invention, and can thus be used as a safe and low toxic drug for the treatment/prevention, etc. for these diseases. A compound derived from the compound obtained by the screening can also be similarly used.

The compound obtained by the screening method may form a salt, and as the salts of the compound, there may be used salts with physiologically acceptable acids (e.g., inorganic acids or organic acids) or bases (e.g., alkali metals), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A medicine comprising the compound or salts thereof obtained by the above screening method may be manufactured in a manner similar to the method for preparing the medicine comprising the protein of the present invention described hereinabove.

Since the medicine thus obtained is safe and low toxic, it can be administered to humans or other mammals (e.g., rat, mouse, guinea pig, rabbit, sheep, swine, bovine, horse, cat, dog, monkey, etc.).

The dose of the above compound or its salt may vary depending on its action, target disease, subject to be administered, route for administration, etc. When the compound is orally administered, the compound is administered to adult (as 60 kg) as a patient with hyperlipemia generally in a daily dose of approximately 0.1 mg to 100 mg, preferably approximately 1.0 mg to 50 mg, more preferably approximately 1.0 to 20 mg. When the compound is parenterally administered, a single dose of the compound may vary depending on subject to be administered, target disease, etc. When the compound is administered in the form of an injection to adult (as 60 kg body weight) as a patient with hyperlipemia, it is convenient to administer the compound by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

[7b] Method of Screening a Compound that Promotes or Inhibits the Activities of a Promoter for the DNA of the Present Invention The present invention provides a method of screening a compound or its salt that promotes or inhibits the activities of a promoter for the DNA of the present invention, which comprises administering a test compound to a non-human mammal deficient in expression of the DNA of the present invention and detecting expression of the reporter gene.

In the screening method described above, the non-human mammal deficient in expression of the DNA of the present invention is selected from the aforesaid non-human mammal deficient in expression of the DNA of the present invention for an animal, in which the DNA of the present invention is inactivated by introducing a reporter gene and the reporter gene can be expressed under the control of a promoter for the DNA of the present invention.

The same examples given above for the test compound apply to the test compound.

As the reporter gene, the same specific examples given above apply to the reporter gene, with β-galactosidase (lacZ), soluble alkaline phosphatase gene, luciferase gene, etc. being preferred.

In the non-human mammal deficient in expression of the DNA of the present invention wherein the DNA of the present invention is substituted with a reporter gene, the reporter gene is present under the control of a promoter for the DNA of the present invention. Thus, the activity of the promoter can be detected by tracing the expression of a substance encoded by the reporter gene.

For example, when a part of the DNA region encoding the protein of the present invention is substituted with, e.g., β-galactosidase gene (lacZ) derived from *Escherichia coli*, β-galactosidase is expressed in a tissue where the protein of the present invention should originally be expressed, in place of the protein of the present invention. Thus, the expression state of the protein of the present invention can be readily observed in vivo in an animal, by staining with a reagent, e.g., 5-bromo-4-chloro-3-indolyl-β-galactopyranoside (X-gal), which is a substrate for β-galactosidase. Specifically, a mouse deficient in the protein of the present invention, or its tissue section, is fixed with glutaraldehyde, etc. After washing with phosphate buffered saline (PBS), the system is reacted with a staining solution containing X-gal at room temperature or about 37° C. for approximately 30 minutes to 1 hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening methods supra are compounds selected from the test compounds described above, which promote or inhibit the promoter activity for the DNA of the present invention.

The compound obtained by the screening methods may be in the form of salts. The salts of the compound used are salts with physiologically acceptable acids (e.g., inorganic acids) or bases (e.g., organic acids), and physiologically acceptable acid addition salts are preferred. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The compound or its salt that promotes the activity of the promoter for the DNA encoding the protein A of the present invention can promote the expression of protein A of the present invention to promote the functions of the protein, and is thus useful as a medicine such as a prophylactic/therapeutic agent for diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc.

The compound or its salt that inhibits the promoter activity for the DNA encoding the protein A of the present invention can inhibit the expression of the protein A of the present invention to inhibit the functions of the protein, and is thus useful as a medicine such as a prophylactic/therapeutic agent for diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc.

The compound or its salt that promotes the promoter activity for the DNA encoding the protein B of the present invention can promote the expression of the protein B of the present invention to promote the functions of the protein, and is thus useful as a medicine such as a prophylactic/therapeutic agent for diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc., preferably respiratory diseases, renal diseases, digestive diseases etc.

The compound or its salt that inhibits the promoter activity for the DNA encoding the protein B of the present invention can inhibit the expression of the protein B of the present invention to inhibit the functions of the protein, and is thus useful as a medicine such as a prophylactic/therapeutic agent for diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc., preferably respiratory diseases, renal diseases, digestive diseases etc.

The compound or its salt that promotes the promoter activity for the DNA encoding the protein C of the present invention can promote the expression of the protein C of the present invention to promote the functions of the protein, and is thus useful as a medicine such as a prophylactic/therapeutic agent for diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc.

The compound or its salt that inhibits the promoter activity for the DNA encoding the protein C of the present invention can inhibit the expression of the protein C of the present invention to inhibit the functions of the protein, and is thus useful as a medicine such as a prophylactic/therapeutic agent for diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc.

The compound or its salt that promotes the promoter activity for the DNA encoding the protein D of the present invention can promote the expression of the protein D of the present invention to promote the functions of the protein, and is thus useful as a medicine such as a prophylactic/therapeutic agent for diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

The compound or its salt that inhibits the promoter activity for the DNA encoding the protein D of the present invention can inhibit the expression of the protein D of the present invention to inhibit the functions of the protein, and is thus useful as a medicine such as a prophylactic/therapeutic agent for diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

Further, a compound derived from the compound obtained in the above screening can also be used similarly.

The medicine comprising the compound or its salt obtained by the screening method can be produced in a manner similar to the method for preparing the medicine comprising the protein of the present invention or its salt described hereinabove.

Since the thus obtained medicine is safe and low toxic, and can be administered to, for example, human and warm-blooded animal (e.g., rat, mouse, guinea pig, rabbit, sheep, swine, bovine, horse, cat, dog, monkey, etc.).

The dose of the compound or its salt may vary depending on target disease, subject to be administered, route for administration, etc. When the compound promoting the promoter activity for the DNA of the present invention is orally administered, the compound is administered to adult (as 60 kg) as a patient with hyperlipemia generally in a daily dose of approximately 0.1 mg to 100 mg, preferably approximately 1.0 mg to 50 mg, more preferably approximately 1.0 to 20 mg. When the compound is parenterally administered, a single dose of the compound may vary depending on subject to be administered, target disease, etc. When the compound promoting the promoter activity for the DNA of the present invention is administered in the form of an injection to adult (as 60 kg body weight) as a patient with hyperlipemia, it is convenient to administer the compound by intravenous injection in a daily dose of approximately 0.01 to 30 mg, preferably approximately 0.1 to 20 mg, more preferably approximately 0.1 to 10 mg. For other animal species, the corresponding dose as converted per 60 kg weight can be administered.

On the other hand, when the compound inhibiting the promoter activity for the DNA of the present invention is orally administered, the compound is administered to adult (as 60 kg) as a patient with hyperlipemia generally in a daily dose of approximately 0.1 mg to 100 mg, preferably approximately 1.0 mg to 50 mg, more preferably approximately 1.0 to 20 mg. When the compound is parenterally administered, a single dose of the compound may vary depending on subject to be administered, target disease, etc. When the compound inhibiting the promoter activity for the DNA of the present invention is administered in the form of an injection to adult (as 60 kg body weight) as a patient with hyperlipemia, it is convenient to administer the compound by intravenous injection in a daily dose of approximately 0.01 to 30 mg, preferably approximately 0.1 to 20 mg, more preferably approximately 0.1 to 10 mg. For other animal species, the corresponding dose as converted per 60 kg weight can be administered.

Thus, the non-human mammal deficient in expression of the DNA of the present invention is extremely useful in screening a compound or its salt that promotes or inhibits the activity of a promoter for the DNA of the present invention, and can contribute significantly to elucidation of causes for various diseases attributable to deficient expression of the DNA of the present invention or development of a prophylactic/therapeutic agent for the diseases.

Further, genes encoding various proteins are ligated downstream DNA containing a promoter region for the protein of the present invention and injected into a fertilized egg of an animal to create a transgenic animal by which the protein of the present invention can be specifically synthesized and examined for its action in the living body. When a suitable reporter gene is ligated to the promoter region to establish a cell strain expressing the same, the cell strain can be used as a system of searching for a low-molecular compound having an action of specifically promoting or suppressing the ability of the cell strain to produce the protein of the present invention in vivo.

[8] Determination of a Ligand to the Protein D of the Present Invention

The protein D of the present invention or its partial peptide or its salts are useful as reagents for searching and determining ligands to the protein D of the present invention or its salts.

That is, the present invention provides a method for determining a ligand to the protein D of the present invention, which comprises bringing the protein D of the present invention or its partial peptide or its salts, into contact with a test compound.

Examples of the test compound include publicly known ligands (e.g., angiotensin, bombesin, canavinoid, cholecystokinin, glutamine, serotonin, melatonin, neuropeptide Y, opioid, purines, vasopressin, oxytocin, PACAP (e.g., PACAP27, PACAP38), secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, a chemokine superfamily (e.g., CXC chemokine subfamily such as IL-8, GROα, GROβ, GROγ, NAP-2, ENA-78, GCP-2, PF4, IP10, Mig, PBSF/SDF-1, etc.; CC chemokine subfamily such as MCAF/MCP-1, MCP-2, MCP-3, MCP-4, eotaxin, RANTES, MIP1-α, MIP-1β, HCC-1, MIP-3α/LARC, MIP-3β/ELC, I-309, TARC, MIPF-1, MIPF-2/eotaxin-2, MDC, DC-CK1/PARC, SLC, etc.; C chemokine subfamily such as lymphotactin; and CX3C chemokine subfamily such as fractalkine, etc.), endothelin, enterogastrin, histamine, neurotensin, TRH, pancreatic polypeptide, galanin, lysophosphatidic acid (LPA), sphingosine 1-phosphate, vanilloid, nucleotide, etc.) as well as other substances, for example, tissue extracts and cell culture supernatants from mammals (e.g., humans, mice, rats, swine, bovine, sheep, monkeys, etc.). For example, the tissue extract or cell culture supernatant is added to the protein D of the present invention and fractionated while assaying the cation channel activities, etc. to finally give a single ligand.

In more detail, the method for determining ligands of the present invention comprises determining compounds (e.g., peptides, proteins, non-peptide compounds, synthetic compounds, fermentation products, nucleotides, etc.) or salts thereof that bind to the protein D of the present invention to provide cation channel activities (e.g., $Ca^{2+}$ channel activity etc.), using the protein D of the present invention, or by the ligand binding assay using the constructed recombinant protein D expression system.

The method for determining ligands according to the present invention is characterized, for example, by measurement of the amount of the test compound bound to the protein D or its partial peptide, or by assaying the cation channel activities, etc., when the test compound is brought into contact with the protein D of the present invention or its partial peptide.

More specifically, the present invention provides:

(i) A method for determining ligands to the protein D of the present invention or its salt, which comprises bringing a labeled test compound into contact with the protein D of the present invention or its salt or the partial peptide of the present invention or its salt and measuring the amount of the labeled test compound bound to the protein or its salt or to the partial peptide or its salt;

(ii) A method for determining ligands to the protein D of the present invention or its salt, which comprises bringing a labeled test compound into contact with cells or cell membrane fraction containing the protein D of the present invention, and measuring the amount of the labeled test compound bound to the cells or the membrane fraction;

(iii) A method for determining ligands to the protein D of the present invention, which comprises culturing a transformant containing the DNA encoding the protein D of the present invention, bringing a labeled test compound into contact with the protein D expressed on the cell membrane by said culturing, and measuring the amount of the labeled test compound bound to the protein D or its salt; and (iv) A method for determining ligands to the protein D of the present invention or its salt, which comprises bringing a test compound into contact with cells containing the protein D of the present invention and measuring the protein D-mediated cation channel activities (e.g., $Ca^{2+}$ channel activity etc.).

It is particularly preferred to perform the tests (i) to (iii) described above thereby confirming that the test compound can bind to the protein D of the present invention, followed by the test (iv) described above.

As the protein D used in the method of determining ligands, any material comprising the protein D of the present invention or the partial peptide of the present invention may be used, but the protein produced in a large amount by animal cells is appropriate.

The protein D of the present invention can be manufactured by the expression method described above, preferably by expressing DNA encoding the protein D in mammalian or insect cells. As DNA fragments encoding the desired portion of the protein, complementary DNA is generally used but not necessarily limited thereto. For example, gene fragments or synthetic DNA may also be used. For introducing a DNA fragment encoding the protein D of the present invention into host animal cells and efficiently expressing the same, it is preferred to insert the DNA fragment downstream a polyhedrin promoter of nuclear polyhedrosis virus (NPV), which is a baculovirus having insect hosts, an SV40-derived promoter, a retrovirus promoter, a metallothionein promoter, a human heat shock promoter, a cytomegalovirus promoter, an SRα promoter or the like. The amount and quality of the channel expressed can be determined by a publicly known method. For example, this determination can be made by the method described in the literature (Nambi, P., et al., J. Biol. Chem., 267, 19555-19559 (1992)).

Accordingly, the subject containing the protein D of the present invention, its partial peptides or salts thereof in the method for determining the ligand according to the present invention may be the protein D, its partial peptides or salts thereof purified by publicly known methods, cells containing the protein D, or membrane fractions of such cells.

In the ligand determination method of the present invention where cells containing the protein D of the present invention are used, the cells may be fixed with glutaraldehyde, formalin, etc. The cells can be fixed by publicly known methods.

The cells containing the protein D of the present invention are host cells that have expressed the protein D. As the host cells, *Escherichia coli, Bacillus subtilis*, yeast, insect cells, animal cells and the like are used.

The cell membrane fraction refers to a fraction abundant in cell membrane obtained by cell disruption and subsequent fractionation by a publicly known method. Cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), and the resulting supernatant is then centrifuged at a higher speed (15,000 rpm to 30,000 rpm) normally for 30 minutes to 2 hours. The precipitate thus obtained is used as the membrane fraction. The membrane fraction is rich in the protein D expressed and membrane components such as cell-derived phospholipids and membrane proteins.

The amount of the protein D in the protein D-containing cells or membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the methods (i) through (iii) supra for determination of a ligand to the protein D of the present invention or its salt, an appropriate protein D fraction and a labeled test compound are required.

The protein D fraction is preferably a fraction of naturally occurring protein D or a recombinant channel fraction having an equivalent activity to that of the natural protein. Herein, the term "equivalent activity" is intended to mean a ligand binding activity, a cation channel activity or the like that is equivalent to that possessed by the naturally occurring protein.

Preferred examples of labeled test compounds include angiotensin, bombesin, canavinoid, cholecystokinin, glutamine, serotonin, melatonin, neuropeptide Y, opioid, purines, vasopressin, oxytocin, PACAP (e.g., PACAP27, PACAP38), secretin, glucagon, calcitonin, adrenomedulin, somatostatin, GHRH, CRF, ACTH, GRP, PTH, VIP (vasoactive intestinal polypeptide), somatostatin, dopamine, motilin, amylin, bradykinin, CGRP (calcitonin gene-related peptide), leukotrienes, pancreastatin, prostaglandins, thromboxane, adenosine, adrenaline, a chemokine superfamily (e.g., CXC chemokine subfamily such as IL-8, GROα, GROβ, GROγ, NAP-2, ENA-78, GCP-2, PF4, IP10, Mig, PBSF/SDF-1, etc.; CC chemokine subfamily such as MCAF/MCP-1, MCP-2, MCP-3, MCP-4, eotaxin, RANTES, MIP1-α, MIP-1β, HCC-1, MIP-3α/LARC, MIP-3β/ELC, I-309, TARC, MIPF-1, MIPF-2/eotaxin-2, MDC, DC-CK1/PARC, SLC, etc.; C chemokine subfamily such as lymphotactin; and CX3C chemokine subfamily such as/fractalkine, etc.), endothelin, enterogastrin, histamin, neurotensin, TRH, pancreatic polypeptide, galanin, lysophosphatidic acid (LPA) or sphingosine 1-phosphate, vanilloid, nucleotide etc.), which are labeled with [$^3$H], [$^{125}$I], [$^{14}$C], [$^{35}$S], etc.

Specifically, the ligand to the protein D of the present invention or its salt is determined by the following procedures. First, a standard channel preparation is prepared by suspending cells containing the protein D of the present invention or the membrane fraction thereof in a buffer appropriate for use in the determination method. Any buffer can be used so long as it does not inhibit the ligand-protein D binding, such buffers including a phosphate buffer or a Tris-HCl buffer having pH of 4 to 10 (preferably pH of 6 to 8). For the purpose of minimizing non-specific binding, a surfactant such as CHAPS, TWEEN-80™ (Polyoxyethylene (20) Sorbitan Monooleate) (manufactured by Kao-Atlas Inc.), digitonin or deoxycholate, and various proteins such as bovine serum albumin or gelatin, may optionally be added to the buffer. Further for the purpose of suppressing the degradation of the receptors or ligands by proteases, a protease inhibitor such as PMSF, leupeptin, E-64 (manufactured by Peptide Institute, Inc.) and pepstatin may also be added. A given amount (5,000 to 500,000 cpm) of the test compound labeled with [$^3$H], [$^{125}$I], [$^{14}$C], [$^{35}$S] or the like is added to 0.01 ml to 10 ml of the protein solution. To determine the amount of non-specific binding (NSB), a reaction tube containing an unlabeled test compound in large excess is also prepared. The reaction is carried out at approximately 0 to 50° C., preferably about 4 to 37° C. for about 20 minutes to about 24 hours, preferably about 30 minutes to about 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. A test compound exceeding 0 cpm in count obtained by subtracting nonspecific binding (NSB) from the total binding (B) (B minus NSB) can be selected as a ligand to the protein D of the present invention or its salt.

The method (iv) above for determination of a ligand to the protein D of the present invention or its salt can be performed as follows. The protein D-mediated cation channel activities (e.g., $Ca^{2+}$ channel activity etc.) may be determined by a publicly known method, or using an assay kit commercially available. Specifically, cells containing the protein D are first cultured on a multi-well plate, etc. Prior to the ligand determination, the medium is replaced with fresh medium or with an appropriate non-cytotoxic buffer, followed by incorporation of a fluorescent $Ca^{2+}$ probe (for example, Fura-2, Fuo-3 or the like) and subsequent measurement of fluorescence density by FLIPR (Molecular Devices, Ltd.) etc. for a given period of time in the presence of a test compound, etc. The kit of the present invention for determination of the ligand that binds to the protein D of the present invention or its salt comprises the protein D of the present invention or its salt, the partial peptide of the present invention or its salt, cells comprising the protein D of the present invention, or the membrane fraction of the cells containing the protein D of the present invention.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |

The substituents, protective groups and reagents, which are frequently used throughout the specification, are shown by the following abbreviations.

| | |
|---|---|
| Me | methyl |
| Et | ethyl |
| Bu | butyl |
| Ph | phenyl |
| TC | thiazolidine-4(R)-carboxamide |
| Tos | p-toluenesulfonyl |
| CHO | formyl |
| Bzl | benzyl |
| $Cl_2Bzl$ | 2,6-dichlorobenzyl |
| Bom | benzyloxymethyl |
| Z | benzyloxycarbonyl |
| Cl-Z | 2-chlorobenzyloxycarbonyl |
| Br-Z | 2-bromobenzyloxycarbonyl |
| Boc | t-butoxycarbonyl |
| DNP | dinitrophenyl |
| Trt | trityl |
| Bum | t-butoxymethyl |
| Fmoc | N-9-fluorenylmethoxycarbonyl |
| HOBt | 1-hydroxybenztriazole |
| HOOBt | 3,4-dihydro-3-hydroxy-4-oxo-1,2,3-benzotriazine |

-continued

| | |
|---|---|
| HONB | 1-hydroxy-5-norbornene-2,3-dicarboxyimide |
| DCC | N,N'-dicyclohexylcarbodiimide |

The sequence identification numbers in the sequence listing of the specification indicate the following sequences, respectively.

[SEQ ID NO. 1]

This shows the amino acid sequence of human TCH230 (SEQ ID NO:1) protein consisting of 377 amino acids, which was obtained in Example 1.

[SEQ ID NO: 2]

This shows the base sequence of DNA encoding human TCH230 protein having the amino acid sequence represented by SEQ ID NO. 1.

[SEQ ID NO: 3]

This shows the base sequence of primer OF used in Example 1.

[SEQ ID NO: 4]

This shows the base sequence of primer OR1 used in Example 1.

[SEQ ID NO: 5]

This shows the base sequence of primer OF1 used in Example 1.

[SEQ ID NO: 6]

This shows the base sequence of primer OR used in Example 1.

[SEQ ID NO: 7]

This shows the base sequence of primer SP6 used in Examples 1 and 13.

[SEQ ID NO: 8]

This shows the base sequence of primer T7 used in Examples 1, 13, 18, 25 and 33.

[SEQ ID NO: 9]

This shows the base sequence of primer B1 used in Examples 1 and 18.

[SEQ ID NO. 10]

This shows the base sequence of primer F1 used in Examples 1 and 18.

[SEQ ID NO. 11]

This shows the base sequence of cDNA derived from human small intestine cDNA comprising the full-length TCH230 gene obtained in Example 1.

[SEQ ID NO. 12]

This shows the base sequence of cDNA derived from human skeletal muscle cDNA comprising the full-length TCH230 gene obtained in Example 1.

[SEQ ID NO. 13]

This shows the base sequence of DNA encoding human TCH230 (SEQ ID NO:1) protein comprising the amino acid sequence represented by SEQ ID NO. 14.

[SEQ ID NO. 14]

This shows the amino acid sequence of human TCH230 (SEQ ID NO:1) protein comprising an amino acid sequence encoded by the base sequence represented by SEQ ID NO. 13.

[SEQ ID NO. 15]

This shows the base sequence of primer TF used in Examples 2, 19 and 38.

[SEQ ID NO. 16]

This shows the base sequence of primer TR used in Examples 2, 19 and 38.

[SEQ ID NO. 17]

This shows the base sequence of TaqMan probe T1 used in Examples 2, 19 and 38.

[SEQ ID NO. 18]

This shows the amino acid sequence of human TCH234 (SEQ ID NO:18) protein obtained in Example 1.

[SEQ ID NO. 19]

This shows the base sequence of DNA encoding human TCH234 (SEQ ID NO:18) protein having the amino acid sequence represented by SEQ ID NO. 19.

[SEQ ID NO: 20]

This shows the base sequence of primer AP1 used in Example 3.

[SEQ ID NO: 21]

This shows the base sequence of primer rr0 used in Example 3.

[SEQ ID NO: 22]

This shows the base sequence of primer AP2 used in Example 3.

[SEQ ID NO: 23]

This shows the base sequence of primer rr1 used in Example 3.

[SEQ ID NO: 24]

This shows the base sequence of primer ff1 used in Example 4.

[SEQ ID NO: 25]

This shows the base sequence of primer ff2 used in Examples 4, 5 and 25.

[SEQ ID NO: 26]

This shows the base sequence of primer ORFF1 used in Example 5.

[SEQ ID NO: 27]

This shows the base sequence of primer ORFR1 used in Example 5.

[SEQ ID NO: 28]

This shows the base sequence of primer ORFF2 used in Example 5.

[SEQ ID NO: 29]

This shows the base sequence of primer ORFR2 used in Example 5.

[SEQ ID NO: 30]

This shows the base sequence of primer M13F used in Example 5.

[SEQ ID NO: 31]

This shows the base sequence of primer M13R used in Example 5.

[SEQ ID NO: 32]

This shows the base sequence of primer TMF used in Examples 6, 27, 28 and 38.

[SEQ ID NO: 33]

This shows the base sequence of primer TMR used in Examples 6, 27, 28 and 38.

[SEQ ID NO: 34]

This shows the base sequence of primer F2 used in Example 5.

[SEQ ID NO: 35]

This shows the base sequence of primer F3 used in Examples 5 and 25.

[SEQ ID NO: 36]

This shows the base sequence of primer R1 used in Example 5.

[SEQ ID NO: 37]

This shows the base sequence of primer R2 used in Examples 5 and 25.

[SEQ ID NO: 38]

This shows the base sequence of TaqMan probe P1 used in Examples 6, 27, 28 and 38.

[SEQ ID NO: 39]

This shows the base sequence of cDNA obtained in Example 3.

[SEQ ID NO: 40]

This shows the base sequence of cDNA obtained in Example 4.

[SEQ ID NO: 41]

This shows the base sequence of cDNA obtained in Example 5.

[SEQ ID NO: 42]

This shows the amino acid sequence of human TCH212 (SEQ ID NO:42) protein obtained in Example 7.

[SEQ ID NO: 43]

This shows the base sequence of DNA encoding human TCH212 protein having the amino acid sequence represented by SEQ ID NO: 42.

[SEQ ID NO: 44]

This shows the base sequence of primer A3 used in Example 7.

[SEQ ID NO: 45]

This shows the base sequence of primer B3 used in Example 7.

[SEQ ID NO: 46]

This shows the base sequence of primer SP6 used in Example 7.

[SEQ ID NO: 47]

This shows the base sequence of primer T7 used in Example 7.

[SEQ ID NO: 48]

This shows the base sequence of primer A2 used in Examples 7 and 33.

[SEQ ID NO: 49]

This shows the base sequence of primer B1 used in Examples 7 and 33.

[SEQ ID NO: 50]

This shows the base sequence of primer B2 used in Examples 7 and 33.

[SEQ ID NO: 51]

This shows the base sequence of primer F1 used in Examples 7 and 33.

[SEQ ID NO: 52]

This shows the base sequence of primer F2 used in Examples 7 and 33.

[SEQ ID NO: 53]
This shows the base sequence of primer F3 used in Examples 7 and 33.

[SEQ ID NO: 54]
This shows the base sequence of primer F4 used in Examples 7 and 33.

[SEQ ID NO: 55]
This shows the base sequence of primer F5 used in Examples 7 and 33.

[SEQ ID NO: 56]
This shows the base sequence of primer R1 used in Examples 7 and 33.

[SEQ ID NO: 57]
This shows the base sequence of primer R2 used in Examples 7 and 33.

[SEQ ID NO: 58]
This shows the base sequence of primer R3 used in Examples 7 and 33.

[SEQ ID NO: 59]
This shows the base sequence of primer R4 used in Examples 7 and 33.

[SEQ ID NO: 60]
This shows the base sequence of cDNA comprising the full-length human TCH212 (SEQ ID NO:42) gene obtained in Example 7.

[SEQ ID NO: 61]
This shows the base sequence of cDNA comprising the full-length human TCH212 (SEQ ID NO:42) clone #2 obtained in Example 7.

[SEQ ID NO: 62]
This shows the base sequence of ORF in human TCH212 (SEQ ID NO:42) clone #2 obtained in Example 7.

[SEQ ID NO: 63]
This shows the base sequence of primer TF used in Examples 8 and 38.

[SEQ ID NO: 64]
This shows the base sequence of primer TR used in Examples 8 and 38.

[SEQ ID NO: 65]
This shows the base sequence of TaqMan probe T1 used in Examples 8 and 38.

[SEQ ID NO: 66]
This shows the amino acid sequence of human TCH200 (SEQ ID NO:66) protein.

[SEQ ID NO: 67]
This shows the base sequence of DNA encoding human TCH200 protein comprising the amino acid sequence represented by SEQ ID NO: 66.

[SEQ ID NO: 68]
This shows the base sequence of primer API used in Example 9.

[SEQ ID NO: 69]
This shows the base sequence of primer R1 used in Example 9.

[SEQ ID NO: 70]
This shows the base sequence of primer AP2 used in Example 9.

[SEQ ID NO: 71]
This shows the base sequence of primer rr2 used in Example 9.

[SEQ ID NO: 72]
This shows the base sequence of primer M13F used in Example 9.

[SEQ ID NO: 73]
This shows the base sequence of primer M13R used in Example 9.

[SEQ ID NO: 74]
This shows the base sequence of primer rr4 used in Example 9.

[SEQ ID NO: 75]
This shows the base sequence of primer rr6 used in Example 9.

[SEQ ID NO: 76]
This shows the base sequence of primer r1 used in Example 10.

[SEQ ID NO: 77]
This shows the base sequence of primer r2 used in Example 10.

[SEQ ID NO: 78]
This shows the base sequence of primer f1 used in Example 10.

[SEQ ID NO: 79]
This shows the base sequence of primer f2 used in Example 10.

[SEQ ID NO: 80]
This shows the base sequence of primer f4 used in Example 10.

[SEQ ID NO: 81]
This shows the base sequence of primer F0 used in Example 11.

[SEQ ID NO: 82]
This shows the base sequence of primer R7 used in Example 11.

[SEQ ID NO: 83]
This shows the base sequence of primer F00 used in Example 11.

[SEQ ID NO: 84]
This shows the base sequence of primer R00 used in Example 11.

[SEQ ID NO: 85]
This shows the base sequence of primer F1 used in Example 11.

[SEQ ID NO: 86]
This shows the base sequence of primer F2 used in Example 11.

[SEQ ID NO: 87]
This shows the base sequence of primer F5 used in Example 11.

[SEQ ID NO: 88]
This shows the base sequence of primer F7 used in Example 11.

[SEQ ID NO: 89]
This shows the base sequence of primer ff3 used in Example 11.

[SEQ ID NO: 90]
This shows the base sequence of primer ff4 used in Example 11.

[SEQ ID NO: 91]
This shows the base sequence of primer f3 used in Example 11.

[SEQ ID NO: 92]
This shows the base sequence of primer rr1 used in Example 11.

[SEQ ID NO: 93]
This shows the base sequence of primer rr3 used in Example 11.

[SEQ ID NO: 94]
This shows the base sequence of primer TMF used in Examples 12, 37 and 38.

[SEQ ID NO: 95]
This shows the base sequence of primer TMR used in Examples 12, 37 and 38.

[SEQ ID NO: 96]
This shows the base sequence of TaqMan probe P1 used in Examples 12, 37 and 38.

[SEQ ID NO: 97]
This shows the base sequence of cDNA obtained in Example 9.

[SEQ ID NO: 98]
This shows the base sequence of cDNA obtained in Example 9.

[SEQ ID NO: 99]
This shows the base sequence of cDNA obtained in Example 10.

[SEQ ID NO. 100]
This shows the base sequence of cDNA obtained in Example 10.

[SEQ ID NO. 101]
This shows the base sequence of cDNA obtained in Example 10.

[SEQ ID NO. 102]
This shows the base sequence of cDNA obtained in Example 11.

[SEQ ID NO. 103]
This shows the base sequence of DNA encoding human TCH200 protein comprising the amino acid sequence represented by SEQ ID NO: 66.

[SEQ ID NO. 104]
This shows the amino acid sequence of mouse TCH230 (SEQ ID NO:112) protein consisting of 373 amino acids, which was obtained in Example 13.

[SEQ ID NO. 105]
This shows the base sequence of DNA encoding mouse TCH230 (SEQ ID NO:112) protein having the amino acid sequence represented by SEQ ID NO. 104.

[SEQ ID NO. 106]
This shows the base sequence of primer m230A1 used in Example 13.

[SEQ ID NO. 107]
This shows the base sequence of primer m230B2 used in Example 13.

[SEQ ID NO. 108]
This shows the base sequence of primer m230F1 used in Example 13.

[SEQ ID NO. 109]
This shows the base sequence of primer m230F2 used in Example 13.

[SEQ ID NO. 110]
This shows the base sequence of primer m230R1 used in Example 13.

[SEQ ID NO. 111]
This shows the base sequence of primer m230R2 used in Example 13.

[SEQ ID NO. 112]
This shows the base sequence of cDNA comprising the full-length mouse TCH230 (SEQ ID NO:112) gene obtained in Example 13.

[SEQ ID NO. 113]
This shows the base sequence of primer m230TF used in Examples 14, 15 and 40.

[SEQ ID NO. 114]
This shows the base sequence of primer m230TR used in Examples 14, 15 and 40.

[SEQ ID NO. 115]
This shows the base sequence of TaqMan probe m230T1 used in Examples 14, 15 and 40.

[SEQ ID NO. 116]
This shows the base sequence of a partial sequence of rat TCH230 gene cDNA identified in Example 16.

[SEQ ID NO. 117]
This shows the base sequence of primer r230OF used in Example 16.

[SEQ ID NO. 118]
This shows the base sequence of primer r230OR used in Example 16.

[SEQ ID NO. 119]
This shows the base sequence of primer r230TF used in Example 17.

[SEQ ID NO. 120]
This shows the base sequence of primer r230TR used in Example 17.

[SEQ ID NO. 121]
This shows the base sequence of TaqMan probe r230T1 used in Example 17.

[SEQ ID NO. 122]
This shows the base sequence of primer 230OF2 used in Example 18.

[SEQ ID NO. 123]
This shows the base sequence of primer 230OR2 used in Example 18.

[SEQ ID NO. 124]
This shows the base sequence of primer BGHRV used in Example 18.

[SEQ ID NO. 125]
This shows the base sequence of a partial sequence of mouse TCH234 gene cDNA identified in Example 21.

[SEQ ID NO. 126]
This shows the base sequence of primer m234-1485F used in Example 21.

[SEQ ID NO. 127]

This shows the base sequence of primer m234-1801R used in Example 21.

[SEQ ID NO. 128]

This shows the base sequence of primer m234-TMF used in Examples 22 and 39.

[SEQ ID NO. 129]

This shows the base sequence of primer m234-TMR used in Examples 22 and 39.

[SEQ ID NO. 130]

This shows the base sequence of primer m234T1 used in Examples 22 and 39.

[SEQ ID NO. 131]

This shows the base sequence of a partial sequence of rat TCH234 gene cDNA identified in Example 23.

[SEQ ID NO. 132]

This shows the base sequence of primer r234-815F used in Example 23.

[SEQ ID NO. 133]

This shows the base sequence of primer r234-1177R used in Example 23.

[SEQ ID NO. 134]

This shows the base sequence of primer r234-TMF used in Example 24.

[SEQ ID NO. 135]

This shows the base sequence of primer r234-TMR used in Example 24.

[SEQ ID NO. 136]

This shows the base sequence of primer r234-P1 used in Example 24.

[SEQ ID NO. 137]

This shows the base sequence of primer 234OF used in Example 25.

[SEQ ID NO. 138]

This shows the base sequence of primer 234OR used in Example 25.

[SEQ ID NO. 139]

This shows the base sequence of primer 234F21 used in Example 25.

[SEQ ID NO. 140]

This shows the base sequence of primer 234F22 used in Example 25.

[SEQ ID NO. 141]

This shows the base sequence of primer 234F23 used in Example 25.

[SEQ ID NO. 142]

This shows the base sequence of primer 234R24 used in Example 25.

[SEQ ID NO. 143]

This shows the base sequence of a partial sequence of mouse TCH212 (SEQ ID NO:143) gene cDNA identified in Example 29.

[SEQ ID NO. 144]

This shows the base sequence of primer m212A1 used in Examples 29 and 31.

[SEQ ID NO. 145]

This shows the base sequence of primer m212B1 used in Examples 29 and 31.

[SEQ ID NO. 146]

This shows the base sequence of primer m212TF used in Example 30.

[SEQ ID NO. 147]

This shows the base sequence of primer m212TR used in Example 30.

[SEQ ID NO. 148]

This shows the base sequence of TaqMan probe m212T1 used in Example 30.

[SEQ ID NO. 149]

This shows the base sequence of a partial sequence of rat TCH212 gene cDNA identified in Example 31.

[SEQ ID NO. 150]

This shows the base sequence of primer r212TF used in Example 32.

[SEQ ID NO. 151]

This shows the base sequence of primer r212TR used in Example 32.

[SEQ ID NO. 152]

This shows the base sequence of primer r212T1 used in Example 32.

[SEQ ID NO. 153]

This shows the base sequence of primer 212OF used in Example 33.

[SEQ ID NO. 154]

This shows the base sequence of primer 212OR used in Example 33.

[SEQ ID NO. 155]

This shows the base sequence of a partial sequence of mouse TCH200 gene cDNA identified in Example 34.

[SEQ ID NO. 156]

This shows the base sequence of primer m200A1 used in Example 34.

[SEQ ID NO. 157]

This shows the base sequence of primer m200B1 used in Example 34.

[SEQ ID NO. 158]

This shows the base sequence of primer m200A2 used in Examples 34 and 35.

[SEQ ID NO. 159]

This shows the base sequence of primer m200B2 used in Examples 34 and 35.

[SEQ ID NO. 160]

This shows the base sequence of TaqMan probe m200T1 used in Example 35.

[SEQ ID NO. 161]

This shows the base sequence of primer TCH200F used in Example 36.

[SEQ ID NO. 162]

This shows the base sequence of primer TCH200R used in Example 36.

[SEQ ID NO. 163]

This shows the base sequence of primer T7 used in Example 36.

[SEQ ID NO. 164]

This shows the base sequence of primer AF used in Example 36.

[SEQ ID NO. 165]

This shows the base sequence of primer BF used in Example 36.

[SEQ ID NO. 166]

This shows the base sequence of primer CF used in Example 36.

[SEQ ID NO. 167]

This shows the base sequence of primer DF used in Example 36.

[SEQ ID NO. 168]

This shows the base sequence of primer BGH RV used in Example 36.

[SEQ ID NO. 169]

This shows the base sequence of primer DR used in Example 36.

[SEQ ID NO. 170]

This shows the base sequence of primer CR used in Example 36.

[SEQ ID NO. 171]

This shows the base sequence of primer BR used in Example 36.

[SEQ ID NO. 172]

This shows the base sequence of primer AR used in Example 36.

Transformant *Escherichia coli* TOP10/PCR-BluntII-TCH230 obtained in Example 1 later described has been deposited with International Patent Organism Depositary (IPOD), National Institute of Advanced Industrial Science and Technology (AIST) at Central 6, 1-1-1, Higashi, Tsukuba, Ibaraki, Japan (zip code: 305-8566), under the Accession Number FERM BP-7869 since Jan. 17, 2002, and with Institute for Fermentation, Osaka (IFO) at 17-85, Juso-honmachi 2-chome, Yodogawa-ku, Osaka, Japan (zip code: 532-8686), under the Accession Number IFO 16749 since Jan. 17, 2002.

Transformant *Escherichia coli* TOP10/PCR-BluntII-TCH234 obtained in Example 3 later described has been deposited with International Patent Organism Depositary (IPOD), National Institute of Advanced Industrial Science and Technology (AIST) at Central 6, 1-1-1, Higashi, Tsukuba, Ibaraki, Japan (zip code: 305-8566), under the Accession Number FERM BP-7906 since Feb. 18, 2002, and with Institute for Fermentation, Osaka (IFO) at 17-85, Juso-honmachi 2-chome, Yodogawa-ku, Osaka, Japan (zip code: 532-8686), under the Accession Number IFO 16758 since Feb. 7, 2002.

Transformant *Escherichia coli* JM109/PCR-BluntII-TCH212 obtained in Example 7 later described has been deposited with International Patent Organism Depositary (IPOD), National Institute of Advanced Industrial Science and Technology (AIST) at Central 6, 1-1-1, Higashi, Tsukuba, Ibaraki, Japan (zip code: 305-8566), under the Accession Number FERM BP-7888 since Feb. 12, 2002, and with Institute for Fermentation, Osaka (IFO) at 17-85, Juso-honmachi 2-chome, Yodogawa-ku, Osaka, Japan (zip code: 532-8686), under the Accession Number IFO 16755 since Jan. 31, 2002.

Transformant *Escherichia coli* TOP10/PCR-BluntII-TCH200 obtained in Example 9 later described has been deposited with International Patent Organism Depositary (IPOD), National Institute of Advanced Industrial Science and Technology (AIST) at Central 6, 1-1-1, Higashi, Tsukuba, Ibaraki, Japan (zip code: 305-8566), under the Accession Number FERM BP-7874 since Feb. 4, 2002, and with Institute for Fermentation, Osaka (IFO) at 17-85, Juso-honmachi 2-chome, Yodogawa-ku, Osaka, Japan (zip code: 532-8686), under the Accession Number IFO 16750 since Jan. 22, 2002.

Hereinafter, the present invention will be specifically described by reference to the Examples, but is not limited thereto. The gene manipulation procedures using *Escherichia coli* were performed in accordance with the methods described in the Molecular Cloning.

Example 1

Cloning of Human TCH230 (SEQ ID NO:1) Gene cDNA

Using two primer DNAs, i.e. primer OF (SEQ ID NO: 3) and primer OR1 (SEQ ID NO: 4), human small intestine Marathon-Ready cDNA and human skeletal muscle Marathon-Ready cDNA (both of which were manufactured by Clontech) were subjected to primary PCR with Pyrobest DNA Polymerase (Takara Shuzo Co., Ltd.) under the following conditions (1) to (3):

(1) reaction at 94° C. for 2 minutes, (2) 30 cycles each consisting of reaction at 98° C. for 10 seconds, at 68° C. for 30 seconds and at 72° C. for 3 minutes, and (3) reaction at 72° C. for 10 minutes.

Using the primary PCR product as a template, nested PCR was conducted with primer OF1 (SEQ ID NO: 5), primer OR (SEQ ID NO: 6) and Pyrobest DNA polymerase (Takara Shuzo Co., Ltd.) under the following conditions (4) to (6):

(4) reaction at 94° C. for 2 minutes, (5) 35 cycles each consisting of reaction at 98° C. for 10 seconds, at 68° C. for 30 seconds, and at 72° C. for 3 minutes, (6) reaction at 72° C. for 10 minutes.

The resulting amplification product was cloned by using the Zero Blunt TOPO Cloning Kit (Invitrogen, Inc.), to give plasmid pCR-BluntII-TCH230.

This product was reacted with primer DNAs [primer SP6 (SEQ ID NO: 7), primer T7 (SEQ ID NO: 8), primer B1 (SEQ ID NO: 9), primer F1 (SEQ ID NO. 10)] and BigDye Terminator Cycle Sequencing Kit (Applied Biosystems), and the base sequence of the inserted cDNA fragment was determined by DNA sequencer ABI PRISM 3100 DNA analyzer (Applied Biosystems). The result indicated that the clone obtained from human small intestine cDNA had 1152-base sequence (SEQ ID NO. 11). The cDNA fragment (SEQ ID NO: 2) coded for a 377-amino acid sequence (SEQ ID NO. 1), and the protein having the amino acid sequence was designated human TCH230 (SEQ ID NO:1) protein.

A transformant having a plasmid comprising the cDNA fragment was designated *Escherichia coli* TOP10/pCR-BluntII-TCH230.

In the clone obtained from the human skeletal muscle cDNA, base substitution was recognized in one site (position 340 in the base sequence represented by SEQ ID NO. 11). This base substitution A340G is accompanied by amino acid substitution of Ile→Val, and it is considered that there is a possibility to be derived from single nucleotide polymorphisms (SNPs). The base sequence of the full-length cDNA possessed by this clone is shown in SEQ ID NO. 12, and the base sequence of ORF in this base sequence is shown in SEQ ID NO. 13. The amino acid sequence encoded by the base sequence represented by SEQ ID NO. 13 is shown in SEQ ID NO. 14.

When homology with owl by using Blast P [Nucleic Acids Res., 25, 3389, 1997] was examined, the cDNA encoding human TCH230 (SEQ ID NO:1) protein was revealed to be a novel gene belonging to sodium-dependent bile acid transporter family (FIG. 1). This protein showed 46% homology at the base level and 44% homology at the amino acid level with reported human ileum sodium-dependent bile acid transporter ISBT [J. Biol. Chem., 270, 27228, 1995].

Example 2

Analysis of Distribution of Human TCH230 (SEQ ID NO:1) Gene Product in Tissues

Using two primer DNAs, i.e. primer TF (SEQ ID NO. 15) and primer TR (SEQ ID NO. 16), designed from the sequence of human TCH230 (SEQ ID NO:1), and TaqMan probe T1 (SEQ ID NO. 17), the expression level of human TCH230 (SEQ ID NO:1) by cDNA in each human tissue was measured by TaqMan PCR. The PCR reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out. The cDNA in each tissue used in measurement is shown in Table 1.

TABLE 1

| cDNA (manufactured by Clontech) | Tissues |
|---|---|
| Human MTC panel I | heart, brain, placenta, lung, liver, skeletal muscle, kidney, pancreas |
| Human MTC panel II | spleen, thymus, prostate, testis, ovary, small intestine, colon, peripheral blood leukocyte |
| Human digestive system MTC panel | liver, esophagus, stomach, duodenum, jejunum, ileum, ileocecum, caecum, ascending colon, transverse colon, descending colon, rectum |
| Human fetal MTC panel | fetal brain, fetal lung, fetal liver, fetal kidney, fetal heart, fetal skeletal muscle, fetal spleen, fetal thymus |
| Human tumor MTC panel | breast cancer (GI-101), lung cancer (LX-1), colon cancer (CX-1), lung cancer (GI-117), prostate cancer (PC3), colon cancer (GI-112), ovarian cancer (GI-102), pancreatic cancer (GI-103) |

The results are shown in FIGS. 2, 3, 4 and 5.

The human TCH230 (SEQ ID NO:1) gene product (mRNA) in human MTC panels I and II was slightly expressed in the heart, brain, liver, skeletal muscle, kidney, colon and peripheral blood leukocyte, expressed at a certain degree in the placenta, lung, pancreas, spleen, thymus, prostate and small intestine, and expressed strongly in the testis and ovary. In human digestive system MTC panel, strong expression was observed in every region from the stomach to rectum (particularly strong expression was observed in the esophagus). Strong expression was also observed in the liver. In human fetal MTC panel, slight expression was observed in the fetal heart, fetal skeletal muscle and fetal spleen, certain expression was observed in the fetal brain, fetal liver, fetal kidney and fetal lung, and strong expression was observed in the fetal thymus. In human tumor MTC panel, slight expression was observed in the lung cancer, colon cancer, prostate cancer and pancreatic cancer, certain expression was observed in the breast cancer, and strong expression was observed in the ovarian cancer.

Example 3

Cloning of the 5'-Upstream Terminus of cDNA Encoding Human TCH234 (SEQ ID NO:18) Protein The 5'-upstream base sequence of cDNA encoding human TCH234 (SEQ ID NO:18) protein was revealed by 5'RACE PCR cloning.

Using two primer DNAs, i.e. primer AP1 (SEQ ID NO: 20) and primer rr0 (SEQ ID NO: 21), human pancreas Marathon-Ready cDNA (Clontech) was subjected to primary PCR with Advantage 2 DNA Polymerase (Clontech) under the following conditions (1) to (3):

(1) reaction at 94° C. for 30 seconds, (2) 35 cycles each consisting of reaction at 94° C. for 10 seconds and at 68° C. for 2 minutes, and (3) reaction at 68° C. for 5 minutes.

Using the primary PCR product as a template, nested PCR was conducted with primer AP2 (SEQ ID NO: 22), primer rr1 (SEQ ID NO: 23) and Advantage 2 DNA Polymerase (Clontech) under the following conditions (4) to (6):

(4) reaction at 94° C. for 30 seconds, (5) 30 cycles each consisting of reaction at 94° C. for 10 seconds and at 68° C. for 2 minutes, and (6) reaction at 68° C. for 5 minutes.

One (1) μl each of exonuclease I and shrimp alkaline phosphatase in PCR Product Pre-Sequencing Kit (USB) were added to 5 μl of the nested PCR reaction solution and reacted at 37° C. for 15 minutes and at 85° C. for 15 minutes. The solution was reacted by using primer rr1 (SEQ ID NO: 23) and BigDye Terminator Cycle Sequencing Kit (Applied Biosystems), and the base sequence of the amplified DNA fragment was determined by DNA sequencer ABI PRISM 3100 DNA analyzer (Applied Biosystems). As a result, the base sequence represented by SEQ ID NO: 39 was obtained.

Example 4

Cloning of the 3'-Downstream Terminus of cDNA Encoding Human TCH234 (SEQ ID NO:18) Protein The 3'-downstream base sequence of cDNA encoding human TCH234 (SEQ ID NO:18) protein was revealed by 3'RACE PCR cloning.

Using two primer DNAs, i.e. primer AP1 (SEQ ID NO: 20) and primer ffl (SEQ ID NO: 24), human pancreas Marathon-Ready cDNA (Clontech) was subjected to primary PCR with Advantage 2 DNA Polymerase (Clontech) under the following conditions (1) to (3):

(1) reaction at 94° C. for 30 seconds, (2) 35 cycles each consisting of reaction at 94° C. for 10 seconds and at 68° C. for 2 minutes, and (3) reaction at 68° C. for 5 minutes.

Using the primary PCR product as a template, nested PCR was conducted with primer AP2 (SEQ ID NO: 22), primer ff2 (SEQ ID NO: 25) and Advantage 2 DNA Polymerase (Clontech) under the following conditions (4) to (6):

(4) reaction at 94° C. for 30 seconds, (5) 30 cycles each consisting of reaction at 94° C. for 10 seconds and at 68° C. for 2 minutes, and (6) reaction at 68° C. for 5 minutes.

One (1) μl each of exonuclease I and shrimp alkaline phosphatase in PCR Product Pre-Sequencing Kit (USB) were added to 5 μl of the nested PCR reaction solution and reacted at 37° C. for 15 minutes and at 85° C. for 15 minutes. The solution was reacted by using primer ff2 (SEQ ID NO: 25) and BigDye Terminator Cycle Sequencing Kit (Applied Biosystems), and the base sequence of the amplified DNA fragment was determined by DNA sequencer ABI PRISM 3100 DNA analyzer (Applied Biosystems). As a result, the base sequence represented by SEQ ID NO: 40 was obtained.

Example 5

Cloning of cDNA Encoding Human TCH234 (SEQ ID NO:18) Protein

Using two primer DNAs, i.e. primer ORFF1 (SEQ ID NO: 26) and primer ORFR1 (SEQ ID NO: 27), human pancreas Marathon-Ready cDNA (Clontech) was subjected to primary PCR with pfu turbo DNA Polymerase (Stratagene) under the following conditions (1) to (3):

(1) reaction at 94° C. for 30 seconds, (2) 35 cycles each consisting of reaction at 94° C. for 10 seconds, at 54° C. for 5 seconds and at 72° C. for 2.5 minutes, and (3) reaction at 72° C. for 5 minutes.

Using the primary PCR product as a template, nested PCR was conducted with primer ORFF2 (SEQ ID NO: 28), primer ORFR2 (SEQ ID NO: 29) and pfu turbo DNA Polymerase (Stratagene) under the following conditions (4) to (6):

(4) reaction at 94° C. for 30 seconds, (5) 30 cycles each consisting of reaction at 94° C. for 10 seconds, at 55° C. for 5 seconds and at 72° C. for 2.5 minutes, and (6) reaction at 72° C. for 5 minutes.

The nested PCR reaction solution was purified by QIAquick PCR Purification Kit (Qiagen). This DNA was cloned into pCR-Blunt II-TOPO vector according to a protocol of the Zero Blunt TOPO PCR Cloning Kit (Invitrogen, Inc.). The resulting product was transformed into *Escherichia coli* TOP10 competent cell (Invitrogen, Inc.), and clones having the cDNA insert fragment were selected in a kanamycin-containing LB agar medium to give transformants. The respective clones were cultured overnight in a kanamycin-containing LB medium, and plasmid DNAs were prepared by QIAwell 8 Plasmid Kit (Qiagen) to give pCR-BluntII-TCH234 plasmid clones #1, #2 and #3. These were reacted with primer DNAs [primer M13F (SEQ ID NO: 30), primer M13R (SEQ ID NO: 31), primer ORFF2 (SEQ ID NO: 28), primer ORFR2 (SEQ ID NO: 29), primer TMF (SEQ ID NO: 32), primer TMR (SEQ ID NO: 33), primer F2 (SEQ ID NO: 34), primer F3 (SEQ ID NO: 35), primer R1 (SEQ ID NO: 36), primer R2 (SEQ ID NO: 37), primer ff2 (SEQ ID NO: 25)] and BigDye Terminator Cycle Sequencing Kit (Applied Biosystems), and the base sequences of the inserted cDNA fragments were determined by a DNA sequencer ABI PRISM 3100 DNA analyzer (Applied Biosystems). As a result, the acquired 3 clones contained the same DNA fragment and had a 2426-base sequence (SEQ ID NO: 41). The fragment (SEQ ID NO. 19) encoded a 798-amino acid sequence (SEQ ID NO. 18), and the protein comprising the amino acid sequence represented by SEQ ID NO. 18 was designated human TCH234 protein.

A transformant comprising the cDNA fragment was designated *Escherichia coli* TOP10/pCR-BluntII-TCH234.

When homology with OWL was examined using Blast P [Nucleic Acids Res., 25, 3389, 1997], the cDNA was revealed to be a novel gene belonging to $Na^+/H^+$ exchange transporter (FIG. 6).

Human TCH234 exhibited 53% homology at the amino acid level with $Na^+/H^+$ exchange transporter NHE2 [Genomics, 30, 25, 1995] and 84% homology at the amino acid level with rat NHE4 (J. Biol. Chem., 267, 9331, 1992), and the protein was estimated to have a 13-times transmembrane structure.

Example 6

Analysis of Distribution of Human TCH234 (SEQ ID NO:18) Gene Product in Tissues Using 2 primer DNAs, i.e. primer TMF (SEQ ID NO: 32) and primer TMR (SEQ ID NO: 33), designed from the sequence of human TCH234 (SEQ ID NO:18), and TaqMan probe P1 (SEQ ID NO: 38), the expression level of human TCH234 (SEQ ID NO:18) by cDNA (Human MTC panels I and II: Clontech) in each human tissue (heart, brain, placenta, lung, liver, skeletal muscle, kidney, pancreas, spleen, thymus, prostate, testis, ovary, small intestine, colon, peripheral blood leukocyte) was measured by TaqMan PCR. The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 7:
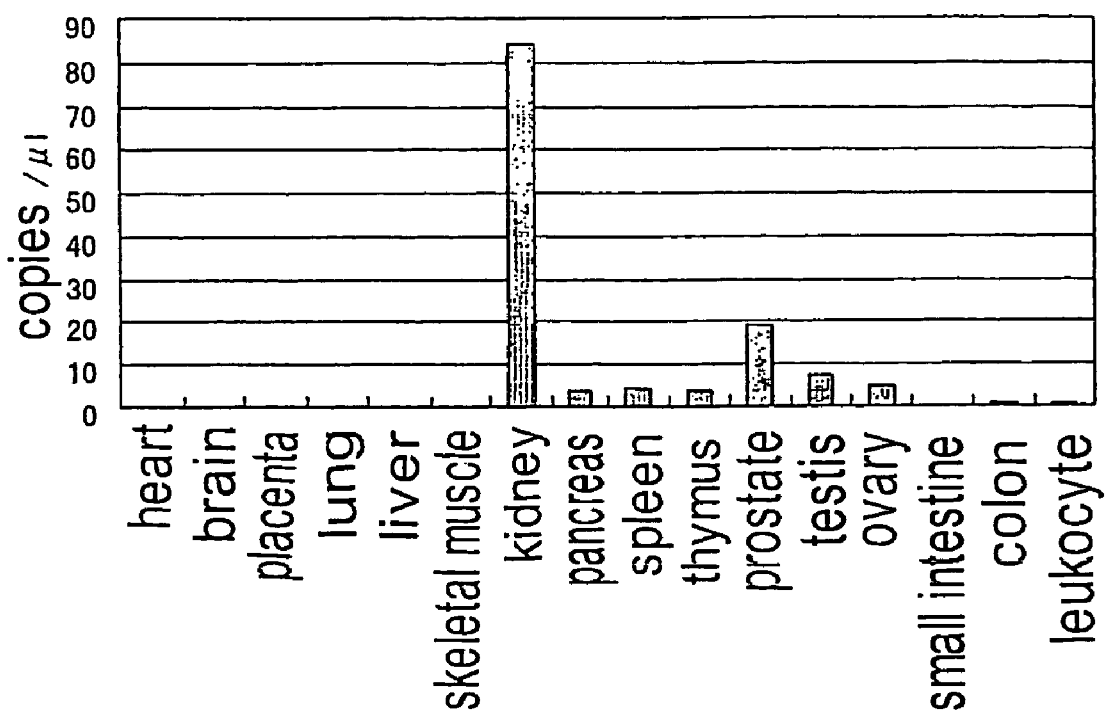
FIG. 7 shows the expression level of human TCH234 (SEQ ID NO:18) gene product in each tissue. The expression level is represented in terms of copy number per μl of cDNA solution.

The results are shown in FIG. 7. The human TCH234 (SEQ ID NO:18) gene product (mRNA) was strongly expressed in the kidney. Certain expression was recognized in the prostate, pancreas, testis, spleen, thymus and ovary.

Example 7

Cloning of Human TCH212 (SEQ ID NO:42) Gene cDNA

Using two primer DNAs, i.e. primer A3 (SEQ ID NO: 44) and primer OB3 (SEQ ID NO: 45), human testis Marathon-Ready cDNA (Clontech) was subjected to primary PCR with Pyrobest DNA Polymerase (Takara Shuzo Co., Ltd.) under the following conditions (1) to (3):

(1) reaction at 94° C. for 2 minutes, (2) 35 cycles each consisting of reaction at 98° C. for 10 seconds, at 68° C. for 30 seconds and at 72° C. for 7 minutes, and (3) reaction at 72° C. for 10 minutes.

The amplified product was cloned with the Zero Blunt TOPO Cloning Kit (Invitrogen, Inc.) to give plasmid pCR-BluntII-TCH212.

This product was reacted with primer DNAs [primer SP6 (SEQ ID NO: 46), primer T7 (SEQ ID NO: 47), primer A2 (SEQ ID NO: 48), primer B1 (SEQ ID NO: 49), primer B2 (SEQ ID NO: 50), primer F1 (SEQ ID NO: 51), primer F2 (SEQ ID NO: 52), primer F3 (SEQ ID NO: 53), primer F4 (SEQ ID NO: 54), primer F5 (SEQ ID NO: 55), primer R1 (SEQ ID NO: 56), primer R2 (SEQ ID NO: 57), primer R3 (SEQ ID NO: 58), primer R4 (SEQ ID NO: 59)] and BigDye Terminator Cycle Sequencing Kit (Applied Biosystems), and the base sequence of the inserted cDNA fragment was determined by DNA sequencer ABI PRISM 3100 DNA analyzer (Applied Biosystems). The acquired clone had a 3643-base sequence (SEQ ID NO: 60). The cDNA fragment (SEQ ID NO: 43) coded for a 1148-amino acid sequence (SEQ ID NO: 42), and the protein having the amino acid sequence was designated human TCH212 protein.

Base substitution was recognized at one site (position 1592 in the base sequence of SEQ ID NO: 60) in the acquired clone (designated clone #2). This base substitution C1592T was not accompanied by amino acid substitution and it is considered that the substitution is derived from single nucleotide polymorphisms (SNPs). The base sequence of the full-length cDNA possessed by this clone is shown in SEQ ID NO: 61, and the base sequence of ORF in this base sequence is shown in SEQ ID NO: 62.

A transformant having a plasmid comprising cDNA comprising the base sequence represented by SEQ ID NO: 60 was designated *Escherichia coli* JM109/pCR-BluntII-TCH212.

When homology with owl was examined using Blast P [Nucleic Acids Res., 25, 3389, 1997], the cDNA encoding human TCH212 (SEQ ID NO:42) was revealed to be a novel gene belonging to P-type ATPase family (FIGS. 8A-8C). The human TCH212 (SEQ ID NO:42) exhibited 60% homology at the base level and 67% homology at the amino acid level with reported human P-type ATPase 8A1 (ATP8A1) [Biochem. Biophys. Res. Commun., 257, 333-339, 1999] and 86% homology at the base level and 95% homology at the amino acid level with reported mouse P-type ATPase 8A2 [Physiol. Genomics (Online), 1, 139-150, 1999].

Example 8

Analysis of Distribution of Human TCH212 (SEQ ID NO:42) Gene Product in Tissues Using two primer DNAs, i.e. primer TF (SEQ ID NO: 63) primer TR (SEQ ID NO: 64), designed from the sequence of human TCH212 (SEQ ID NO:42), and TaqMan probe T1 (SEQ ID NO: 65), the expression level of human TCH212 (SEQ ID NO:42) in each human tissue was measured by TaqMan PCR. The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out. The cDNA in each kind of tissue used in measurement is shown in Table 2.

TABLE 2

| cDNA (manufactured by Clontech) | Tissues |
|---|---|
| Human MTC panel I | heart, brain, placenta, lung, liver, skeletal muscle, kidney, pancreas |
| Human MTC panel II | spleen, thymus, prostate, testis, ovary, small intestine, colon, peripheral blood leukocyte |
| Human fetal MTC panel | fetal brain, fetal lung, fetal liver, fetal kidney, fetal heart, fetal skeletal muscle, fetal spleen, fetal thymus |
| Human tumor MTC panel | breast cancer (GI-101), lung cancer (LX-1), colon cancer (CX-1), lung cancer (GI-117), prostate cancer (PC3), colon cancer (GI-112), ovarian cancer (GI-102), pancreatic cancer (GI-103) |

Figure 9:
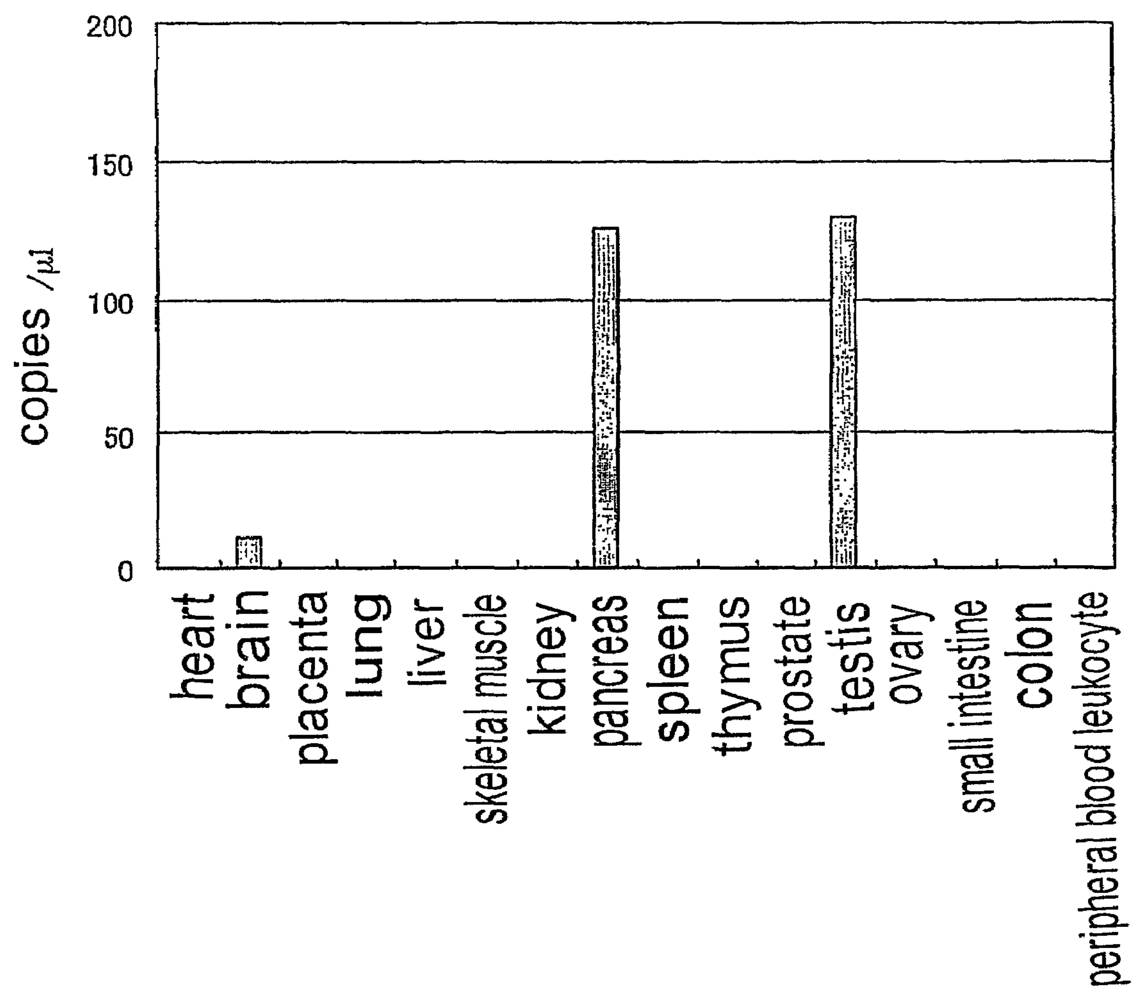
FIG. 9 shows the expression level of human TCH212 (SEQ ID NO:42) gene product in each tissue. The expression level is represented in terms of copy number per μl of cDNA solution.
Figure 10:
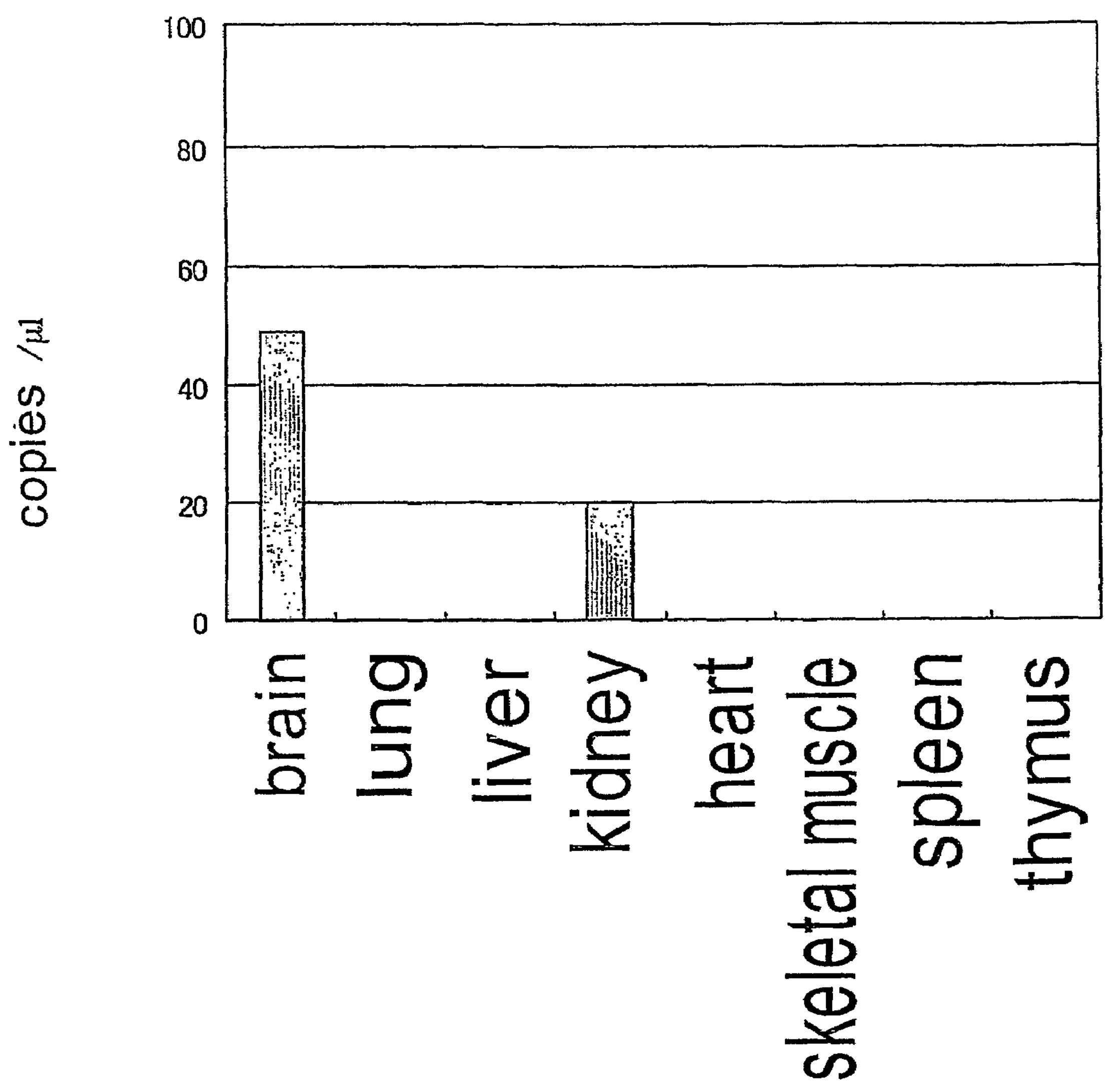
FIG. 10 shows the expression level of human TCH212 (SEQ ID NO:42) gene product in each tissue. The expression level is represented in terms of copy number per μl of cDNA solution.
Figure 31:
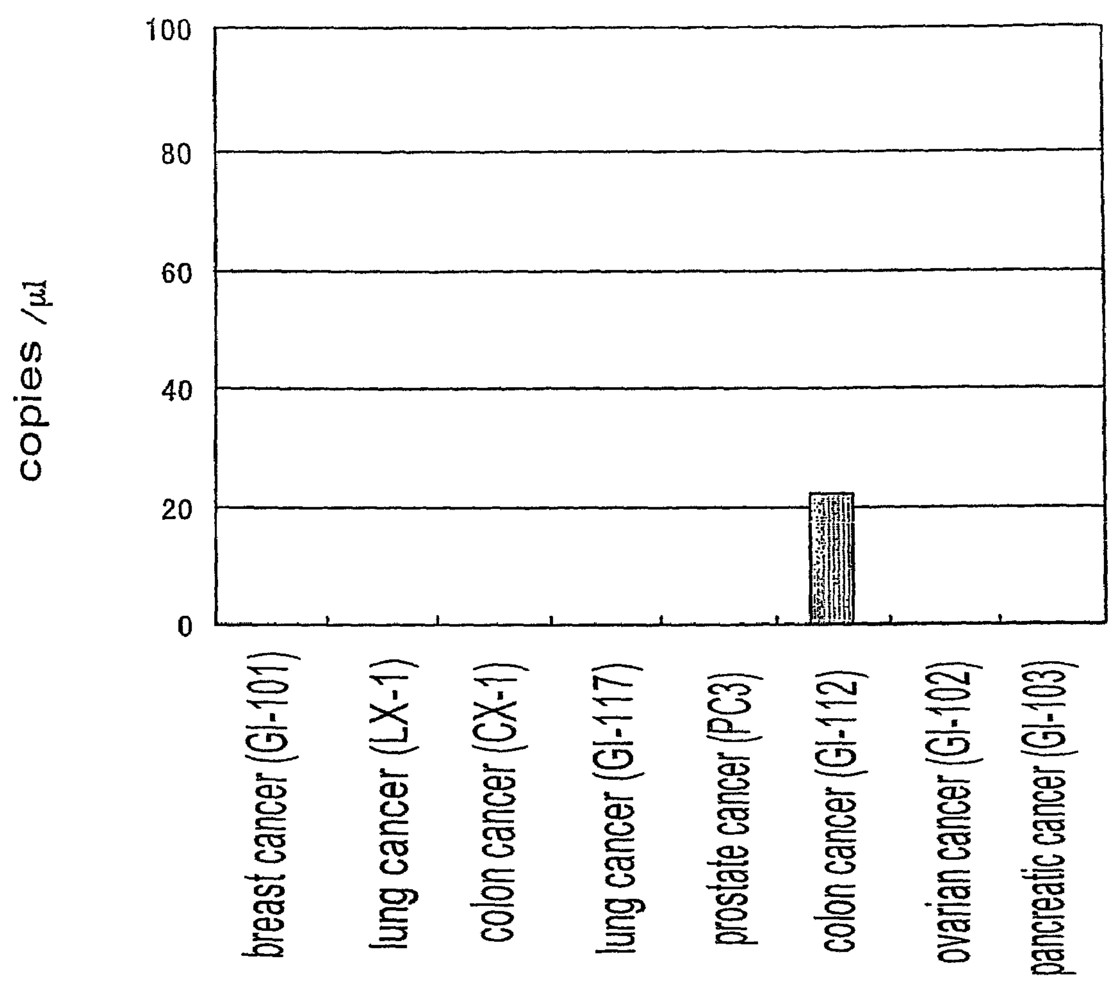
FIG. 31 shows the expression level of human TCH212 (SEQ ID NO:42) gene product in each tissue. The expression level is represented as copy number per μl of cDNA solution.

The results are shown in FIGS. 9, 10 and 31.

In human MTC panels I and II, the human TCH212 (SEQ ID NO:42) gene product (mRNA) was expressed at a certain degree in the brain and strongly expressed in the pancreas and testis.

In human fetal MTC panel, certain expression was observed in the fetal kidney, and strong expression was observed in the fetal brain.

In human tumor MTC panel, slight expression was observed in the colon cancer (GI-112).

Example 9

Cloning of the 5'-Upstream Terminus of cDNA Encoding Human TCH200 (SEQ ID NO:66) Protein The 5'-upstream base sequence of cDNA encoding human TCH200 (SEQ ID NO:66) protein was revealed by 5'RACE PCR cloning.

Using human small intestine Marathon-Ready cDNA (Clontech) as a template, PCR reaction was carried out with primer AP1 (SEQ ID NO: 68) and primer R1 (SEQ ID NO: 69), and by using this PCR reaction solution as a template, PCR reaction was carried out with primer AP2 (SEQ ID NO: 70) and primer rr2 (SEQ ID NO: 71). The composition of the PCR reaction solution and reaction conditions are shown below. A reaction solution of 2.5 μl of human small intestine Marathon-Ready cDNA, 5 μM primer AP1, 5 μM primer R1, 0.4 mM dNTPs and 0.5 μl Advantage2 Polymerase mix (Clontech) was adjusted to 25 μl with a buffer attached to Advantage2 Polymerase mix (Clontech), and then heated at 94° C. for 30 seconds and subjected to 35 cycles of reaction each at 94° C. for 5 seconds and at 68° C. for 4 minutes in thermal cycler 9700 (Applied Biosystems). Then, a mixture consisting of 2.5 μl solution obtained by diluting the above PCR reaction solution (reacted with AP1/R1) 50-fold with tricine-EDTA buffer, 5 μM primer AP2, 5 μM primer rr2, 0.4 mM dNTPs and 0.5 μl Advantage2 Polymerase mix (Clontech) was adjusted to 25 μl with a buffer attached to Advantage2 Polymerase mix (Clontech), and then heated at 94° C. for 30 seconds and subjected to 30 cycles of reaction each at 94° C. for 5 seconds and at 68° C. for 4 minutes in thermal cycler 9700 (Applied Biosystems). The amplified DNA was separated by 1.5% agarose gel electrophoresis, and DNA of about 700-base in length was cut off with a razor, and then the DNA was recovered with QIAquick Gel Extraction Kit (Qiagen). This DNA was cloned into PCR2.1-TOPO vector according to the protocol of TOPO TA Cloning Kit (Invitrogen, Inc.). The product was transformed into *Escherichia coli* TOP10 competent cell (Invitrogen, Inc.), and clones having the cDNA insert fragment were selected in an ampicillin-containing LB agar medium to give transformants. The respective clones were cultured overnight in an ampicillin-containing LB medium, and the plasmid DNA was prepared by QIAwell 8 Plasmid Kit (Qiagen). The plasmid DNA was reacted with primer DNAs [pritner M13F (SEQ ID NO: 72), primer M13R (SEQ ID NO: 73), primer rr2 (SEQ ID NO: 71)] and BigDye Terminator Cycle Sequencing Kit (Applied Biosystems), and the base sequence of the inserted cDNA fragment was determined by DNA sequencer ABI PRISM 3100 DNA analyzer (Applied Biosystems). As a result, the base sequence shown in SEQ ID NO: 97 was obtained.

Then, primer rr4 (SEQ ID NO: 74) and primer rr6 (SEQ ID NO: 75) were designed on the basis of the base sequence shown in SEQ ID NO: 97. To obtain further upstream base sequence, PCR reaction with primer AP1 (SEQ ID NO: 68) and primer rr4 (SEQ ID NO: 74) was conducted, and using this PCR reaction solution as a template, PCR reaction was conducted with primer AP2 (SEQ ID NO: 70) and primer rr6 (SEQ ID NO: 75). The composition of the PCR reaction solution and reaction conditions are shown below. A reaction solution of 2.5 μl of human small intestine Marathon-Ready cDNA, 5 μM primer AP1, 5 μM primer rr4, 0.4 mM dNTPs and 0.5 μl Advantage2 Polymerase mix (Clontech) was adjusted to 25 μl with a buffer attached to Advantage2 Polymerase mix (Clontech), and then heated at 94° C. for 30 seconds and subjected to 35 cycles of reaction each at 94° C. for 5 seconds and at 68° C. for 1.5 minutes in thermal cycler 9700 (Applied Biosystems). Then, a mixture consisting of 2.5 μl solution obtained by diluting the above PCR reaction solution (reacted with AP1/rr4) 50-fold with tricine-EDTA buffer, 0.5 μM primer AP2, 0.5 μM primer rr6, 0.4 mM dNTPs and 0.5 μl Advantage2 Polymerase mix (Clontech) was adjusted to 25 μl with a buffer attached to Advantage2 Polymerase mix (Clontech), and then heated at 94° C. for 30 seconds and subjected to 30 cycles of reaction each at 94° C. for 5 seconds and at 68° C. for 1.5 minutes in thermal cycler 9700 (Applied Biosystems). The amplified DNA of about 280-base in length was confirmed by 1.5% agarose gel electrophoresis, and 1 μl each of exonuclease I and shrimp alkaline phosphatase in PCR Product Pre-Sequencing Kit (USB) were added to 5 μl of the PCR reaction solution (reacted with AP2/rr6) and reacted at 37° C. for 15 minutes and at 85° C. for 15 minutes. This reaction solution was diluted 3-fold with ultrapure water, and reacted with primer rr6 (SEQ ID NO: 75) and BigDye Terminator Cycle Sequencing Kit (Applied Biosystems), and the base sequence of the amplified DNA fragment was determined by DNA sequencer ABI PRISM 3100 DNA analyzer (Applied Biosystems). As a result, the base sequence shown in SEQ ID NO: 98 was obtained.

Example 10

Cloning of the 3'-Downstream Terminus of cDNA Encoding Human TCH200 (SEQ ID NO:66) Protein For cloning of the 3'-downstream terminus, PCR reaction was carried out using human small intestine Marathon-Ready cDNA (Clontech) as a template with primer API (SEQ ID NO: 68) and primer r1 (SEQ ID NO: 76), and by using this PCR reaction solution as a template, PCR reaction was carried out with primer AP2 (SEQ ID NO: 70) and primer r2 (SEQ ID NO: 77). The composition of the PCR reaction solution and reaction conditions are shown below. A reaction solution of 2.5 μl of human small intestine Marathon-Ready cDNA, 5 μM primerAPI, 5 μM primer r1, 0.4 mM dNTPs and 0.5 μl Advantage2 Polymerase mix (Clontech) was adjusted to 25 μl with a buffer attached to Advantage2 Polymerase mix (Clontech), and then heated at 94° C. for 30 seconds and subjected to 35 cycles of reaction each at 94° C. for 5 seconds and at 68° C. for 4 minutes in thermal cycler 9700 (Applied Biosystems). Then, a mixture consisting of 2.5 μl solution obtained by diluting the above PCR reaction solution (reacted with API/r1) 50-fold with tricine-EDTA buffer, 5 μM primer AP2, 5 μM primer r2, 0.4 mM dNTPs and 0.5 μl Advantage2 Polymerase mix (Clontech) was adjusted to 25 μl with a buffer attached to Advantage2 Polymerase mix (Clontech), and then heated at 94° C. for 30 seconds and subjected to 30 cycles of reaction each at 94° C. for 5 seconds and at 68° C. for 4 minutes in thermal cycler 9700 (Applied Biosystems). The amplified DNA was separated by 1.5% agarose gel electrophoresis, and DNA of about 600-base in length was cut off with a razor, and then the DNA was recovered with QIAquick Gel Extraction Kit (Qiagen). This DNA was cloned into PCR2.1-TOPO vector according to the protocol of TOPO TA Cloning Kit (Invitrogen, Inc.). The product was transformed into *Escherichia coli* TOP10 competent cell (Invitrogen, Inc.), and clones having the cDNA insert fragment were selected in an ampicillin-containing LB agar medium to give transformants. The respective clones were cultured overnight in an ampicillin-containing LB medium, and plasmid DNA was prepared by QIAwell 8 Plasmid Kit (Qiagen). The plasmid DNA was reacted with primer DNAs [primer M13F (SEQ ID NO: 72), primer M13R (SEQ ID NO: 73), primer r2 (SEQ ID NO: 77)] and BigDye Terminator Cycle Sequencing Kit (Applied Biosystems), and the base sequence of the inserted cDNA fragment was determined by DNA sequencer ABI PRISM 3100 DNA analyzer (Applied Biosystems). As a result, the base sequence shown in SEQ ID NO: 99 was obtained.

To further obtain the base sequence of the 3'-downstream terminus, PCR reaction was conducted with primer API (SEQ ID NO: 68) and primer f1 (SEQ ID NO: 78), and by using this PCR reaction solution as a template, PCR reaction was conducted with primer AP2 (SEQ ID NO: 70) and primer f2 (SEQ ID NO: 79). The composition of the PCR reaction solution and reaction conditions are shown below. A reaction solution consisting of 2.5 μl of human small intestine Marathon-Ready cDNA, 5 μM primer AP1, 5 μM primer f1, 0.4 mM dNTPs and 0.5 μl Advantage2 Polymerase mix (Clontech) was adjusted to 25 μl with a buffer attached to Advantage2 Polymerase mix (Clontech), and then heated at 94° C. for 30 seconds and subjected to 35 cycles of reaction each at 94° C. for 5 seconds and at 68° C. for 1.5 minutes in thermal cycler 9700 (Applied Biosystems). Then, a mixture consisting of 2.5 μl solution obtained by diluting the above PCR reaction solution (reacted with AP1/f1) 50-fold with tricine-EDTA buffer, 5 μM primer AP2, 5 μM primer f2, 0.4 mM dNTPs and 0.5 μl Advantage2 Polymerase mix (Clontech) was adjusted to 25 μl with a buffer attached to Advantage2 Polymerase mix (Clontech), and then heated at 94° C. for 30 seconds and subjected to 30 cycles of reaction each at 94° C. for 5 seconds and at 68° C. for 1.5 minutes in thermal cycler 9700 (Applied Biosystems). The amplified DNA of about 300-base in length was confirmed by 1.5% agarose gel electrophoresis, and 1 μl each of exonuclease I and shrimp alkaline phosphatase in PCR Product Pre-Sequencing Kit (USB) were added to 5 μl of the PCR reaction solution (reacted with AP2/f2) and reacted at 37° C. for 15 minutes and at 85° C. for 15 minutes. This reaction solution was diluted 3-fold with ultrapure water, and reacted with primer f2 (SEQ ID NO: 79) and BigDye Terminator Cycle Sequencing Kit (Applied Biosystems), and the base sequence of the amplified DNA fragment was determined by DNA sequencer ABI PRISM 3100 DNA analyzer (Applied Biosystems). As a result, the base sequence shown in SEQ ID NO. 100 was obtained.

Then, primer f4 (SEQ ID NO: 80) was designed on the basis of the base sequence shown in SEQ ID NO. 100. To obtain further downstream base sequence, first PCR reaction was carried out with primer API (SEQ ID NO: 68) and primer f2 (SEQ ID NO: 79), and by using this PCR reaction solution as a template, second PCR reaction was conducted with primer AP2 (SEQ ID NO: 70) and primer f4 (SEQ ID NO: 80). The composition of the PCR reaction solution and reaction conditions are shown below. A reaction solution consisting of 2.5 μl human testis Marathon-Ready cDNA, 5 μM primer API, 5 μM primer f2, 0.4 mM dNTPs and 0.5 μl Advantage2 Polymerase mix (Clontech) was adjusted to 25 μl with a buffer attached to Advantage2 Polymerase mix (Clontech), and then heated at 94° C. for 30 seconds and subjected to 35 cycles of reaction each at 94° C. for 5 seconds and at 68° C. for 1.5 minutes in thermal cycler 9700 (Applied Biosystems). Then, a mixture consisting of 2.5 μl solution obtained by diluting the above PCR reaction solution (reacted with AP1/f2) 50-fold with tricine-EDTA buffer, 5 μM primer AP2, 5 μM primer f4, 0.4 mM dNTPs and 0.5 μl Advantage2

Polymerase mix (Clontech) was adjusted to 25 μl with a buffer attached to Advantage2 Polymerase mix (Clontech), and then heated at 94° C. for 30 seconds and subjected to 30 cycles of reaction each at 94° C. for 5 seconds and at 68° C. for 1.5 minutes in thermal cycler 9700 (Applied Biosystems). The amplified DNA of about 150-base in length was confirmed by 1.5% agarose gel electrophoresis, and 1 μl each of exonuclease I and shrimp alkaline phosphatase in PCR Product Pre-Sequencing Kit (USB) were added to 5 μl of the PCR reaction solution (reacted with AP2/f4) and reacted at 37° C. for 15 minutes and at 85° C. for 15 minutes. This reaction solution was diluted 3-fold with ultrapure water, and reacted with primer DNAs [primer AP2 (SEQ ID NO: 70) and primer f4 (SEQ ID NO: 80)] and BigDye Terminator Cycle Sequencing Kit (Applied Biosystems), and the base sequence of the amplified DNA fragment was determined by DNA sequencer ABI PRISM 3100 DNA analyzer (Applied Biosystems). As a result, the base sequence shown in SEQ ID NO. 101 was obtained.

Example 11

Cloning of cDNA Encoding Human TCH200 (SEQ ID NO:66) Protein

Cloning of cDNA encoding human TCH200 (SEQ ID NO:66) protein was conducted by nested PCR.

For cloning of cDNA encoding human TCH200 (SEQ ID NO:66) protein, primer F0 (SEQ ID NO: 81), primer R7 (SEQ ID NO: 82), primer F00 (SEQ ID NO: 83) and primer R00 (SEQ ID NO: 84) were designed on the basis of the base sequences (SEQ ID NOS: 97, 98, 99, 100 and 101) obtained in Examples 1 and 2. First PCR reaction was carried out by using human small intestine Marathon-Ready cDNA (Clontech) as a template with primer F0 and primer R7. Using this PCR reaction solution as a template, second PCR reaction was conducted with primer F00 and primer R00. The composition of the PCR reaction solution and reaction conditions are shown below. A reaction solution consisting of 2.0 μl human small intestine Marathon-Ready cDNA, 12.5 μM primer F0, 12.5 μM primer R7, 0.4 mM dNTPs and 0.5 μl pfu turbo DNA Polymerase (Stratagene) was adjusted to 20 μl with a buffer attached to Advantage2 Polymerase mix (Clontech), and then heated at 94° C. for 30 seconds and subjected to 35 cycles of reaction each at 94° C. for 10 seconds, at 56° C. for 5 seconds and at 72° C. for 2.5 minutes in thermal cycler 9700 (Applied Biosystems). Then, a mixture consisting of 1 μl of this PCR reaction solution (reacted with R0/R7), 12.5 μM primer F00, 12.5 μM primer R00, 0.4 mM dNTPs and 0.5 μl Advantage2 Polymerase mix (Clontech) was adjusted to 20 μl with a buffer attached to Advantage2 Polymerase mix (Clontech), and then heated at 94° C. for 30 seconds and subjected to 30 cycles of reaction each at 94° C. for 10 seconds, 56° C. for 5 seconds and at 72° C. for 2.5 minutes in thermal cycler 9700 (Applied Biosystems). The amplified DNA was separated by 1.5% agarose gel electrophoresis, and DNA of about 2376-base in length was cut off with a razor, and then the DNA was recovered with QIAquick Gel Extraction Kit (Qiagen). This DNA was cloned into pCR-Blunt II-TOPO vector according to the protocol of the Zero Blunt TOPO PCR Cloning Kit (Invitrogen, Inc.). The product was transformed into *Escherichia coli* TOP10 competent cell (Invitrogen, Inc.), and clones having the cDNA insert fragment were selected in a kanamycin-containing LB agar medium to give transformants. The respective clones were cultured overnight in a kanamycin-containing LB medium, and plasmid DNAs were prepared by QIAwell 8 Plasmid Kit (Qiagen) to give pCR-BluntII-TCH200 plasmid clones #1, #2 and #3. These were reacted with primer DNAs [primer M13F (SEQ ID NO: 72), primer M13R (SEQ ID NO: 73), primer F00 (SEQ ID NO: 83), primer R00 (SEQ ID NO: 84), primer F1 (SEQ ID NO: 85), primer F2 (SEQ ID NO: 86), primer F5 (SEQ ID NO: 87), primer F7 (SEQ ID NO: 88), primer R1 (SEQ ID NO: 69), primer ff3 (SEQ ID NO: 89), primer ff4 (SEQ ID NO: 90), primer f2 (SEQ ID NO: 80), primer B3 (SEQ ID NO: 91), primer rr1 (SEQ ID NO: 92), primer rr2 (SEQ ID NO: 71) and primer rr3 (SEQ ID NO: 93)] and BigDye Terminator Cycle Sequencing Kit (Applied Biosystems), and the base sequences of the inserted cDNA fragments were determined by DNA sequencer ABI PRISM 3100 DNA analyzer (Applied Biosystems). As a result, the obtained 2 clones had the same DNA fragment and had a 2376-base sequence (SEQ ID NO. 102). The fragment (SEQ ID NO: 97) coded for a 791-amino acid sequence (SEQ ID NO: 66), and the protein comprising the amino acid sequence represented by SEQ ID NO: 66 was designated human TCH200 (SEQ ID NO:66) protein.

A transformant having the plasmid comprising the cDNA fragment (SEQ ID NO. 102) was designated *Escherichia coli* TOP10/pCR-BluntII-TCH200.

The obtained sequence (SEQ ID NO. 102) was examined for homology in a public genome database, and as a result, base substitution was recognized at one site (substitution of C with A at position 558 in the base sequence represented by SEQ ID NO: 67) (SEQ ID NO. 103). This base substitution C558A was not accompanied by amino acid substitution, and it is considered that the substitution is derived from single nucleotide polymorphisms (SNPs).

When homology with GENEMBL was conducted by using Blast P [Nucleic Acids Res., 25, 3389, 1997], the cDNA comprising the base sequence represented by SEQ ID NO: 67 was revealed to be a novel gene belonging to human vanilloid receptor (FIG. 11). The TCH200 protein showed 58% homology at the base level and 43% homology at the amino acid level with reported human vanilloid receptor human VR1 [Biochemical and Biophysical Research Communications, 281, 1183, 2001], and the human TCH200 (SEQ ID NO:66) protein was estimated to have a 6-times transmembrane structure.

Example 12

Analysis of Distribution of Human TCH200 (SEQ ID NO:66) Gene Product in Tissues

By using two primer DNAs, i.e. primer TMF (SEQ ID NO: 94) and primer TMR (SEQ ID NO: 95), designed from the sequence of human TCH200 (SEQ ID NO:66), and TaqMan probe P1 (SEQ ID NO: 96), the expression level of human TCH200 (SEQ ID NO:66) by cDNA (human MTC panels I and II: Clontech) in each human tissue (heart, brain, placenta, lung, liver, skeletal muscle, kidney, pancreas, spleen, thymus, prostate, testis, ovary, small intestine, large intestine, peripheral blood leukocyte) was measured by TaqMan PCR. The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 12:
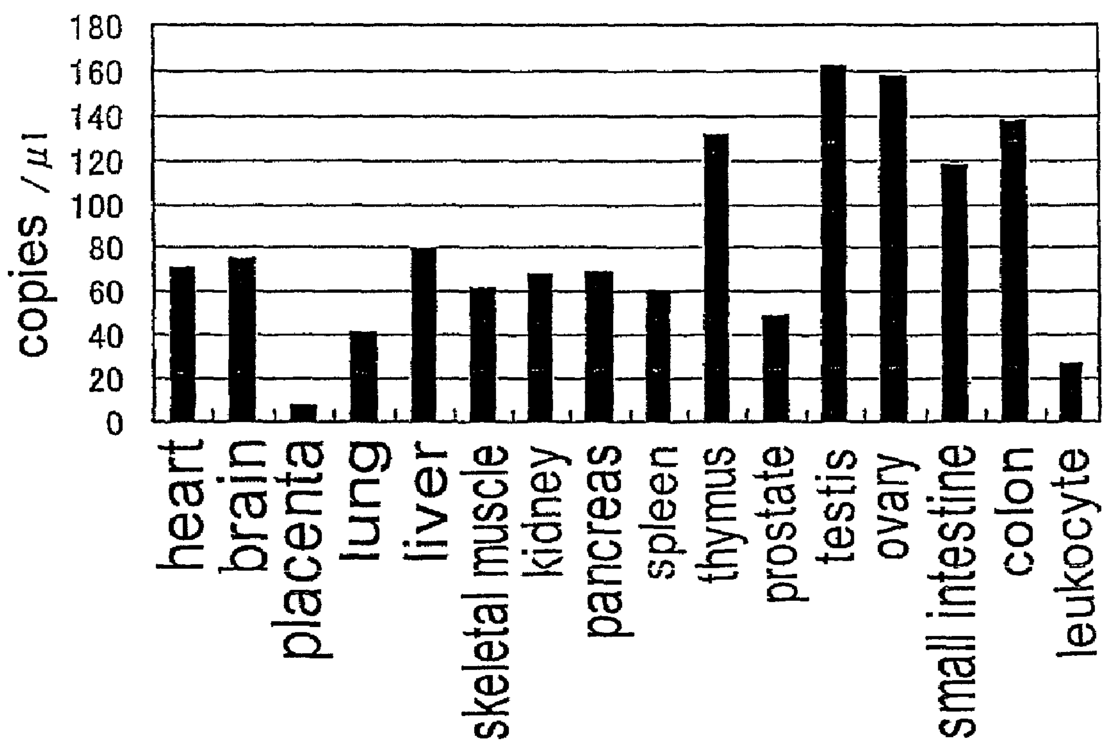
FIG. 12 shows the expression level of human TCH200 (SEQ ID NO:66) gene product in each tissue. The expression level is represented in terms of copy number per μl of cDNA solution.

The results are shown in FIG. 12. The human TCH200 (SEQ ID NO:66) gene product (mRNA) was strongly expressed in various tissues. Particularly in the thymus, testis, ovary, small intestine and colon, the human TCH200 (SEQ ID NO:66) gene product was expressed relatively strongly, but was hardly expressed in the placenta.

Example 13

Cloning of cDNA Encoding Mouse TCH230 (SEQ ID NO:112) Protein

Using two primer DNAs, i.e. primer m230A1 (SEQ ID NO. 106) and primer m230B2 (SEQ ID NO. 107), mouse testis Marathon-Ready cDNA (Clontech) was subjected to primary PCR with Pyrobest DNA Polymerase (Takara Bio) under the following conditions (1) to (3):

(1) reaction at 94° C. for 2 minutes, (2) 30 cycles each consisting of reaction at 98° C. for 10 seconds and at 72° C. for 2 minutes, and (3) reaction at 72° C. for 10 minutes.

The resulting amplification product was cloned by Zero Blunt TOPO Cloning kit (Invitrogen, Inc.) to give plasmid pCR-BluntII-mTCH230.

The product was reacted with primer DNAs [primer SP6 (SEQ ID NO: 7), primer T7 (SEQ ID NO: 8), primer m230F1 (SEQ ID NO. 108), primer m230F2 (SEQ ID NO. 109), primer m230R1 (SEQ ID NO. 110) and primer m230R2 (SEQ ID NO. 111)] and BigDye Terminator Cycle Sequencing Kit (Applied Biosystems), and the base sequence of the inserted cDNA fragment was determined by DNA sequencer ABI PRISM 3100 DNA analyzer (Applied Biosystems). As a result, the clone had a 1237-base sequence (SEQ ID NO. 112). The cDNA fragment (SEQ ID NO. 105) encoded a 373-amino acid sequence (SEQ ID NO. 104), and the protein having the amino acid sequence was designated mouse TCH230 (SEQ ID NO:112) protein.

A transformant having the plasmid comprising the cDNA fragment was designated *Escherichia coli* TOP10/PCR-BluntII-mTCH230.

The mouse TCH230 (SEQ ID NO:112) exhibited 74% homology at the base level and 70% homology at the amino acid level with human TCH230 (SEQ ID NO: 1), and it was revealed that mouse TCH230 (SEQ ID NO:112) is a mouse ortholog of human TCH230 (SEQ ID NO:1) (FIG. 13).

Example 14

Analysis of Distribution of Mouse TCH230 (SEQ ID NO:112) Gene Product in Tissues Using two primer DNAs, i.e. primer m230TF (SEQ ID NO. 113) and primer m230TR (SEQ ID NO. 114), designed from the sequence of mouse TCH230 (SEQ ID NO:112), and TaqMan probe m230T1 (SEQ ID NO. 115), the expression level of mouse TCH230 (SEQ ID NO:112) by cDNA (mouse MTC panels I and II: Clontech) in each mouse tissue (bone marrow, eye, lymph node, smooth muscle, prostate, thymus, stomach, uterus, heart, brain, spleen, lung, liver, skeletal muscle, kidney, testis, embryo (7th day), embryo (11th day), embryo (15th day), embryo (17th day)) were measured by TaqMan PCR. The PCR reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 14:
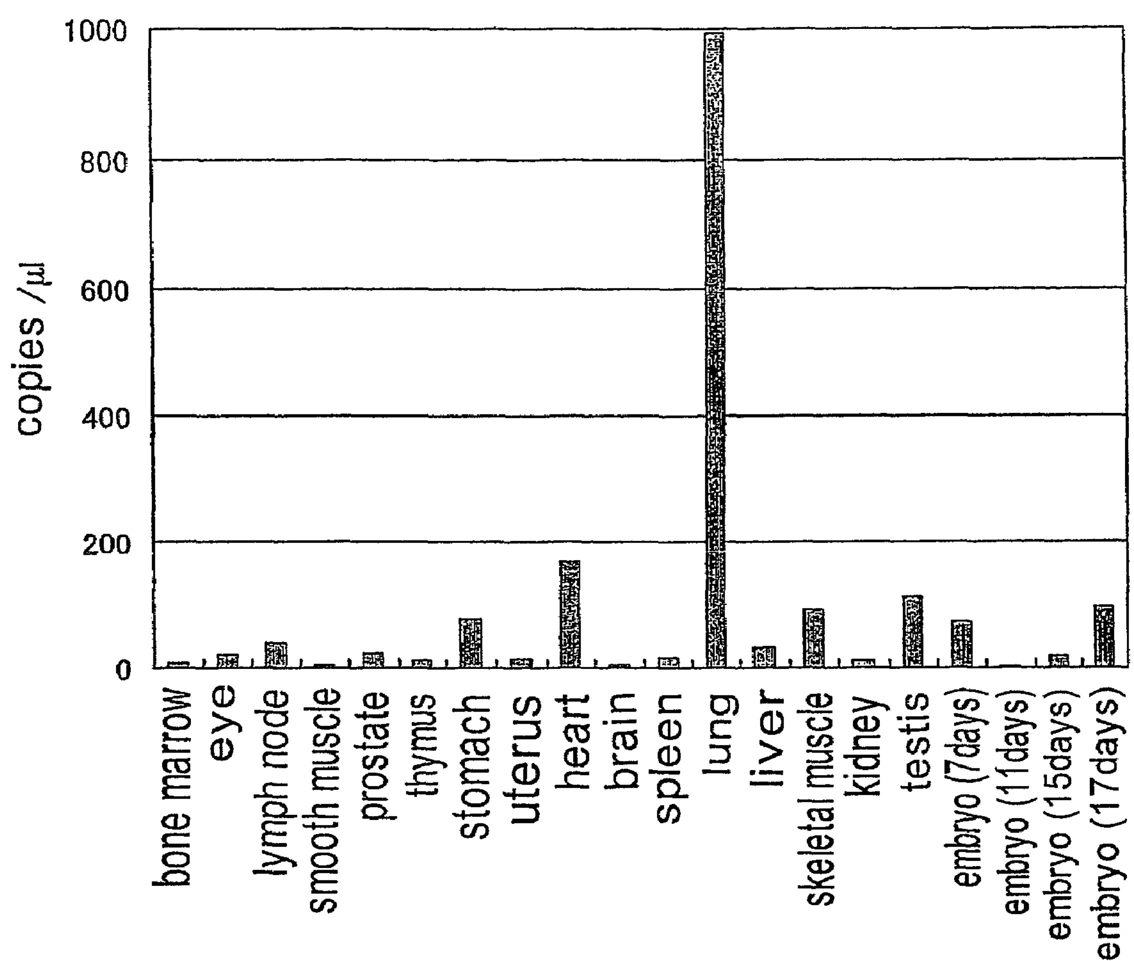
FIG. 14 shows the expression level of mouse TCH230 (SEQ ID NO:112) gene product in each tissue cDNA. The expression level is represented in terms of copy number per μl of cDNA solution.

The results are shown in FIG. 14.

In mouse MTC panels I and II, the mouse TCH230 (SEQ ID NO:112) gene product (mRNA) was expressed slightly in the eye, lymph node, prostate, thymus, uterus, spleen, liver, kidney and embryo (15th day), expressed at a certain degree in the stomach, skeletal muscle, testis, embryo (7th day) and embryo (17th day), expressed strongly in the heart, and expressed most strongly in the lung.

Example 15

Analysis of Distribution of Mouse TCH230 (SEQ ID NO:112) Gene Product in Tissues of 7-Week-Old BALB/c Mouse (1) Preparation of cDNA from Each Tissue in Normal Mouse Using ISOGEN (Nippon Gene) or RNeasy Mini Kit (Qiagen), total RNA was prepared from each kind ofussue in 7-week-old BALB/c mouse [cerebrum, cerebellum, hippocampus, medulla oblongata, spinal cord, ischiatic nerve, skin, skeletal muscle, eyeball, heart, lung, trachea, pancreas, kidney, liver, anterior stomach, pyloric stomach, duodenum, jejunoileum, caecum, colon, rectum, spleen, thymus, bone marrow, ovary, uterus, prostate, testis (ovary and uterus were collected from female mice, and other organs were from male mice, and each was collected from 1 to 10 mice)]. The prepared total RNA was subjected to reverse transcription reaction by using TaqMan Reverse Transcription Reagents (Applied Biosystems) to prepare cDNA.

(2) Analysis of Distribution of Mouse TCH230 (SEQ ID NO:112) Gene Product in Tissues The expression level (copy number) of mouse TCH230 (SEQ ID NO:112) by cDNA in each kind of mouse tissue was measured by TaqMan PCR with two primer DNAs, i.e. primer m230TF (SEQ ID NO. 113) and primer m230TR (SEQ ID NO. 114) used in Example 14 and TaqMan probe m230T1 (SEQ ID NO. 115). The same cDNA was also measured for the expression level (copy number) of rodent glyceraldehyde-3-phosphate dehydrogenase (GAPDH) by using TaqMan rodent GAPDH control reagents (Applied Biosystems). The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 15:
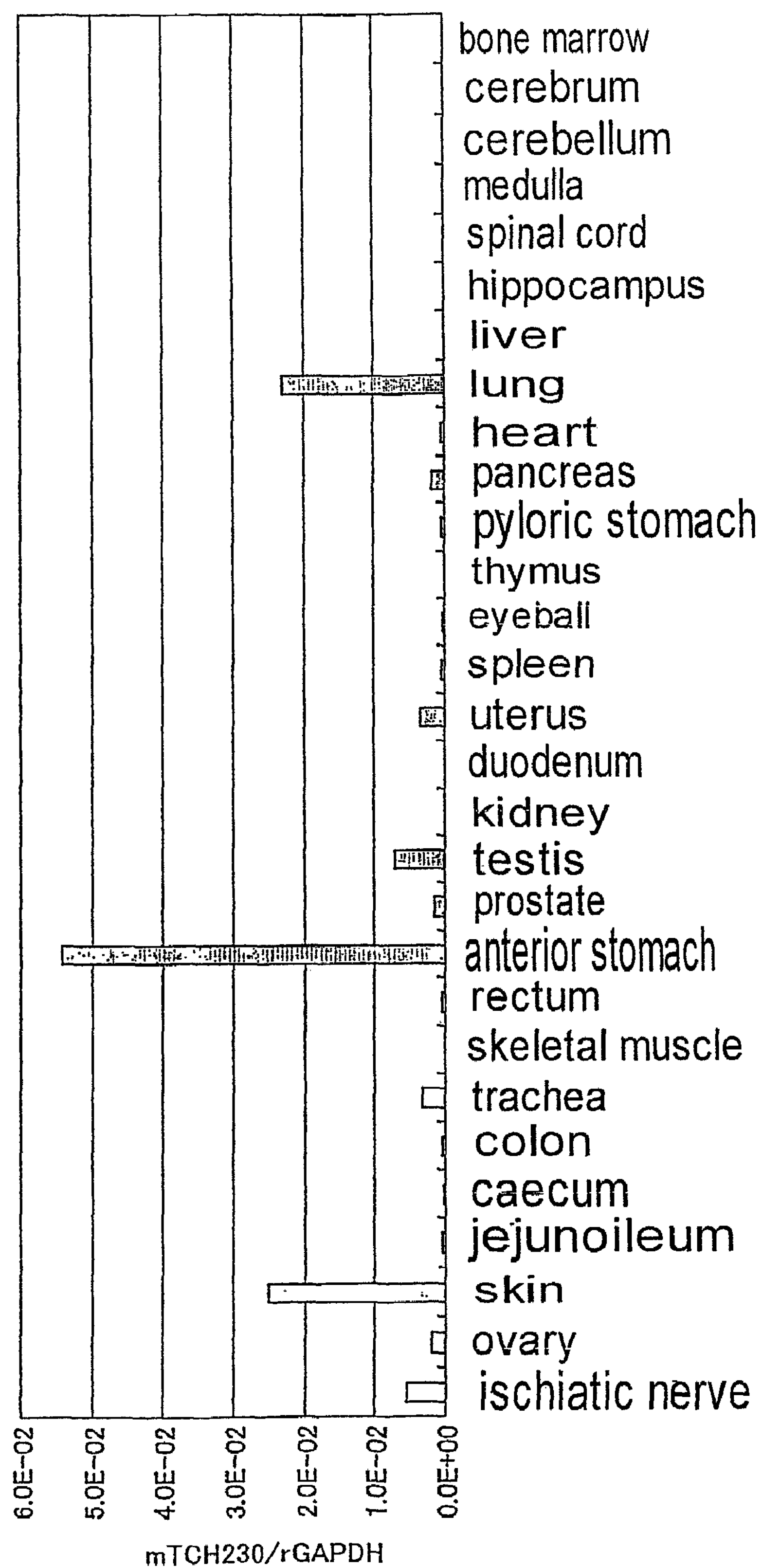
FIG. 15 shows the expression level of mouse TCH230 (SEQ ID NO:112) gene product in each tissue. The expression level is represented as (copy number of mouse TCH230 (SEQ ID NO:112) per μl of cDNA solution/copy number of rodent GAPDH by equivalent amount of tissue cDNA).

The results are shown in FIG. 15.

In the tissues of 7-week-old BALB/c mice, the mouse TCH230 (SEQ ID NO:112) gene product (mRNA) was expressed slightly in the ovary, jejunoileum, caecum, colon, rectum, prostate, spleen, eyeball, pyloric stomach, pancreas and heart, expressed at a certain degree in the ischiatic nerve, trachea, testis and uterus, expressed highly in the skin and lung, and expressed at the highest degree in the anterior stomach.

Example 16

Identification of a Partial Sequence of Rat TCH230 Gene

Using two primer DNAs, i.e. primer r230OF (SEQ ID NO. 117) and primer r230OR (SEQ ID NO. 118), rat testis Marathon-Ready cDNA (Clontech) was subjected to PCR with Advantage 2 DNA Polymerase (Clontech) under the following conditions (1) to (3):

(1) reaction at 95° C. for 1 minute, (2) 35 cycles each consisting of reaction at 95° C. for 30 seconds and at 68° C. for 3 minutes, and (3) reaction at 68° C. for 3 minutes.

The resulting amplification product was subjected to gel electrophoresis, and a fragment of about 1.0 kb was cut off, purified by QIAquick Gel Extraction Kit (Qiagen) and reacted by using primer r230OF (SEQ ID NO. 117), primer r230OR (SEQ ID NO. 118) and BigDye Terminator Cycle Sequencing Kit (Applied Biosystems), and the base sequence of the product amplified by PCR was determined by DNA sequencer ABI PRISM 3100 DNA analyzer (Applied Biosystems). As a result, a partial sequence of rat TCH230 gene cDNA having a 1046-base sequence represented by SEQ ID NO. 116 was identified.

Example 17

(1) Preparation of cDNA from Each Tissue in Normal Rat

Using RNeasy Mini Kit (Qiagen), total RNA was prepared from each kind of tissue (cerebrum, cerebellum, liver, kidney, prostate, heart, lung, duodenum, jejunoileum, colon, skin, eyeball) in 12-week-old male Wistar rats. The prepared total RNA was subjected to reverse transcription reaction with TaqMan Reverse Transcription Reagents (Applied Biosystems) to prepare cDNA.

(2) Analysis of Distribution of Rat TCH230 Gene Product in Tissues

The expression level (copy number) of rat TCH230 by cDNA in each rat tissue was measured by TaqMan PCR with two primer DNAs, i.e. primer r230TF (SEQ ID NO. 119) and primer r230TR (SEQ ID NO. 120), designed from the sequence of SEQ ID NO. 116, and TaqMan probe r230T1 (SEQ ID NO. 121). The same cDNA was also measured for the expression level (copy number) of rodent glyceraldehyde-3-phosphate dehydrogenase (GAPDH) by using TaqMan rodent GAPDH control reagents (Applied Biosystems). The PCR reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 16:
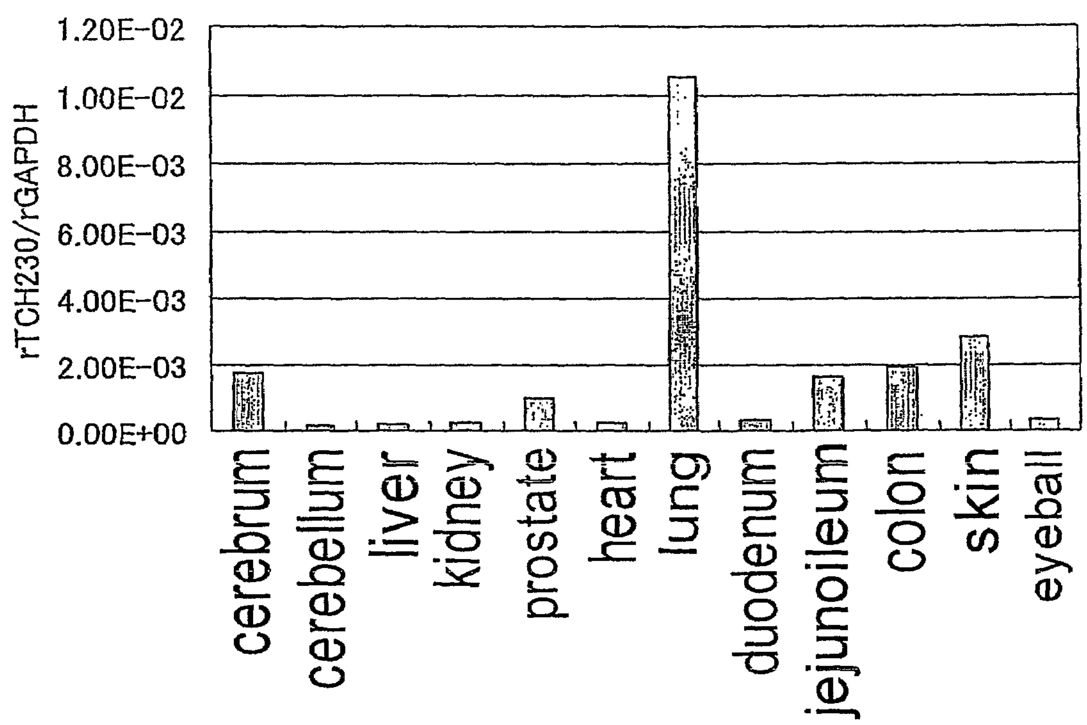
FIG. 16 shows the expression level of rat TCH230 gene product in each tissue. The expression level is represented as (copy number of rat TCH230 per μl of cDNA solution/copy number of rodent GAPDH by equivalent amount of tissue cDNA).

The results are shown in FIG. 16.

The TCH230 gene product (mRNA) was expressed in all tissues in the 12-week-old Wistar rats, and particularly in the cerebrum, prostate, jejunoileum, colon and skin, high expression was observed, and the highest expression was observed in the lung.

Example 18

Construction of Human TCH230 (SEQ ID NO:1) Expression Vector

Human TCH230 (SEQ ID NO. 1) expression vector was constructed by the following method.

Using 10 ng of plasmid obtained in Example 1 as a template, PCR was conducted with primer 230OF2 (SEQ ID NO. 122) and primer 230OR2 (SEQ ID NO. 123) and Pyrobest DNA Polymerase (Takara Bio) under the following conditions (1) to (3). The 5'-terminal side primer 230OF2 and the 3'-terminal side primer 230OR2 were designed such that Hind III site and Xba I site were added respectively to the 5'-terminal side for cloning into a vector.

(1) reaction at 98° C. for 2 minutes, (2) 30 cycles each consisting of reaction at 98° C. for 10 seconds, at 65° C. for 30 seconds and at 72° C. for 3.5 minutes, and (3) reaction at 72° C. for 10 minutes.

The PCR reaction solution was subjected to gel electrophoresis, and a major band was purified. The PCR fragment thus obtained was digested with restriction enzymes Hind III and Xba I at 37° C. for 1 hour, and the reaction solution was subjected to gel electrophoresis and purified. The product was ligated to Hind III site and Xba I site of an animal cell expression vector pcDNA3.1(+) (Invitrogen, Inc.) by Takara ligation kit ver. 2 (Takara Bio). This ligation reaction solution was precipitated with ethanol and used to transform a competent cell *Escherichia coli* TOP10 (Invitrogen, Inc.). From a plurality of colonies thus obtained, a plasmid was prepared, and this base sequence was reacted by using primer DNAs [primer BGH RV (SEQ ID NO. 124), primer T7 (SEQ ID NO: 8), primer B1 (SEQ ID NO: 9), primer F1 (SEQ ID NO. 10)] and BigDye Terminator Cycle Sequencing Kit (Applied Biosystems), and the base sequence was confirmed by DNA sequencer ABI PRISM 3100 DNA analyzer (Applied Biosystems). The transformant having this plasmid was designated *Escherichia coli* TOP10/pCDNA3.1(+)-TCH230.

Example 19

Preparation of Human TCH230 (SEQ ID NO:1) Expressing CHO Cell Strain and Measurement of the Expression Level of the Introduced Gene

*Escherichia coli* TOP10/pCDNA3.1(+)-TCH230 was cultured, and from this *Escherichia coli*, plasmid DNA was prepared by EndoFree Plasmid Maxi Kit (Qiagen). This plasmid DNA was introduced into CHO dhfr− cells by using FuGENE 6 Transfection Reagent (Roche) according to its attached protocol. A mixture of 2 μg of plasmid DNA and transfection reagents was added to a 6 cm Petri dish on which $3\times10^5$ CHO dhfr$^-$ cells had been plated before 24 hours. The cells were cultured for 1 day in MEMα medium (Invitrogen, Inc.) containing 10% bovine fetal serum (JRH Bioscience), and peeled off by treatment with trypsin, and the recovered cells were plated on a 96-well plate at a density of 10-50 cells/well. After 24 hours, 0.5 mg/ml geneticine (Invitrogen, Inc.) was added to the medium, and then the TCH230 expression cells were selected in a medium containing 0.5-1.0 mg/ml geneticine. 22 wells wherein one to three colonies had grownper well were cultured in a 6-well plate, and from the grown cells, total RNA was prepared by RNeasy Mini Kit or RNeasy 96 Kit (both available from Qiagen). The prepared total RNA was subjected to reverse transcription reaction by TaqMan Reverse Transcription Reagents (Applied Biosystems) to prepare cDNA. This was examined for the expression level of TCH230 by TaqMan PCR with primer TF (SEQ ID NO. 15) and primer TR (SEQ ID NO. 16) used in Example 2 and TaqMan probe T1 (SEQ ID NO. 17). The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out. As cell strains (polyclonal) highly expressing human TCH230 (SEQ ID NO:1) gene, clone Nos. 19 and 26 were selected. Each strain was inoculated into a 96-well plate at a density of 0.5 cell/well, and then cultured for 7 to 10 days in a medium containing geneticine, to give a monoclonal clone. Total RNA was prepared and the expression level of human TCH230 (SEQ ID NO:1) gene was measured by TaqMan PCR. As cell strains (monoclonal) expressing human TCH230 (SEQ ID NO:1), clone No. 19-6 were selected.

Example 20

Measurement of Incorporation of [6,7-$^3$H(N)]-estrone sulfate and [1,2,6,7-$^3$H(N)]-dehydroepiandrosterone sulfate into the Human TCH230 (SEQ ID NO: 1)-Expressing CHO Cell Strain Incorporation of [6,7-$^3$H(N)]-estrone sulfate and [1,2,6,7-$^3$H(N)]-dehydroepiandrosterone sulfate (hereinafter also referred to as [1,2,6,7-$^3$H(N)]-DHEA-S) into the human TCH230 (SEQ ID NO:1)-expressing CHO cell strain clone No. 19-6 obtained in Example 19 was measured.

The human TCH230 (SEQ ID NO:1) expressing CHO cell strain clone No. 19-6 was inoculated at a density of $4\times10^4$ cells/well in a 96 well plate, and cultured at 37° C. for 24 hours in MEMα medium (Invitrogen, Inc.) containing 5 mM sodium butyrate. The medium was removed, and the cells were washed 3 times with 150 μL NMDG buffer (140 mM N-methyl-D(−)-glucamine, 5.4 mM KCl, 0.34 mM $Na_2HPO_4$, 0.44 mM $KH_2PO_4$, 1.26 mM $CaCl_2$, 0.41 mM $MgSO_4$, 0.49 mM $MgCl_2$, 5.55 mM glucose, pH 7.4-7.6), and incubated in 150 μL NMDG buffer at 37° C. for 1 hour. The buffer was replaced with 90 μL NaCl buffer (140 mM NaCl, 5.4 mM KCl, 0.34 mM $Na_2HPO_4$, 0.44 mM $KH_2PO_4$, 1.26 mM $CaCl_2$, 0.41 mM $MgSO_4$, 0.49 mM $MgCl_2$, 5.55 mM glucose, pH 7.4-7.6) or 90 μL NMDG buffer, followed by adding 10 μL of 2.5 μM estrone sulfate, ammonium salt, [6,7-$^3$H(N)]— or 1.37 μM dehydroepiandrosterone sulfate, sodium salt, [1,2,6,7-$^3$H(N)]— (all of which are available from Perkin-Elmer Life Science). The cells were incubated at 37° C. for 1 hour, and the buffer was removed, then washed 3 times with 200 μL PBS (Takara Bio) and lysed with 10 μL of 0.1N NaOH. 100 μL SuperMix scintillator (Perkin-Elmer Life Science) was added thereto and stirred, and the amount of [6,7-$^3$H(N)]-estrone sulfate or [1,2,6,7-$^3$H(N)]-DHEA-S incorporated into the cells was measured in terms of radioactivity. This measurement was carried out with 1450 MICROBETA PLUS LIQUID SCINTILLATION COUNTER (Perkin-Elmer Life Science). CHO dhfr− cells into which vector pcDNA3.1(+) had been introduced (also referred to hereinafter as Mock) was also subjected to the same procedure and measured for radioactivity.

Figure 17:
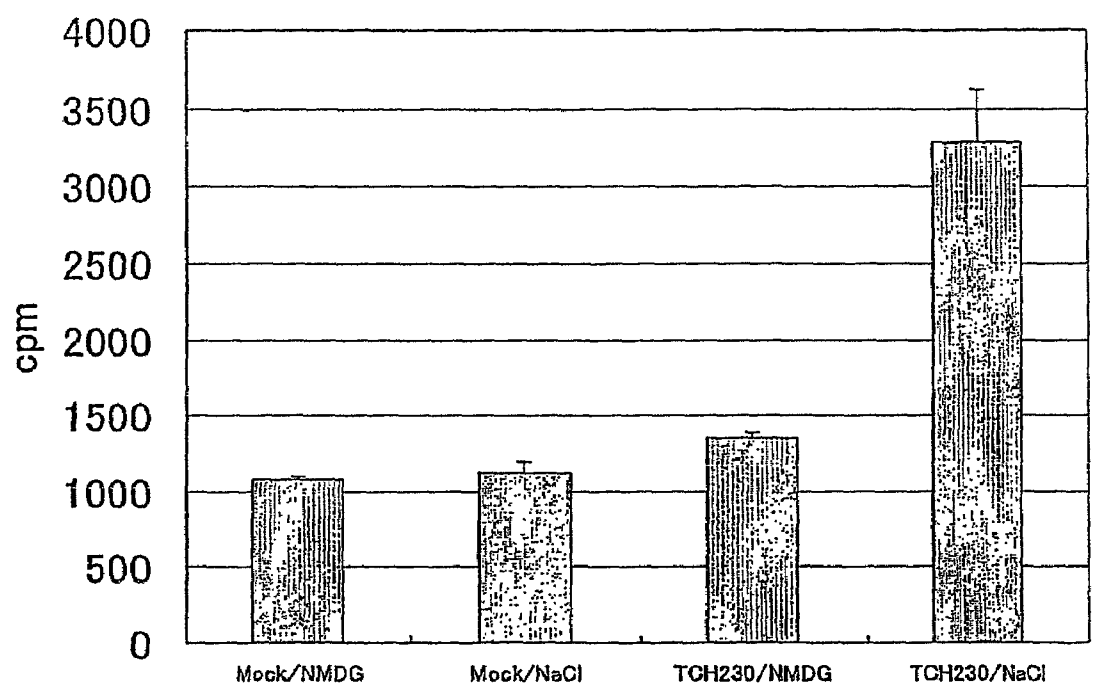
FIG. 17 shows the result of measurement of incorporation of [6,7-$^3$H(N)]-estrone sulfate into human TCH230 (SEQ ID NO:1)-expressing CHO cell strain. The amount of the incorporated compound was expressed as count (cpm) upon incorporation of [6,7-$^3$H(N)]-estrone sulfate for 1 hour. The amount was expressed as the average of the counts in 3 independent wells and standard deviation.
Figure 18:
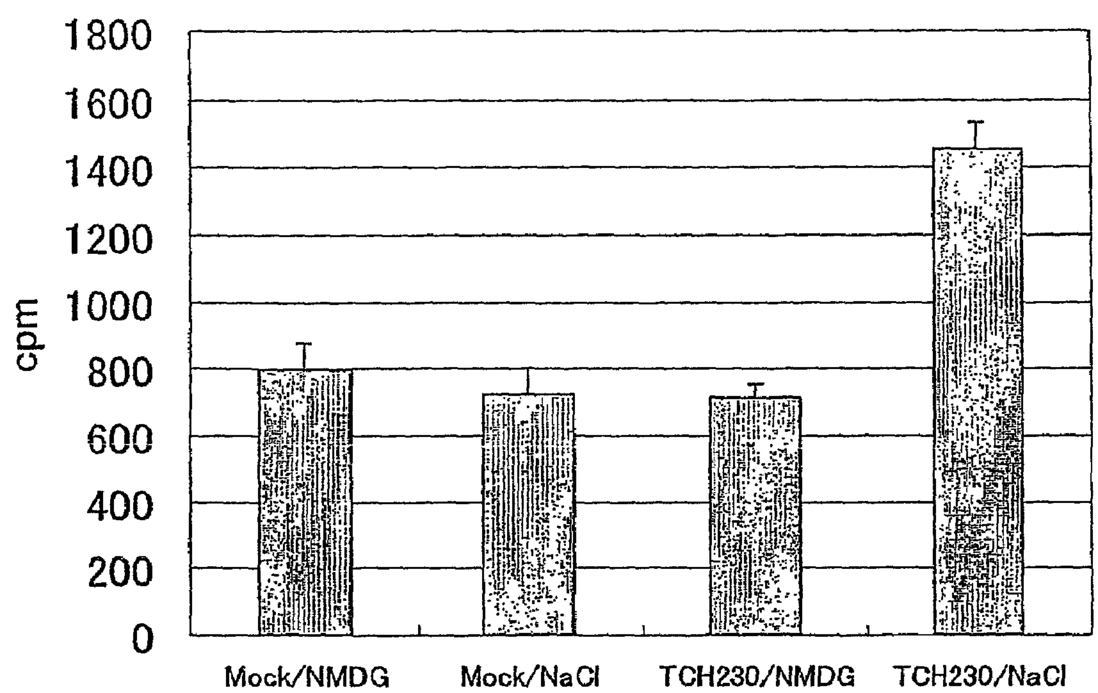
FIG. 18 shows the result of measurement of incorporation of [1,2,6,7-$^3$H(N)]-DHEA-S into human TCH230 (SEQ ID NO:1)-expressing CHO cell strain. The amount of the incorporated compound was represented as count (cpm) upon incorporation of [1,2,6,7-$^3$H(N)]-DHEA-S for 1 hour. The amount was represented as the average of the counts in 3 independent wells and standard deviation.

The result of [6,7-$^3$H(N)]-estrone sulfate is shown in FIG. 17, and the result of [1,2,6,7-$^3$H(N)]-DHEA-S is shown in FIG. 18.

It was thereby revealed that the human TCH230 (SEQ ID NO:1) expressing CHO cells incorporate [6,7-$^3$H(N)]-estrone sulfate and [1,2,6,7-$^3$H(N)]-DHEA-S in the presence of 140 mM NaCl.

Example 21

Identification of a Partial Sequence of Mouse TCH234 Gene

Using two primer DNAs, i.e. primer m234-1485F (SEQ ID NO. 126) and primer m234-1801R (SEQ ID NO. 127), mouse testis Marathon-Ready cDNA (Clontech) was subjected to PCR with Advantage 2 DNA Polymerase (Clontech) under the following conditions (1) to (5):

(1) reaction at 94° C. for 30 seconds, (2) 35 cycles each consisting of reaction at 94° C. for 10 seconds, at 62° C. for 10 seconds and at 68° C. for 30 seconds, and (3) reaction at 68° C. for 3 minutes.

The resulting amplification product was subjected to gel electrophoresis, and a fragment of about 0.3 kb was cut off, purified by QIAquick Gel Extraction Kit (Qiagen) and reacted by using primer m234-1485F (SEQ ID NO. 126), primer m234-1801R (SEQ ID NO. 127) and BigDye Terminator Cycle Sequencing Kit (Applied Biosystems), and the base sequence of the product amplified by PCR was determined by DNA sequencer ABI PRISM 3100 DNA analyzer (Applied Biosystems).

As a result, a partial sequence of mouse TCH234 gene cDNA having a 317-base sequence represented by SEQ ID NO. 125 was identified.

Example 22

Analysis of Distribution of Mouse TCH234 Gene Product in Tissues

The expression level (copy number) of mouse TCH234 by the cDNA prepared in Example 15 in each mouse tissue was measured by TaqMan PCR with two primer DNAs, i.e. primer m234-TMF (SEQ ID NO. 128) and primer m234-TMR (SEQ ID NO. 129), designed from the base sequence represented by SEQ ID NO. 125, and TaqMan probe m234T1 (SEQ ID NO. 130). The same cDNA was also measured for the expression level (copy number) of rodent glyceraldehyde-3-phosphate dehydrogenase (GAPDH) by using TaqMan rodent GAPDH control reagents (Applied Biosystems). The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 19:
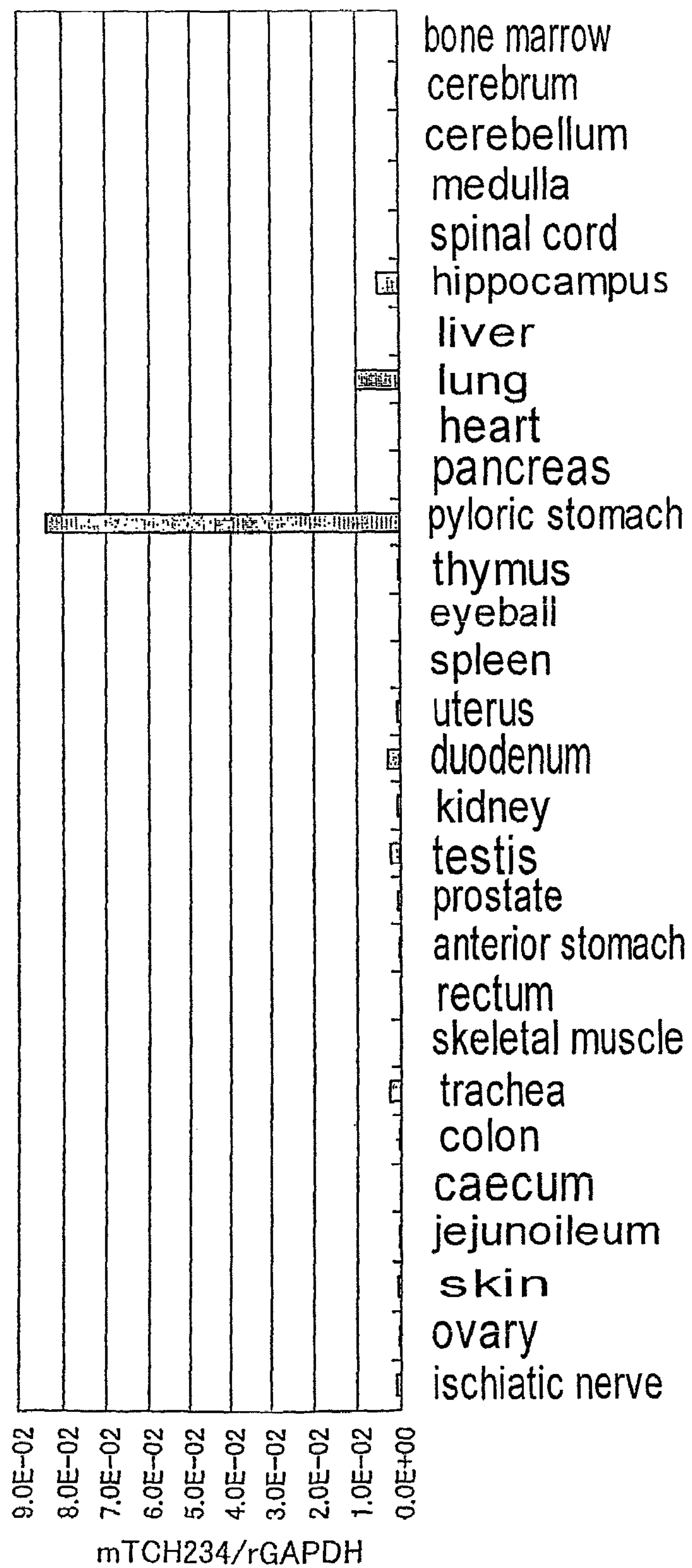
FIG. 19 shows the expression level of mouse TCH234 gene product in each tissue. The expression level is represented as (copy number of mouse TCH234 per μl of cDNA solution/copy number of rodent GAPDH by equivalent amount ofussue cDNA).

The results are shown in FIG. 19.

In each kind of tissue of 7-week-old BALB/c mouse, the mouse TCH234 gene product (mRNA) was expressed slightly in the ischiatic nerve, ovary, skin, jejunoileum, colon, anterior stomach, prostate, kidney, uterus, thymus and cerebrum, expressed at a certain degree in the lung, hippocampus, duodenum, testis and trachea, and expressed particularly highly in the pyloric stomach.

Example 23

Identification of a Partial Sequence of Rat TCH234 Gene

Using two primer DNAs, i.e. primer r234-815F (SEQ ID NO. 132) and primer r234-1177R (SEQ ID NO. 133), rat kidney Marathon-Ready cDNA (Clontech) was subjected to PCR with Advantage 2 DNA Polymerase (Clontech) under the following conditions (1) to (3):

(1) reaction at 94° C. for 30 seconds, (2) 35 cycles each consisting of reaction at 94° C. for 10 seconds, at 62° C. for 10 seconds and at 68° C. for 30 seconds, and (3) reaction at 68° C. for 3 minutes.

The resulting amplification product was subjected to gel electrophoresis, and a fragment of about 0.35 kb was cut off, purified by QIAquick Gel Extraction Kit (Qiagen) and reacted by using primer r234-815F (SEQ ID NO. 132), primer m234-1177R (SEQ ID NO. 133) and BigDye Terminator Cycle Sequencing Kit (Applied Biosystems), and the base sequence of the product amplified by PCR was determined by DNA sequencer ABI PRISM 3100 DNA analyzer (Applied Biosystems). As a result, a partial sequence of rat TCH234 gene cDNA having a 363-base sequence represented by SEQ ID NO. 131 was identified.

Example 24

Analysis of Distribution of Rat TCH234 Gene Product in Tissues

The expression level (copy number) of rat TCH234 by the cDNA prepared in Example 17 in each rat tissue was measured by TaqMan PCR with two primer DNAs, i.e. primer r234-TMF (SEQ ID NO. 134) and primer r234-TMR (SEQ ID NO. 135), designed from the base sequence represented by SEQ ID NO. 131, and TaqMan probe r234-P1 (SEQ ID NO. 136). The same cDNA was also measured for the expression level (copy number) of rodent glyceraldehyde-3-phosphate dehydrogenase (GAPDH) by using TaqMan rodent GAPDH control reagents (Applied Biosystems). The PCR reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 20:
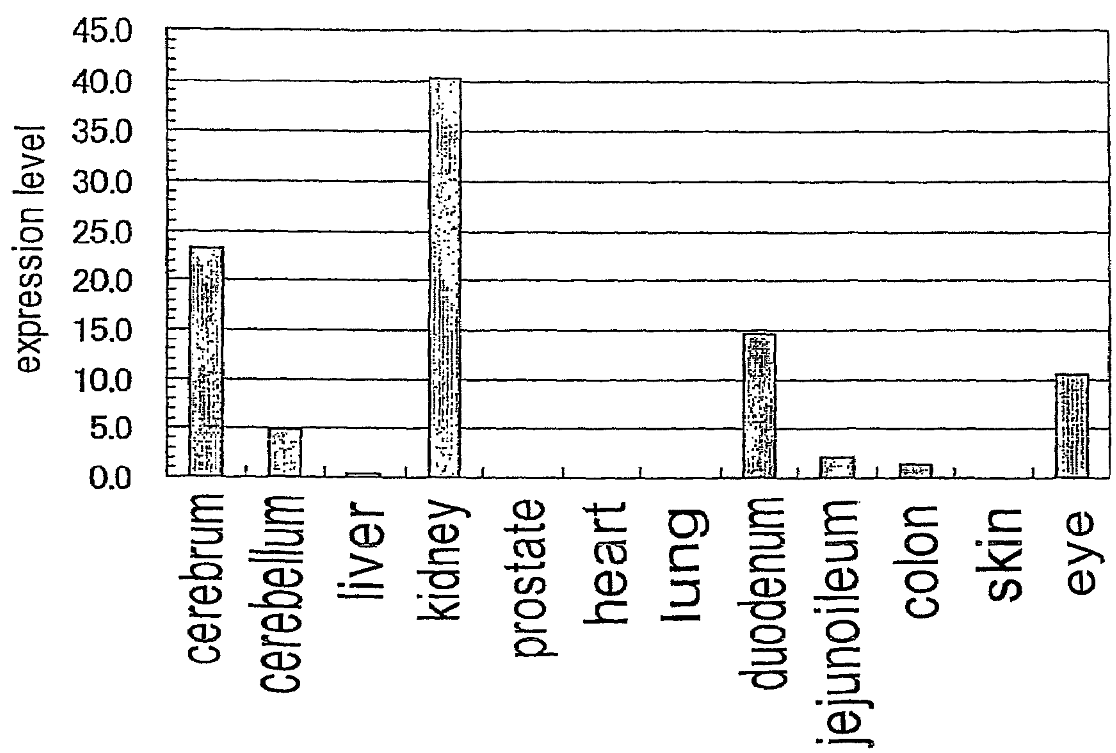
FIG. 20 shows the expression level of rat TCH234 gene product in each tissue. In the figure, the expression level shown on the ordinate is represented as ((copy number of rat TCH234 per μl of cDNA solution)/(copy number of rodent GAPDH by equivalent amount of tissue cDNA)×100,000)).

The results are shown in FIG. 20.

In each kind of tissue of 12-week-old Wistar rat, the rat TCH234 gene product (mRNA) was expressed at a certain degree in the cerebellum, liver, jejunoileum and colon, expressed highly in the cerebrum, duodenum and eye and expressed most highly in the kidney.

Example 25

Construction of Human TCH234 (SEQ ID NO:18) Expression Vector

Human TCH234 (SEQ ID NO. 18) expression vector was constructed by the following method.

Using 10 ng plasmid obtained in Example 5 as a template, PCR was conducted with primer 234OF (SEQ ID NO. 137) and primer 2340R (SEQ ID NO. 138) and Pyrobest DNA Polymerase (Takara Bio) under the following conditions (1) to (3). The 5'-terminal side primer 234OF and the 3'-terminal side primer 234OR were designed such that Hind III site and Xba I site were added respectively to the 5'-terminal side for cloning into a vector.

(1) reaction at 94° C. for 1 minute, (2) 25 cycles each consisting of reaction at 94° C. for 30 seconds, at 55° C. for 30 seconds and at 72° C. for 3 minutes, and (3) reaction at 72° C. for 5 minutes.

The PCR reaction solution was subjected to gel electrophoresis, and a major band was purified. The PCR fragment thus obtained was digested with restriction enzymes Hind III and Xba I at 37° C. for 1 hour, and the reaction solution was subjected to gel electrophoresis and purified. The product was ligated to Hind III site and Xba I site of an animal cell expression vector pcDNA3.1(+) (Invitrogen, Inc.) by using Takara ligation kit ver. 2 (Takara Bio). This ligation reaction solution was used to transform a competent cell *Escherichia coli* JM109 (Takara Bio).

From a plurality of colonies thus obtained, a plasmid was prepared, and this base sequence was reacted by using primer DNAs [primer BGH RV (SEQ ID NO. 124), primer T7 (SEQ ID NO: 8), primer F3 (SEQ ID NO: 35), primer R2 (SEQ ID NO: 37), primer ff2 (SEQ ID NO: 25), primer 234F21 (SEQ ID NO. 139), primer 234F22 (SEQ ID NO. 140), primer 234F23 (SEQ ID NO. 141), primer 234R24 (SEQ ID NO. 142)] and BigDye Terminator Cycle Sequencing Kit (Applied Biosystems), and the base sequence was confirmed by DNA sequencer ABI PRISM 3100 DNA analyzer (Applied Biosystems). The transformant having this plasmid was designated *Escherichia coli* JM109/pCDNA3.1(+)-TCH234.

Example 26

Preparation of Human TCH234 (SEQ ID NO:18)-Expressing CHO Cell Strain

The *Escherichia coli* JM109/pCDNA3.1 (+)-TCH234 was cultured, and from this *Escherichia coli*, plasmid DNA was prepared by EndoFree Plasmid Maxi Kit (Qiagen). This plasmid DNA was introduced into CHO dhfr− cells by using FuGENE 6 Transfection Reagent (Roche) according to its attached protocol. A mixture of 2 μg of plasmid DNA and transfection reagents was added to a Petri dish of 6 cm in diameter on which $3\times10^5$ CHO dhfr$^-$ cells had been plated before 24 hours. The cells were cultured for one (1) day in MEMα medium (Invitrogen, Inc.) containing 10% bovine fetal serum (JRH Bioscience), and peeled off by treatment with trypsin, and the recovered cells were suitably diluted and plated on a 10 cm Petri dish. After 24 hours, 0.5 mg/ml geneticine (Invitrogen, Inc.) was added to the medium, and for 10 days thereafter, human TCH234 (SEQ ID NO:18)-expressing cells were selected in MEM medium containing 0.5-1.0 mg/ml geneticine. 104 grown colonies of monoclonal human TCH234 (SEQ ID NO:18)-expressing cells were selected in the geneticine-containing selective medium.

Example 27

Measurement of the Expression Level of the Introduced Gene in the Human TCH234 (SEQ ID NO:18) Expressing CHO Cell Strain by TaqMan PCR The human TCH234 (SEQ ID NO:18) expressing CHO cell strain prepared in Example 26 was cultured in a 96-well plate, and from the grown cells, total RNA was prepared by using SV 96 Total RNA Isolation System (Promega). The prepared total RNA was subjected to reverse transcription reaction by TaqMan Reverse Transcription Reagents (Applied Biosystems) to prepare cDNA. This was measured for the expression level of human TCH234 (SEQ ID NO:18) by TaqMan PCR with primer TMF (SEQ ID NO: 32) and primer TMR (SEQ ID NO: 33), used in Example 6, and TaqMan probe P1 (SEQ ID NO: 38). The PCR reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out. As a cell strain highly expressing human TCH234 (SEQ ID NO:18) gene, clone No. 104 was selected.

Example 28

Analysis of Tissue Distribution of Human TCH234 (SEQ ID NO:18) Gene Product in Human Digestive Tissues The expression level (copy number) of human TCH234 (SEQ ID NO:18) by cDNA (human digestive system MTC panel; Clontech) in each human digestive tract tissue (liver, esophagus, stomach, duodenum, jejunoileum, ileocecum, caecum, ascending colon, transverse colon, descending colon, rectum) was measured by TaqMan PCR with primer TMF (SEQ ID NO: 32) and primer TMR (SEQ ID NO: 33), used in Example 6, and TaqMan probe P1 (SEQ ID NO: 38). The same cDNA was also measured for the expression level (copy number) of rodent glyceraldehyde-3-phosphate dehydrogenase (GAPDH) by using TaqMan rodent GAPDH control reagents (Applied Biosystems). The PCR reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 21:
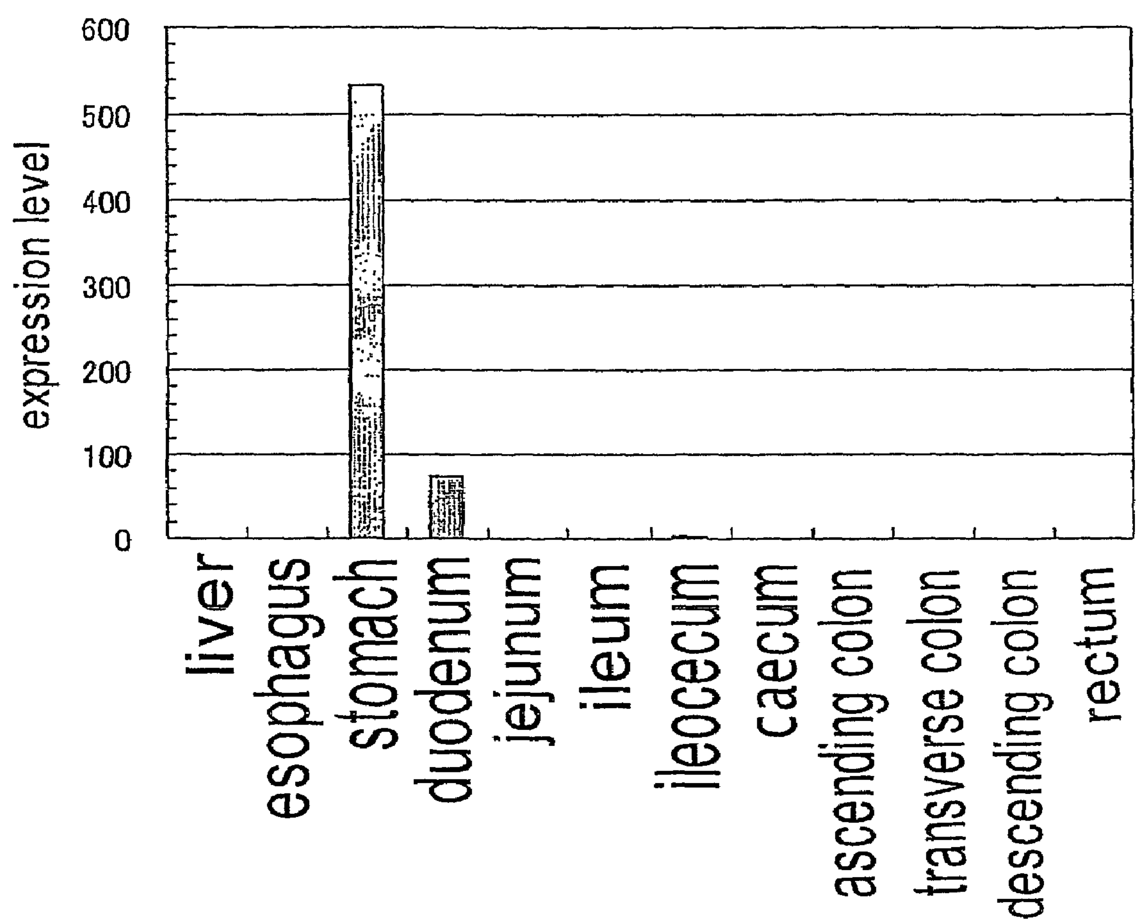
FIG. 21 shows the amount of human TCH234 (SEQ ID NO:18) gene product expressed in each kind of tissue. In the figure, the expression level shown on the ordinate is represented as ((copy number of TCH234 per μl of cDNA solution)/(copy number of GAPDH by equivalent amount of tissue cDNA)×100,000)).

The results are shown in FIG. 21.

In the digestive tract tissues, the human TCH234 (SEQ ID NO:18) gene product (mRNA) was expressed slightly in the ileocecum, expressed highly in the duodenum and expressed most highly in the stomach.

Example 29

Identification of a Partial Sequence of Mouse TCH212 (SEQ ID NO:143) Gene

Using two primer DNAs, i.e. primer m212A1 (SEQ ID NO. 144) and primer m212B1 (SEQ ID NO. 145), mouse testis Marathon-Ready cDNA (Clontech) was subjected to PCR with Advantage 2 DNA Polymerase (Clontech) under the following conditions (1) to (3):

(1) reaction at 95° C. for 1 minute, (2) 35 cycles each consisting of reaction at 95° C. for 30 seconds and at 68° C. for 3 minutes, and (3) reaction at 68° C. for 3 minutes.

The resulting amplification product was subjected to gel electrophoresis, and a fragment of about 0.8 kb was cut off, purified by QIAquick Gel Extraction Kit (Qiagen) and reacted by using primer m212A1 (SEQ ID NO. 144), primer m212B1 (SEQ ID NO. 145) and BigDye Terminator Cycle Sequencing Kit (Applied Biosystems), and the base sequence of the product amplified by PCR was determined by DNA sequencer ABI PRISM 3100 DNA analyzer (Applied Biosystems). As a result, a partial sequence of mouse TCH212 gene cDNA having a 680-base sequence represented by SEQ ID NO. 143 was identified.

Example 30

Analysis of Distribution of Mouse TCH212 (SEQ ID NO:143) Gene Product in Tissues Using two primer DNAs, i.e. primer m212TF (SEQ ID NO: 146) and primer m212TR (SEQ ID NO: 147), designed from the base sequence represented by SEQ ID NO: 143, and TaqMan probe m212T1 (SEQ ID NO: 148), the expression level (copy number) of mouse TCH212 (SEQ ID NO:143) by the cDNA prepared in Example 15 in each mouse tissue was measured by TaqMan PCR. The same cDNA was also measured for the expression level (copy number) of rodent glyceraldehyde-3-phosphate dehydrogenase (GAPDH) by using TaqMan rodent GAPDH control reagents (Applied Biosystems). The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 22:
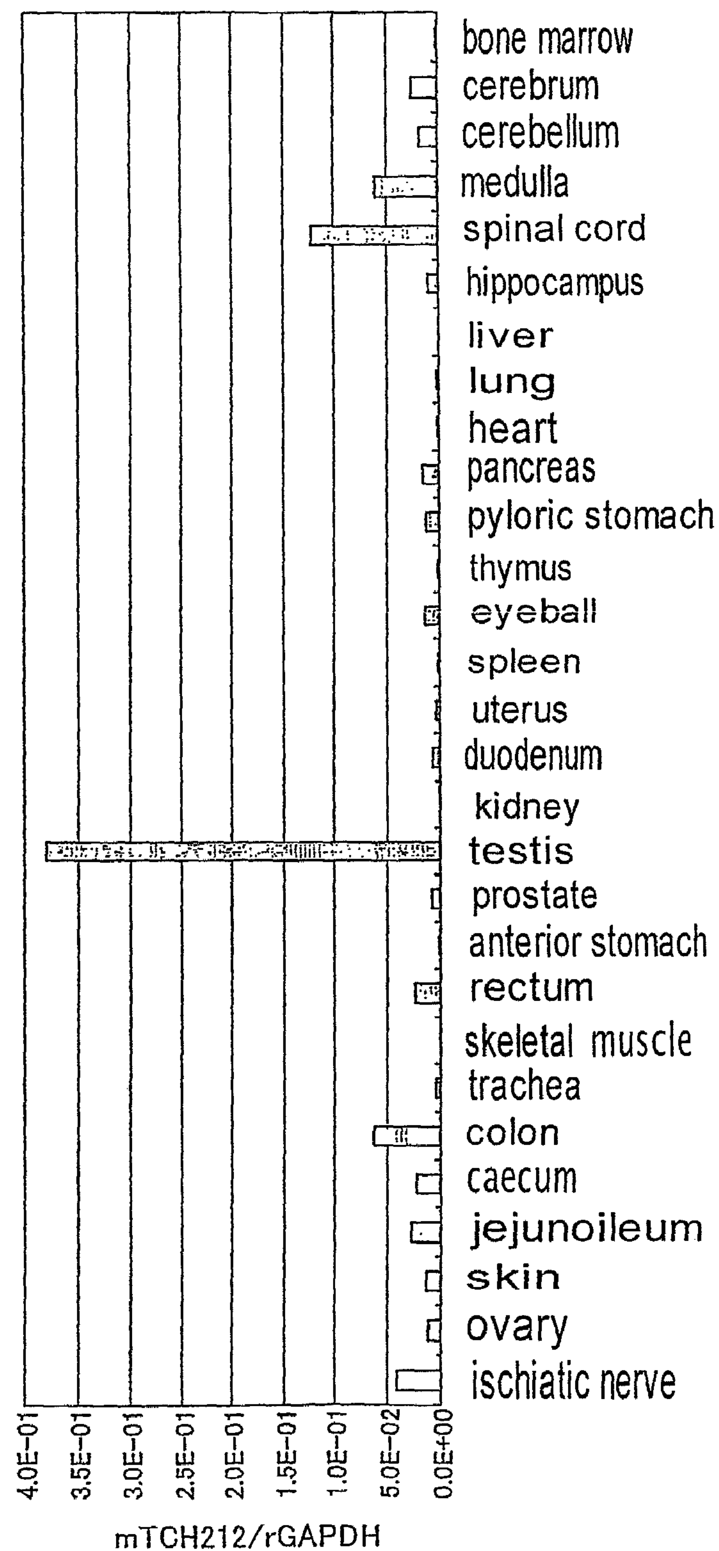
FIG. 22 shows the expression level of mouse TCH212 (SEQ ID NO:143) gene product in each tissue. The expression level is represented as (copy number of mouse TCH212 (SEQ ID NO:143) per μl of cDNA solution)/(copy number of rodent GAPDH by equivalent amount of tissue cDNA).

The results are shown in FIG. 22.

In each kind of tissue in 7-week-old BALB/c mouse, the mouse TCH212 (SEQ ID NO:143) gene product (mRNA) was expressed slightly in the trachea, anterior stomach, prostate, duodenum, uterus, spleen, eyeball, thymus, pyloric stomach, heart, lung, hippocampus and bone marrow, expressed at a certain degree in the ovary, skin, jejunoileum, caecum, rectum, pancreas, cerebellum and cerebrum, expressed highly in the ischiatic nerve, colon, medulla oblongata and spinal cord and expressed most highly in the testis.

Example 31

Identification of a Partial Sequence of Rat TCH212 Gene

Using two primer DNAs, i.e. primer m212A1 (SEQ ID NO. 144) and primer m212B1 (SEQ ID NO. 145) used in Example 29, rat testis Marathon-Ready cDNA (Clontech) was subjected to PCR with Advantage 2 DNA Polymerase (Clontech) under the following conditions (1) to (3):

(1) reaction at 95° C. for 1 minute, (2) 35 cycles each consisting of reaction at 95° C. for 30 seconds, at 60° C. for 30 seconds and at 68° C. for 3 minutes, and (3) reaction at 68° C. for 3 minutes.

The resulting amplification product was subjected to gel electrophoresis, and a fragment of about 0.8 kb was excised, purified by QIAquick Gel Extraction Kit (Qiagen) and reacted by using primer m212A1 (SEQ ID NO. 144), primer m212B1 (SEQ ID NO. 145) and BigDye Terminator Cycle Sequencing Kit (Applied Biosystems), and the base sequence of the product amplified by PCR was determined by DNA sequencer ABI PRISM 3100 DNA analyzer (Applied Biosystems). As a result, a partial sequence of rat TCH212 gene cDNA having a 771-base sequence represented by SEQ ID NO. 149 was identified.

Example 32

Analysis of Distribution of Rat TCH212 Gene Product in Tissues

Using two primer DNAs, i.e. primer r212TF (SEQ ID NO. 150) and primer r212TR (SEQ ID NO. 151), designed from the base sequence represented by SEQ ID NO: 149, and TaqMan probe r212T1 (SEQ ID NO. 152), the expression level (copy number) of rat TCH212 by the cDNA prepared in Example 17 in each rat tissue was measured by TaqMan PCR. The same cDNA was also measured for the expression level (copy number) of rodent glyceraldehyde-3-phosphate dehydrogenase (GAPDH) by using TaqMan rodent GAPDH control reagents (Applied Biosystems). The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 23:
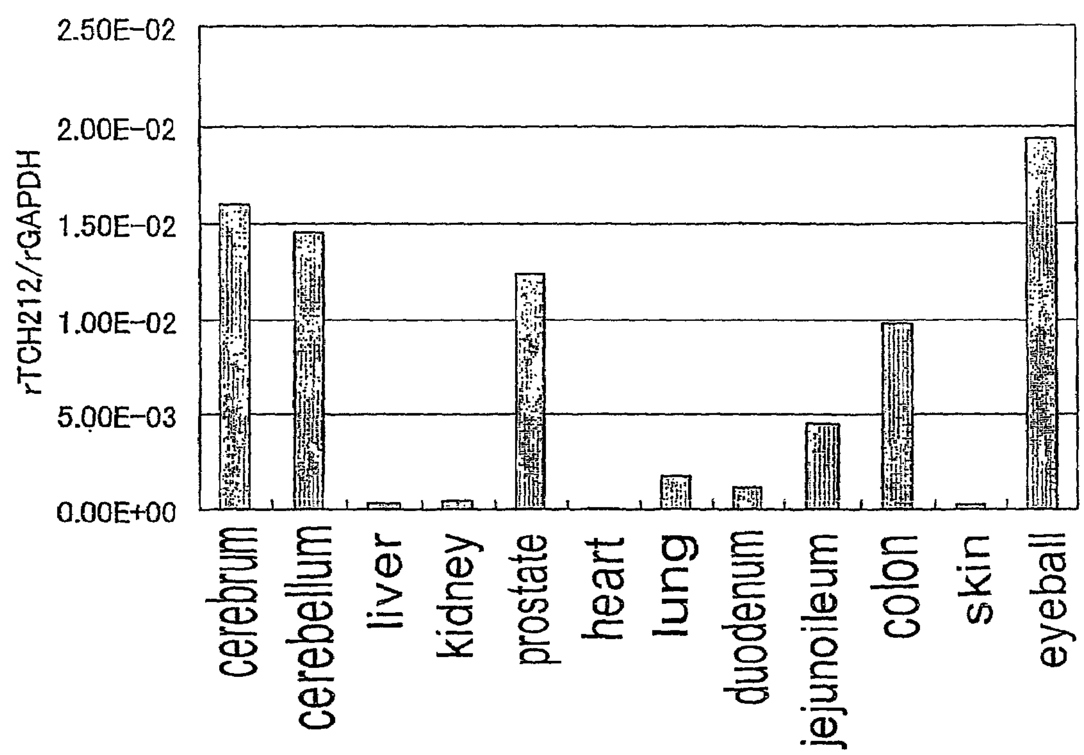
FIG. 23 shows the expression level of rat TCH212 gene product in each tissue. The expression level is represented as (copy number of rat TCH212 per μl of cDNA solution)/(copy number of rodent GAPDH by equivalent amount of tissue cDNA).

The results are shown in FIG. 23.

In all tissues in 12-week-old Wistar rat, the rat TCH212 gene product (mRNA) was expressed; particularly in the lung, duodenum and jejunoileum, certain expression was observed, and in the cerebrum, cerebellum, prostate, colon and eyeball, high expression was observed.

Example 33

Construction of Human TCH212 (SEQ ID NO:42) Expression Vector

Human TCH212 (SEQ ID NO: 42) expression vector was constructed by the following method.

Using 10 ng of plasmid obtained in Example 7 as a template, PCR was conducted with primer 2120F (SEQ ID NO. 153) and primer 2120R (SEQ ID NO. 154) and KOD DNA Polymerase (Toyobo) under the following conditions (1) to (3). The 5'-terminal side primer 2120F and the 3'-terminal side primer 2120R were designed such that BamH I site and Not I site were added respectively to the 5'-terminal side for cloning into a vector.

(1) reaction at 94° C. for 2 minutes, (2) 35 cycles each consisting of reaction at 94° C. for 15 seconds, at 60° C. for 30 seconds and at 68° C. for 3.5 minutes, and (3) reaction at 68° C. for 3 minutes.

The PCR reaction solution was subjected to gel electrophoresis, and a major band was purified. The PCR fragment thus obtained was digested with restriction enzymes Bam HI and Not I at 37° C. for 1 hour, and the reaction solution was subjected to gel electrophoresis and purified. The product was ligated to Bam HI site and Not I site of an animal cell expression vector pcDNA3.1(+) (Invitrogen, Inc.) by using Takara ligation kit ver. 2 (Takara Bio). This ligation reaction solution was used to transform a competent cell *Escherichia coli* JM109 (Takara Bio).

From a plurality of colonies thus obtained, a plasmid was prepared, and with respect to 2 clones wherein a fragment of about 3.5 kbp was confirmed to be inserted, the base sequence was reacted by using primer DNAs [primer BGH RV (SEQ ID NO. 124), primer T7 (SEQ ID NO: 8), primer A2 (SEQ ID NO: 48), primer B1 (SEQ ID NO: 49), primer B2 (SEQ ID NO: 50), primer F1 (SEQ ID NO: 51), primer F2 (SEQ ID NO: 52), primer F3 (SEQ ID NO: 53), primer F4 (SEQ ID NO: 54), primer F5 (SEQ ID NO: 55), primer R1 (SEQ ID NO: 56), primer R2 (SEQ ID NO: 57), primer R3 (SEQ ID NO: 58), primer R4 (SEQ ID NO: 59)] and BigDye Terminator Cycle Sequencing Kit (Applied Biosystems), and the base sequence was determined by DNA sequencer ABI PRISM 3100 DNA analyzer (Applied Biosystems). As a result, one-base substitution was observed in both the clones as compared with SEQ ID NO: 43. That is, in "clone 1", C at position 1185 in SEQ ID NO: 43 was changed into A, and in "clone 2", A at position 2509 was changed into T, and the change in both cases was a change to a termination codon on the frame.

Accordingly, the following correction was conducted. To introduce a termination codon on the same frame into an upstream from an initiation codon, the plasmid DNA in "clone 2" was cleaved with Nhe I, blunt-ended, re-cyclized by ligation and introduced into *Escherichia coli* JM109. The plasmid DNA in the resulting "modified clone 2" was cleaved with Bst EII and Not I, to remove a DNA fragment (about 1.1 kbp) having the one-base substitution at position 2509. Separately, the plasmid DNA in "clone 1" was cleaved with Bst EII and Not I to prepare a DNA fragment (about 1.1 kbp) of predetermined sequence. The above 2 DNA fragments were ligated and introduced into *Escherichia coli* JM109. After transformation, the transformant was cultured on agar medium at 30° C. for 2 days, and from a colony appearing on the second day, plasmid was extracted. This clone was determined for its base sequence in the same manner as described above, and confirmed to agree with SEQ ID NO: 43. The transformant having this plasmid was designated *Escherichia coli* JM109/pCDNA3.1 (+)-NheBlunt-TCH212.

Example 34

Identification of a Partial Sequence of Mouse TCH 200 Gene

Using two primer DNAs, i.e. primer m200A1 (SEQ ID NO. 156) and primer m200B1 (SEQ ID NO. 157), the mouse skin cDNA prepared in Example 15 was subjected to PCR with Advantage 2 DNA Polymerase (Clontech) under the following conditions (1) to (5):

(1) reaction at 94° C. for 3 minutes, (2) 5 cycles each consisting of reaction at 94° C. for 5 seconds and at 72° C. for 1 minute, (3) 5 cycles each consisting of reaction at 94° C. for 5 seconds and at 70° C. for 1 minute, (4) 25 cycles each consisting of reaction at 94° C. for 5 seconds and at 68° C. for 1 minute, and (5) reaction at 70° C. for 10 minutes.

The resulting amplification product was subjected to gel electrophoresis, and a fragment of about 1.1 kb was excised and purified by QIAquick Gel Extraction Kit (Qiagen). The purified product was reacted by using primer m200A1 (SEQ ID NO. 156), primer m200B1 (SEQ ID NO. 157) and BigDye Terminator Cycle Sequencing Kit (Applied Biosystems), and the base sequence of the product amplified by PCR was determined by DNA sequencer ABI PRISM 3100 DNA analyzer (Applied Biosystems). From the determined sequence, two primer DNAs, i.e. primer m200A2 (SEQ ID NO. 158) and primer m200B2 (SEQ ID NO. 159) were designed and used in determination of the base sequence of the PCR amplification product. As a result, a partial sequence of mouse TCH200 gene cDNA having a 1064-base sequence represented by SEQ ID NO. 155 was identified.

Example 35

Analysis of Distribution of Mouse TCH200 Gene Product in Tissues

The expression level (copy number) of mouse TCH200 by the cDNA prepared in Example 15 in each mouse tissue was measured by TanMan PCR with TaqMan probe m200T1 (SEQ ID NO. 160) designed from the base sequence represented by SEQ ID NO. 155, and two primer DNAs, i.e. primer m200A2 (SEQ ID NO. 158) and primer m200B2 (SEQ ID NO. 159) used in Example 34. The same cDNA was also measured for the expression level (copy number) of rodent glyceraldehyde-3-phosphate dehydrogenase (GAPDH) by using TaqMan rodent GAPDH control reagents (Applied Biosystems). The PCR reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

Figure 24:
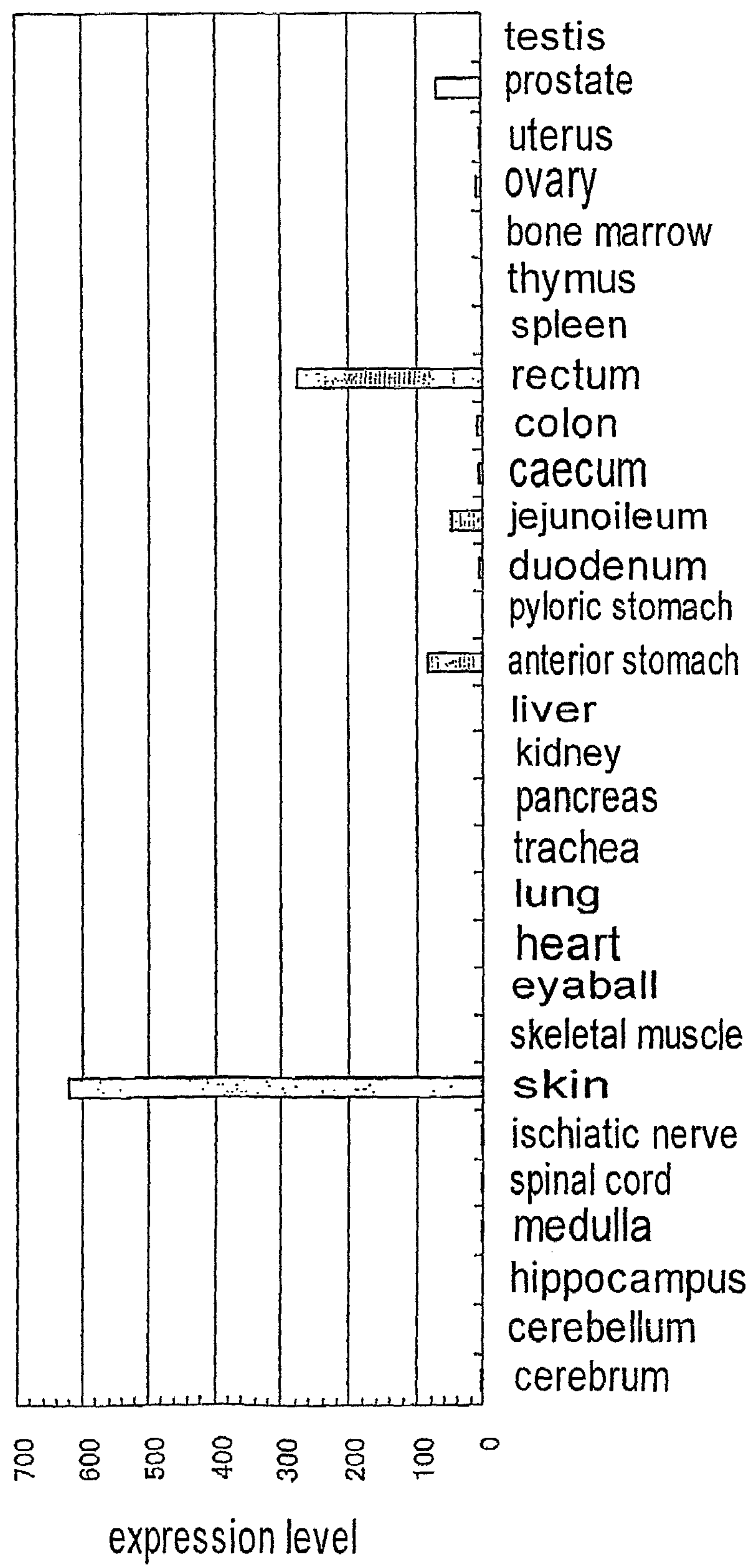
FIG. 24 shows the expression level of mouse TCH200 gene product in each tissue. The expression level is represented as ((copy number of mouse TCH200 per μl of cDNA solution)/(copy number of rodent GAPDH by equivalent amount of tissue cDNA)×100,000)).

The results are shown in FIG. 24.

In each tissue in 7-week-old BALB/c mouse, the mouse TCH200 gene product (mRNA) was expressed at a certain degree in the cerebrum, medulla oblongata, spinal cord, ischiatic nerve, duodenum, caecum, colon, ovary and uterus, expressed highly in the anterior stomach, jejunoileum and prostate and expressed most highly in the skin and rectum.

Example 36

Construction of Human TCH200 (SEQ ID NO:66) Expression Vector

Human TCH200 (SEQ ID NO: 66) expression vector was constructed by the following method.

Using the plasmid obtained in Example 11 as a template, PCR was conducted with primer TCH200F (SEQ ID NO. 161) and primer TCH200R (SEQ ID NO. 162) and Pyrobest DNA Polymerase (Takara Bio) under the following conditions (1) to (5). The 5'-terminal side primer TCH200F and the 3'-terminal side primer TCH200R were designed such that Kpn I site and Not I site were added respectively to the 5'-terminal side for cloning into a vector.

(1) reaction at 98° C. for 5 seconds, (2) 2 cycles each consisting of reaction at 98° C. for 5 seconds and at 68° C. for 290 seconds, (3) 23 cycles each consisting of reaction at 98° C. for 5 seconds and at 66° C. for 290 seconds, (4) 3 cycles each consisting of reaction at 98° C. for 5 seconds and at 64° C. for 290 seconds, and (5) reaction at 72° C. for 7 minutes.

The PCR reaction solution was subjected to gel electrophoresis, and a major band was purified. The PCR fragment thus obtained was digested with restriction enzymes KpnI and NotI at 37° C. for 1 hour, and the reaction solution was subjected to gel electrophoresis and purified. The product was ligated to KpnI site and NotI site of an animal cell expression vector pcDNA3.1 (+) (Invitrogen, Inc.) by using Takara ligation kit ver. 2 (Takara Bio). This ligation reaction solution was used to transform *Escherichia coli* JM109 (Takara Bio) by the heat shock method. From a plurality of colonies thus obtained, plasmid was prepared, and this base sequence was reacted with primer DNAs [primer T7 (SEQ ID NO. 163), primer AF (SEQ ID NO. 164), primer BF (SEQ ID NO. 165), primer CF (SEQ ID NO. 166), primer DF (SEQ ID NO. 167), primer BGH RV (SEQ ID NO. 168), primer DR (SEQ ID NO. 169), primer CR (SEQ ID NO. 170), primer BR (SEQ ID NO. 171), primer AR (SEQ ID NO. 172)] and BigDye Terminator Cycle Sequencing Kit (Applied Biosystems), and the base sequence was confirmed by DNA sequencer ABI PRISM 3100 DNA analyzer (Applied Biosystems). The transformant having this plasmid was designated *Escherichia coli* JM109/pCDNA3.1(+)/TCH200.

Example 37

Preparation of Human TCH200 (SEQ ID NO:66)-Expressing CHO Cell Strain and Measurement of the Expression Level of the Introduced Gene The *Escherichia coli* JM109/pCDNA3.1(+)/TCH200 was cultured, and from the *Escherichia coli*, plasmid DNA was prepared by using EndoFree Plasmid Maxi Kit (Qiagen). This plasmid DNA was introduced into CHO-K1 cell by Nucleofector (Amakusa) and Cell Line Nucleofector Kit T (Amakusa) according to their attached protocol. The CHO-K1 cells at a density of $1\times10^6$ were suspended at ordinary temperature in 100 μl of solution T to which supplements attached to the kit had been added, and then 2 μg of plasmid DNA was mixed with the resulting suspension and introduced into a cuvette and subjected to Nucleofetor program U-27. Immediately, 500 μl of RPMI1640 medium (Nikken Seibutsu Igaku Kenkyusho) containing 10% fetal bovine serum (ICN Biomedicals), which has been pre-warmed at 37° C., was added thereto, and 1 ml of Ham's F12 medium (Nikken Seibutsu Igaku Kenkyusho) containing 10% fetal bovine serum was added thereto, and the suspension was dropped onto a 6-well plate, which has been pre-warmed at 37° C., and cultured. After 3 days, the medium was replaced with the medium containing 0.4 mg/ml geneticine (Invitrogen, Inc.) to initiate selection of human TCH200 (SEQ ID NO:66) expression cells. Four days after selection was initiated, the transfected cells were peeled off, and the recovered cells were inoculated at a density of 100 cells/well in FBS-Ham's F12 medium containing 10% bovine fetal serum in a 24-well plate. After 4 days, the number of colonies grown in each well and the approximate number of cells per colony were measured, whereby the number of cells per well was calculated, and on the basis of this number, the cells were inoculated such that one cell was put in one well on a 96-well plate, to order to produce a monoclonal cell expressing human TCH200 (SEQ ID NO:66).

From the grown monoclonal cells expressing human TCH200 (SEQ ID NO:66), total RNA was prepared by RNeasy 96 Kit (Qiagen). The prepared total RNA was subjected to reverse transcription reaction by TaqMan Reverse Transcription Reagents (Applied Biosystems) to prepare cDNA. The cDNA was measured for the expression level of human TCH200 (SEQ ID NO:66) by TaqMan PCR with primer TMF (SEQ ID NO: 94) and primer TMR (SEQ ID NO: 95) used in Example 12 and TaqMan probe P1 (SEQ ID NO: 96).

The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out. As a cell strain highly expressing human TCH200 (SEQ ID NO:66) gene, clone No. G10 was selected.

Example 38

Analysis of Expression of Human TCH230 (SEQ ID NO:1), Human TCH234 (SEQ ID NO:18), Human TCH212 (SEQ ID NO:42) and Human TCH200 (SEQ ID NO:66) Gene in Commercial Normal Human Cells (1) Preparation of Normal Human Cell cDNA Normal human cells were purchased from Cambrex BioScience Walkersvill and cultured according to a method attached to the product. The cells used in the experiment and the mediums used in culturing the cells are shown in Table 3.

TABLE 3

| No. | Cell | Medium |
|---|---|---|
| 1 | Umbilical cord vein endothelial cell C-2517 | Bullet Kit EGM CC-3124 |
| 2 | Main artery endothelial cell CC-2535 | Bullet Kit EGM-2 CC-3162 |
| 3 | Coronary artery endothelial cell CC-2585 | Bullet Kit EGM-2MV CC-3202 |
| 4 | Main artery smooth muscle cell CC-2571 | Bullet Kit SmGM-2 CC-3182 |
| 5 | Coronary artery smooth muscle cell CC-2583 | Bullet Kit SmGM-2 CC-3182 |
| 6 | Uterus smooth muscle cell CC-2562 | Bullet Kit SmGM-2 CC-3182 |
| 7 | Bronchial smooth muscle cell CC-2576 | Bullet Kit SmGM-2 CC-3182 |
| 8 | Skeletal muscle satellite cell CC-2561 | Bullet Kit SkGM CC-3160 |
| 9 | Mammary gland epithelial cell CC-2551 | Bullet Kit MEGM CC-3150 |
| 10 | Bronchial epithelial cell (with RA) CC-2540 | Bullet Kit SAGM CC-3118 |
| 11 | Bronchial epithelial cell (without RA) CC-2541 | Bullet Kit SAGM CC-3118 |
| 12 | Lung fibroblast CC-2512 | Bullet Kit FGM-2 CC-3132 |
| 13 | Kidney proximal urine tubule epithelial cell CC-2553 | Bullet Kit REGM CC-3190 |
| 14 | Mesangial cell CC-2559 | Bullet Kit MsGM CC-3146 |
| 15 | Kidney cortex epithelial cell CC-2554 | Bullet Kit REGM CC-3190 |
| 16 | Mesenchyme stem cell PT-2501 | Bullet Kit MSCGM PT-3001 |
| 17 | Knee joint cartilage cell CC-2550 | Bullet Kit CGM CC-3216 |
| 18 | Osteoblast CC-2538 | Bullet Kit OGM CC-3207 |

Each cell was cultured in a 75 $cm^2$ culture flask until the cell became subconfluent, and the cells were recovered by treatment with trypsin-EDTA. From the recovered cells, total RNA was prepared by using ISOGEN (Nippon Gene) or RNeasy Mini Kit (Qiagen) (in either case, contaminant DNA was removed by treatment with DNase). The prepared total RNA was subjected to reverse transcription reaction with TaqMan Reverse Transcription Reagents (Applied Biosystems) to prepare cDNA.

(2) Analysis of Expression of Human TCH230 (SEQ ID NO:1), Human TCH234 (SEQ ID NO:18), Human TCH212 (SEQ ID NO:42) and Human TCH200 (SEQ ID NO:66) Genes in the Commercial Normal Human Cells The expression level (Ct value) of each cDNA was measured in the following manner by using TaqMan PCR. Primer TF (SEQ ID NO. 15) and primer TR (SEQ ID NO. 16) used in Example 2 and TaqMan probe T1 (SEQ ID NO. 17) were used for human TCH230 (SEQ ID NO:1); primer TMF (SEQ ID NO: 32) and primer TMR (SEQ ID NO: 33) used in Example 6 and TaqMan probe P1 (SEQ ID NO: 38) were used for human TCH234 (SEQ ID NO:18); primer TF (SEQ ID NO: 63) and primer TR (SEQ ID NO: 64) used in Example 8 and TaqMan probe T1 (SEQ ID NO: 65) were used for human TCH212 (SEQ ID NO:42); and primer TMF (SEQ ID NO: 94) and primer TMR (SEQ ID NO: 95) used in Example 12 and TaqMan probe P1 (SEQ ID NO: 96) were used for human TCH200 (SEQ ID NO:66). The same cDNA was also examined for the expression level (Ct value) of glyceraldehyde-3-phosphate dehydrogenase (GAPDH) by using TaqMan GAPDH control reagents (Applied Biosystems). The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

On the basis of measurements obtained by the above method, the relative expression level of each TCH gene (human TCH230 (SEQ ID NO:1), human TCH234 (SEQ ID NO:18), human TCH212 (SEQ ID NO:42) and human TCH200 (SEQ ID NO:66)) to GAPDH was calculated according to the following equation:

$$\text{Relative expression level} = \tfrac{1}{2}^{A-B}$$

wherein A represents the Ct value of human TCH230 (SEQ ID NO:1) gene, human TCH234 (SEQ ID NO:18) gene, human TCH212 (SEQ ID NO:42) gene or human TCH200 (SEQ ID NO:66) gene, and B represents the Ct value of GAPDH gene.

Figure 25:
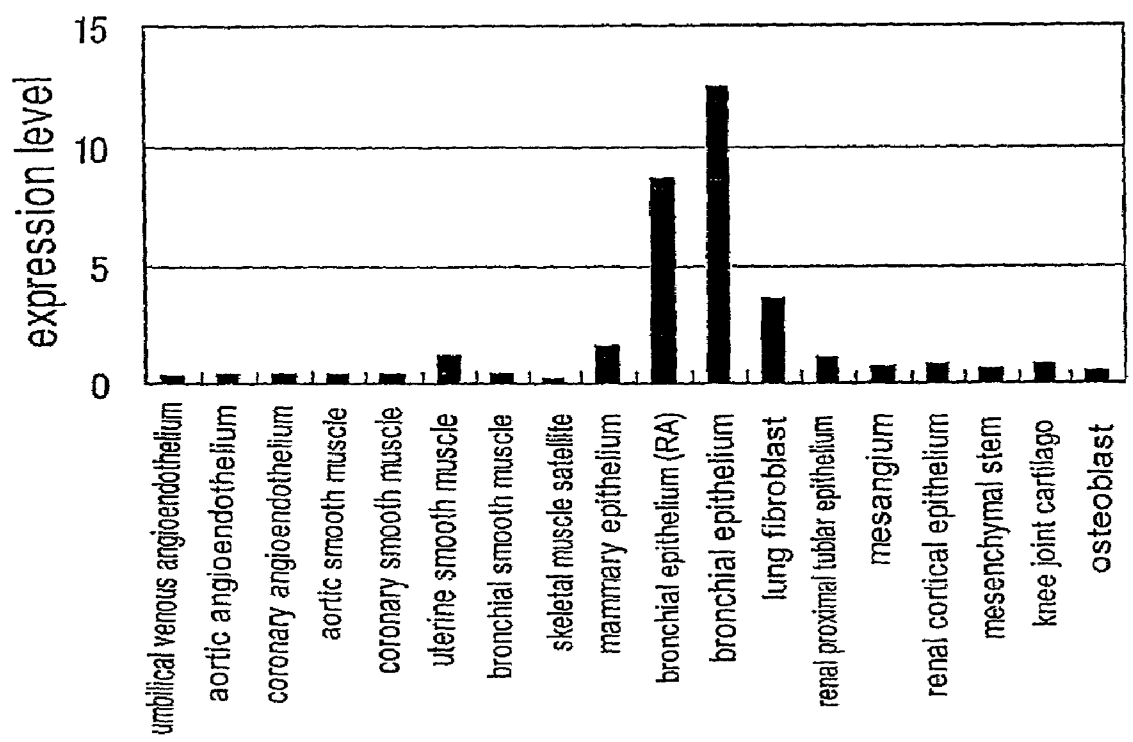
FIG. 25 shows the expression level of human TCH230 (SEQ ID NO:1) gene product in normal cells. The expression level is represented as (relative expression amount×10,000).

The result of human TCH230 (SEQ ID NO:1) gene is shown in FIG. 25.

Human TCH230 was expressed at a certain degree in the main artery endothelial cell, coronary artery endothelial cell, main artery smooth muscle cell, coronary artery smooth muscle cell, uterus smooth muscle cell, mammary gland epithelial cell, lung fibroblast, kidney proximal urine tubule epithelial cell, mesangial cell, kidney cortex epithelial cell, knee joint cartilage cell and osteoblast and expressed strongly in the bronchial epithelial cell (with RA) and bronchial epithelial cell (without RA).

Figure 26:
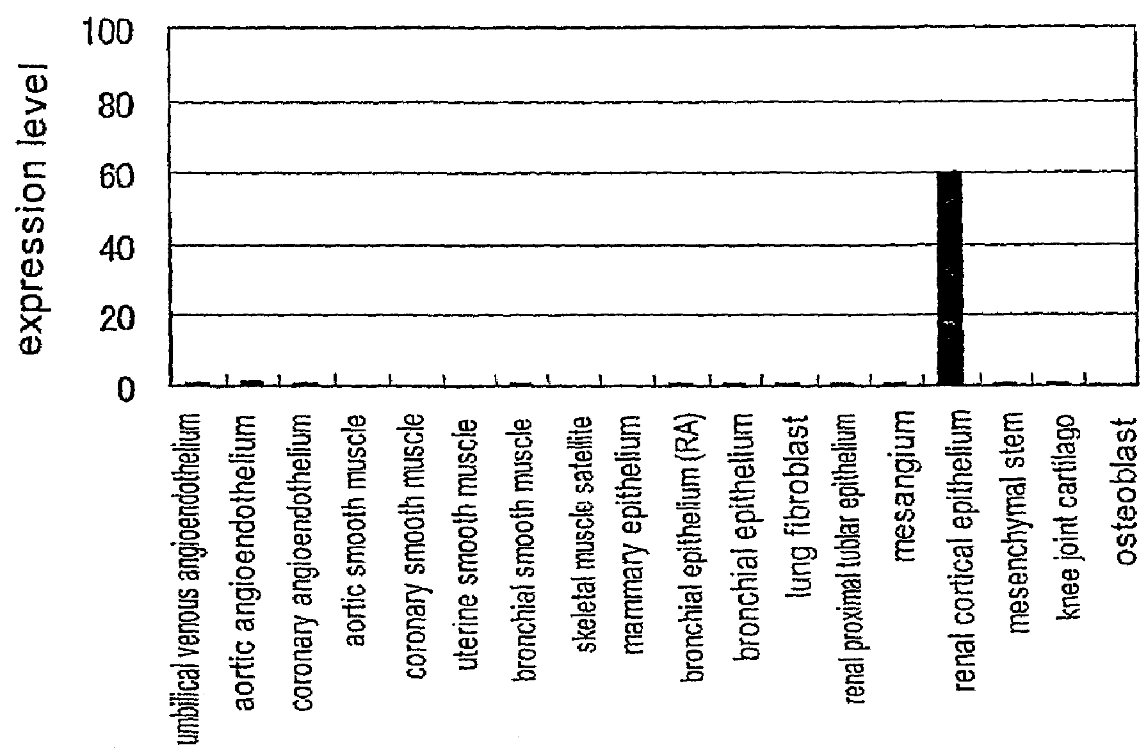
FIG. 26 shows the expression level of human TCH234 (SEQ ID NO:18) gene product in normal cells. The expression level is represented as (relative expression amount×10,000).

The result of human TCH234 (SEQ ID NO:18) gene is shown in FIG. 26.

Human TCH234 was expressed at a certain degree in the main artery endothelial cell, coronary artery endothelial cell and kidney proximal urine tubule epithelial cell and expressed particularly strongly in the kidney cortex epithelial cell.

Figure 27:
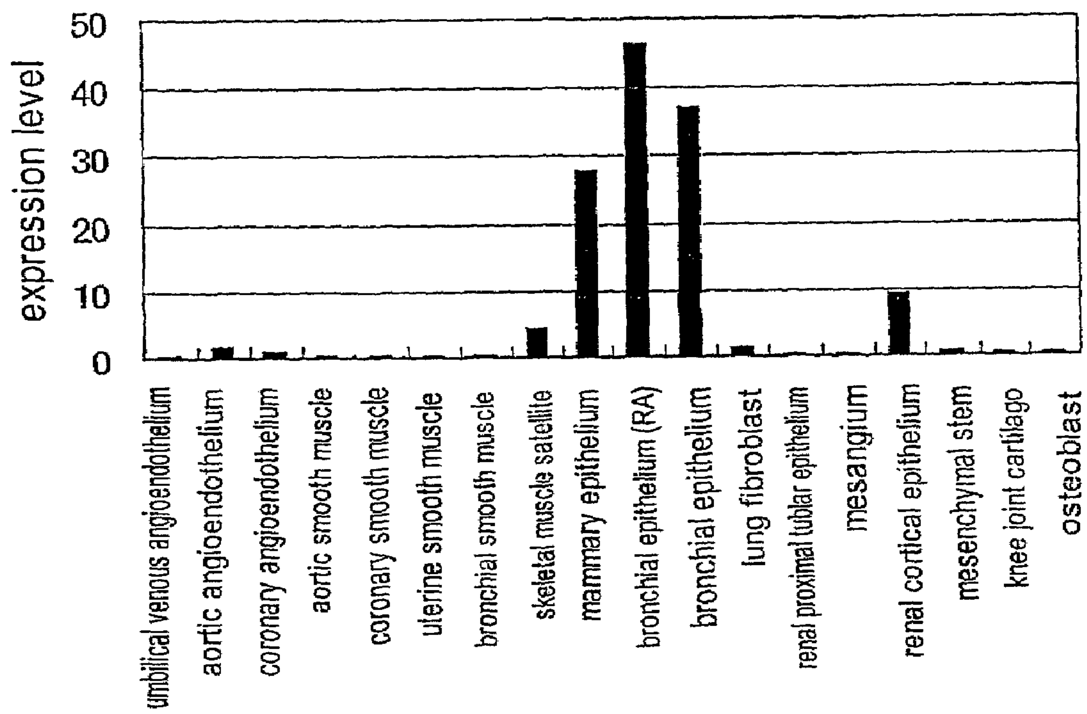
FIG. 27 shows the expression level of human TCH200 (SEQ ID NO:66) gene product in normal cells. The expression level is represented as (relative expression amount×10,000).

The result of human TCH200 (SEQ ID NO:66) gene is shown in FIG. 27.

Human TCH200 was expressed at a certain degree in the main artery endothelial cell, coronary artery endothelial cell, main artery smooth muscle cell, skeletal muscle satellite cell and lung fibroblast, expressed strongly in the kidney cortex epithelial cell, and expressed particularly strongly in the mammary gland epithelial cell, bronchial epithelial cell (with RA) and bronchial epithelial cell (without RA).

Human TCH212 was not expressed in any cells.

Example 39

Analysis of Expression of Mouse TCH234 and Mouse TCH212 (SEQ ID NO:143) Gene Products in the Lung of Chronic Obstructive Pulmonary Disease (COPD) Model Mouse (1) Preparation of COPD Model Mouse by Exposure to Cigarette Smoke and Preparation of Lung cDNA A COPD model was prepared by giving mainstream smoke generated from Kentucky Reference Cigarette 1R1 to C57BL/6N mice (6-week-old, Charles River Japan) for 1 to 4 hours/day at the interval of 5 days/week for 6 months in total. That is, Kentucky Reference Cigarette 1R1 was attached to a cigarette smoke generator (SG-200, Shibata Kagaku), and mainstream smoke was collected under the condition of 35 ml/puff, 10 puff/min, and 25 puff/cigarette. The obtained mainstream smoke was diluted to a density of 3% (V/V) with air, and then sent to an acrylic exposure chamber where mice were present, and the cigarette smoke was given to the mice under spontaneous respiration. As a control group, normal mice were used.

On the day after final exposure was finished, the mice were killed under pentobarbital anesthesia, and after washing bronchial pulmonary alveoli, lungs were removed. The removed lungs were frozen in liquid nitrogen, then milled with a frozen-tissue milling device, and immersed in ISOGEN (Nippon Gene) in a 10-fold excess amount relative to the wet lungs. From a group exposed to cigarette smoke for 1 month (n=10), its control group (n=6), a group exposed to cigarette smoke for 3 months (n=8), its control group (n=8), a group exposed to cigarette smoke for 6 months (n=8), and its control group (n=8), total RNA was extracted by using ISOGEN according to its attached manual. Contaminant DNA was removed by using QIAGEN RNeasy Mini Kit (Qiagen) and RNase-Free DNAse set (Qiagen). The prepared total RNA was subjected to reverse transcription reaction with TaqMan Reverse Transcription Reagents (Applied Biosystems) to prepare cDNA.

(2) Analysis of Expression of Mouse TCH234 Gene Product in COPD Model Mouse Lung Using two primer DNAs, i.e. primer m234-TMF (SEQ ID NO. 128) and primer m234-TMR (SEQ ID NO. 129) used in Example 22 and TaqMan probe m234T1 (SEQ ID NO. 130), the expression level (Ct value) of mouse TCH234 by the COPD model mouse lung cDNA prepared in (1) above was measured by TaqMan PCR. The same cDNA was also measured for the expression level (Ct value) of 18S rRNA by using Eukaryotic 18S rRNA Pre-Developed TaqMan Assay Reagents (Applied Biosystems). The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

On the basis of measurements obtained by the above method, the relative expression level of mouse TCH234 to 18S rRNA was calculated according to the following equation:

$$\text{Relative expression level} = \tfrac{1}{2}^{A-B}$$

wherein A represents the Ct value of mouse TCH234 gene, and B represents the Ct value of 18S rRNA gene.

In statistical analysis, SAS software (manufactured by SAS) was used, and $p<0.05$ was regarded as significant in Student's t test.

Figure 28:
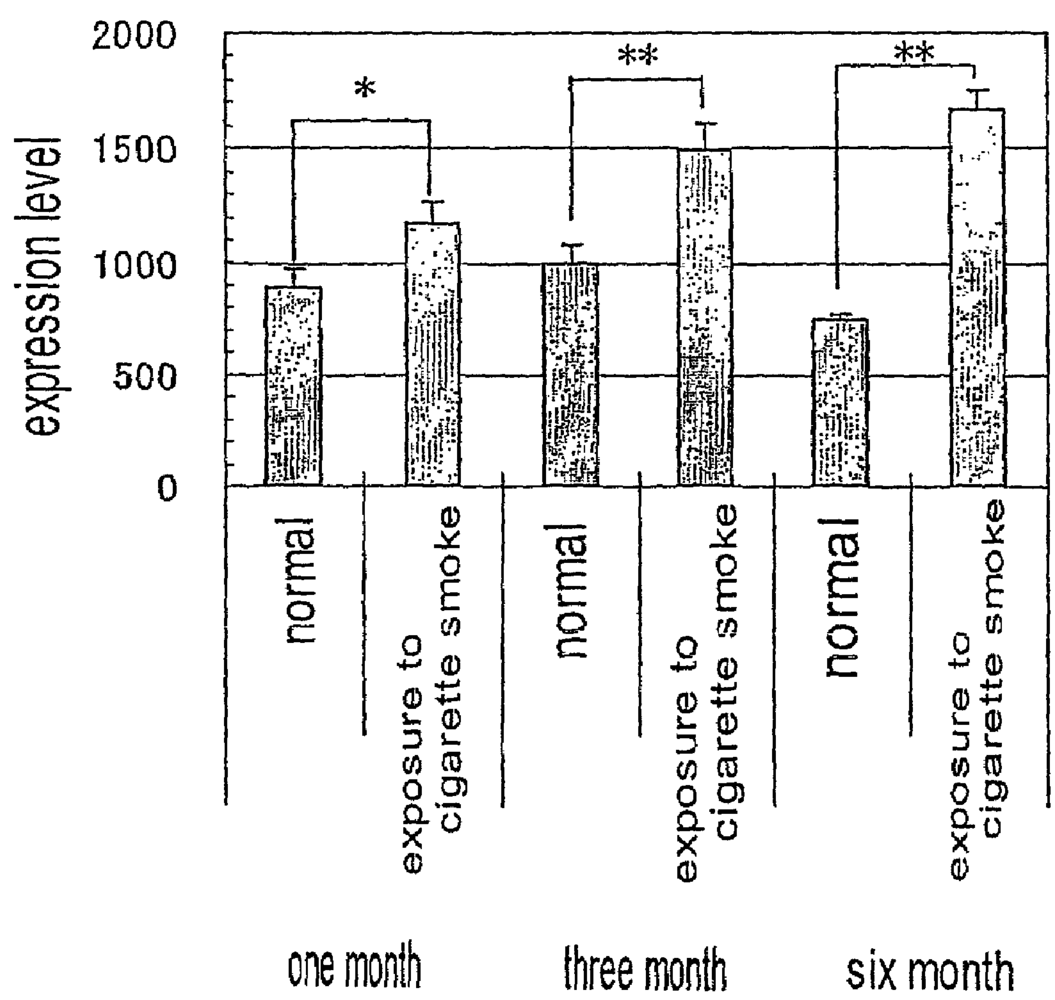
FIG. 28 shows the expression level of mouse TCH234 gene product in COPD model mouse lung. The expression level is represented as (relative expression amount×100,000,000). The result shows the average and standard error in each group.

The result is shown in FIG. 28.

In the lungs of COPD model mice in all the groups exposed to cigarette smoke for 1, 3 and 6 months, a significant increase in expression was observed (1 month, p=0.0415; 3 months, p=0.0058; 6 months, p=0.0001). From this result, TCH234 was considered to participate in respiratory diseases such as COPD.

(3) Analysis of Expression of Mouse TCH212 (SEQ ID NO:143) Gene Product in COPD Model Mouse Lung Using two primer DNAs, i.e. primer m212TF (SEQ ID NO. 146) and primer m212TR (SEQ ID NO. 147) used in Example 30 and TaqMan probe m212T1 (SEQ ID NO. 148), the expression level (Ct value) of mouse TCH212 (SEQ ID NO:143) in the COPD model mouse lung cDNA prepared in (1) above was measured by TaqMan PCR, and the relative expression to 18S rRNA was calculated in the same manner as in (2) above. Statistical analysis was conducted in the same manner as in (2) above.

Figure 29:
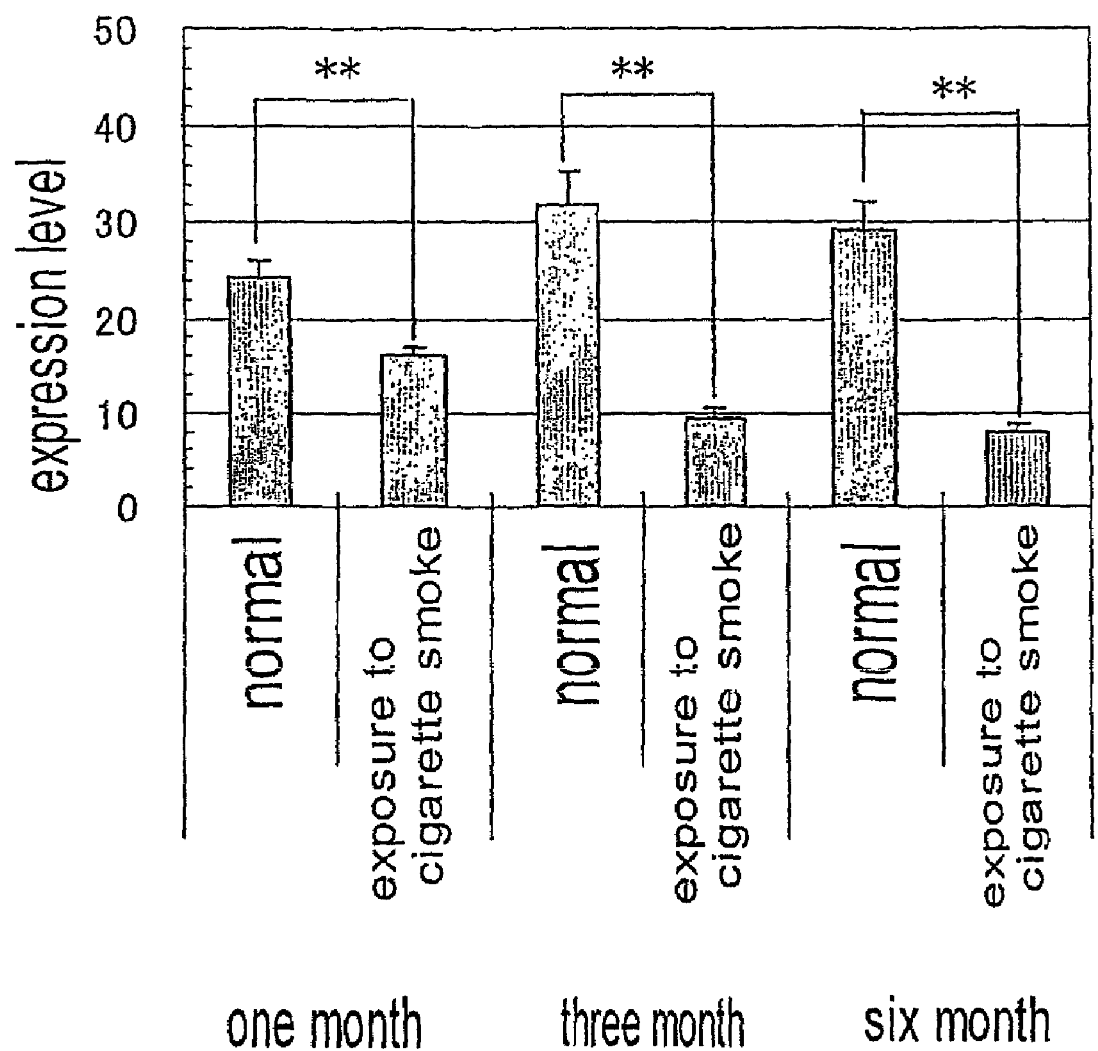
FIG. 29 shows the expression level of mouse TCH212 (SEQ ID NO:143) gene product in COPD model mouse lung. The expression level is represented as (relative expression amount×100,000,000). The result shows the average and standard error in each group.

The results are shown in FIG. 29. In the lungs of COPD model mice in all the groups exposed to cigarette smoke for 1, 3 and 6 months, a significant decrease in expression was observed (1 month, p=0.0014; 3 months, p=0.0004; 6 months, p=0.0001). From this result, TCH212 was considered to participate in respiratory diseases such as COPD.

Example 40

Analysis of Expression of Mouse TCH230 (SEQ ID NO:112) Gene Product in the Large Intestine in Colitis Model Mice (1) Preparation of Colitis Model Mice by Administration of DSS and Preparation of Large Intestine cDNA Colitis model mice were prepared by administering DSS (Dextran Sulfate Sodium 5000, Wako Pure Chemical Industries, Ltd.) into BALB/cA mice (male, 6-week-old, Nippon Clea).

That is, the mice were allowed 5% DSS solution ad libitum, and on the second day when the symptom of diarrhea appeared and on the seventh day when bleeding also appeared, the animals were slaughtered in a carbon dioxide gas, and a part of the large intestine (5 cm from the anal verge) was excised. As a control group, normal mice were used. The removed large intestines from 3 mice were washed with physiological saline and extracted by using ISOGEN (Nippon Gene) according to its attached manual, to give total RNA. Contaminant DNA was removed by using QIAGEN RNeasy Mini kit and RNase-Free DNAse set (Qiagen). The prepared total RNA was subjected to reverse transcription reaction with TaqMan Reverse Transcription Reagents (Applied Biosystems) to prepare cDNA.

(2) Analysis of Expression of Mouse TCH230 (SEQ ID NO:112) Gene Product in Colitis Model Mouse Large Intestine Using two primer DNAs, i.e. primer m230TF (SEQ ID NO. 113) and primer m230TR (SEQ ID NO. 114) used in Example 14 and TaqMan probe m230T1 (SEQ ID NO. 115), the expression level (Ct value) of mouse TCH230 (SEQ ID NO:112) by the colitis model mouse large intestine cDNA prepared in (1) above was measured by TaqMan PCR. The same cDNA was also measured for the expression level (Ct value) of 18S rRNA by using eukaryotic 18S rRNA Pre-Developed TaqMan Assay Reagents (Applied Biosystems). The reaction involved a reaction at 50° C. for 2 minutes and at 95° C. for 10 minutes and 40 cycles each consisting of a reaction at 95° C. for 15 seconds and at 60° C. for 1 minute by using TaqMan Universal PCR Master Mix (Applied Biosystems) in ABI PRISM 7900 sequence detection system (Applied Biosystems), and simultaneously detection was carried out.

On the basis of measurements obtained by the above method, the relative expression level of mouse TCH230 (SEQ ID NO:112) to 18S rRNA was calculated according to the following equation:

$$\text{Relative expression level}=\tfrac{1}{2}^{A-B}$$

wherein A represents the Ct value of mouse TCH230 (SEQ ID NO:112) gene, and B represents the Ct value of 18S rRNA gene.

Figure 30:
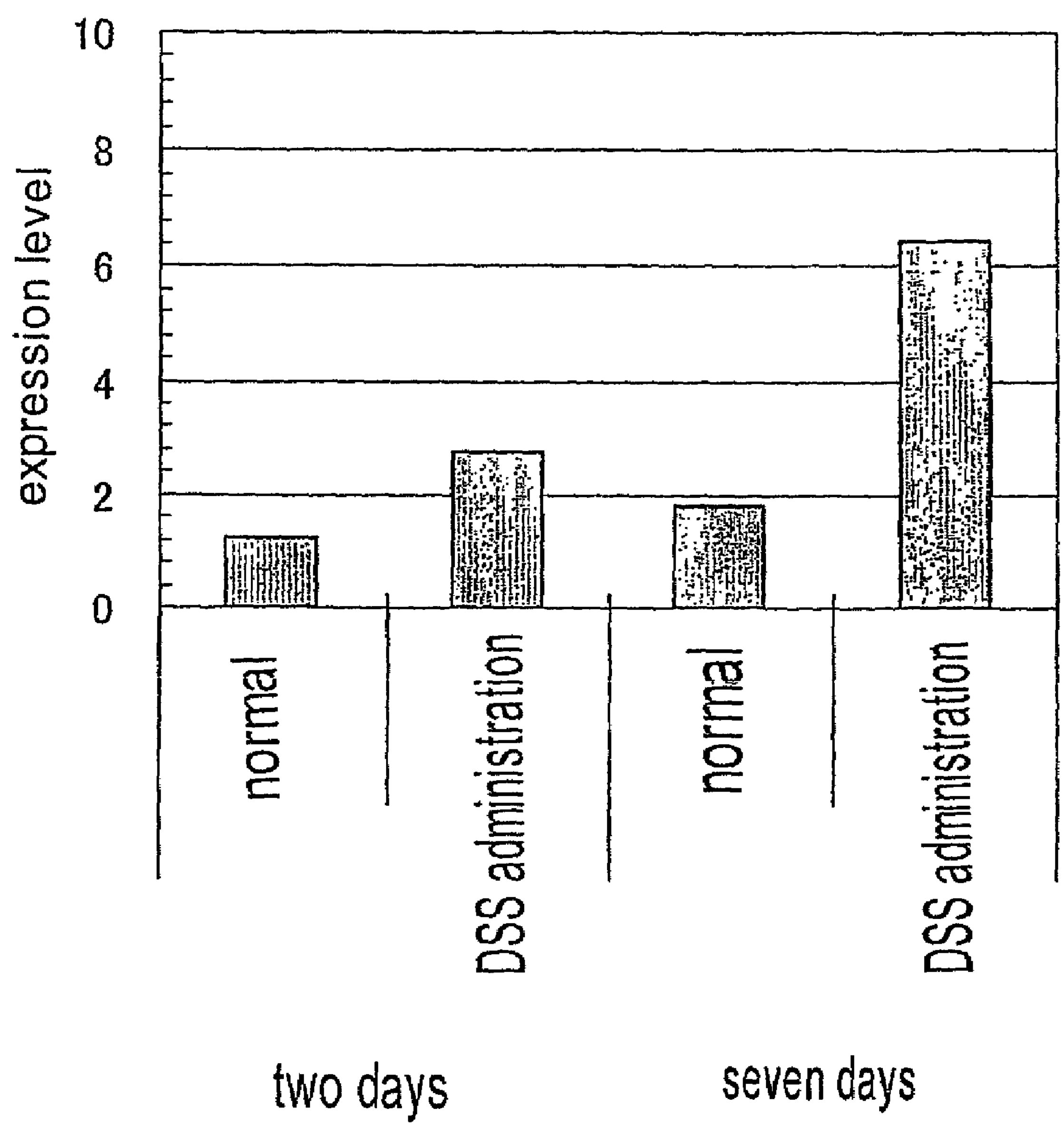
FIG. 30 shows the expression level of mouse TCH230 (SEQ ID NO:112) gene product in the large intestine of colitis model mouse. The expression level is represented as (relative expression amount×10,000,000). The result shows the average of duplicate measurements by independent TaqMan PCR.

The result is shown in FIG. 30.

An increase in expression of mouse TCH230 (SEQ ID NO:112) was observed on both the second and seventh days in the large intestines of colitis model mice given DSS. From this result, TCH230 was considered to participate in colitis such as ulcerous colitis, Crohn's disease and ischemic colitis.

INDUSTRIAL APPLICABILITY

The protein A of the present invention, the polynucleotide encoding the same, the antibody thereto, and the antisense polynucleotide are useful as diagnostic markers etc. for diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc. The protein A of the present invention, the polynucleotide encoding the same and the antibody thereto are useful for screening a compound or a salt thereof that promotes or inhibits the activity of the protein, a compound or a salt thereof that promotes or inhibits the expression of the gene for the protein, and a compound or a salt thereof that promotes or inhibits the expression of the protein. The compound or a salt thereof that promotes or inhibits the activity of the protein, the compound or a salt thereof that promotes or inhibits the expression of the gene for the protein, etc., can be used as prophylactic/therapeutic agents for diseases such as hyperlipemia, genital diseases (e.g., prostatic hypertrophy, prostatitis, testis neurosis, ovarian cystoma etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, bronchial asthma etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), diabetes, hypothyroidism, circulatory diseases (e.g., cardiac insufficiency, arrhythmia, long QT syndrome, arteriosclerosis, angina etc.), pancreatic diseases (e.g., pancreatic function insufficiency such as pancreatitis, pancreatic cystic fibrosis etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably hyperlipemia, arteriosclerosis, genital diseases, digestive diseases etc.

The protein B of the present invention, the polynucleotide encoding the same, the antibody thereto, and the antisense polynucleotide are useful as diagnostic markers etc. for diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc., preferably respiratory diseases, renal diseases, digestive diseases etc. The protein B of the present invention, the polynucleotide encoding the same and the antibody thereto are useful for screening a compound or a salt thereof that promotes or inhibits the activity of the protein, or a compound or a salt thereof that promotes or inhibits the expression of the protein. The compound or a salt thereof that promotes or inhibits the activity of the protein, the compound or a salt thereof that promotes or inhibits the expression of the gene for the protein or the compound or a salt thereof that promotes or inhibits the expression of the protein can be used as prophylactic/therapeutic agents for diseases such as renal diseases (e.g., renal insufficiency, uremia etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), pancreatic diseases (e.g., pancreatic function insufficiency such as pancreatitis, pancreatic cystic fibrosis etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), thymic diseases, immune disorders (e.g., immune disorders accompanying leukocyte abnormalities, spleen function insufficiency or thymic abnormalities), genital diseases (e.g., prostatic hypertrophy, prostatitis, testis neurosis, ovarian cystoma etc.), spleen diseases, cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.), diabetes, hypertension, ischemia-reperfusion injury, central nerve diseases (e.g., Alzheimer's disease, Parkinson's syndrome, schizophrenia, cerebral vascular dementia, cerebral ischemia, epilepsy etc.) etc., preferably respiratory diseases, renal diseases, digestive diseases etc.

The protein C of the present invention, the polynucleotide encoding the same, the antibody thereto, and the antisense polynucleotide are useful as diagnostic markers etc. for diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc. The protein C of the present invention, the polynucleotide encoding the same and the antibody thereto are useful for screening a compound or a salt thereof that promotes or inhibits the activity of the protein, a compound or a salt thereof that promotes or inhibits the expression of the gene for the protein, or a compound or a salt thereof that promotes or inhibits the expression of the protein. The compound or a salt thereof that promotes or inhibits the activity of the protein, the compound or a salt thereof that promotes or inhibits the expression of the gene for the protein, or the compound or a salt thereof that promotes or inhibits the expression of the protein can be used as prophylactic/therapeutic agents for diseases such as pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), central nerve diseases (e.g., Alzheimer's disease, Parkinson's syndrome, schizophrenia, cerebral vascular dementia, cerebral ischemia, epilepsy etc.), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), diabetes, hyperlipemia, cholestasis, or cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably pancreatic diseases, central nerve diseases, digestive diseases, respiratory diseases etc.

The protein D of the present invention, the polynucleotide encoding the same, the antibody to the same, and the antisense polynucleotide are useful as diagnostic markers for diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc. The protein D of the present invention, the polynucleotide encoding the same and the antibody thereto are useful in screening a compound or a salt thereof that promotes or inhibits the activity of the protein, a compound or a salt thereof that promotes or inhibits the expression of the gene for the protein, a compound or a salt thereof that promotes or inhibits the expression of the protein, a compound or a salt thereof that alters the binding property between the protein and its ligand. The compound or a salt thereof that promotes or inhibits the activity of the protein, the compound or a salt thereof that promotes or inhibits the expression of the gene for the protein, the compound or a salt thereof that promotes or inhibits the expression of the protein, or the compound or a salt thereof that alters the binding property between the protein and its ligand can be used as prophylactic/therapeutic agents for diseases such as inflammatory diseases (e.g., septicemia, pneumonia, encephalitis, meningitis, hepatitis, myocarditis, pleurisy etc.), autoimmune diseases (e.g., myasthenia gravis, glomerulonephritis, multiple sclerosis, Sjogren's syndrome, systemic lupus erythematosus etc.), allergic diseases (e.g., pollinosis, allergic rhinitis, anaphylactic shock, atopic dermatitis etc.), rheumatoid diseases (e.g., chronic articular rheumatism, osteoarthritis, gout etc.), diabetic neurosis, thymic diseases, immune disorders (e.g., immune disorders accompanying leukocyte abnormalities, spleen function insufficiency or thymic abnormalities), digestive diseases (e.g., irritable bowel syndrome, ulcerous colitis, Crohn's disease, ischemic colitis, gastritis, digestive ulcer, rectitis, reflux esophagitis, duodenitis etc.), respiratory diseases (e.g., chronic obstructive pulmonary disease, asthma etc.), circulatory diseases (e.g., cardiac insufficiency, arrhythmia, long QT syndrome, arteriosclerosis, angina etc.), hepatic diseases (e.g., hepatocirrhosis etc.), renal diseases (e.g., renal insufficiency, uremia etc.), muscular diseases (e.g., muscular dystrophy etc.), pancreatic diseases (e.g., pancreatic function insufficiency such as pancreatitis, pancreatic cystic fibrosis etc.), genital diseases (e.g., prostatic hypertrophy, prostatitis, testis neurosis, ovarian cystoma etc.), burns, pain syndrome (e.g., cancerous sharp pain, referred pain etc.), cancers (e.g., testis tumor, ovarian cancer, breast cancer, esophagus cancer, lung cancer, kidney cancer, hepatoma, non-small cell lung cancer, prostate cancer, stomach cancer, bladder cancer, uterine cervix cancer, colon cancer, rectum cancer, pancreatic cancer, thymoma, myoma etc.) etc., preferably inflammatory diseases, rheumatoid diseases, diabetic neurosis etc.

The invention claimed is:

1. A kit for screening a compound or its salt that promotes or inhibits the activity of a protein comprising the amino acid of SEQ ID NO:1 or its salt, said kit comprising in one or more containers:

(a) an isolated protein comprising the amino acid sequence of SEQ ID NO:1 or its salt;

(b) a substrate of the protein; and (c) a lipid bilayer.

2. The kit according to claim 1, wherein the substrate of the protein is a steroid hormone.

3. The kit according to claim 2, wherein the steroid hormone is selected from the group consisting of estrogen and androgen.

4. The kit according to claim 3, wherein the estrogen is estrone or metabolites thereof and the androgen is dehydroepiandrosterone or metabolites thereof.

* * * * *

```
                            SEQUENCE LISTING

<160> NUMBER OF SEQ ID NOS: 178

<210> SEQ ID NO 1
<211> LENGTH: 377
<212> TYPE: PRT
<213> ORGANISM: Human

<400> SEQUENCE: 1

Met Arg Ala Asn Cys Ser Ser Ser Ser Ala Cys Pro Ala Asn Ser Ser
                5                   10                  15

Glu Glu Glu Leu Pro Val Gly Leu Glu Val His Gly Asn Leu Glu Leu
            20                  25                  30

Val Phe Thr Val Val Ser Thr Val Met Met Gly Leu Leu Met Phe Ser
        35                  40                  45

Leu Gly Cys Ser Val Glu Ile Arg Lys Leu Trp Ser His Ile Arg Arg
    50                  55                  60

Pro Trp Gly Ile Ala Val Gly Leu Leu Cys Gln Phe Gly Leu Met Pro
65                  70                  75                  80

Phe Thr Ala Tyr Leu Leu Ala Ile Ser Phe Ser Leu Lys Pro Val Gln
                85                  90                  95

Ala Ile Ala Val Leu Ile Met Gly Cys Cys Pro Gly Gly Thr Ile Ser
            100                 105                 110

Asn Ile Phe Thr Phe Trp Val Asp Gly Asp Met Asp Leu Ser Ile Ser
        115                 120                 125

Met Thr Thr Cys Ser Thr Val Ala Ala Leu Gly Met Met Pro Leu Cys
    130                 135                 140

Ile Tyr Leu Tyr Thr Trp Ser Trp Ser Leu Gln Gln Asn Leu Thr Ile
145                 150                 155                 160

Pro Tyr Gln Asn Ile Gly Ile Thr Leu Val Cys Leu Thr Ile Pro Val
                165                 170                 175

Ala Phe Gly Val Tyr Val Asn Tyr Arg Trp Pro Lys Gln Ser Lys Ile
            180                 185                 190

Ile Leu Lys Ile Gly Ala Val Val Gly Gly Val Leu Leu Leu Val Val
        195                 200                 205

Ala Val Ala Gly Val Val Leu Ala Lys Gly Ser Trp Asn Ser Asp Ile
    210                 215                 220

Thr Leu Leu Thr Ile Ser Phe Ile Phe Pro Leu Ile Gly His Val Thr
225                 230                 235                 240

Gly Phe Leu Leu Ala Leu Phe Thr His Gln Ser Trp Gln Arg Cys Arg
                245                 250                 255

Thr Ile Ser Leu Glu Thr Gly Ala Gln Asn Ile Gln Met Cys Ile Thr
            260                 265                 270

Met Leu Gln Leu Ser Phe Thr Ala Glu His Leu Val Gln Met Leu Ser
        275                 280                 285

Phe Pro Leu Ala Tyr Gly Leu Phe Gln Leu Ile Asp Gly Phe Leu Ile
    290                 295                 300

Val Ala Ala Tyr Gln Thr Tyr Lys Arg Arg Leu Lys Asn Lys His Gly
305                 310                 315                 320
```

-continued

```
Lys Lys Asn Ser Gly Cys Thr Glu Val Cys His Thr Arg Lys Ser Thr
              325                 330                 335

Ser Ser Arg Glu Thr Asn Ala Phe Leu Glu Val Asn Glu Glu Gly Ala
            340                 345                 350

Ile Thr Pro Gly Pro Pro Gly Pro Met Asp Cys His Arg Ala Leu Glu
        355                 360                 365

Pro Val Gly His Ile Thr Ser Cys Glu
    370                 375
```

<210> SEQ ID NO 2
<211> LENGTH: 1131
<212> TYPE: DNA
<213> ORGANISM: Human

<400> SEQUENCE: 2

```
atgagagcca attgttccag cagctcagcc tgccctgcca acagttcaga ggaggagctg     60

ccagtgggac tggaggtgca tggaaacctg gagctcgttt tcacagtggt gtccactgtg    120

atgatggggc tgctcatgtt ctctttggga tgttccgtgg agatccggaa gctgtggtcg    180

cacatcagga gaccctgggg cattgctgtg ggactgctct gccagtttgg gctcatgcct    240

tttacagctt atctcctggc cattagcttt tctctgaagc cagtccaagc tattgctgtt    300

ctcatcatgg gctgctgccc ggggggcacc atctctaaca ttttcacctt ctgggttgat    360

ggagatatgg atctcagcat cagtatgaca acctgttcca ccgtggccgc cctgggaatg    420

atgccactct gcatttatct ctacacctgg tcctggagtc ttcagcagaa tctcaccatt    480

ccttatcaga acataggaat taccettgtg tgcctgacca ttcctgtggc ctttggtgtc    540

tatgtgaatt acagatggcc aaaacaatcc aaaatcattc tcaagattgg ggccgttgtt    600

ggtggggtcc tccttctggt ggtcgcagtt gctggtgtgg tcctggcgaa aggatcttgg    660

aattcagaca tcacccttct gaccatcagt ttcatctttc ctttgattgg ccatgtcacg    720

ggttttctgc tggcactttt tacccaccag tcttggcaaa ggtgcaggac aatttcctta    780

gaaactggag ctcagaatat tcagatgtgc atcaccatgc tccagttatc tttcactgct    840

gagcacttgg tccagatgtt gagtttccca ctggcctatg gactcttcca gctgatagat    900

ggatttctta ttgttgcagc atatcagacg tacaagagga gattgaagaa caaacatgga    960

aaaaagaact caggttgcac agaagtctgc catacgagga aatcgacttc ttccagagag   1020

accaatgcct tcttggaggt gaatgaagaa ggtgccatca ctcctgggcc accagggcca   1080

atggattgcc acagggctct cgagccagtt ggccacatca cttcatgtga a            1131
```

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3

```
aatgctgcct taaggagatg agga                                            24
```

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
cactggccct accaacaaga ttca 24

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
atgagagcca attgttccag cagc 24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ccagccagct agtccctgct attc 24

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
atttaggtga cactatag 18

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
aatacgactc actatagg 19

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ttcgccagga ccacaccagc aact 24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
agttgctggt gtggtcctgg cgaa 24

<210> SEQ ID NO 11
<211> LENGTH: 1152
<212> TYPE: DNA

-continued

<213> ORGANISM: Human

<400> SEQUENCE: 11

```
atgagagcca attgttccag cagctcagcc tgccctgcca acagttcaga ggaggagctg     60
ccagtgggac tggaggtgca tggaaacctg gagctcgttt tcacagtggt gtccactgtg    120
atgatggggc tgctcatgtt ctctttggga tgttccgtgg agatccggaa gctgtggtcg    180
cacatcagga gaccctgggg cattgctgtg ggactgctct gccagtttgg gctcatgcct    240
tttacagctt atctcctggc cattagcttt tctctgaagc cagtccaagc tattgctgtt    300
ctcatcatgg gctgctgccc ggggggcacc atctctaaca ttttcacctt ctgggttgat    360
ggagatatgg atctcagcat cagtatgaca acctgttcca ccgtggccgc cctgggaatg    420
atgccactct gcatttatct ctacacctgg tcctggagtc ttcagcagaa tctcaccatt    480
ccttatcaga acataggaat taccettgtg tgcctgacca ttcctgtggc ctttggtgtc    540
tatgtgaatt acagatggcc aaaacaatcc aaaatcattc tcaagattgg ggccgttgtt    600
ggtggggtcc tccttctggt ggtcgcagtt gctggtgtgg tcctggcgaa aggatcttgg    660
aattcagaca tcacccttct gaccatcagt ttcatctttc ctttgattgg ccatgtcacg    720
ggttttctgc tggcactttt tacccaccag tcttggcaaa ggtgcaggac aatttcctta    780
gaaactggag ctcagaatat tcagatgtgc atcaccatgc tccagttatc tttcactgct    840
gagcacttgg tccagatgtt gagtttccca ctggcctatg gactcttcca gctgatagat    900
ggatttctta ttgttgcagc atatcagacg tacaagagga gattgaagaa caaacatgga    960
aaaaagaact caggttgcac agaagtctgc catacgagga aatcgacttc ttccagagag   1020
accaatgcct tcttggaggt gaatgaagaa ggtgccatca ctcctgggcc accagggcca   1080
atggattgcc acagggctct cgagccagtt ggccacatca cttcatgtga atagcaggga   1140
ctagctggct gg                                                       1152
```

<210> SEQ ID NO 12
<211> LENGTH: 1152
<212> TYPE: DNA
<213> ORGANISM: Human

<400> SEQUENCE: 12

```
atgagagcca attgttccag cagctcagcc tgccctgcca acagttcaga ggaggagctg     60
ccagtgggac tggaggtgca tggaaacctg gagctcgttt tcacagtggt gtccactgtg    120
atgatggggc tgctcatgtt ctctttggga tgttccgtgg agatccggaa gctgtggtcg    180
cacatcagga gaccctgggg cattgctgtg ggactgctct gccagtttgg gctcatgcct    240
tttacagctt atctcctggc cattagcttt tctctgaagc cagtccaagc tattgctgtt    300
ctcatcatgg gctgctgccc ggggggcacc atctctaacg ttttcacctt ctgggttgat    360
ggagatatgg atctcagcat cagtatgaca acctgttcca ccgtggccgc cctgggaatg    420
atgccactct gcatttatct ctacacctgg tcctggagtc ttcagcagaa tctcaccatt    480
ccttatcaga acataggaat taccettgtg tgcctgacca ttcctgtggc ctttggtgtc    540
tatgtgaatt acagatggcc aaaacaatcc aaaatcattc tcaagattgg ggccgttgtt    600
ggtggggtcc tccttctggt ggtcgcagtt gctggtgtgg tcctggcgaa aggatcttgg    660
aattcagaca tcacccttct gaccatcagt ttcatctttc ctttgattgg ccatgtcacg    720
ggttttctgc tggcactttt tacccaccag tcttggcaaa ggtgcaggac aatttcctta    780
gaaactggag ctcagaatat tcagatgtgc atcaccatgc tccagttatc tttcactgct    840
```

```
gagcacttgg tccagatgtt gagtttccca ctggcctatg gactcttcca gctgatagat    900

ggatttctta ttgttgcagc atatcagacg tacaagagga gattgaagaa caaacatgga    960

aaaaagaact caggttgcac agaagtctgc catacgagga aatcgacttc ttccagagag   1020

accaatgcct tcttggaggt gaatgaagaa ggtgccatca ctcctgggcc accagggcca   1080

atggattgcc acagggctct cgagccagtt ggccacatca cttcatgtga atagcaggga   1140

ctagctggct gg                                                       1152
```

<210> SEQ ID NO 13
<211> LENGTH: 1131
<212> TYPE: DNA
<213> ORGANISM: Human

<400> SEQUENCE: 13

```
atgagagcca attgttccag cagctcagcc tgccctgcca acagttcaga ggaggagctg     60

ccagtgggac tggaggtgca tggaaacctg gagctcgttt tcacagtggt gtccactgtg    120

atgatggggc tgctcatgtt ctctttggga tgttccgtgg agatccggaa gctgtggtcg    180

cacatcagga gaccctgggg cattgctgtg ggactgctct gccagtttgg gctcatgcct    240

tttacagctt atctcctggc cattagcttt tctctgaagc cagtccaagc tattgctgtt    300

ctcatcatgg gctgctgccc ggggggcacc atctctaacg ttttcacctt ctgggttgat    360

ggagatatgg atctcagcat cagtatgaca acctgttcca ccgtggccgc cctgggaatg    420

atgccactct gcatttatct ctacacctgg tcctggagtc ttcagcagaa tctcaccatt    480

ccttatcaga acataggaat tacccttgtg tgcctgacca ttcctgtggc ctttggtgtc    540

tatgtgaatt acagatggcc aaaacaatcc aaaatcattc tcaagattgg ggccgttgtt    600

ggtggggtcc tccttctggt ggtcgcagtt gctggtgtgg tcctggcgaa aggatcttgg    660

aattcagaca tcacccttct gaccatcagt ttcatctttc ctttgattgg ccatgtcacg    720

ggttttctgc tggcactttt tacccaccag tcttggcaaa ggtgcaggac aatttcctta    780

gaaactggag ctcagaatat tcagatgtgc atcaccatgc tccagttatc tttcactgct    840

gagcacttgg tccagatgtt gagtttccca ctggcctatg gactcttcca gctgatagat    900

ggatttctta ttgttgcagc atatcagacg tacaagagga gattgaagaa caaacatgga    960

aaaaagaact caggttgcac agaagtctgc catacgagga aatcgacttc ttccagagag   1020

accaatgcct tcttggaggt gaatgaagaa ggtgccatca ctcctgggcc accagggcca   1080

atggattgcc acagggctct cgagccagtt ggccacatca cttcatgtga a            1131
```

<210> SEQ ID NO 14
<211> LENGTH: 377
<212> TYPE: PRT
<213> ORGANISM: Human

<400> SEQUENCE: 14

```
Met Arg Ala Asn Cys Ser Ser Ser Ser Ala Cys Pro Ala Asn Ser Ser
                5                   10                  15

Glu Glu Glu Leu Pro Val Gly Leu Glu Val His Gly Asn Leu Glu Leu
            20                  25                  30

Val Phe Thr Val Val Ser Thr Val Met Met Gly Leu Leu Met Phe Ser
        35                  40                  45

Leu Gly Cys Ser Val Glu Ile Arg Lys Leu Trp Ser His Ile Arg Arg
    50                  55                  60
```

-continued

```
Pro Trp Gly Ile Ala Val Gly Leu Leu Cys Gln Phe Gly Leu Met Pro
65                  70                  75                  80

Phe Thr Ala Tyr Leu Leu Ala Ile Ser Phe Ser Leu Lys Pro Val Gln
                85                  90                  95

Ala Ile Ala Val Leu Ile Met Gly Cys Cys Pro Gly Gly Thr Ile Ser
            100                 105                 110

Asn Val Phe Thr Phe Trp Val Asp Gly Asp Met Asp Leu Ser Ile Ser
        115                 120                 125

Met Thr Thr Cys Ser Thr Val Ala Ala Leu Gly Met Met Pro Leu Cys
    130                 135                 140

Ile Tyr Leu Tyr Thr Trp Ser Trp Ser Leu Gln Gln Asn Leu Thr Ile
145                 150                 155                 160

Pro Tyr Gln Asn Ile Gly Ile Thr Leu Val Cys Leu Thr Ile Pro Val
                165                 170                 175

Ala Phe Gly Val Tyr Val Asn Tyr Arg Trp Pro Lys Gln Ser Lys Ile
            180                 185                 190

Ile Leu Lys Ile Gly Ala Val Val Gly Gly Val Leu Leu Leu Val Val
        195                 200                 205

Ala Val Ala Gly Val Val Leu Ala Lys Gly Ser Trp Asn Ser Asp Ile
    210                 215                 220

Thr Leu Leu Thr Ile Ser Phe Ile Phe Pro Leu Ile Gly His Val Thr
225                 230                 235                 240

Gly Phe Leu Leu Ala Leu Phe Thr His Gln Ser Trp Gln Arg Cys Arg
                245                 250                 255

Thr Ile Ser Leu Glu Thr Gly Ala Gln Asn Ile Gln Met Cys Ile Thr
            260                 265                 270

Met Leu Gln Leu Ser Phe Thr Ala Glu His Leu Val Gln Met Leu Ser
        275                 280                 285

Phe Pro Leu Ala Tyr Gly Leu Phe Gln Leu Ile Asp Gly Phe Leu Ile
    290                 295                 300

Val Ala Ala Tyr Gln Thr Tyr Lys Arg Arg Leu Lys Asn Lys His Gly
305                 310                 315                 320

Lys Lys Asn Ser Gly Cys Thr Glu Val Cys His Thr Arg Lys Ser Thr
                325                 330                 335

Ser Ser Arg Glu Thr Asn Ala Phe Leu Glu Val Asn Glu Glu Gly Ala
            340                 345                 350

Ile Thr Pro Gly Pro Pro Gly Pro Met Asp Cys His Arg Ala Leu Glu
        355                 360                 365

Pro Val Gly His Ile Thr Ser Cys Glu
    370                 375
```

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
tctgccatac gaggaaatcg a 21

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
caggagtgat ggcaccttct tc 22

<210> SEQ ID NO 17
<211> LENGTH: 28
<212> TYPE: DNA
<213> ORGANISM: Artificial Sequence
<220> FEATURE:
<223> OTHER INFORMATION: Probe

<400> SEQUENCE: 17
tcttccagag agaccaatgc cttcttgg 28

<210> SEQ ID NO 18
<211> LENGTH: 798
<212> TYPE: PRT
<213> ORGANISM: Human

<400> SEQUENCE: 18

```
Met Ala Leu Gln Met Phe Val Thr Tyr Ser Pro Trp Asn Cys Leu Leu
1               5                   10                  15

Leu Leu Val Ala Leu Glu Cys Ser Glu Ala Ser Ser Asp Leu Asn Glu
            20                  25                  30

Ser Ala Asn Ser Thr Ala Gln Tyr Ala Ser Asn Ala Trp Phe Ala Ala
        35                  40                  45

Ala Ser Ser Glu Pro Glu Glu Gly Ile Ser Val Phe Glu Leu Asp Tyr
    50                  55                  60

Asp Tyr Val Gln Ile Pro Tyr Glu Val Thr Leu Trp Ile Leu Leu Ala
65                  70                  75                  80

Ser Leu Ala Lys Ile Gly Phe His Leu Tyr His Arg Leu Pro Gly Leu
                85                  90                  95

Met Pro Glu Ser Cys Leu Leu Ile Leu Val Gly Ala Leu Val Gly Gly
            100                 105                 110

Ile Ile Phe Gly Thr Asp His Lys Ser Pro Pro Val Met Asp Ser Ser
        115                 120                 125

Ile Tyr Phe Leu Tyr Leu Leu Pro Pro Ile Val Leu Glu Gly Gly Tyr
    130                 135                 140

Phe Met Pro Thr Arg Pro Phe Phe Glu Asn Ile Gly Ser Ile Leu Trp
145                 150                 155                 160

Trp Ala Val Leu Gly Ala Leu Ile Asn Ala Leu Gly Ile Gly Leu Ser
                165                 170                 175

Leu Tyr Leu Ile Cys Gln Val Lys Ala Phe Gly Leu Gly Asp Val Asn
            180                 185                 190

Leu Leu Gln Asn Leu Leu Phe Gly Ser Leu Ile Ser Ala Val Asp Pro
        195                 200                 205

Val Ala Val Leu Ala Val Phe Glu Glu Ala Arg Val Asn Glu Gln Leu
    210                 215                 220

Tyr Met Met Ile Phe Gly Glu Ala Leu Leu Asn Asp Gly Ile Thr Val
225                 230                 235                 240

Val Leu Tyr Asn Met Leu Ile Ala Phe Thr Lys Met His Lys Phe Glu
                245                 250                 255

Asp Ile Glu Thr Val Asp Ile Leu Ala Gly Cys Ala Arg Phe Ile Val
            260                 265                 270

Val Gly Leu Gly Gly Val Leu Phe Gly Ile Val Phe Gly Phe Ile Ser
        275                 280                 285
```

-continued

```
Ala Phe Ile Thr Arg Phe Thr Gln Asn Ile Ser Ala Ile Glu Pro Leu
    290                 295                 300

Ile Val Phe Met Phe Ser Tyr Leu Ser Tyr Leu Ala Ala Glu Thr Leu
305                 310                 315                 320

Tyr Leu Ser Gly Ile Leu Ala Ile Thr Ala Cys Ala Val Thr Met Lys
                325                 330                 335

Lys Tyr Val Glu Glu Asn Val Ser Gln Thr Ser Tyr Thr Thr Ile Lys
            340                 345                 350

Tyr Phe Met Lys Met Leu Ser Ser Val Ser Glu Thr Leu Ile Phe Ile
        355                 360                 365

Phe Met Gly Val Ser Thr Val Gly Lys Asn His Glu Trp Asn Trp Ala
    370                 375                 380

Phe Ile Cys Phe Thr Leu Ala Phe Cys Gln Ile Trp Arg Ala Ile Ser
385                 390                 395                 400

Val Phe Ala Leu Phe Tyr Ile Ser Asn Gln Phe Arg Thr Phe Pro Phe
                405                 410                 415

Ser Ile Lys Asp Gln Cys Ile Ile Phe Tyr Ser Gly Val Arg Gly Ala
            420                 425                 430

Gly Ser Phe Ser Leu Ala Phe Leu Leu Pro Leu Ser Leu Phe Pro Arg
        435                 440                 445

Lys Lys Met Phe Val Thr Ala Thr Leu Val Val Ile Tyr Phe Thr Val
    450                 455                 460

Phe Ile Gln Gly Ile Thr Val Gly Pro Leu Val Arg Tyr Leu Asp Val
465                 470                 475                 480

Lys Lys Thr Asn Lys Lys Glu Ser Ile Asn Glu Glu Leu His Ile Arg
                485                 490                 495

Leu Met Asp His Leu Lys Ala Gly Ile Glu Asp Val Cys Gly His Trp
            500                 505                 510

Ser His Tyr Gln Val Arg Asp Lys Phe Lys Lys Phe Asp His Arg Tyr
        515                 520                 525

Leu Arg Lys Ile Leu Ile Arg Lys Asn Leu Pro Lys Ser Ser Ile Val
    530                 535                 540

Ser Leu Tyr Lys Lys Leu Glu Met Lys Gln Ala Ile Glu Met Val Glu
545                 550                 555                 560

Thr Gly Ile Leu Ser Ser Thr Ala Phe Ser Ile Pro His Gln Ala Gln
                565                 570                 575

Arg Ile Gln Gly Ile Lys Arg Leu Ser Pro Glu Asp Val Glu Ser Ile
            580                 585                 590

Arg Asp Ile Leu Thr Ser Asn Met Tyr Gln Val Arg Gln Arg Thr Leu
        595                 600                 605

Ser Tyr Asn Lys Tyr Asn Leu Lys Pro Gln Thr Ser Glu Lys Gln Ala
    610                 615                 620

Lys Glu Ile Leu Ile Arg Arg Gln Asn Thr Leu Arg Glu Ser Met Arg
625                 630                 635                 640

Lys Gly His Ser Leu Pro Trp Gly Lys Pro Ala Gly Thr Lys Asn Ile
                645                 650                 655

Arg Tyr Leu Ser Tyr Pro Tyr Gly Asn Pro Gln Ser Ala Gly Arg Asp
            660                 665                 670

Thr Arg Ala Ala Gly Phe Ser Asp Asp Asp Ser Ser Asp Pro Gly Ser
        675                 680                 685

Pro Ser Ile Thr Phe Ser Ala Cys Ser Arg Ile Gly Ser Leu Gln Lys
    690                 695                 700

Gln Glu Ala Gln Glu Ile Ile Pro Met Lys Ser Leu His Arg Gly Arg
```

-continued

```
705                 710                 715                 720

Lys Ala Phe Ser Phe Gly Tyr Gln Arg Asn Thr Ser Gln Glu Glu Tyr
                725                 730                 735

Leu Gly Gly Val Arg Arg Val Ala Leu Arg Pro Lys Pro Leu Phe His
            740                 745                 750

Ala Val Asp Glu Glu Gly Glu Ser Gly Gly Glu Ser Glu Gly Lys Ala
        755                 760                 765

Ser Leu Val Glu Val Arg Ser Arg Trp Thr Ala Asp His Gly His Ser
    770                 775                 780

Arg Asp His His Arg Ser His Ser Pro Leu Leu Gln Lys Lys
785                 790                 795


<210> SEQ ID NO 19
<211> LENGTH: 2394
<212> TYPE: DNA
<213> ORGANISM: Human

<400> SEQUENCE: 19

atggctctgc agatgttcgt gacttacagt ccttggaatt gtttgctact gctagtggct      60

cttgagtgtt ctgaagcatc ttctgatttg aatgaatctg caaattccac tgctcagtat     120

gcatctaacg cttggtttgc tgctgccagc tcagagccag aggaagggat atctgttttt     180

gaactggatt atgactatgt gcaaattcct tatgaggtca ctctctggat acttctagca     240

tcccttgcaa aaataggctt ccacctctac cacaggctgc caggcctcat gccagaaagc     300

tgcctcctca tcctggtggg ggcgctggtg ggcggcatca tcttcggcac cgaccacaaa     360

tcacctccgg tcatggactc cagcatctac ttcctgtatc tcctgccacc catcgttctg     420

gagggcggct acttcatgcc cacccggccc ttctttgaga acatcggctc catcctgtgg     480

tgggcagtat tgggggccct gatcaacgcc ttgggcattg gcctctccct ctacctcatc     540

tgccaggtga aggcctttgg cctgggcgac gtcaacctgc tgcagaacct gctgttcggc     600

agcctgatct ccgccgtgga cccagtggcc gtgctagccg tgtttgagga agcgcgcgtg     660

aacgagcagc tctacatgat gatctttggg gaggccctgc tcaatgatgg cattactgtg     720

gtcttataca atatgttaat tgcctttaca aagatgcata aatttgaaga catagaaact     780

gtcgacattt tggctggatg tgcccgattc atcgttgtgg ggcttggagg ggtattgttt     840

ggcatcgttt ttggatttat ttctgcattt atcacacgtt tcactcagaa tatctctgca     900

attgagccac tcatcgtctt catgttcagc tatttgtctt acttagctgc tgaaaccctc     960

tatctctccg gcatcctggc aatcacagcc tgcgcagtaa caatgaaaaa gtacgtggaa    1020

gaaaacgtgt cccagacatc atacacgacc atcaagtact tcatgaagat gctgagcagc    1080

gtcagcgaga ccttgatctt catcttcatg ggtgtgtcca ctgtgggcaa gaatcacgag    1140

tggaactggg ccttcatctg cttcaccctg gccttctgcc aaatctggag agccatcagc    1200

gtatttgctc tcttctatat cagtaaccag tttcggactt tcccctctc catcaaggac    1260

cagtgcatca ttttctacag tggtgttcga ggagctggaa gtttttcact tgcatttttg    1320

cttcctctgt ctcttttcc taggaagaaa atgtttgtca ctgctactct agtagttata    1380

tactttactg tatttattca gggaatcaca gttggccctc tggtcaggta cctggatgtt    1440

aaaaaaacca ataaaaaaga atccatcaat gaagagcttc atattcgtct gatggatcac    1500

ttaaaggctg gaatcgaaga tgtgtgtggg cactggagtc actaccaagt gagagacaag    1560

tttaagaagt ttgatcatag atacttacgg aaaatcctca tcagaaagaa cctacccaaa    1620
```

-continued

```
tcaagcattg tttctttgta caagaagctg gaaatgaagc aagccatcga gatggtggag   1680

actgggatac tgagctctac agctttctcc ataccccatc aggcccagag gatacaagga   1740

atcaaaagac tttcccctga agatgtggag tccataaggg acattctgac atccaacatg   1800

taccaagttc ggcaaaggac cctgtcctac aacaaataca acctcaaacc ccaaacaagt   1860

gagaagcagg ctaaagagat tctgatccgc cgccagaaca ccttaaggga gagcatgagg   1920

aaaggtcaca gcctgccctg gggaaagccg gctggcacca agaatatccg ctacctctcc   1980

taccccctacg ggaatcctca gtctgcagga agagacacaa gggctgctgg gttctcagat   2040

gatgacagca gtgatccagg atccccatcc atcacgttca gcgcatgctc tcggataggg   2100

tcacttcaga agcaagaggc acaagaaata ataccaatga agagcctaca cagaggaagg   2160

aaggcattca gctttggtta tcaaagaaac acaagccaag aagagtactt gggtggagta   2220

aggagggtgg ccttaagacc caaacctctg tttcatgcag tggatgagga gggtgagtct   2280

ggaggggaga gtgagggcaa ggcctctttg gttgaggttc ggtcgaggtg gacagctgac   2340

catggacaca gcagggacca tcacaggtcc catagtcctt tgctccaaaa aaaa         2394
```

```
<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20

ccatcctaat acgactcact atagggc                                         27


<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21

gcatgaagta gccgccctcc agaacga                                         27


<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22

actcactata gggctcgagc ggc                                             23


<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23

cagaacgatg ggtggcagga gatacagga                                       29


<210> SEQ ID NO 24
<211> LENGTH: 29
<212> TYPE: DNA
<213> ORGANISM: Artificial Sequence
```

<220> FEATURE:
<223> OTHER INFORMATION: Primer

<400> SEQUENCE: 24
cgccgccaga acaccttaag ggagagcat 29

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
ggctggcacc aagaatatcc gctacct 27

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
tccacacagg ggtgtaggta g 21

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
tgtggacaat aacactattt t 21

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
aggtaggaga agcccacagg aatg 24

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
caataacact attttttttg gagc 24

<210> SEQ ID NO 30
<211> LENGTH: 17
<212> TYPE: DNA
<213> ORGANISM: Artificial Sequence
<220> FEATURE:
<223> OTHER INFORMATION: Primer

<400> SEQUENCE: 30
caggaaacag ctatgac 17

<210> SEQ ID NO 31
<211> LENGTH: 16
<212> TYPE: DNA
<213> ORGANISM: Artificial Sequence
<220> FEATURE:
<223> OTHER INFORMATION: Primer

<400> SEQUENCE: 31
gtaaaacgac ggccag 16

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
cccttctttg agaacatcgg c 21

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
aatgcccaag gcgttgatc 19

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
acagcctgcg cagtaacaat gaaaaagt 28

<210> SEQ ID NO 35
<211> LENGTH: 23
<212> TYPE: DNA
<213> ORGANISM: Artificial Sequence
<220> FEATURE:
<223> OTHER INFORMATION: Primer

<400> SEQUENCE: 35
ttgtacaaga agctggaaat gaa 23

<210> SEQ ID NO 36
<211> LENGTH: 25
<212> TYPE: DNA
<213> ORGANISM: Artificial Sequence
<220> FEATURE:
<223> OTHER INFORMATION: Primer

<400> SEQUENCE: 36
acttgatggt cgtgtatgat gtctg 25

<210> SEQ ID NO 37
<211> LENGTH: 26
<212> TYPE: DNA
<213> ORGANISM: Artificial Sequence
<220> FEATURE:
<223> OTHER INFORMATION: Primer

<400> SEQUENCE: 37
ctgggcctga tggggtatgg agaaag 26

<210> SEQ ID NO 38
<211> LENGTH: 25
<212> TYPE: DNA
<213> ORGANISM: Artificial Sequence
<220> FEATURE:
<223> OTHER INFORMATION: Probe

<400> SEQUENCE: 38
ccatcctgtg gtgggcagta ttggg 25

<210> SEQ ID NO 39
<211> LENGTH: 511
<212> TYPE: DNA
<213> ORGANISM: Human

<400> SEQUENCE: 39
aggtggatgc agtcactctc tagaagcctc cccgacttca gatgtgtggc acacatccac 60
acaggggtgt aggtaggaga agcccacagg aatggctctg cagatgttcg tgacttacag 120
tccttggaat tgtttgctac tgctagtggc tcttgagtgt tctgaagcat cttctgattt 180
gaatgaatct gcaaattcca ctgctcagta tgcatctaac gcttggtttg ctgctgccag 240
ctcagagcca gaggaaggga tatctgtttt tgaactggat tatgactatg tgcaaattcc 300
ttatgaggtc actctctgga tacttctagc atcccttgca aaaataggct tccacctcta 360
ccacaggctg ccaggcctca tgccagaaag ctgcctcctc atcctggtgg gggcgctggt 420
gggcggcatc atcttcggca ccgaccacaa atcacctccg gtcatggact ccagcatcta 480
cttcctgtat ctcctgccac ccatcgttct g 511

<210> SEQ ID NO 40
<211> LENGTH: 462
<212> TYPE: DNA
<213> ORGANISM: Human

<400> SEQUENCE: 40
ggctggcacc aagaatatcc gctacctctc ctacccctac gggaatcctc agtctgcagg 60
aagagacaca agggctgctg ggttctcaga tgatgacagc agtgatccag gatccccatc 120
catcacgttc agcgcatgct ctcggatagg gtcacttcag aagcaagagg cacaagaaat 180
aataccaatg aagagcctac acagaggaag gaaggcattc agctttggtt atcaaagaaa 240
cacaagccaa gaagagtact tgggtggagt aaggagggtg gccttaagac ccaaacctct 300
gtttcatgca gtggatgagg agggtgagtc tggaggggag agtgagggca aggcctcttt 360
ggttgaggtt cggtcgaggt ggacagctga ccatggacac agcagggacc atcacaggtc 420
ccatagtcct ttgctccaaa aaaaatagtg ttattgtcca ca 462

<210> SEQ ID NO 41
<211> LENGTH: 2426
<212> TYPE: DNA
<213> ORGANISM: Human

<400> SEQUENCE: 41
aggtaggaga agcccacagg aatggctctg cagatgttcg tgacttacag tccttggaat 60
tgtttgctac tgctagtggc tcttgagtgt tctgaagcat cttctgattt gaatgaatct 120

-continued

```
gcaaattcca ctgctcagta tgcatctaac gcttggtttg ctgctgccag ctcagagcca    180
gaggaaggga tatctgtttt tgaactggat tatgactatg tgcaaattcc ttatgaggtc    240
actctctgga tacttctagc atcccttgca aaaataggct tccacctcta ccacaggctg    300
ccaggcctca tgccagaaag ctgcctcctc atcctggtgg gggcgctggt gggcggcatc    360
atcttcggca ccgaccacaa atcacctccg gtcatggact ccagcatcta cttcctgtat    420
ctcctgccac ccatcgttct ggagggcggc tacttcatgc ccacccggcc cttctttgag    480
aacatcggct ccatcctgtg gtgggcagta ttgggggccc tgatcaacgc cttgggcatt    540
ggcctctccc tctacctcat ctgccaggtg aaggcctttg gcctgggcga cgtcaacctg    600
ctgcagaacc tgctgttcgg cagcctgatc tccgccgtgg acccagtggc cgtgctagcc    660
gtgtttgagg aagcgcgcgt gaacgagcag ctctacatga tgatctttgg ggaggccctg    720
ctcaatgatg gcattactgt ggtcttatac aatatgttaa ttgcctttac aaagatgcat    780
aaatttgaag acatagaaac tgtcgacatt ttggctggat gtgcccgatt catcgttgtg    840
gggcttggag ggtattgttt tggcatcgtt tttggattta tttctgcatt tatcacacgt    900
ttcactcaga atatctctgc aattgagcca ctcatcgtct tcatgttcag ctatttgtct    960
tacttagctg ctgaaaccct ctatctctcc ggcatcctgg caatcacagc ctgcgcagta   1020
acaatgaaaa agtacgtgga agaaaacgtg tcccagacat catacacgac catcaagtac   1080
ttcatgaaga tgctgagcag cgtcagcgag accttgatct tcatcttcat gggtgtgtcc   1140
actgtgggca agaatcacga gtggaactgg gccttcatct gcttcaccct ggccttctgc   1200
caaatctgga gagccatcag cgtatttgct ctcttctata tcagtaacca gtttcggact   1260
ttccccttct ccatcaagga ccagtgcatc attttctaca gtggtgttcg aggagctgga   1320
agtttttcac ttgcattttt gcttcctctg tctctttttc ctaggaagaa aatgtttgtc   1380
actgctactc tagtagttat atactttact gtatttattc agggaatcac agttggccct   1440
ctggtcaggt acctggatgt taaaaaaacc aataaaaaag aatccatcaa tgaagagctt   1500
catattcgtc tgatggatca cttaaaggct ggaatcgaag atgtgtgtgg gcactggagt   1560
cactaccaag tgagagacaa gtttaagaag tttgatcata gatacttacg gaaaatcctc   1620
atcagaaaga acctacccaa atcaagcatt gtttctttgt acaagaagct ggaaatgaag   1680
caagccatcg agatggtgga gactgggata ctgagctcta cagctttctc catacccat    1740
caggcccaga ggatacaagg aatcaaaaga ctttcccctg aagatgtgga gtccataagg   1800
gacattctga catccaacat gtaccaagtt cggcaaagga ccctgtccta caacaaatac   1860
aacctcaaac cccaaacaag tgagaagcag gctaaagaga ttctgatccg ccgccagaac   1920
accttaaggg agagcatgag gaaaggtcac agcctgccct ggggaaagcc ggctggcacc   1980
aagaatatcc gctacctctc ctacccctac gggaatcctc agtctgcagg aagagacaca   2040
agggctgctg ggttctcaga tgatgacagc agtgatccag gatccccatc catcacgttc   2100
agcgcatgct ctcggatagg gtcacttcag aagcaagagg cacaagaaat aataccaatg   2160
aagagcctac acagaggaag gaaggcattc agctttggtt atcaaagaaa cacaagccaa   2220
gaagagtact tgggtggagt aaggagggtg gccttaagac ccaaacctct gtttcatgca   2280
gtggatgagg agggtgagtc tggaggggag agtgagggca aggcctcttt ggttgaggtt   2340
cggtcgaggt ggacagctga ccatggacac agcagggacc atcacaggtc ccatagtcct   2400
ttgctccaaa aaaaatagtg ttattg                                        2426
```

<210> SEQ ID NO 42
<211> LENGTH: 1148
<212> TYPE: PRT
<213> ORGANISM: Human

<400> SEQUENCE: 42

```
Met Ser Arg Ala Thr Ser Val Gly Asp Gln Leu Glu Ala Pro Ala Arg
                5                   10                  15

Thr Ile Tyr Leu Asn Gln Pro His Leu Asn Lys Phe Arg Asp Asn Gln
            20                  25                  30

Ile Ser Thr Ala Lys Tyr Ser Val Leu Thr Phe Leu Pro Arg Phe Leu
        35                  40                  45

Tyr Glu Gln Ile Arg Arg Ala Ala Asn Ala Phe Phe Leu Phe Ile Ala
    50                  55                  60

Leu Leu Gln Gln Ile Pro Asp Val Ser Pro Thr Gly Arg Tyr Thr Thr
65                  70                  75                  80

Leu Val Pro Leu Ile Ile Ile Leu Thr Ile Ala Gly Ile Lys Glu Ile
                85                  90                  95

Val Glu Asp Phe Lys Arg His Lys Ala Asp Asn Ala Val Asn Lys Lys
            100                 105                 110

Lys Thr Ile Val Leu Arg Asn Gly Met Trp His Thr Ile Met Trp Lys
        115                 120                 125

Glu Val Ala Val Gly Asp Ile Val Lys Val Val Asn Gly Gln Tyr Leu
    130                 135                 140

Pro Ala Asp Val Val Leu Leu Ser Ser Ser Glu Pro Gln Ala Met Cys
145                 150                 155                 160

Tyr Val Glu Thr Ala Asn Leu Asp Gly Glu Thr Asn Leu Lys Ile Arg
                165                 170                 175

Gln Gly Leu Ser His Thr Ala Asp Met Gln Thr Arg Glu Val Leu Met
            180                 185                 190

Lys Leu Ser Gly Thr Ile Glu Cys Glu Gly Pro Asn Arg His Leu Tyr
        195                 200                 205

Asp Phe Thr Gly Asn Leu Asn Leu Asp Gly Lys Ser Leu Val Ala Leu
    210                 215                 220

Gly Pro Asp Gln Ile Leu Leu Arg Gly Thr Gln Leu Arg Asn Thr Gln
225                 230                 235                 240

Trp Val Phe Gly Ile Val Val Tyr Thr Gly His Asp Thr Lys Leu Met
                245                 250                 255

Gln Asn Ser Thr Lys Ala Pro Leu Lys Arg Ser Asn Val Glu Lys Val
            260                 265                 270

Thr Asn Val Gln Ile Leu Val Leu Phe Gly Ile Leu Leu Val Met Ala
        275                 280                 285

Leu Val Ser Ser Ala Gly Ala Leu Tyr Trp Asn Arg Ser His Gly Glu
    290                 295                 300

Lys Asn Trp Tyr Ile Lys Lys Met Asp Thr Thr Ser Asp Asn Phe Gly
305                 310                 315                 320

Tyr Asn Leu Leu Thr Phe Ile Ile Leu Tyr Asn Asn Leu Ile Pro Ile
                325                 330                 335

Ser Leu Leu Val Thr Leu Glu Val Val Lys Tyr Thr Gln Ala Leu Phe
            340                 345                 350

Ile Asn Trp Asp Thr Asp Met Tyr Tyr Ile Gly Asn Asp Thr Pro Ala
        355                 360                 365

Met Ala Arg Thr Ser Asn Leu Asn Glu Glu Leu Gly Gln Val Lys Tyr
    370                 375                 380
```

-continued

```
Leu Phe Ser Asp Lys Thr Gly Thr Leu Thr Cys Asn Ile Met Asn Phe
385                 390                 395                 400

Lys Lys Cys Ser Ile Ala Gly Val Thr Tyr Gly His Phe Pro Glu Leu
                405                 410                 415

Ala Arg Glu Pro Ser Ser Asp Asp Phe Cys Arg Met Pro Pro Pro Cys
            420                 425                 430

Ser Asp Ser Cys Asp Phe Asp Asp Pro Arg Leu Leu Lys Asn Ile Glu
        435                 440                 445

Asp Arg His Pro Thr Ala Pro Cys Ile Gln Glu Phe Leu Thr Leu Leu
    450                 455                 460

Ala Val Cys His Thr Val Val Pro Glu Lys Asp Gly Asp Asn Ile Ile
465                 470                 475                 480

Tyr Gln Ala Ser Ser Pro Asp Glu Ala Ala Leu Val Lys Gly Ala Lys
                485                 490                 495

Lys Leu Gly Phe Val Phe Thr Ala Arg Thr Pro Phe Ser Val Ile Ile
            500                 505                 510

Glu Ala Met Gly Gln Glu Gln Thr Phe Gly Ile Leu Asn Val Leu Glu
        515                 520                 525

Phe Ser Ser Asp Arg Lys Arg Met Ser Val Ile Val Arg Thr Pro Ser
    530                 535                 540

Gly Arg Leu Arg Leu Tyr Cys Lys Gly Ala Asp Asn Val Ile Phe Glu
545                 550                 555                 560

Arg Leu Ser Lys Asp Ser Lys Tyr Met Glu Glu Thr Leu Cys His Leu
                565                 570                 575

Glu Tyr Phe Ala Thr Glu Gly Leu Arg Thr Leu Cys Val Ala Tyr Ala
            580                 585                 590

Asp Leu Ser Glu Asn Glu Tyr Glu Glu Trp Leu Lys Val Tyr Gln Glu
        595                 600                 605

Ala Ser Thr Ile Leu Lys Asp Arg Ala Gln Arg Leu Glu Glu Cys Tyr
    610                 615                 620

Glu Ile Ile Glu Lys Asn Leu Leu Leu Leu Gly Ala Thr Ala Ile Glu
625                 630                 635                 640

Asp Arg Leu Gln Ala Gly Val Pro Glu Thr Ile Ala Thr Leu Leu Lys
                645                 650                 655

Ala Glu Ile Lys Ile Trp Val Leu Thr Gly Asp Lys Gln Glu Thr Ala
            660                 665                 670

Ile Asn Ile Gly Tyr Ser Cys Arg Leu Val Ser Gln Asn Met Ala Leu
        675                 680                 685

Ile Leu Leu Lys Glu Asp Ser Leu Asp Ala Thr Arg Ala Ala Ile Thr
    690                 695                 700

Gln His Cys Thr Asp Leu Gly Asn Leu Leu Gly Lys Glu Asn Asp Val
705                 710                 715                 720

Ala Leu Ile Ile Asp Gly His Thr Leu Lys Tyr Ala Leu Ser Phe Glu
                725                 730                 735

Val Arg Arg Ser Phe Leu Asp Leu Ala Leu Ser Cys Lys Ala Val Ile
            740                 745                 750

Cys Cys Arg Val Ser Pro Leu Gln Lys Ser Glu Ile Val Asp Val Val
        755                 760                 765

Lys Lys Arg Val Lys Ala Ile Thr Leu Ala Ile Gly Asp Gly Ala Asn
    770                 775                 780

Asp Val Gly Met Ile Gln Thr Ala His Val Gly Val Gly Ile Ser Gly
785                 790                 795                 800

Asn Glu Gly Met Gln Ala Thr Asn Asn Ser Asp Tyr Ala Ile Ala Gln
```

```
                805                 810                 815

Phe Ser Tyr Leu Glu Lys Leu Leu Leu Val His Gly Ala Trp Ser Tyr
            820                 825                 830

Asn Arg Val Thr Lys Cys Ile Leu Tyr Cys Phe Tyr Lys Asn Val Val
        835                 840                 845

Leu Tyr Ile Ile Glu Leu Trp Phe Ala Phe Val Asn Gly Phe Ser Gly
    850                 855                 860

Gln Ile Leu Phe Glu Arg Trp Cys Ile Gly Leu Tyr Asn Val Ile Phe
865                 870                 875                 880

Thr Ala Leu Pro Pro Phe Thr Leu Gly Ile Phe Glu Arg Ser Cys Thr
                885                 890                 895

Gln Glu Ser Met Leu Arg Phe Pro Gln Leu Tyr Lys Ile Thr Gln Asn
            900                 905                 910

Gly Glu Gly Phe Asn Thr Lys Val Phe Trp Gly His Cys Ile Asn Ala
        915                 920                 925

Leu Val His Ser Leu Ile Leu Phe Trp Phe Pro Met Lys Ala Leu Glu
    930                 935                 940

His Asp Thr Val Leu Thr Ser Gly His Ala Thr Asp Tyr Leu Phe Val
945                 950                 955                 960

Gly Asn Ile Val Tyr Thr Tyr Val Val Val Thr Val Cys Leu Lys Ala
                965                 970                 975

Gly Leu Glu Thr Thr Ala Trp Thr Lys Phe Ser His Leu Ala Val Trp
            980                 985                 990

Gly Ser Met Leu Thr Trp Leu Val Phe Phe Gly Ile Tyr Ser Thr Ile
        995                 1000                1005

Trp Pro Thr Ile Pro Ile Ala Pro Asp Met Arg Gly Gln Ala Thr Met
   1010                1015                1020

Val Leu Ser Ser Ala His Phe Trp Leu Gly Leu Phe Leu Val Pro Thr
1025                1030                1035                1040

Ala Cys Leu Ile Glu Asp Val Ala Trp Arg Ala Ala Lys His Thr Cys
               1045                1050                1055

Lys Lys Thr Leu Leu Glu Glu Val Gln Glu Leu Glu Thr Lys Ser Arg
           1060                1065                1070

Val Leu Gly Lys Ala Val Leu Arg Asp Ser Asn Gly Lys Arg Leu Asn
       1075                1080                1085

Glu Arg Asp Arg Leu Ile Lys Arg Leu Gly Arg Lys Thr Pro Pro Thr
   1090                1095                1100

Leu Phe Arg Gly Ser Ser Leu Gln Gln Gly Val Pro His Gly Tyr Ala
1105                1110                1115                1120

Phe Ser Gln Glu Glu His Gly Ala Val Ser Gln Glu Glu Val Ile Arg
               1125                1130                1135

Ala Tyr Asp Thr Thr Lys Lys Lys Ser Arg Lys Lys
           1140                1145
```

<210> SEQ ID NO 43
<211> LENGTH: 3444
<212> TYPE: DNA
<213> ORGANISM: Human

<400> SEQUENCE: 43

```
atgtcccggg ccacgtctgt tggagaccag ctggaggcac ccgcccgcac catttacctc      60

aaccaaccgc atctcaacaa attccgcgac aaccagatca gtacggccaa gtacagcgtg     120

ttgacatttc tacctcgatt cttgtatgag cagattagaa gagctgctaa tgccttcttt     180
```

-continued

```
ctcttcattg ccttattaca gcaaattcca gatgtatctc caacaggaag atataccacc    240
ctggtgccat tgatcattat tttaacaatt gcaggcatca aagagattgt agaagatttt    300
aagcgacaca aggcagacaa tgcagttaac aaaaagaaaa caatagtgtt aagaaatggt    360
atgtggcata ccattatgtg gaaagaggtg gcagtgggag acattgtgaa ggtcgtcaat    420
gggcagtatc ttccagcaga tgtggtcctg ctgtcatcca gtgaacctca ggcaatgtgt    480
tatgttgaaa cagctaatct ggatggggag acgaacctta aaatacgtca gggtttgagt    540
cacactgctg acatgcaaac acgtgaagtt ctgatgaagt tatctggaac tatagagtgt    600
gaagggccca accgccacct ctatgacttc actggaaact tgaacttaga tgggaaaagc    660
cttgttgccc ttgggcctga ccagatctta ttaagaggta cacagcttag aaatactcag    720
tgggtctttg gcatagttgt ttatactgga cacgacacca aactcatgca gaattcaacc    780
aaagcgcctc tcaagagatc aaatgttgag aaggtgacta acgtgcagat cctggtgttg    840
tttggcatcc tcttggtcat ggccttggtg agctcggcgg gggccctgta ctggaacagg    900
tctcatggtg aaaagaactg gtacatcaag aagatggaca ccacctcaga taattttgga    960
tacaacctac tgacgttcat catcttatac aacaatctta ttcccatcag tctgttggtg   1020
actcttgagg ttgtgaagta tactcaagcc cttttcataa actgggacac agatatgtat   1080
tatataggaa atgacactcc tgccatggcc aggacatcaa accttaatga agagcttggg   1140
caggtgaaat atctcttttc tgacaagact ggaacgctta catgcaatat catgaacttt   1200
aagaagtgca gcattgccgg agtaacctat ggtcacttcc cagaattggc aagagagccg   1260
tcttcagatg acttctgtcg gatgcctcct ccctgtagtg attcctgtga ctttgatgac   1320
cccaggctgt tgaagaacat tgaggatcgc catcccacag ccccttgcat tcaggagttc   1380
ctcacccttc tggccgtgtg ccacacggtt gttcctgaga aggatggaga taacatcatc   1440
taccaggcct cttccccaga tgaagctgct ttggtgaaag gagctaaaaa gctgggcttt   1500
gtcttcacag ccagaacacc attctcagtc atcatagaag cgatgggaca ggaacaaaca   1560
ttcggaatcc ttaatgtcct ggaattttct agtgacagaa aaagaatgtc tgtaattgtt   1620
cgaactcctt caggacgact tcggctttac tgtaaagggg ctgataatgt gatttttgag   1680
agactttcaa aagactcaaa atatatggag gaaacattat gccatctgga atactttgcc   1740
acggaaggct tgcggactct ctgtgtggct tatgctgatc tctctgagaa tgagtatgag   1800
gagtggctga aagtctatca ggaagccagc accatattga aggacagagc tcaacggttg   1860
gaagagtgtt acgagatcat tgagaagaat ttgctgctac ttggagccac agccatagaa   1920
gatcgccttc aagcaggagt tccagaaacc atcgcaacac tgttgaaggc agaaattaaa   1980
atatgggtgt tgacaggaga caaacaagaa actgcgatta atatagggta ttcctgccga   2040
ttggtatcgc agaatatggc ccttatccta ttgaaggagg actctttgga tgccacaagg   2100
gcagccatta ctcagcactg cactgacctt gggaatttgc tgggcaagga aaatgacgtg   2160
gccctcatca tcgatggcca caccctgaag tacgcgctct ccttcgaagt ccggaggagt   2220
ttcctggatt tggcactctc gtgcaaagcg gtcatatgct gcagagtgtc tcctctgcag   2280
aagtctgaga tagtggatgt ggtgaagaag cgggtgaagg ccatcaccct cgccatcgga   2340
gacggcgcca acgatgtcgg gatgatccag acagcccacg tgggtgtggg aatcagtggg   2400
aatgaaggca tgcaggccac caacaactcg gattacgcca tcgcacagtt ttcctactta   2460
gagaagcttc tgttggttca tggagcctgg agctacaacc gggtgaccaa gtgcatcttg   2520
tactgcttct ataagaacgt ggtcctgtat attattgagc tttggttcgc ctttgttaat   2580
```

```
ggattttctg ggcagatttt atttgaacgt tggtgcatcg gcctgtacaa tgtgattttc   2640

accgctttgc cgcccttcac tctgggaatc tttgagaggt cttgcactca ggagagcatg   2700

ctcaggtttc cccagctcta caaaatcacc cagaatggcg aaggcttcaa cacaaaggtt   2760

ttctggggtc actgcatcaa cgccttggtc cactccctca tcctcttctg gtttcccatg   2820

aaagctctgg agcatgatac tgtgttgaca agtggtcatg ctaccgacta tttatttgtt   2880

ggaaatattg tttacacata tgttgttgtt actgtttgtc tgaaagctgg tttggagacc   2940

acagcttgga ctaaattcag tcatctggct gtctggggaa gcatgctgac ctggctggtg   3000

tttttggca tctactcgac catctggccc accattccca ttgctccaga tatgagagga   3060

caggcaacta tggtcctgag ctccgcacac ttctggttgg gattatttct ggttcctact   3120

gcctgtttga ttgaagatgt ggcatggaga gcagccaagc acacctgcaa aaagacattg   3180

ctggaggagg tgcaggagct ggaaaccaag tctcgagtcc tgggaaaagc ggtgctgcgg   3240

gatagcaatg gaaagaggct gaacgagcgc gaccgcctga tcaagaggct gggccggaag   3300

acgcccccga cgctgttccg ggcagctcc ctgcagcagg gcgtcccgca tgggtatgct   3360

ttttctcaag aagaacacgg agctgttagt caggaagaag tcatccgtgc ttatgacacc   3420

accaaaaaga aatccaggaa gaaa                                          3444
```

<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44

```
ctttgggcta taagaaggca gag                                             23
```

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45

```
aggtttgcga gggaatatgt aact                                            24
```

<210> SEQ ID NO 46
<211> LENGTH: 18
<212> TYPE: DNA
<213> ORGANISM: Artificial Sequence
<220> FEATURE:
<223> OTHER INFORMATION: Primer

<400> SEQUENCE: 46

```
atttaggtga cactatag                                                   18
```

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47

```
aatacgactc actataggg                                                  19
```

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
tcaagaagat ggacaccacc tcag 24

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
gccagtttat gaaaagggct tgag 24

<210> SEQ ID NO 50
<211> LENGTH: 24
<212> TYPE: DNA
<213> ORGANISM: Artificial Sequence
<220> FEATURE:
<223> OTHER INFORMATION: Primer

<400> SEQUENCE: 50
ttcgccagga ccacaccagc aact 24

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
tcgcagtttc ttgtttgtct cctg 24

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
acctcaggca atgtgttatg 20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
agcgatggga caggaacaaa 20

<210> SEQ ID NO 54
<211> LENGTH: 24
<212> TYPE: DNA
<213> ORGANISM: Artificial Sequence
<220> FEATURE:
<223> OTHER INFORMATION: Primer -continued

<400> SEQUENCE: 54
agttgctggt gtggtcctgg cgaa 24

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
ctgggcagat tttatttgaa 20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
cctgagctcc gcacacttct 20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
cataacacat tgcctgaggt 20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
ttcaaataaa atctgcccag 20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
agaagtgtgc ggagctcagg 20

<210> SEQ ID NO 60
<211> LENGTH: 3643
<212> TYPE: DNA
<213> ORGANISM: Human

<400> SEQUENCE: 60
ctttgggcta taagaaggca gaggatgaga tgtcccgggc cacgtctgtt ggagaccagc 60
tggaggcacc cgcccgcacc atttacctca accaaccgca tctcaacaaa ttccgcgaca 120
accagatcag tacggccaag tacagcgtgt tgacatttct acctcgattc ttgtatgagc 180

-continued

```
agattagaag agctgctaat gccttctttc tcttcattgc cttattacag caaattccag    240

atgtatctcc aacaggaaga tataccaccc tggtgccatt gatcattatt ttaacaattg    300

caggcatcaa agagattgta gaagatttta agcgacacaa ggcagacaat gcagttaaca    360

aaaagaaaac aatagtgtta agaaatggta tgtggcatac cattatgtgg aaagaggtgg    420

cagtgggaga cattgtgaag gtcgtcaatg ggcagtatct tccagcagat gtggtcctgc    480

tgtcatccag tgaacctcag gcaatgtgtt atgttgaaac agctaatctg gatggggaga    540

cgaaccttaa aatacgtcag ggtttgagtc acactgctga catgcaaaca cgtgaagttc    600

tgatgaagtt atctggaact atagagtgtg aagggcccaa ccgccacctc tatgacttca    660

ctggaaactt gaacttagat gggaaaagcc ttgttgccct tgggcctgac cagatcttat    720

taagaggtac acagcttaga aatactcagt gggtctttgg catagttgtt tatactggac    780

acgacaccaa actcatgcag aattcaacca aagcgcctct caagagatca aatgttgaga    840

aggtgactaa cgtgcagatc ctggtgttgt ttggcatcct cttggtcatg gccttggtga    900

gctcggcggg ggccctgtac tggaacaggt ctcatggtga aaagaactgg tacatcaaga    960

agatggacac cacctcagat aattttggat acaacctact gacgttcatc atcttataca   1020

acaatcttat tcccatcagt ctgttggtga ctcttgaggt tgtgaagtat actcaagccc   1080

ttttcataaa ctgggacaca gatatgtatt atataggaaa tgacactcct gccatggcca   1140

ggacatcaaa ccttaatgaa gagcttgggc aggtgaaata tctcttttct gacaagactg   1200

gaacgcttac atgcaatatc atgaacttta agaagtgcag cattgccgga gtaacctatg   1260

gtcacttccc agaattggca agagagccgt cttcagatga cttctgtcgg atgcctcctc   1320

cctgtagtga ttcctgtgac tttgatgacc ccaggctgtt gaagaacatt gaggatcgcc   1380

atcccacagc cccttgcatt caggagttcc tcacccttct ggccgtgtgc cacacggttg   1440

ttcctgagaa ggatggagat aacatcatct accaggcctc ttccccagat gaagctgctt   1500

tggtgaaagg agctaaaaag ctgggctttg tcttcacagc cagaacacca ttctcagtca   1560

tcatagaagc gatgggacag gaacaaacat tcggaatcct taatgtcctg gaattttcta   1620

gtgacagaaa aagaatgtct gtaattgttc gaactccttc aggacgactt cggctttact   1680

gtaaaggggc tgataatgtg atttttgaga gactttcaaa agactcaaaa tatatggagg   1740

aaacattatg ccatctggaa tactttgcca cggaaggctt gcggactctc tgtgtggctt   1800

atgctgatct ctctgagaat gagtatgagg agtggctgaa agtctatcag gaagccagca   1860

ccatattgaa ggacagagct caacggttgg aagagtgtta cgagatcatt gagaagaatt   1920

tgctgctact tggagccaca gccatagaag atcgccttca agcaggagtt ccagaaacca   1980

tcgcaacact gttgaaggca gaaattaaaa tatgggtgtt gacaggagac aaacaagaaa   2040

ctgcgattaa tatagggtat tcctgccgat tggtatcgca gaatatggcc cttatcctat   2100

tgaaggagga ctctttggat gccacaaggg cagccattac tcagcactgc actgaccttg   2160

ggaatttgct gggcaaggaa aatgacgtgg ccctcatcat cgatggccac accctgaagt   2220

acgcgctctc cttcgaagtc cggaggagtt tcctggattt ggcactctcg tgcaaagcgg   2280

tcatatgctg cagagtgtct cctctgcaga agtctgagat agtggatgtg gtgaagaagc   2340

gggtgaaggc catcaccctc gccatcggag acggcgccaa cgatgtcggg atgatccaga   2400

cagcccacgt gggtgtggga atcagtggga atgaaggcat gcaggccacc aacaactcgg   2460

attacgccat cgcacagttt tcctacttag agaagcttct gttggttcat ggagcctgga   2520

gctacaaccg ggtgaccaag tgcatcttgt actgcttcta taagaacgtg gtcctgtata   2580
```

ttattgagct ttggttcgcc tttgttaatg gattttctgg gcagatttta tttgaacgtt 2640
ggtgcatcgg cctgtacaat gtgattttca ccgctttgcc gcccttcact ctgggaatct 2700
ttgagaggtc ttgcactcag gagagcatgc tcaggtttcc ccagctctac aaaatcaccc 2760
agaatggcga aggcttcaac acaaaggttt tctggggtca ctgcatcaac gccttggtcc 2820
actccctcat cctcttctgg tttcccatga aagctctgga gcatgatact gtgttgacaa 2880
gtggtcatgc taccgactat ttatttgttg gaaatattgt ttacacatat gttgttgtta 2940
ctgtttgtct gaaagctggt ttggagacca cagcttggac taaattcagt catctggctg 3000
tctggggaag catgctgacc tggctggtgt tttttggcat ctactcgacc atctggccca 3060
ccattcccat tgctccagat atgagaggac aggcaactat ggtcctgagc tccgcacact 3120
tctggttggg attatttctg gttcctactg cctgtttgat tgaagatgtg gcatggagag 3180
cagccaagca cacctgcaaa aagacattgc tggaggaggt gcaggagctg gaaaccaagt 3240
ctcgagtcct gggaaaagcg gtgctgcggg atagcaatgg aaagaggctg aacgagcgcg 3300
accgcctgat caagaggctg ggccggaaga cgcccccgac gctgttccgg ggcagctccc 3360
tgcagcaggg cgtcccgcat gggtatgctt tttctcaaga agaacacgga gctgttagtc 3420
aggaagaagt catccgtgct tatgacacca ccaaaaagaa atccaggaag aaataagaca 3480
tgaattttcc tgactgatct taggaaagag attcagtttg ttgcacccag tgttaacaca 3540
tctttgtcag agaagactgg cgtcagcagc caaaacacca ggaaacacat ttctgtggcc 3600
ttagccaagc agtttgttag ttacatattc cctcgcaaac cta 3643

<210> SEQ ID NO 61
<211> LENGTH: 3643
<212> TYPE: DNA
<213> ORGANISM: Human

<400> SEQUENCE: 61
ctttgggcta taagaaggca gaggatgaga tgtcccgggc cacgtctgtt ggagaccagc 60
tggaggcacc cgcccgcacc atttacctca accaaccgca tctcaacaaa ttccgcgaca 120
accagatcag tacggccaag tacagcgtgt tgacatttct acctcgattc ttgtatgagc 180
agattagaag agctgctaat gccttctttc tcttcattgc cttattacag caaattccag 240
atgtatctcc aacaggaaga tataccaccc tggtgccatt gatcattatt ttaacaattg 300
caggcatcaa agagattgta gaagatttta agcgacacaa ggcagacaat gcagttaaca 360
aaaagaaaac aatagtgtta agaaatggta tgtggcatac cattatgtgg aaagaggtgg 420
cagtgggaga cattgtgaag gtcgtcaatg ggcagtatct tccagcagat gtggtcctgc 480
tgtcatccag tgaacctcag gcaatgtgtt atgttgaaac agctaatctg gatggggaga 540
cgaaccttaa aatacgtcag ggtttgagtc acactgctga catgcaaaca cgtgaagttc 600
tgatgaagtt atctggaact atagagtgtg aagggcccaa ccgccacctc tatgacttca 660
ctggaaactt gaacttagat gggaaaagcc ttgttgccct tgggcctgac cagatcttat 720
taagaggtac acagcttaga aatactcagt gggtctttgg catagttgtt tatactggac 780
acgacaccaa actcatgcag aattcaacca aagcgcctct caagagatca aatgttgaga 840
aggtgactaa cgtgcagatc ctggtgttgt ttggcatcct cttggtcatg gccttggtga 900
gctcggcggg ggccctgtac tggaacaggt ctcatggtga aaagaactgg tacatcaaga 960
agatggacac cacctcagat aattttggat acaacctact gacgttcatc atcttataca 1020

-continued

```
acaatcttat tcccatcagt ctgttggtga ctcttgaggt tgtgaagtat actcaagccc   1080
ttttcataaa ctgggacaca gatatgtatt atataggaaa tgacactcct gccatggcca   1140
ggacatcaaa ccttaatgaa gagcttgggc aggtgaaata tctcttttct gacaagactg   1200
gaacgcttac atgcaatatc atgaacttta agaagtgcag cattgccgga gtaacctatg   1260
gtcacttccc agaattggca agagagccgt cttcagatga cttctgtcgg atgcctcctc   1320
cctgtagtga ttcctgtgac tttgatgacc ccaggctgtt gaagaacatt gaggatcgcc   1380
atcccacagc cccttgcatt caggagttcc tcacccttct ggccgtgtgc cacacggttg   1440
ttcctgagaa ggatggagat aacatcatct accaggcctc ttccccagat gaagctgctt   1500
tggtgaaagg agctaaaaag ctgggctttg tcttcacagc cagaacacca ttctcagtca   1560
tcatagaagc gatgggacag gaacaaacat tcggaatcct taatgtcctg gaattttcta   1620
gtgacagaaa aagaatgtct gtaattgttc gaactccttc aggacgactt cggctttact   1680
gtaaaggggc tgataatgtg atttttgaga gactttcaaa agactcaaaa tatatggagg   1740
aaacattatg ccatctggaa tactttgcca cggaaggctt gcggactctc tgtgtggctt   1800
atgctgatct ctctgagaat gagtatgagg agtggctgaa agtctatcag gaagccagca   1860
ccatattgaa ggacagagct caacggttgg aagagtgtta cgagatcatt gagaagaatt   1920
tgctgctact tggagccaca gccatagaag atcgccttca agcaggagtt ccagaaacca   1980
tcgcaacact gttgaaggca gaaattaaaa tatgggtgtt gacaggagac aaacaagaaa   2040
ctgcgattaa tatagggtat tcctgccgat tggtatcgca gaatatggcc cttatcctat   2100
tgaaggagga ctctttggat gccacaaggg cagccattac tcagcactgc actgaccttg   2160
ggaatttgct gggcaaggaa aatgacgtgg ccctcatcat cgatggccac accctgaagt   2220
acgcgctctc cttcgaagtc cggaggagtt tcctggattt ggcactctcg tgcaaagcgg   2280
tcatatgctg cagagtgtct cctctgcaga agtctgagat agtggatgtg gtgaagaagc   2340
gggtgaaggc catcaccctc gccatcggag acggcgccaa cgatgtcggg atgatccaga   2400
cagcccacgt gggtgtggga atcagtggga atgaaggcat gcaggccacc aacaactcgg   2460
attacgccat cgcacagttt tcctacttag agaagcttct gttggttcat ggagcctgga   2520
gctacaaccg ggtgaccaag tgcatcttgt actgcttcta taagaacgtg gtcctgtata   2580
ttattgagct ttggttcgcc tttgttaatg gattttctgg gcagatttta tttgaacgtt   2640
ggtgcatcgg cctgtacaat gtgattttca ccgctttgcc gcccttcact ctgggaatct   2700
ttgagaggtc ttgcactcag gagagcatgc tcaggtttcc ccagctctac aaaatcaccc   2760
agaatggcga aggcttcaac acaaaggttt tctggggtca ctgcatcaac gccttggtcc   2820
actccctcat cctcttctgg tttcccatga aagctctgga gcatgatact gtgttgacaa   2880
gtggtcatgc taccgactat ttatttgttg gaaatattgt ttacacatat gttgttgtta   2940
ctgtttgtct gaaagctggt ttggagacca cagcttggac taaattcagt catctggctg   3000
tctggggaag catgctgacc tggctggtgt tttttggcat ctactcgacc atctggccca   3060
ccattcccat tgctccagat atgagaggac aggcaactat ggtcctgagc tccgcacact   3120
tctggttggg attatttctg gttcctactg cctgtttgat tgaagatgtg gcatggagag   3180
cagccaagca cacctgcaaa aagacattgc tggaggaggt gcaggagctg gaaaccaagt   3240
ctcgagtcct gggaaaagcg gtgctgcggg atagcaatgg aaagaggctg aacgagcgcg   3300
accgcctgat caagaggctg ggccggaaga cgcccccgac gctgttccgg ggcagctccc   3360
tgcagcaggg cgtcccgcat gggtatgctt tttctcaaga agaacacgga gctgttagtc   3420
```

```
aggaagaagt catccgtgct tatgacacca ccaaaaagaa atccaggaag aaataagaca   3480

tgaattttcc tgactgatct taggaaagag attcagtttg ttgcacccag tgttaacaca   3540

tctttgtcag agaagactgg cgtcagcagc caaaacacca ggaaacacat ttctgtggcc   3600

ttagccaagc agtttgttag ttacatattc cctcgcaaac cta                     3643


<210> SEQ ID NO 62
<211> LENGTH: 3444
<212> TYPE: DNA
<213> ORGANISM: Human

<400> SEQUENCE: 62

atgtcccggg ccacgtctgt tggagaccag ctggaggcac ccgcccgcac catttacctc     60

aaccaaccgc atctcaacaa attccgcgac aaccagatca gtacggccaa gtacagcgtg    120

ttgacatttc tacctcgatt cttgtatgag cagattagaa gagctgctaa tgccttcttt    180

ctcttcattg ccttattaca gcaaattcca gatgtatctc caacaggaag atataccacc    240

ctggtgccat tgatcattat tttaacaatt gcaggcatca aagagattgt agaagatttt    300

aagcgacaca aggcagacaa tgcagttaac aaaaagaaaa caatagtgtt aagaaatggt    360

atgtggcata ccattatgtg gaaagaggtg gcagtgggag acattgtgaa ggtcgtcaat    420

gggcagtatc ttccagcaga tgtggtcctg ctgtcatcca gtgaacctca ggcaatgtgt    480

tatgttgaaa cagctaatct ggatggggag acgaacctta aaatacgtca gggtttgagt    540

cacactgctg acatgcaaac acgtgaagtt ctgatgaagt tatctggaac tatagagtgt    600

gaagggccca accgccacct ctatgacttc actggaaact tgaacttaga tgggaaaagc    660

cttgttgccc ttgggcctga ccagatctta ttaagaggta cacagcttag aaatactcag    720

tgggtctttg gcatagttgt ttatactgga cacgacacca aactcatgca gaattcaacc    780

aaagcgcctc tcaagagatc aaatgttgag aaggtgacta acgtgcagat cctggtgttg    840

tttggcatcc tcttggtcat ggccttggtg agctcggcgg gggccctgta ctggaacagg    900

tctcatggtg aaaagaactg gtacatcaag aagatggaca ccacctcaga taattttgga    960

tacaacctac tgacgttcat catcttatac aacaatctta ttcccatcag tctgttggtg   1020

actcttgagg ttgtgaagta tactcaagcc cttttcataa actgggacac agatatgtat   1080

tatataggaa atgacactcc tgccatggcc aggacatcaa accttaatga agagcttggg   1140

caggtgaaat atctcttttc tgacaagact ggaacgctta catgcaatat catgaacttt   1200

aagaagtgca gcattgccgg agtaacctat ggtcacttcc cagaattggc aagagagccg   1260

tcttcagatg acttctgtcg gatgcctcct ccctgtagtg attcctgtga ctttgatgac   1320

cccaggctgt tgaagaacat tgaggatcgc catcccacag ccccttgcat tcaggagttc   1380

ctcacccttc tggccgtgtg ccacacggtt gttcctgaga aggatggaga taacatcatc   1440

taccaggcct cttccccaga tgaagctgct ttggtgaaag gagctaaaaa gctgggcttt   1500

gtcttcacag ccagaacacc attctcagtc atcatagaag cgatgggaca ggaacaaaca   1560

tttggaatcc ttaatgtcct ggaattttct agtgacagaa aaagaatgtc tgtaattgtt   1620

cgaactcctt caggacgact tcggctttac tgtaaagggg ctgataatgt gatttttgag   1680

agactttcaa aagactcaaa atatatggag gaaacattat gccatctgga atactttgcc   1740

acggaaggct tgcggactct ctgtgtggct tatgctgatc tctctgagaa tgagtatgag   1800

gagtggctga aagtctatca ggaagccagc accatattga aggacagagc tcaacggttg   1860
```

-continued

```
gaagagtgtt acgagatcat tgagaagaat ttgctgctac ttggagccac agccatagaa   1920

gatcgccttc aagcaggagt tccagaaacc atcgcaacac tgttgaaggc agaaattaaa   1980

atatgggtgt tgacaggaga caaacaagaa actgcgatta atatagggta ttcctgccga   2040

ttggtatcgc agaatatggc ccttatccta ttgaaggagg actctttgga tgccacaagg   2100

gcagccatta ctcagcactg cactgacctt gggaatttgc tgggcaagga aaatgacgtg   2160

gccctcatca tcgatggcca caccctgaag tacgcgctct ccttcgaagt ccggaggagt   2220

ttcctggatt tggcactctc gtgcaaagcg gtcatatgct gcagagtgtc tcctctgcag   2280

aagtctgaga tagtggatgt ggtgaagaag cgggtgaagg ccatcaccct cgccatcgga   2340

gacggcgcca acgatgtcgg gatgatccag acagcccacg tgggtgtggg aatcagtggg   2400

aatgaaggca tgcaggccac caacaactcg gattacgcca tcgcacagtt ttcctactta   2460

gagaagcttc tgttggttca tggagcctgg agctacaacc gggtgaccaa gtgcatcttg   2520

tactgcttct ataagaacgt ggtcctgtat attattgagc tttggttcgc ctttgttaat   2580

ggattttctg ggcagatttt atttgaacgt tggtgcatcg gcctgtacaa tgtgattttc   2640

accgctttgc cgcccttcac tctgggaatc tttgagaggt cttgcactca ggagagcatg   2700

ctcaggtttc cccagctcta caaaatcacc cagaatggcg aaggcttcaa cacaaaggtt   2760

ttctggggtc actgcatcaa cgccttggtc cactccctca tcctcttctg gtttcccatg   2820

aaagctctgg agcatgatac tgtgttgaca agtggtcatg ctaccgacta tttatttgtt   2880

ggaaatattg tttacacata tgttgttgtt actgtttgtc tgaaagctgg tttggagacc   2940

acagcttgga ctaaattcag tcatctggct gtctggggaa gcatgctgac ctggctggtg   3000

tttttggca tctactcgac catctggccc accattccca ttgctccaga tatgagagga   3060

caggcaacta tggtcctgag ctccgcacac ttctggttgg gattatttct ggttcctact   3120

gcctgtttga ttgaagatgt ggcatggaga gcagccaagc acacctgcaa aaagacattg   3180

ctggaggagg tgcaggagct ggaaaccaag tctcgagtcc tgggaaaagc ggtgctgcgg   3240

gatagcaatg gaaagaggct gaacgagcgc gaccgcctga tcaagaggct gggccggaag   3300

acgcccccga cgctgttccg ggcagctcc ctgcagcagg gcgtcccgca tgggtatgct   3360

ttttctcaag aagaacacgg agctgttagt caggaagaag tcatccgtgc ttatgacacc   3420

accaaaaaga aatccaggaa gaaa                                          3444
```

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63

```
cgcagaatat ggcccttatc c                                               21
```

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64

```
cattttcctt gcccagcaaa                                                 20
```

<210> SEQ ID NO 65
<211> LENGTH: 28
<212> TYPE: DNA
<213> ORGANISM: Artificial Sequence
<220> FEATURE:
<223> OTHER INFORMATION: Probe

<400> SEQUENCE: 65
ccattactca gcactgcact gaccttgg 28

<210> SEQ ID NO 66
<211> LENGTH: 791
<212> TYPE: PRT
<213> ORGANISM: Human

<400> SEQUENCE: 66

```
Met Lys Ala His Pro Lys Glu Met Val Pro Leu Met Gly Lys Arg Val
                5                   10                  15

Ala Ala Pro Ser Gly Asn Pro Ala Val Leu Pro Glu Lys Arg Pro Ala
            20                  25                  30

Glu Ile Thr Pro Thr Lys Lys Ser Ala His Phe Phe Leu Glu Ile Glu
        35                  40                  45

Gly Phe Glu Pro Asn Pro Thr Val Ala Lys Thr Ser Pro Pro Val Phe
    50                  55                  60

Ser Lys Pro Met Asp Ser Asn Ile Arg Gln Cys Ile Ser Gly Asn Cys
65                  70                  75                  80

Asp Asp Met Asp Ser Pro Gln Ser Pro Gln Asp Asp Val Thr Glu Thr
                85                  90                  95

Pro Ser Asn Pro Asn Ser Pro Ser Ala Gln Leu Ala Lys Glu Glu Gln
            100                 105                 110

Arg Arg Lys Lys Arg Arg Leu Lys Lys Arg Ile Phe Ala Ala Val Ser
        115                 120                 125

Glu Gly Cys Val Glu Glu Leu Val Glu Leu Leu Val Glu Leu Gln Glu
    130                 135                 140

Leu Cys Arg Arg Arg His Asp Glu Asp Val Pro Asp Phe Leu Met His
145                 150                 155                 160

Lys Leu Thr Ala Ser Asp Thr Gly Lys Thr Cys Leu Met Lys Ala Leu
                165                 170                 175

Leu Asn Ile Asn Pro Asn Thr Lys Glu Ile Val Arg Ile Leu Leu Ala
            180                 185                 190

Phe Ala Glu Glu Asn Asp Ile Leu Gly Arg Phe Ile Asn Ala Glu Tyr
        195                 200                 205

Thr Glu Glu Ala Tyr Glu Gly Gln Thr Ala Leu Asn Ile Ala Ile Glu
    210                 215                 220

Arg Arg Gln Gly Asp Ile Ala Ala Leu Leu Ile Ala Ala Gly Ala Asp
225                 230                 235                 240

Val Asn Ala His Ala Lys Gly Ala Phe Phe Asn Pro Lys Tyr Gln His
                245                 250                 255

Glu Gly Phe Tyr Phe Gly Glu Thr Pro Leu Ala Leu Ala Ala Cys Thr
            260                 265                 270

Asn Gln Pro Glu Ile Val Gln Leu Leu Met Glu His Glu Gln Thr Asp
        275                 280                 285

Ile Thr Ser Arg Asp Ser Arg Gly Asn Asn Ile Leu His Ala Leu Val
    290                 295                 300

Thr Val Ala Glu Asp Phe Lys Thr Gln Asn Asp Phe Val Lys Arg Met
305                 310                 315                 320
```

-continued

```
Tyr Asp Met Ile Leu Leu Arg Ser Gly Asn Trp Glu Leu Glu Thr Thr
                325                 330                 335

Arg Asn Asn Asp Gly Leu Thr Pro Leu Gln Leu Ala Ala Lys Met Gly
            340                 345                 350

Lys Ala Glu Ile Leu Lys Tyr Ile Leu Ser Arg Glu Ile Lys Glu Lys
        355                 360                 365

Arg Leu Arg Ser Leu Ser Arg Lys Phe Thr Asp Trp Ala Tyr Gly Pro
    370                 375                 380

Val Ser Ser Ser Leu Tyr Asp Leu Thr Asn Val Asp Thr Thr Thr Asp
385                 390                 395                 400

Asn Ser Val Leu Glu Ile Thr Val Tyr Asn Thr Asn Ile Asp Asn Arg
                405                 410                 415

His Glu Met Leu Thr Leu Glu Pro Leu His Thr Leu Leu His Met Lys
            420                 425                 430

Trp Lys Lys Phe Ala Lys His Met Phe Phe Leu Ser Phe Cys Phe Tyr
        435                 440                 445

Phe Phe Tyr Asn Ile Thr Leu Thr Leu Val Ser Tyr Tyr Arg Pro Arg
    450                 455                 460

Glu Glu Glu Ala Ile Pro His Pro Leu Ala Leu Thr His Lys Met Gly
465                 470                 475                 480

Trp Leu Gln Leu Leu Gly Arg Met Phe Val Leu Ile Trp Ala Met Cys
                485                 490                 495

Ile Ser Val Lys Glu Gly Ile Ala Ile Phe Leu Leu Arg Pro Ser Asp
            500                 505                 510

Leu Gln Ser Ile Leu Ser Asp Ala Trp Phe His Phe Val Phe Phe Ile
        515                 520                 525

Gln Ala Val Leu Val Ile Leu Ser Val Phe Leu Tyr Leu Phe Ala Tyr
    530                 535                 540

Lys Glu Tyr Leu Ala Cys Leu Val Leu Ala Met Ala Leu Gly Trp Ala
545                 550                 555                 560

Asn Met Leu Tyr Tyr Thr Arg Gly Phe Gln Ser Met Gly Met Tyr Ser
                565                 570                 575

Val Met Ile Gln Lys Val Ile Leu His Asp Val Leu Lys Phe Leu Phe
            580                 585                 590

Val Tyr Ile Val Phe Leu Leu Gly Phe Gly Val Ala Leu Ala Ser Leu
        595                 600                 605

Ile Glu Lys Cys Pro Lys Asp Asn Lys Asp Cys Ser Ser Tyr Gly Ser
    610                 615                 620

Phe Ser Asp Ala Val Leu Glu Leu Phe Lys Leu Thr Ile Gly Leu Gly
625                 630                 635                 640

Asp Leu Asn Ile Gln Gln Asn Ser Lys Tyr Pro Ile Leu Phe Leu Phe
                645                 650                 655

Leu Leu Ile Thr Tyr Val Ile Leu Thr Phe Val Leu Leu Leu Asn Met
            660                 665                 670

Leu Ile Ala Leu Met Gly Glu Thr Val Glu Asn Val Ser Lys Glu Ser
        675                 680                 685

Glu Arg Ile Trp Arg Leu Gln Arg Ala Arg Thr Ile Leu Glu Phe Glu
    690                 695                 700

Lys Met Leu Pro Glu Trp Leu Arg Ser Arg Phe Arg Met Gly Glu Leu
705                 710                 715                 720

Cys Lys Val Ala Glu Asp Asp Phe Arg Leu Cys Leu Arg Ile Asn Glu
                725                 730                 735

Val Lys Trp Thr Glu Trp Lys Thr His Val Ser Phe Leu Asn Glu Asp
```

-continued

```
            740                   745                   750

Pro Gly Pro Val Arg Arg Thr Ala Asp Phe Asn Lys Ile Gln Asp Ser
        755                   760                   765

Ser Arg Asn Asn Ser Lys Thr Thr Leu Asn Ala Phe Glu Glu Val Glu
    770                   775                   780

Glu Phe Pro Glu Thr Ser Val
785                   790


<210> SEQ ID NO 67
<211> LENGTH: 2373
<212> TYPE: DNA
<213> ORGANISM: Human

<400> SEQUENCE: 67

atgaaagccc accccaagga gatggtgcct ctcatgggca agagagttgc tgcccccagt      60

gggaaccctg ccgtcctgcc agagaagagg ccggcggaga tcaccccccac aaagaagagt     120

gcacacttct tcctggagat agaagggttt gaacccaacc ccacagttgc caagacctct     180

cctcctgtct tctccaagcc catggattcc aacatccggc agtgcatctc tggtaactgt     240

gatgacatgg actcccccca gtctcctcaa gatgatgtga cagagacccc atccaatccc     300

aacagcccca gtgcacagct ggccaaggaa gagcagagga ggaaaaagag gcggctgaag     360

aagcgcatct ttgcagccgt gtctgagggc tgcgtggagg agttggtaga gttgctggtg     420

gagctgcagg agctttgcag gcggcgccat gatgaggatg tgcctgactt cctcatgcac     480

aagctgacgg cctccgacac ggggaagacc tgcctgatga aggccttgtt aaacatcaac     540

cccaacacca aggagatcgt gcggatcctg cttgcctttg ctgaagagaa cgacatcctg     600

ggcaggttca tcaacgccga gtacacagag gaggcctatg aagggcagac ggcgctgaac     660

atcgccatcg agcggcggca gggggacatc gcagccctgc tcatcgccgc cggcgccgac     720

gtcaacgcgc acgccaaggg ggccttcttc aaccccaagt accaacacga aggcttctac     780

ttcggtgaga cgcccctggc cctggcagca tgcaccaacc agcccgagat tgtgcagctg     840

ctgatggagc acgagcagac ggacatcacc tcgcgggact cacgaggcaa caacatcctt     900

cacgccctgg tgaccgtggc cgaggacttc aagacgcaga atgactttgt gaagcgcatg     960

tacgacatga tcctactgcg gagtggcaac tgggagctgg agaccactcg caacaacgat    1020

ggcctcacgc cgctgcagct ggccgccaag atgggcaagg cggagatcct gaagtacatc    1080

ctcagtcgtg agatcaagga gaagcggctc cggagcctgt ccaggaagtt caccgactgg    1140

gcgtacggac ccgtgtcatc ctccctctac gacctcacca acgtggacac caccacggac    1200

aactcagtgc tggaaatcac tgtctacaac accaacatcg acaaccggca tgagatgctg    1260

accctggagc cgctgcacac gctgctgcat atgaagtgga agaagtttgc caagcacatg    1320

ttctttctgt ccttctgctt ttatttcttc tacaacatca ccctgaccct cgtctcgtac    1380

taccgccccc gggaggagga ggccatcccg cacccttgg ccctgacgca caagatgggg    1440

tggctgcagc tcctagggag gatgtttgtg ctcatctggg ccatgtgcat ctctgtgaaa    1500

gagggcattg ccatcttcct gctgagaccc tcggatctgc agtccatcct ctcggatgcc    1560

tggttccact ttgtcttttt tatccaagct gtgcttgtga tactgtctgt cttcttgtac    1620

ttgtttgcct acaaagagta cctcgcctgc ctcgtgctgg ccatggccct gggctgggcg    1680

aacatgctct actatacgcg gggtttccag tccatgggca tgtacagcgt catgatccag    1740

aaggtcattt tgcatgatgt tctgaagttc ttgtttgtat atatcgtgtt tttgcttgga    1800
```

-continued

```
tttggagtag ccttggcctc gctgatcgag aagtgtccca aagacaacaa ggactgcagc   1860

tcctacggca gcttcagcga cgcagtgctg gaactcttca agctcaccat aggcctgggt   1920

gacctgaaca tccagcagaa ctccaagtat cccattctct ttctgttcct gctcatcacc   1980

tatgtcatcc tcacctttgt tctcctcctc aacatgctca ttgctctgat gggcgagact   2040

gtggagaacg tctccaagga gagcgaacgc atctggcgcc tgcagagagc caggaccatc   2100

ttggagtttg agaaaatgtt accagaatgg ctgaggagca gattccggat gggagagctg   2160

tgcaaagtgg ccgaggatga tttccgactg tgtttgcgga tcaatgaggt gaagtggact   2220

gaatggaaga cgcacgtctc cttccttaac gaagacccgg ggcctgtaag acgaacagca   2280

gatttcaaca aaatccaaga ttcttccagg aacaacagca aaaccactct caatgcattt   2340

gaagaagtcg aggaattccc ggaaacctcg gtg                                2373
```

<210> SEQ ID NO 68
<211> LENGTH: 27
<212> TYPE: DNA
<213> ORGANISM: Artificial Sequence
<220> FEATURE:
<223> OTHER INFORMATION: Primer

<400> SEQUENCE: 68

```
ccatcctaat acgactcact atagggc                                         27
```

<210> SEQ ID NO 69
<211> LENGTH: 23
<212> TYPE: DNA
<213> ORGANISM: Artificial Sequence
<220> FEATURE:
<223> OTHER INFORMATION: Primer

<400> SEQUENCE: 69

```
cgggggcggt agtacgagac gag                                             23
```

<210> SEQ ID NO 70
<211> LENGTH: 23
<212> TYPE: DNA
<213> ORGANISM: Artificial Sequence
<220> FEATURE:
<223> OTHER INFORMATION: Primer

<400> SEQUENCE: 70

```
actcactata gggctcgagc ggc                                             23
```

<210> SEQ ID NO 71
<211> LENGTH: 28
<212> TYPE: DNA
<213> ORGANISM: Artificial Sequence
<220> FEATURE:
<223> OTHER INFORMATION: Primer

<400> SEQUENCE: 71

```
cagcaaaggc aagcaggatc cgcactat                                        28
```

<210> SEQ ID NO 72
<211> LENGTH: 17
<212> TYPE: DNA
<213> ORGANISM: Artificial Sequence
<220> FEATURE:
<223> OTHER INFORMATION: Primer

<400> SEQUENCE: 72

```
caggaaacag ctatgac                                                    17
```

<210> SEQ ID NO 73
<211> LENGTH: 16
<212> TYPE: DNA
<213> ORGANISM: Artificial Sequence
<220> FEATURE:
<223> OTHER INFORMATION: Primer

<400> SEQUENCE: 73
gtaaaacgac ggccag 16

<210> SEQ ID NO 74
<211> LENGTH: 28
<212> TYPE: DNA
<213> ORGANISM: Artificial Sequence
<220> FEATURE:
<223> OTHER INFORMATION: Primer

<400> SEQUENCE: 74
gtgcactggg gctgttggga ttggatgg 28

<210> SEQ ID NO 75
<211> LENGTH: 28
<212> TYPE: DNA
<213> ORGANISM: Artificial Sequence
<220> FEATURE:
<223> OTHER INFORMATION: Primer

<400> SEQUENCE: 75
atggctggtg aggttctggg tggtcgtg 28

<210> SEQ ID NO 76
<211> LENGTH: 29
<212> TYPE: DNA
<213> ORGANISM: Artificial Sequence
<220> FEATURE:
<223> OTHER INFORMATION: Primer

<400> SEQUENCE: 76
tgaggaggag aacaaaggtg aggatgaca 29

<210> SEQ ID NO 77
<211> LENGTH: 27
<212> TYPE: DNA
<213> ORGANISM: Artificial Sequence
<220> FEATURE:
<223> OTHER INFORMATION: Primer

<400> SEQUENCE: 77
actgcgtcgc tgaagctgcc gtaggag 27

<210> SEQ ID NO 78
<211> LENGTH: 29
<212> TYPE: DNA
<213> ORGANISM: Artificial Sequence
<220> FEATURE:
<223> OTHER INFORMATION: Primer

<400> SEQUENCE: 78
tcccattctc tttctgttcc tgctcatca 29

<210> SEQ ID NO 79
<211> LENGTH: 29
<212> TYPE: DNA
<213> ORGANISM: Artificial Sequence
<220> FEATURE:

<223> OTHER INFORMATION: Primer

<400> SEQUENCE: 79
tgtcatcctc acctttgttc tcctcctca 29

<210> SEQ ID NO 80
<211> LENGTH: 28
<212> TYPE: DNA
<213> ORGANISM: Artificial Sequence
<220> FEATURE:
<223> OTHER INFORMATION: Primer

<400> SEQUENCE: 80
aacgaagacc cggggcctgt aagacgaa 28

<210> SEQ ID NO 81
<211> LENGTH: 21
<212> TYPE: DNA
<213> ORGANISM: Artificial Sequence
<220> FEATURE:
<223> OTHER INFORMATION: Primer

<400> SEQUENCE: 81
ccgccgcctc agccacagtc c 21

<210> SEQ ID NO 82
<211> LENGTH: 22
<212> TYPE: DNA
<213> ORGANISM: Artificial Sequence
<220> FEATURE:
<223> OTHER INFORMATION: Primer

<400> SEQUENCE: 82
gctctgggtt ccgcttctac ac 22

<210> SEQ ID NO 83
<211> LENGTH: 24
<212> TYPE: DNA
<213> ORGANISM: Artificial Sequence
<220> FEATURE:
<223> OTHER INFORMATION: Primer

<400> SEQUENCE: 83
atgaaagccc accccaagga gatg 24

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
ctacaccgag gtttccggga attc 24

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
tggagcacga gcagacggac atca 24

<210> SEQ ID NO 86
<211> LENGTH: 25
<212> TYPE: DNA
<213> ORGANISM: Artificial Sequence
<220> FEATURE:
<223> OTHER INFORMATION: Primer

<400> SEQUENCE: 86
gcggatcctg cttgcctttg ctgaa 25

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
cgcgggactc acgaggcaac aaca 24

<210> SEQ ID NO 88
<211> LENGTH: 24
<212> TYPE: DNA
<213> ORGANISM: Artificial Sequence
<220> FEATURE:
<223> OTHER INFORMATION: Primer

<400> SEQUENCE: 88
ggctgggcga acatgctcta ctat 24

<210> SEQ ID NO 89
<211> LENGTH: 29
<212> TYPE: DNA
<213> ORGANISM: Artificial Sequence
<220> FEATURE:
<223> OTHER INFORMATION: Primer

<400> SEQUENCE: 89
cgctgctgca tatgaagtgg aagaagttt 29

<210> SEQ ID NO 90
<211> LENGTH: 29
<212> TYPE: DNA
<213> ORGANISM: Artificial Sequence
<220> FEATURE:
<223> OTHER INFORMATION: Primer

<400> SEQUENCE: 90
cagacggaca tcacctcgcg ggactcacg 29

<210> SEQ ID NO 91
<211> LENGTH: 29
<212> TYPE: DNA
<213> ORGANISM: Artificial Sequence
<220> FEATURE:
<223> OTHER INFORMATION: Primer

<400> SEQUENCE: 91
gagagctgtg caaagtggcc gaggatgat 29

<210> SEQ ID NO 92
<211> LENGTH: 28
<212> TYPE: DNA
<213> ORGANISM: Artificial Sequence
<220> FEATURE:
<223> OTHER INFORMATION: Primer -continued

<400> SEQUENCE: 92
gagtcccgcg aggtgatgtc cgtctgct 28

<210> SEQ ID NO 93
<211> LENGTH: 28
<212> TYPE: DNA
<213> ORGANISM: Artificial Sequence
<220> FEATURE:
<223> OTHER INFORMATION: Primer

<400> SEQUENCE: 93
caactcctcc acgcagccct cagacacg 28

<210> SEQ ID NO 94
<211> LENGTH: 21
<212> TYPE: DNA
<213> ORGANISM: Artificial Sequence
<220> FEATURE:
<223> OTHER INFORMATION: Primer

<400> SEQUENCE: 94
gcctgacttc ctcatgcaca a 21

<210> SEQ ID NO 95
<211> LENGTH: 19
<212> TYPE: DNA
<213> ORGANISM: Artificial Sequence
<220> FEATURE:
<223> OTHER INFORMATION: Primer

<400> SEQUENCE: 95
aggccttcat caggcaggt 19

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
ctgacggcct ccgacacggg 20

<210> SEQ ID NO 97
<211> LENGTH: 697
<212> TYPE: DNA
<213> ORGANISM: Human

<400> SEQUENCE: 97
tgcaatgaga gcttcccgcc gcctcagcca cagtcccacc cgggggcctt gggccccaga 60
catgcggtga tctcagggca agggttgcca cgaccaccca gaacctcacc agccatgaaa 120
gcccacccca aggagatggt gcctctcatg ggcaagagag ttgctgcccc cagtgggaac 180
cctgccgtcc tgccagagaa gaggccggcg gagatcaccc ccacaaagaa gagtgcacac 240
ttcttcctgg agatagaagg gtttgaaccc aaccccacag ttgccaagac ctctcctcct 300
gtcttctcca agcccatgga ttccaacatc cggcagtgca tctctggtaa ctgtgatgac 360
atggactccc cccagtctcc tcaagatgat gtgacagaga ccccatccaa tcccaacagc 420
cccagtgcac agctggccaa ggaagagcag aggaggaaaa agaggcggct gaagaagcgc 480
atctttgcag ccgtgtctga gggctgcgtg gaggagttgg tagagttgct ggtggagctg 540
caggagcttt gcaggcggcg ccatgatgag gatgtgcctg acttcctcat gcacaagctg 600
acggcctccg acacggggaa gacctgcctg atgaaggcct tgttaaacat caaccccaac 660
accaaggaga tagtgcggat cctgcttgcc tttgctg 697

<210> SEQ ID NO 98
<211> LENGTH: 275
<212> TYPE: DNA
<213> ORGANISM: Human

<400> SEQUENCE: 98
ttcttgagca gtgcgtcatg gttgtgtgag tttgtgtcaa acttgctgta ggtctgcttg 60
aggatctgcc cagtccggcg gctgccgtct tccagcctcc ccatcagcgt ttggatgcct 120
tcctctaggt cctttaggag gtgatagtca tcgctgtccc tgcaatgaga gcttcccgcc 180
gcctcagcca cagtcccacc cgggggcctt gggccccaga catgcggtga tctcagggca 240
agggttgcac gaccacccag aacctcacca gccat 275

<210> SEQ ID NO 99
<211> LENGTH: 586
<212> TYPE: DNA
<213> ORGANISM: Human

<400> SEQUENCE: 99
agaagtttgc caagcacatg ttctttctgt ccttctgctt ttatttcttc tacaacatca 60
ccctgaccct cgtctcgtac taccgccccc gggaggagga ggccatcccg caccccttgg 120
ccctgacgca caagatgggg tggctgcagc tcctagggag gatgtttgtg ctcatctggg 180
ccatgtgcat ctctgtgaaa gagggcattg ccatcttcct gctgagaccc tcggatctgc 240
agtccatcct ctcggatgcc tggttccact ttgtcttttt tatccaagct gtgcttgtga 300
tactgtctgt cttcttgtac ttgtttgcct acaaagagta cctcgcctgc ctcgtgctgg 360
ccatggccct gggctgggcg aacatgctct actatacgcg gggtttccag tccatgggca 420
tgtacagcgt catgatccag aaggtcattt tgcatgatgt tctgaagttc ttgtttgtat 480
atatcgtgtt tttgcttgga tttggagtag ccttggcctc gctgatcgag aagtgtccca 540
aagacaacaa ggactgcagc tcctacggca gcttcagcga cgcagt 586

<210> SEQ ID NO 100
<211> LENGTH: 307
<212> TYPE: DNA
<213> ORGANISM: Human

<400> SEQUENCE: 100
tgtcatcctc acctttgttc tcctcctcaa catgctcatt gctctgatgg gcgagactgt 60
ggagaacgtc tccaaggaga gcgaacgcat ctggcgcctg cagagagcca ggaccatctt 120
ggagtttgag aaaatgttac cagaatggct gaggagcaga ttccggatgg gagagctgtg 180
caaagtggcc gaggatgatt tccgactgtg tttgcggatc aatgaggtga agtggactga 240
atggaagacg cacgtctcct tccttaacga agacccgggg cctgtaagac gaacagcaga 300
tttcaac 307

<210> SEQ ID NO 101
<211> LENGTH: 156
<212> TYPE: DNA
<213> ORGANISM: Human

<400> SEQUENCE: 101

-continued aacgaagacc cggggcctgt aagacgaaca gcagatttca acaaaatcca agattcttcc 60
aggaacaaca gcaaaaccac tctcaatgca tttgaagaag tcgaggaatt cccggaaacc 120
tcggtgtaga agcggaaccc agagctggtg tgcgcg 156

<210> SEQ ID NO 102
<211> LENGTH: 2376
<212> TYPE: DNA
<213> ORGANISM: Human

<400> SEQUENCE: 102
atgaaagccc accccaagga gatggtgcct ctcatgggca agagagttgc tgcccccagt 60
gggaaccctg ccgtcctgcc agagaagagg ccggcggaga tcacccccac aaagaagagt 120
gcacacttct tcctggagat agaagggttt gaacccaacc ccacagttgc caagacctct 180
cctcctgtct tctccaagcc catggattcc aacatccggc agtgcatctc tggtaactgt 240
gatgacatgg actcccccca gtctcctcaa gatgatgtga cagagacccc atccaatccc 300
aacagcccca gtgcacagct ggccaaggaa gagcagagga ggaaaaagag gcggctgaag 360
aagcgcatct ttgcagccgt gtctgagggc tgcgtggagg agttggtaga gttgctggtg 420
gagctgcagg agctttgcag gcggcgccat gatgaggatg tgcctgactt cctcatgcac 480
aagctgacgg cctccgacac ggggaagacc tgcctgatga aggccttgtt aaacatcaac 540
cccaacacca aggagatcgt gcggatcctg cttgcctttg ctgaagagaa cgacatcctg 600
ggcaggttca tcaacgccga gtacacagag gaggcctatg aagggcagac ggcgctgaac 660
atcgccatcg agcggcggca gggggacatc gcagccctgc tcatcgccgc cggcgccgac 720
gtcaacgcgc acgccaaggg ggccttcttc aaccccaagt accaacacga aggcttctac 780
ttcggtgaga cgcccctggc cctggcagca tgcaccaacc agcccgagat tgtgcagctg 840
ctgatggagc acgagcagac ggacatcacc tcgcgggact cacgaggcaa caacatcctt 900
cacgccctgg tgaccgtggc cgaggacttc aagacgcaga atgactttgt gaagcgcatg 960
tacgacatga tcctactgcg gagtggcaac tgggagctgg agaccactcg caacaacgat 1020
ggcctcacgc cgctgcagct ggccgccaag atgggcaagg cggagatcct gaagtacatc 1080
ctcagtcgtg agatcaagga gaagcggctc cggagcctgt ccaggaagtt caccgactgg 1140
gcgtacggac ccgtgtcatc ctccctctac gacctcacca acgtggacac caccacggac 1200
aactcagtgc tggaaatcac tgtctacaac accaacatcg acaaccggca tgagatgctg 1260
accctggagc cgctgcacac gctgctgcat atgaagtgga agaagtttgc caagcacatg 1320
ttctttctgt ccttctgctt ttatttcttc tacaacatca ccctgaccct cgtctcgtac 1380
taccgccccc gggaggagga ggccatcccg cacccccttgg ccctgacgca caagatgggg 1440
tggctgcagc tcctagggag gatgtttgtg ctcatctggg ccatgtgcat ctctgtgaaa 1500
gagggcattg ccatcttcct gctgagaccc tcggatctgc agtccatcct ctcggatgcc 1560
tggttccact ttgtcttttt tatccaagct gtgcttgtga tactgtctgt cttcttgtac 1620
ttgtttgcct acaaagagta cctcgcctgc ctcgtgctgg ccatggccct gggctgggcg 1680
aacatgctct actatacgcg gggtttccag tccatgggca tgtacagcgt catgatccag 1740
aaggtcattt tgcatgatgt tctgaagttc ttgtttgtat atatcgtgtt tttgcttgga 1800
tttggagtag ccttggcctc gctgatcgag aagtgtccca aagacaacaa ggactgcagc 1860
tcctacggca gcttcagcga cgcagtgctg gaactcttca agctcaccat aggcctgggt 1920
gacctgaaca tccagcagaa ctccaagtat cccattctct ttctgttcct gctcatcacc 1980

-continued

```
tatgtcatcc tcacctttgt tctcctcctc aacatgctca ttgctctgat gggcgagact   2040

gtggagaacg tctccaagga gagcgaacgc atctggcgcc tgcagagagc caggaccatc   2100

ttggagtttg agaaaatgtt accagaatgg ctgaggagca gattccggat gggagagctg   2160

tgcaaagtgg ccgaggatga tttccgactg tgtttgcgga tcaatgaggt gaagtggact   2220

gaatggaaga cgcacgtctc cttccttaac gaagacccgg ggcctgtaag acgaacagca   2280

gatttcaaca aaatccaaga ttcttccagg aacaacagca aaaccactct caatgcattt   2340

gaagaagtcg aggaattccc ggaaacctcg gtgtag                              2376
```

<210> SEQ ID NO 103
<211> LENGTH: 2373
<212> TYPE: DNA
<213> ORGANISM: Human

<400> SEQUENCE: 103

```
atgaaagccc accccaagga gatggtgcct ctcatgggca agagagttgc tgcccccagt     60

gggaaccctg ccgtcctgcc agagaagagg ccggcggaga tcaccccccac aaagaagagt   120

gcacacttct tcctggagat agaagggttt gaacccaacc ccacagttgc caagacctct   180

cctcctgtct tctccaagcc catggattcc aacatccggc agtgcatctc tggtaactgt   240

gatgacatgg actcccccca gtctcctcaa gatgatgtga cagagacccc atccaatccc   300

aacagcccca gtgcacagct ggccaaggaa gagcagagga ggaaaaagag gcggctgaag   360

aagcgcatct ttgcagccgt gtctgagggc tgcgtggagg agttggtaga gttgctggtg   420

gagctgcagg agctttgcag gcggcgccat gatgaggatg tgcctgactt cctcatgcac   480

aagctgacgg cctccgacac ggggaagacc tgcctgatga aggccttgtt aaacatcaac   540

cccaacacca aggagatagt gcggatcctg cttgcctttg ctgaagagaa cgacatcctg   600

ggcaggttca tcaacgccga gtacacagag gaggcctatg aagggcagac ggcgctgaac   660

atcgccatcg agcggcggca gggggacatc gcagccctgc tcatcgccgc cggcgccgac   720

gtcaacgcgc acgccaaggg ggccttcttc aaccccaagt accaacacga aggcttctac   780

ttcggtgaga cgcccctggc cctggcagca tgcaccaacc agcccgagat tgtgcagctg   840

ctgatggagc acgagcagac ggacatcacc tcgcgggact cacgaggcaa caacatcctt   900

cacgccctgg tgaccgtggc cgaggacttc aagacgcaga atgactttgt gaagcgcatg   960

tacgacatga tcctactgcg gagtggcaac tgggagctgg agaccactcg caacaacgat  1020

ggcctcacgc cgctgcagct ggccgccaag atgggcaagg cggagatcct gaagtacatc  1080

ctcagtcgtg agatcaagga gaagcggctc cggagcctgt ccaggaagtt caccgactgg  1140

gcgtacggac ccgtgtcatc ctccctctac gacctcacca acgtggacac caccacggac  1200

aactcagtgc tggaaatcac tgtctacaac accaacatcg acaaccggca tgagatgctg  1260

accctggagc cgctgcacac gctgctgcat atgaagtgga agaagtttgc caagcacatg  1320

ttctttctgt ccttctgctt ttatttcttc tacaacatca ccctgaccct cgtctcgtac  1380

taccgccccc gggaggagga ggccatcccg cacccccttgg ccctgacgca caagatgggg  1440

tggctgcagc tcctagggag gatgtttgtg ctcatctggg ccatgtgcat ctctgtgaaa  1500

gagggcattg ccatcttcct gctgagaccc tcggatctgc agtccatcct ctcggatgcc  1560

tggttccact ttgtcttttt tatccaagct gtgcttgtga tactgtctgt cttcttgtac  1620

ttgtttgcct acaaagagta cctcgcctgc ctcgtgctgg ccatggccct gggctgggcg  1680
```

-continued

```
aacatgctct actatacgcg gggtttccag tccatgggca tgtacagcgt catgatccag   1740

aaggtcattt tgcatgatgt tctgaagttc ttgtttgtat atatcgtgtt tttgcttgga   1800

tttggagtag ccttggcctc gctgatcgag aagtgtccca aagacaacaa ggactgcagc   1860

tcctacggca gcttcagcga cgcagtgctg gaactcttca agctcaccat aggcctgggt   1920

gacctgaaca tccagcagaa ctccaagtat cccattctct ttctgttcct gctcatcacc   1980

tatgtcatcc tcacctttgt tctcctcctc aacatgctca ttgctctgat gggcgagact   2040

gtggagaacg tctccaagga gagcgaacgc atctggcgcc tgcagagagc caggaccatc   2100

ttggagtttg agaaaatgtt accagaatgg ctgaggagca gattccggat gggagagctg   2160

tgcaaagtgg ccgaggatga tttccgactg tgtttgcgga tcaatgaggt gaagtggact   2220

gaatggaaga cgcacgtctc cttccttaac gaagacccgg ggcctgtaag acgaacagca   2280

gatttcaaca aaatccaaga ttcttccagg aacaacagca aaaccactct caatgcattt   2340

gaagaagtcg aggaattccc ggaaacctcg gtg                                 2373
```

```
<210> SEQ ID NO 104
<211> LENGTH: 373
<212> TYPE: PRT
<213> ORGANISM: Mouse

<400> SEQUENCE: 104

Met Ser Thr Asp Cys Ala Gly Asn Ser Thr Cys Pro Val Asn Ser Thr
                5                   10                  15

Glu Glu Asp Pro Pro Val Gly Met Glu Gly His Ala Asn Leu Lys Leu
            20                  25                  30

Leu Phe Thr Val Leu Ser Ala Val Met Val Gly Leu Val Met Phe Ser
        35                  40                  45

Phe Gly Cys Ser Val Glu Ser Gln Lys Leu Trp Leu His Leu Arg Arg
    50                  55                  60

Pro Trp Gly Ile Ala Val Gly Leu Leu Ser Gln Phe Gly Leu Met Pro
65                  70                  75                  80

Leu Thr Ala Tyr Leu Leu Ala Ile Gly Phe Gly Leu Lys Pro Phe Gln
                85                  90                  95

Ala Ile Ala Val Leu Met Met Gly Ser Cys Pro Gly Gly Thr Ile Ser
            100                 105                 110

Asn Val Leu Thr Phe Trp Val Asp Gly Asp Met Asp Leu Ser Ile Ser
        115                 120                 125

Met Thr Thr Cys Ser Thr Val Ala Ala Leu Gly Met Met Pro Leu Cys
    130                 135                 140

Leu Tyr Ile Tyr Thr Arg Ser Trp Thr Leu Thr Gln Asn Leu Val Ile
145                 150                 155                 160

Pro Tyr Gln Ser Ile Gly Ile Thr Leu Val Ser Leu Val Val Pro Val
                165                 170                 175

Ala Ser Gly Val Tyr Val Asn Tyr Arg Trp Pro Lys Gln Ala Thr Val
            180                 185                 190

Ile Leu Lys Val Gly Ala Ile Leu Gly Gly Met Leu Leu Leu Val Val
        195                 200                 205

Ala Val Thr Gly Met Val Leu Ala Lys Gly Trp Asn Thr Asp Val Thr
    210                 215                 220

Leu Leu Val Ile Ser Cys Ile Phe Pro Leu Val Gly His Val Thr Gly
225                 230                 235                 240

Phe Leu Leu Ala Phe Leu Thr His Gln Ser Trp Gln Arg Cys Arg Thr
                245                 250                 255
```

-continued

```
Ile Ser Ile Glu Thr Gly Ala Gln Asn Ile Gln Leu Cys Ile Ala Met
            260                 265                 270

Leu Gln Leu Ser Phe Ser Ala Glu Tyr Leu Val Gln Leu Leu Asn Phe
        275                 280                 285

Ala Leu Ala Tyr Gly Leu Phe Gln Val Leu His Gly Leu Leu Ile Val
    290                 295                 300

Ala Ala Tyr Gln Ala Tyr Lys Arg Arg Gln Lys Ser Lys Cys Arg Arg
305                 310                 315                 320

Gln His Pro Asp Cys Pro Asp Val Cys Tyr Glu Lys Gln Pro Arg Glu
                325                 330                 335

Thr Ser Ala Phe Leu Asp Lys Gly Asp Glu Ala Ala Val Thr Leu Gly
            340                 345                 350

Pro Val Gln Pro Glu Gln His His Arg Ala Ala Glu Leu Thr Ser His
        355                 360                 365

Ile Pro Ser Cys Glu
    370
```

```
<210> SEQ ID NO 105
<211> LENGTH: 1119
<212> TYPE: DNA
<213> ORGANISM: Mouse

<400> SEQUENCE: 105

atgagcacag actgtgcggg caactccacc tgccctgtca acagtacgga ggaagacccg      60

cccgtgggaa tggagggcca tgcgaatcta aagctgcttt ttacagtgct ctcggctgtg     120

atggtgggtt tggtcatgtt ctcttttgga tgttctgtgg agagtcagaa gctctggttg     180

cacctcagaa gaccctgggg catcgcagtg ggcctgcttt cccagtttgg acttatgcct     240

ctgacagctt atctgttagc cattggcttc ggtctgaaac cattccaagc tattgctgtc     300

ctcatgatgg ggagctgccc tgggggcacc atctctaatg ttctcacctt ctgggttgat     360

ggagatatgg atctcagcat cagtatgaca acctgttcca cagtggccgc cctgggaatg     420

atgcctctct gcctctacat ctacacccgg tcctggactc tgacacagaa cctcgtcatt     480

ccgtatcaga gcataggaat taccettgtg tccctggtgg ttcctgtggc ttctggcgtc     540

tatgtgaatt ataggtggcc aaagcaagca acggtcattc tcaaggtcgg agccattctg     600

ggtggcatgc tcctcctggt ggtggcagtt actggcatgg tcctggcaaa aggctggaac     660

acagacgtca ctcttctggt catcagctgc attttcccct tggtcggcca tgtcacaggc     720

ttcctgctgg cattcctcac ccaccaatct tggcaaaggt gcaggaccat ttccatagag     780

actggcgctc agaacatcca gctgtgcatc gccatgctgc agctgtcctt ctctgctgag     840

tacctggtcc agctgctaaa ctttgcattg gcctatggac tcttccaagt gctgcacggg     900

ctgctcattg tcgcagcata tcaggcatac aagaggaggc agaagagtaa atgcaggaga     960

cagcacccgg attgcccaga cgtctgctac gagaagcagc ccagagagac cagtgctttc    1020

ttggataaag gggatgaggc tgccgtaact ctggggccag tgcagccaga gcagcaccac    1080

agggctgctg agctgactag ccacattcct tcatgtgaa                           1119

<210> SEQ ID NO 106
<211> LENGTH: 24
<212> TYPE: DNA
<213> ORGANISM: Artificial Sequence
<220> FEATURE:
<223> OTHER INFORMATION: Primer
```

-continued

<400> SEQUENCE: 106
gacctgccca gtgcttgcta ctca 24

<210> SEQ ID NO 107
<211> LENGTH: 24
<212> TYPE: DNA
<213> ORGANISM: Artificial Sequence
<220> FEATURE:
<223> OTHER INFORMATION: Primer

<400> SEQUENCE: 107
tcttcactgg ccacggagga ggat 24

<210> SEQ ID NO 108
<211> LENGTH: 21
<212> TYPE: DNA
<213> ORGANISM: Artificial Sequence
<220> FEATURE:
<223> OTHER INFORMATION: Primer

<400> SEQUENCE: 108
ctattgctgt cctcatgatg g 21

<210> SEQ ID NO 109
<211> LENGTH: 21
<212> TYPE: DNA
<213> ORGANISM: Artificial Sequence
<220> FEATURE:
<223> OTHER INFORMATION: Primer

<400> SEQUENCE: 109
catgctgcag ctgtccttct c 21

<210> SEQ ID NO 110
<211> LENGTH: 21
<212> TYPE: DNA
<213> ORGANISM: Artificial Sequence
<220> FEATURE:
<223> OTHER INFORMATION: Primer

<400> SEQUENCE: 110
ccatcatgag gacagcaata g 21

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
gagaaggaca gctgcagcat g 21

<210> SEQ ID NO 112
<211> LENGTH: 1237
<212> TYPE: DNA
<213> ORGANISM: Mouse

<400> SEQUENCE: 112
gacctgccca gtgcttgcta ctcatgttcc tttgtgttcc tgtgttctaa ttcatgagag 60
gagatgagca cagactgtgc gggcaactcc acctgccctg tcaacagtac ggaggaagac 120
ccgcccgtgg gaatggaggg ccatgcgaat ctaaagctgc tttttacagt gctctcggct 180
gtgatggtgg gtttggtcat gttctctttt ggatgttctg tggagagtca gaagctctgg 240

```
ttgcacctca gaagaccctg gggcatcgca gtgggcctgc tttcccagtt tggacttatg    300

cctctgacag cttatctgtt agccattggc ttcggtctga aaccattcca agctattgct    360

gtcctcatga tggggagctg ccctgggggc accatctcta atgttctcac cttctgggtt    420

gatggagata tggatctcag catcagtatg acaacctgtt ccacagtggc cgccctggga    480

atgatgcctc tctgcctcta catctacacc cggtcctgga ctctgacaca gaacctcgtc    540

attccgtatc agagcatagg aattaccctt gtgtccctgg tggttcctgt ggcttctggc    600

gtctatgtga attataggtg gccaaagcaa gcaacggtca ttctcaaggt cggagccatt    660

ctgggtggca tgctcctcct ggtggtggca gttactggca tggtcctggc aaaaggctgg    720

aacacagacg tcactcttct ggtcatcagc tgcattttcc ccttggtcgg ccatgtcaca    780

ggcttcctgc tggcattcct cacccaccaa tcttggcaaa ggtgcaggac catttccata    840

gagactggcg ctcagaacat ccagctgtgc atcgccatgc tgcagctgtc cttctctgct    900

gagtacctgg tccagctgct aaactttgca ttggcctatg gactcttcca agtgctgcac    960

gggctgctca ttgtcgcagc atatcaggca tacaagagga ggcagaagag taaatgcagg   1020

agacagcacc cggattgccc agacgtctgc tacgagaagc agcccagaga gaccagtgct   1080

ttcttggata aaggggatga ggctgccgta actctggggc cagtgcagcc agagcagcac   1140

cacagggctg ctgagctgac tagccacatt ccttcatgtg aatagtggga ggcacggacc   1200

agcttggccc tccatcctcc tccgtggcca gtgaaga                            1237
```

<210> SEQ ID NO 113
<211> LENGTH: 26
<212> TYPE: DNA
<213> ORGANISM: Artificial Sequence
<220> FEATURE:
<223> OTHER INFORMATION: Primer

<400> SEQUENCE: 113

```
cttctggcgt ctatgtgaat tatagg                                          26
```

<210> SEQ ID NO 114
<211> LENGTH: 19
<212> TYPE: DNA
<213> ORGANISM: Artificial Sequence
<220> FEATURE:
<223> OTHER INFORMATION: Primer

<400> SEQUENCE: 114

```
gagcatgcca cccagaatg                                                  19
```

<210> SEQ ID NO 115
<211> LENGTH: 29
<212> TYPE: DNA
<213> ORGANISM: Artificial Sequence
<220> FEATURE:
<223> OTHER INFORMATION: Probe

<400> SEQUENCE: 115

```
caaagcaagc aacggtcatt ctcaaggtc                                       29
```

<210> SEQ ID NO 116
<211> LENGTH: 1046
<212> TYPE: DNA
<213> ORGANISM: Rat
<220> FEATURE:
<221> NAME/KEY: misc_feature
<222> LOCATION: (811)..(812)

<223> OTHER INFORMATION: a, c, g or t

<400> SEQUENCE: 116

```
gaagacccac ccgtgggaat ggagggacag gggagcctga agcttgtttt cacagtcctg      60
tcggctgtga tggtgggtct ggtcatgttc tcctttggat gttcagtgga gagtcggaag     120
ctctggctgc acctcagaag accctggggc atcgcagtgg gcctgctttg ccagtttggg     180
ctcatgcctc tgacagctta tctgctagcc attggcttcg gtctgaaacc attccaagct     240
attgccgtcc tcatcatggg gagctgccct gggggcaccg tctctaatgt cctcaccttc     300
tgggttgatg gagatatgga cctcagcatc agcatgacga cctgctccac agtggctgct     360
ctgggaatga tgcccctctg cctctacgtc tacacccggt cctggactct tccacagagc     420
ctcaccatcc cgtaccagag cataggaatt acccttgtgt ccctggttgt tcctgtggcc     480
tccggcatct atgtgaatta taggtggcca aagcaagcaa cattcattct caaggtcggg     540
gctgctgttg gcggcatgct cctcctggtg gtggcagtta ccggcgtggt cctggcaaag     600
ggctggaaca tagatgtcac tcttctggtc atcagctgta tttttccctt ggtcggccat     660
gtcatgggct tcctgctggc gttcctcacc caccagtctt ggcaaaggtg caggacgatt     720
tccatagaga ccggagcaca gaacatccag ctgtgcattg ccatgatgca gctgtccttc     780
tctgctgagt acctggtcca gctgttaaac nncgccctgg cctacggact cttccaagtg     840
ctgcacgggc tgctcattgt cgcagcatat caggcataca agaggaggca gaagagtcaa     900
tacaggagac agcacccgga gtgccaagac atcagctctg agaagcagcc cagagagacc     960
agtgccttct tggataaagg ggctgaggct gctgtaactc tggggctaga gcagcaccac    1020
aggaccgctg aactgaccag tcacgt                                         1046
```

<210> SEQ ID NO 117
<211> LENGTH: 23
<212> TYPE: DNA
<213> ORGANISM: Artificial Sequence
<220> FEATURE:
<223> OTHER INFORMATION: Primer

<400> SEQUENCE: 117

```
atgagcgcag actgcgaggg caa                                              23
```

<210> SEQ ID NO 118
<211> LENGTH: 24
<212> TYPE: DNA
<213> ORGANISM: Artificial Sequence
<220> FEATURE:
<223> OTHER INFORMATION: Primer

<400> SEQUENCE: 118

```
tcccactatt cacatgaagg aacg                                             24
```

<210> SEQ ID NO 119
<211> LENGTH: 24
<212> TYPE: DNA
<213> ORGANISM: Artificial Sequence
<220> FEATURE:
<223> OTHER INFORMATION: Primer

<400> SEQUENCE: 119

```
tccggcatct atgtgaatta tagg                                             24
```

<210> SEQ ID NO 120
<211> LENGTH: 20

<212> TYPE: DNA
<213> ORGANISM: Artificial Sequence
<220> FEATURE:
<223> OTHER INFORMATION: Primer

<400> SEQUENCE: 120
taactgccac caccaggagg 20

<210> SEQ ID NO 121
<211> LENGTH: 28
<212> TYPE: DNA
<213> ORGANISM: Artificial Sequence
<220> FEATURE:
<223> OTHER INFORMATION: Probe

<400> SEQUENCE: 121
agcaagcaac attcattctc aaggtcgg 28

<210> SEQ ID NO 122
<211> LENGTH: 36
<212> TYPE: DNA
<213> ORGANISM: Artificial Sequence
<220> FEATURE:
<223> OTHER INFORMATION: Primer

<400> SEQUENCE: 122
taggaagctt gtcgacatga gagccaattg ttccag 36

<210> SEQ ID NO 123
<211> LENGTH: 38
<212> TYPE: DNA
<213> ORGANISM: Artificial Sequence
<220> FEATURE:
<223> OTHER INFORMATION: Primer

<400> SEQUENCE: 123
aatgtctaga actagtctat tcacatgaag tgatgtgg 38

<210> SEQ ID NO 124
<211> LENGTH: 18
<212> TYPE: DNA
<213> ORGANISM: Artificial Sequence
<220> FEATURE:
<223> OTHER INFORMATION: Primer

<400> SEQUENCE: 124
tagaaggcac agtcgagg 18

<210> SEQ ID NO 125
<211> LENGTH: 317
<212> TYPE: DNA
<213> ORGANISM: Mouse

<400> SEQUENCE: 125
ccggaggaac ctgccaaaat caagcatcgt ttctttgtat aagaagctgg agatgaaaca 60
ggccattgag atggtagaga ctgggatact gagctctgtg gcttctccca caccctatca 120
gtctgagagg atacagggaa tcaagcggct ttctcctgaa gacgtggagt ccatgcggga 180
cattctgaca agaagcatgt accaagttcg acaaagaacc ctatcctaca acaaatacaa 240
cctcaaaccc caaacaagtg agaagcaagc caaagagatt ctgatccgtc gccagaacac 300
cttgagggag agcatgc 317

<210> SEQ ID NO 126

<211> LENGTH: 23
<212> TYPE: DNA
<213> ORGANISM: Artificial Sequence
<220> FEATURE:
<223> OTHER INFORMATION: Primer

<400> SEQUENCE: 126
ccggaggaac ctgccaaaat caa 23

<210> SEQ ID NO 127
<211> LENGTH: 26
<212> TYPE: DNA
<213> ORGANISM: Artificial Sequence
<220> FEATURE:
<223> OTHER INFORMATION: Primer

<400> SEQUENCE: 127
gcatgctctc cctcaaggtg ttctgg 26

<210> SEQ ID NO 128
<211> LENGTH: 22
<212> TYPE: DNA
<213> ORGANISM: Artificial Sequence
<220> FEATURE:
<223> OTHER INFORMATION: Primer

<400> SEQUENCE: 128
gatgaaacag gccattgaga tg 22

<210> SEQ ID NO 129
<211> LENGTH: 25
<212> TYPE: DNA
<213> ORGANISM: Artificial Sequence
<220> FEATURE:
<223> OTHER INFORMATION: Primer

<400> SEQUENCE: 129
gattccctgt atcctctcag actga 25

<210> SEQ ID NO 130
<211> LENGTH: 24
<212> TYPE: DNA
<213> ORGANISM: Artificial Sequence
<220> FEATURE:
<223> OTHER INFORMATION: Probe

<400> SEQUENCE: 130
ctgggatact gagctctgtg gctt 24

<210> SEQ ID NO 131
<211> LENGTH: 363
<212> TYPE: DNA
<213> ORGANISM: Rat

<400> SEQUENCE: 131
tcgtgggatg cgggggagta tttttcggca tcatttttgg attcatttcc gcatttatca 60
cacgtttcac tcagaacatc tctgcgatcg agcctctcat cgtcttcatg ttcagctatc 120
tgtcttactt agcagccgag acgctttatc tctccggaat cctggccatc acagcttgtg 180
cagtgacaat gaaaaagtac gtggaagaga acgtgtccca gacgtcgtac acgaccatca 240
agtacttcat gaagatgctg agcagcgtga gcgagaccct catcttcatc ttcatgggcg 300
tgtccaccgt tgggaagaac catgagtgga actgggcttt cgtctgcttc accctggcct 360
tct 363

<210> SEQ ID NO 132
<211> LENGTH: 23
<212> TYPE: DNA
<213> ORGANISM: Artificial Sequence
<220> FEATURE:
<223> OTHER INFORMATION: Primer

<400> SEQUENCE: 132
tcgtgggatg cgggggagta ttt 23

<210> SEQ ID NO 133
<211> LENGTH: 24
<212> TYPE: DNA
<213> ORGANISM: Artificial Sequence
<220> FEATURE:
<223> OTHER INFORMATION: Primer

<400> SEQUENCE: 133
agaaggccag ggtgaagcag acga 24

<210> SEQ ID NO 134
<211> LENGTH: 21
<212> TYPE: DNA
<213> ORGANISM: Artificial Sequence
<220> FEATURE:
<223> OTHER INFORMATION: Primer

<400> SEQUENCE: 134
agcagccgag acgctttatc t 21

<210> SEQ ID NO 135
<211> LENGTH: 26
<212> TYPE: DNA
<213> ORGANISM: Artificial Sequence
<220> FEATURE:
<223> OTHER INFORMATION: Primer

<400> SEQUENCE: 135
tctcttccac gtactttttc attgtc 26

<210> SEQ ID NO 136
<211> LENGTH: 25
<212> TYPE: DNA
<213> ORGANISM: Artificial Sequence
<220> FEATURE:
<223> OTHER INFORMATION: Primer

<400> SEQUENCE: 136
aatcctggcc atcacagctt gtgca 25

<210> SEQ ID NO 137
<211> LENGTH: 35
<212> TYPE: DNA
<213> ORGANISM: Artificial Sequence
<220> FEATURE:
<223> OTHER INFORMATION: Primer

<400> SEQUENCE: 137
gacaagctta tcgatatggc tctgcagatg ttcgt 35

<210> SEQ ID NO 138
<211> LENGTH: 39
<212> TYPE: DNA
<213> ORGANISM: Artificial Sequence
<220> FEATURE:

<223> OTHER INFORMATION: Primer

<400> SEQUENCE: 138
gactctagaa ctagtctatt ttttttggag caaaggact 39

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
ctcctgccac ccatcgttct 20

<210> SEQ ID NO 140
<211> LENGTH: 20
<212> TYPE: DNA
<213> ORGANISM: Artificial Sequence
<220> FEATURE:
<223> OTHER INFORMATION: Primer

<400> SEQUENCE: 140
gctggatgtg cccgattcat 20

<210> SEQ ID NO 141
<211> LENGTH: 20
<212> TYPE: DNA
<213> ORGANISM: Artificial Sequence
<220> FEATURE:
<223> OTHER INFORMATION: Primer

<400> SEQUENCE: 141
catcagcgta tttgctctct 20

<210> SEQ ID NO 142
<211> LENGTH: 20
<212> TYPE: DNA
<213> ORGANISM: Artificial Sequence
<220> FEATURE:
<223> OTHER INFORMATION: Primer

<400> SEQUENCE: 142
tccccaaaga tcatcatgta 20

<210> SEQ ID NO 143
<211> LENGTH: 680
<212> TYPE: DNA
<213> ORGANISM: Mouse

<400> SEQUENCE: 143
tccacggagc ctggagctac aaccgggtga ccaagtgtat cctgtactgt ttctacaaga 60
atgtggtcct ctacatcatc gagctatggt tcgcctttgt gaatggattt tctgggcaga 120
ttttattcga gcgctggtgc atcggcttgt acaatgtgat cttcacggca ttgccgccct 180
tcactctggg gatcttcgag aggtcttgta ctcaggagag catgctcagg ttcccacagc 240
tttacagaat cactcagaac gctgaaggtt tcaacactaa ggttttctgg ggtcactgca 300
tcaatgcctt ggttcattcc ctcatcctct tctgggttcc catgaaagcg ctggagcatg 360
atactccagt aaccagcggt catgccacag actatttgtt tgttggaaat attgtttaca 420
cgtacgttgt ggttacagtt tgtttgaaag ctggtttgga gacgacagct tggacgaaat 480
tcagtcacct ggcggtgtgg ggaagcatgc tgatctggtt ggtgttcttt ggtgtctatt 540

-continued

```
caaccatctg gccgaccatc cccattgctc ctgacatgaa agggcaggca actatggtcc    600

tgagctctgc gtacttctgg ttgggattgt tcctggttcc gactgcgtgt ttgattgaag    660

acgtggcgtg gagagcggcc                                                680


<210> SEQ ID NO 144
<211> LENGTH: 23
<212> TYPE: DNA
<213> ORGANISM: Artificial Sequence
<220> FEATURE:
<223> OTHER INFORMATION: Primer

<400> SEQUENCE: 144

gccatcgcac agttttccta cct                                             23


<210> SEQ ID NO 145
<211> LENGTH: 24
<212> TYPE: DNA
<213> ORGANISM: Artificial Sequence
<220> FEATURE:
<223> OTHER INFORMATION: Primer

<400> SEQUENCE: 145

catcctcttt ccgttactgt ctcg                                            24


<210> SEQ ID NO 146
<211> LENGTH: 19
<212> TYPE: DNA
<213> ORGANISM: Artificial Sequence
<220> FEATURE:
<223> OTHER INFORMATION: Primer

<400> SEQUENCE: 146

aaccatctgg ccgaccatc                                                  19


<210> SEQ ID NO 147
<211> LENGTH: 21
<212> TYPE: DNA
<213> ORGANISM: Artificial Sequence
<220> FEATURE:
<223> OTHER INFORMATION: Primer

<400> SEQUENCE: 147

acgcagagct caggaccata g                                               21


<210> SEQ ID NO 148
<211> LENGTH: 24
<212> TYPE: DNA
<213> ORGANISM: Artificial Sequence
<220> FEATURE:
<223> OTHER INFORMATION: Primer

<400> SEQUENCE: 148

tgcctgccct ttcatgtcag gagc                                            24


<210> SEQ ID NO 149
<211> LENGTH: 771
<212> TYPE: DNA
<213> ORGANISM: Rat

<400> SEQUENCE: 149

gctgcttttg gtccatggag cctggagcta caaccgggtg accaagtgca tcctctactg     60

tttctataag aatgtggtcc tctacatcat tgagctttgg ttcgcctttg ttaatggatt    120
```

-continued

```
ttctgggcag attttatttg agcgctggtg catcggcttg tacaatgtga tcttcacagc    180

attgccaccc ttcactctgg ggatcttcga gaggtcgtgt actcaggaga gcatgctcag    240

gtttccacag ctctacaaaa tcactcagaa cgccgaaggt ttcaacacga aggttttctg    300

gggtcactgc atcaatgcct tggtccactc cctcatcctc ttctgggttc caatgaaagc    360

gctggagcac gatactccgc taaccagtgg tcacgccaca gactatttgt ttgttggaaa    420

tattgtttac acgtacgttg tggtcacagt ttgtttgaaa gctggtttgg agacgacagc    480

ttggactaaa ttcagtcacc tggcagtgtg gggaagcatg ctgatctggt tggtgttctt    540

tggtgtctat tcaaccttct ggccgaccat ccccatcgct cctgacatga aagggcaggc    600

aactatggtc ctgagttctg cccacttctg gttgggtttg ctcctggttc ccactgcgtg    660

tttgatcgag gatgtggcgt ggagagcggc caaacacacc tgcaaaaaga cactgtctgg    720

aggaggttca ggagctggag accaagtccc gagtgtatgg gcaaagcgat g             771


<210> SEQ ID NO 150
<211> LENGTH: 21
<212> TYPE: DNA
<213> ORGANISM: Artificial Sequence
<220> FEATURE:
<223> OTHER INFORMATION: Primer

<400> SEQUENCE: 150

tattcaacct tctggccgac c                                               21


<210> SEQ ID NO 151
<211> LENGTH: 21
<212> TYPE: DNA
<213> ORGANISM: Artificial Sequence
<220> FEATURE:
<223> OTHER INFORMATION: Primer

<400> SEQUENCE: 151

accagaagtg ggcagaactc a                                               21


<210> SEQ ID NO 152
<211> LENGTH: 28
<212> TYPE: DNA
<213> ORGANISM: Artificial Sequence
<220> FEATURE:
<223> OTHER INFORMATION: Primer

<400> SEQUENCE: 152

catagttgcc tgccctttca tgtcagga                                        28


<210> SEQ ID NO 153
<211> LENGTH: 37
<212> TYPE: DNA
<213> ORGANISM: Artificial Sequence
<220> FEATURE:
<223> OTHER INFORMATION: Primer

<400> SEQUENCE: 153

ttggatccgt cgacatgtcc cgggccacgt ctgttgg                              37


<210> SEQ ID NO 154
<211> LENGTH: 43
<212> TYPE: DNA
<213> ORGANISM: Artificial Sequence
<220> FEATURE:
<223> OTHER INFORMATION: Primer

<400> SEQUENCE: 154
```

ccgcggccgc actagtttat ttcttcctgg atttcttttt ggt 43

<210> SEQ ID NO 155
<211> LENGTH: 1064
<212> TYPE: DNA
<213> ORGANISM: Mouse

<400> SEQUENCE: 155
acagcctgag attgtgcagc tgctgatgga gaatgagcag acagacatcg cttcccagga 60
ttcccgggga aacaacatcc tgcacgcgct ggtgacggtg gctgaggact tcaagactca 120
gaatgacttc gttaagcgca tgtatgacat gatcctgctg aggagtggca actgggagct 180
ggagaccatg cgcaacaacg atgggctcac gccactgcag ctggctgcca agatgggcaa 240
ggctgagatc ctgaagtaca tcctcagccg cgagatcaag gagaagcctc tccggagctt 300
gtccaggaag ttcacggact gggcgtatgg gcctgtgtca tcctcactct atgacctcac 360
caatgtagac acaacgacgg ataactctgt gctggaaatc atcgtctaca acaccaacat 420
tgataaccga catgagatgc tgaccctgga gcctctgcat acgctgctac acacgaaatg 480
gaagaaattt gccaagtaca tgttcttctt gtccttctgc ttctatttct tctacaacat 540
caccctgacc cttgtctctt actaccgtcc tcgggaagat gaggatctcc cacacccctt 600
ggccctgaca cacaaaatga gttggcttca gctcctaggg aggatgtttg tcctcatctg 660
ggccacatgc atctctgtga aagaaggcat tgccattttc ctgctgagac cctccgatct 720
tcagtccatc ctgtcagatg cctggtttca ctttgtcttt tttgtccaag ctgtacttgt 780
gatactgtct gtattcttgt acttgtttgc ctacaaagaa tacctcgcct gcctcgtgct 840
ggccatggcc ctgggctggg cgaacatgct ctactacacg agaggcttcc agtctatggg 900
catgtacagc gtcatgatcc agaaggtcat tttgcatgat gtcctcaagt tcttgtttgt 960
ttacatcctg ttcttacttg gatttggagt agcgctggcc tcactgattg agaagtgctc 1020
caaggacaaa aaggactgca gttcctatgg cagcttcagc gaca 1064

<210> SEQ ID NO 156
<211> LENGTH: 27
<212> TYPE: DNA
<213> ORGANISM: Artificial Sequence
<220> FEATURE:
<223> OTHER INFORMATION: Primer

<400> SEQUENCE: 156
gcgtgtacta accagcctga gattgtg 27

<210> SEQ ID NO 157
<211> LENGTH: 25
<212> TYPE: DNA
<213> ORGANISM: Artificial Sequence
<220> FEATURE:
<223> OTHER INFORMATION: Primer

<400> SEQUENCE: 157
gtcgctgaag ctgccatagg aactg 25

<210> SEQ ID NO 158
<211> LENGTH: 22
<212> TYPE: DNA
<213> ORGANISM: Artificial Sequence
<220> FEATURE:
<223> OTHER INFORMATION: Primer

<400> SEQUENCE: 158
ctgagaccct ccgatcttca gt 22

<210> SEQ ID NO 159
<211> LENGTH: 22
<212> TYPE: DNA
<213> ORGANISM: Artificial Sequence
<220> FEATURE:
<223> OTHER INFORMATION: Primer

<400> SEQUENCE: 159
ggcaggcgag gtattctttg ta 22

<210> SEQ ID NO 160
<211> LENGTH: 30
<212> TYPE: DNA
<213> ORGANISM: Artificial Sequence
<220> FEATURE:
<223> OTHER INFORMATION: Probe

<400> SEQUENCE: 160
cctgtcagat gcctggtttc actttgtctt 30

<210> SEQ ID NO 161
<211> LENGTH: 34
<212> TYPE: DNA
<213> ORGANISM: Artificial Sequence
<220> FEATURE:
<223> OTHER INFORMATION: Primer

<400> SEQUENCE: 161
cggggtaccg tcgacatgaa agcccacccc aagg 34

<210> SEQ ID NO 162
<211> LENGTH: 37
<212> TYPE: DNA
<213> ORGANISM: Artificial Sequence
<220> FEATURE:
<223> OTHER INFORMATION: Primer

<400> SEQUENCE: 162
atttgcggcc gcactagtct acaccgaggt ttccggg 37

<210> SEQ ID NO 163
<211> LENGTH: 20
<212> TYPE: DNA
<213> ORGANISM: Artificial Sequence
<220> FEATURE:
<223> OTHER INFORMATION: Primer

<400> SEQUENCE: 163
taatacgact cactataggg 20

<210> SEQ ID NO 164
<211> LENGTH: 24
<212> TYPE: DNA
<213> ORGANISM: Artificial Sequence
<220> FEATURE:
<223> OTHER INFORMATION: Primer

<400> SEQUENCE: 164
gacacgggga agacctgcct gatg 24

<210> SEQ ID NO 165
<211> LENGTH: 23

<212> TYPE: DNA
<213> ORGANISM: Artificial Sequence
<220> FEATURE:
<223> OTHER INFORMATION: Primer

<400> SEQUENCE: 165
gtggcaactg ggagctggag acc 23

<210> SEQ ID NO 166
<211> LENGTH: 24
<212> TYPE: DNA
<213> ORGANISM: Artificial Sequence
<220> FEATURE:
<223> OTHER INFORMATION: Primer

<400> SEQUENCE: 166
gggccatgtg catctctgtg aaag 24

<210> SEQ ID NO 167
<211> LENGTH: 21
<212> TYPE: DNA
<213> ORGANISM: Artificial Sequence
<220> FEATURE:
<223> OTHER INFORMATION: Primer

<400> SEQUENCE: 167
ctgatgggcg agactgtgga g 21

<210> SEQ ID NO 168
<211> LENGTH: 18
<212> TYPE: DNA
<213> ORGANISM: Artificial Sequence
<220> FEATURE:
<223> OTHER INFORMATION: Primer

<400> SEQUENCE: 168
tagaaggcac agtcgagg 18

<210> SEQ ID NO 169
<211> LENGTH: 21
<212> TYPE: DNA
<213> ORGANISM: Artificial Sequence
<220> FEATURE:
<223> OTHER INFORMATION: Primer

<400> SEQUENCE: 169
ctccacagtc tcgcccatca g 21

<210> SEQ ID NO 170
<211> LENGTH: 24
<212> TYPE: DNA
<213> ORGANISM: Artificial Sequence
<220> FEATURE:
<223> OTHER INFORMATION: Primer

<400> SEQUENCE: 170
ctttcacaga gatgcacatg gccc 24

<210> SEQ ID NO 171
<211> LENGTH: 23
<212> TYPE: DNA
<213> ORGANISM: Artificial Sequence
<220> FEATURE:
<223> OTHER INFORMATION: Primer

<400> SEQUENCE: 171
ggtctccagc tcccagttgc cac 23

<210> SEQ ID NO 172
<211> LENGTH: 24
<212> TYPE: DNA
<213> ORGANISM: Artificial Sequence
<220> FEATURE:
<223> OTHER INFORMATION: Primer

<400> SEQUENCE: 172
catcaggcag gtcttccccg tgtc 24

<210> SEQ ID NO 173
<211> LENGTH: 348
<212> TYPE: PRT
<213> ORGANISM: Human

<400> SEQUENCE: 173

```
Met Asn Asp Pro Asn Ser Cys Val Asp Asn Ala Thr Val Cys Ser Gly
1               5                   10                  15

Ala Ser Cys Val Val Pro Glu Ser Asn Phe Asn Asn Ile Leu Ser Val
            20                  25                  30

Val Leu Ser Thr Val Leu Thr Ile Leu Leu Ala Leu Val Met Phe Ser
        35                  40                  45

Met Gly Cys Asn Val Glu Ile Lys Lys Phe Leu Gly His Ile Lys Arg
    50                  55                  60

Pro Trp Gly Ile Cys Val Gly Phe Leu Cys Gln Phe Gly Ile Met Pro
65                  70                  75                  80

Leu Thr Gly Phe Ile Leu Ser Val Ala Phe Asp Ile Leu Pro Leu Gln
                85                  90                  95

Ala Val Val Val Leu Ile Ile Gly Cys Cys Pro Gly Gly Thr Ala Ser
            100                 105                 110

Asn Ile Leu Ala Tyr Trp Val Asp Gly Asp Met Asp Leu Ser Val Ser
        115                 120                 125

Met Thr Thr Cys Ser Thr Leu Leu Ala Leu Gly Met Met Pro Leu Cys
    130                 135                 140

Leu Leu Ile Tyr Thr Lys Met Trp Val Asp Ser Gly Ser Ile Val Ile
145                 150                 155                 160

Pro Tyr Asp Asn Ile Gly Thr Ser Leu Val Ala Leu Val Val Pro Val
                165                 170                 175

Ser Ile Gly Met Phe Val Asn His Lys Trp Pro Gln Lys Ala Lys Ile
            180                 185                 190

Ile Leu Lys Ile Gly Ser Ile Ala Gly Ala Ile Leu Ile Val Leu Ile
        195                 200                 205

Ala Val Val Gly Gly Ile Leu Tyr Gln Ser Ala Trp Ile Ile Ala Pro
    210                 215                 220

Lys Leu Trp Ile Ile Gly Thr Ile Phe Pro Val Ala Gly Tyr Ser Leu
225                 230                 235                 240

Gly Phe Leu Leu Ala Arg Ile Ala Gly Leu Pro Trp Tyr Arg Cys Arg
                245                 250                 255

Thr Val Ala Phe Glu Thr Gly Met Gln Asn Thr Gln Leu Cys Ser Thr
            260                 265                 270

Ile Val Gln Leu Ser Phe Thr Pro Glu Glu Leu Asn Val Val Phe Thr
        275                 280                 285

Phe Pro Leu Ile Tyr Ser Ile Phe Gln Leu Ala Phe Ala Ala Ile Phe
    290                 295                 300
```

```
Leu Gly Phe Tyr Val Ala Tyr Lys Lys Cys His Gly Lys Asn Lys Ala
305                 310                 315                 320

Glu Ile Pro Glu Ser Lys Glu Asn Gly Thr Glu Pro Glu Ser Ser Phe
                325                 330                 335

Tyr Lys Ala Asn Gly Gly Phe Gln Pro Asp Glu Lys
            340                 345


<210> SEQ ID NO 174
<211> LENGTH: 717
<212> TYPE: PRT
<213> ORGANISM: Rat

<400> SEQUENCE: 174

Met Gly Pro Ala Met Leu Arg Ala Phe Ser Ser Trp Lys Trp Leu Leu
1               5                   10                  15

Leu Leu Met Val Leu Thr Cys Leu Glu Ala Ser Ser Tyr Val Asn Glu
            20                  25                  30

Ser Ser Ser Pro Thr Gly Gln Gln Thr Pro Asp Ala Arg Phe Ala Ala
        35                  40                  45

Ser Ser Ser Asp Pro Asp Glu Arg Ile Ser Val Phe Glu Leu Asp Tyr
    50                  55                  60

Asp Tyr Val Gln Ile Pro Tyr Glu Val Thr Leu Trp Ile Leu Leu Ala
65                  70                  75                  80

Ser Leu Ala Lys Ile Gly Phe His Leu Tyr His Arg Leu Pro His Leu
                85                  90                  95

Met Pro Glu Ser Cys Leu Leu Ile Ile Val Gly Ala Leu Val Gly Ser
            100                 105                 110

Ile Ile Phe Gly Thr His His Lys Ser Pro Pro Val Met Asp Ser Ser
        115                 120                 125

Ile Tyr Phe Leu Tyr Leu Leu Pro Pro Ile Val Leu Glu Ser Gly Tyr
    130                 135                 140

Phe Met Pro Thr Arg Pro Phe Phe Glu Asn Ile Gly Ser Ile Leu Trp
145                 150                 155                 160

Trp Ala Gly Leu Gly Ala Leu Ile Asn Ala Phe Gly Ile Gly Leu Ser
                165                 170                 175

Leu Tyr Phe Ile Cys Gln Ile Lys Ala Phe Gly Leu Gly Asp Ile Asn
            180                 185                 190

Leu Leu Gln Asn Leu Leu Phe Gly Ser Leu Ile Ser Ala Val Asp Pro
        195                 200                 205

Val Ala Val Leu Ala Val Phe Glu Glu Ala Arg Val Asn Glu Gln Leu
    210                 215                 220

Tyr Met Met Ile Phe Gly Glu Ala Leu Leu Asn Asp Gly Ile Ser Val
225                 230                 235                 240

Val Leu Tyr Asn Ile Leu Ile Ala Phe Thr Lys Met His Lys Phe Glu
                245                 250                 255

Asp Ile Glu Ala Val Asp Ile Leu Ala Gly Cys Ala Arg Phe Val Ile
            260                 265                 270

Val Gly Cys Gly Gly Val Phe Phe Gly Ile Ile Phe Gly Phe Ile Ser
        275                 280                 285

Ala Phe Ile Thr Arg Phe Thr Gln Asn Ile Ser Ala Ile Glu Pro Leu
    290                 295                 300

Ile Val Phe Met Phe Ser Tyr Leu Ser Tyr Leu Ala Ala Glu Thr Leu
305                 310                 315                 320

Tyr Leu Ser Gly Ile Leu Ala Ile Thr Ala Cys Ala Val Thr Met Lys
                325                 330                 335
```

-continued

```
Lys Tyr Val Glu Glu Asn Val Ser Gln Thr Ser Tyr Thr Thr Ile Lys
            340                 345                 350

Tyr Phe Met Lys Met Leu Ser Ser Val Ser Glu Thr Leu Ile Phe Ile
        355                 360                 365

Phe Met Gly Val Ser Thr Val Gly Lys Asn His Glu Trp Asn Trp Ala
    370                 375                 380

Phe Val Cys Phe Thr Leu Ala Phe Cys Gln Ile Trp Arg Ala Ile Ser
385                 390                 395                 400

Val Phe Thr Leu Phe Tyr Val Ser Asn Gln Phe Arg Thr Phe Pro Phe
                405                 410                 415

Ser Ile Lys Asp Gln Leu Ile Ile Phe Tyr Ser Gly Val Arg Gly Ala
            420                 425                 430

Gly Ser Phe Ser Leu Ala Phe Leu Leu Pro Leu Thr Leu Phe Pro Arg
        435                 440                 445

Lys Lys Leu Phe Val Thr Ala Thr Leu Val Val Thr Tyr Phe Thr Val
    450                 455                 460

Phe Phe Gln Gly Ile Thr Ile Gly Pro Leu Val Arg Tyr Leu Asp Val
465                 470                 475                 480

Arg Lys Thr Asn Lys Lys Glu Ser Ile Asn Glu Glu Leu His Ile Arg
                485                 490                 495

Leu Met Asp His Leu Lys Ala Gly Ile Glu Asp Val Cys Gly Gln Trp
            500                 505                 510

Ser His Tyr Gln Val Arg Asp Lys Phe Lys Lys Phe Asp His Arg Tyr
        515                 520                 525

Leu Arg Lys Ile Leu Ile Arg Arg Asn Gln Pro Lys Ser Ser Ile Val
    530                 535                 540

Ser Leu Tyr Lys Lys Leu Glu Met Lys Gln Ala Ile Glu Met Ala Glu
545                 550                 555                 560

Thr Gly Leu Leu Ser Ser Val Ala Ser Pro Thr Pro Tyr Gln Ser Glu
                565                 570                 575

Arg Ile Gln Gly Ile Lys Arg Leu Ser Pro Glu Asp Val Glu Ser Met
            580                 585                 590

Arg Asp Ile Leu Thr Arg Asn Met Tyr Gln Val Arg Gln Arg Thr Leu
        595                 600                 605

Ser Tyr Asn Lys Tyr Asn Leu Lys Pro Gln Thr Ser Glu Lys Gln Ala
    610                 615                 620

Lys Glu Ile Leu Ile Arg Arg Gln Asn Thr Leu Arg Glu Ser Leu Arg
625                 630                 635                 640

Lys Gly Gln Ser Leu Pro Trp Val Lys Pro Ala Gly Thr Lys Asn Phe
                645                 650                 655

Arg Tyr Leu Ser Phe Pro Tyr Ser Asn Pro Gln Pro Ala Arg Arg Gly
            660                 665                 670

Ala Arg Ala Ala Glu Ser Thr Gly Asn Pro Cys Cys Trp Leu Leu His
        675                 680                 685

Phe Leu Leu Cys Arg Ala Met Val Glu Lys Ile Trp Gly Pro Gly Gly
    690                 695                 700

Gln Glu Thr Gln Pro Arg Leu Leu Cys Arg Asn Leu Asn
705                 710                 715
```

<210> SEQ ID NO 175
<211> LENGTH: 812
<212> TYPE: PRT
<213> ORGANISM: Human

<400> SEQUENCE: 175

```
Met Glu Pro Leu Gly Asn Trp Arg Ser Leu Arg Ala Pro Leu Pro Pro
1               5                   10                  15

Met Leu Leu Leu Leu Leu Leu Gln Val Ala Gly Pro Val Gly Ala Leu
            20                  25                  30

Ala Glu Thr Leu Leu Asn Ala Pro Arg Ala Met Gly Thr Ser Ser Ser
        35                  40                  45

Pro Pro Ser Pro Ala Ser Val Val Ala Pro Gly Thr Thr Leu Phe Glu
    50                  55                  60

Glu Ser Arg Leu Pro Val Phe Thr Leu Asp Tyr Pro His Val Gln Ile
65                  70                  75                  80

Pro Phe Glu Ile Thr Leu Trp Ile Leu Leu Ala Ser Leu Ala Lys Ile
                85                  90                  95

Gly Phe His Leu Tyr His Lys Leu Pro Thr Ile Val Pro Glu Ser Cys
            100                 105                 110

Leu Leu Ile Met Val Gly Leu Leu Leu Gly Gly Ile Ile Phe Gly Val
        115                 120                 125

Asp Glu Lys Ser Pro Pro Ala Met Lys Thr Asp Val Phe Phe Leu Tyr
    130                 135                 140

Leu Leu Pro Pro Ile Val Leu Asp Ala Gly Tyr Phe Met Pro Thr Arg
145                 150                 155                 160

Pro Phe Phe Glu Asn Ile Gly Thr Ile Phe Trp Tyr Ala Val Val Gly
                165                 170                 175

Thr Leu Trp Asn Ser Ile Gly Ile Gly Val Ser Leu Phe Gly Ile Cys
            180                 185                 190

Gln Ile Glu Ala Phe Gly Leu Ser Asp Ile Thr Leu Leu Gln Asn Leu
        195                 200                 205

Leu Phe Gly Ser Leu Ile Ser Ala Val Asp Pro Val Ala Val Leu Ala
    210                 215                 220

Val Phe Glu Asn Ile His Val Asn Glu Gln Leu Tyr Ile Leu Val Phe
225                 230                 235                 240

Gly Glu Ser Leu Leu Asn Asp Ala Val Thr Val Val Leu Tyr Asn Leu
                245                 250                 255

Phe Lys Ser Phe Cys Gln Met Lys Thr Ile Glu Thr Ile Asp Val Phe
            260                 265                 270

Ala Gly Ile Ala Asn Phe Phe Val Val Gly Ile Gly Gly Val Leu Ile
        275                 280                 285

Gly Ile Phe Leu Gly Phe Ile Ala Ala Phe Thr Thr Arg Phe Thr His
    290                 295                 300

Asn Ile Arg Val Ile Glu Pro Leu Phe Val Phe Leu Tyr Ser Tyr Leu
305                 310                 315                 320

Ser Tyr Ile Thr Ala Glu Met Phe His Leu Ser Gly Ile Met Ala Ile
                325                 330                 335

Thr Ala Cys Ala Met Thr Met Asn Lys Tyr Val Glu Glu Asn Val Ser
            340                 345                 350

Gln Lys Ser Tyr Thr Thr Ile Lys Tyr Phe Met Lys Met Leu Ser Ser
        355                 360                 365

Val Ser Glu Thr Leu Ile Phe Ile Phe Met Gly Val Ser Thr Val Gly
    370                 375                 380

Lys Asn His Glu Trp Asn Trp Ala Phe Val Cys Phe Thr Leu Ala Phe
385                 390                 395                 400

Cys Leu Met Trp Arg Ala Leu Gly Val Phe Val Leu Thr Gln Val Ile
                405                 410                 415
```

```
Asn Arg Phe Arg Thr Ile Pro Leu Thr Phe Lys Asp Gln Phe Ile Ile
            420                 425                 430

Ala Tyr Gly Gly Leu Arg Gly Ala Ile Cys Phe Ala Leu Val Phe Leu
        435                 440                 445

Leu Pro Ala Ala Val Phe Pro Arg Lys Lys Leu Phe Ile Thr Ala Ala
    450                 455                 460

Ile Val Val Ile Phe Phe Thr Val Phe Ile Leu Gly Ile Thr Ile Arg
465                 470                 475                 480

Pro Leu Val Glu Phe Leu Asp Val Lys Arg Ser Asn Lys Lys Gln Gln
                485                 490                 495

Ala Val Ser Glu Glu Ile Tyr Cys Arg Leu Phe Asp His Val Lys Thr
            500                 505                 510

Gly Ile Glu Asp Val Cys Gly His Trp Gly His Asn Phe Trp Arg Asp
        515                 520                 525

Lys Phe Lys Lys Phe Asp Asp Lys Tyr Leu Arg Lys Leu Leu Ile Arg
    530                 535                 540

Glu Asn Gln Pro Lys Ser Ser Ile Val Ser Leu Tyr Lys Lys Leu Glu
545                 550                 555                 560

Ile Lys His Ala Ile Glu Met Ala Glu Thr Gly Met Ile Ser Thr Val
                565                 570                 575

Pro Thr Phe Ala Ser Leu Asn Asp Cys Arg Glu Glu Lys Ile Arg Lys
            580                 585                 590

Val Thr Ser Ser Glu Thr Asp Glu Ile Arg Glu Leu Leu Ser Arg Asn
        595                 600                 605

Leu Tyr Gln Ile Arg Gln Arg Thr Leu Ser Tyr Asn Arg His Ser Leu
    610                 615                 620

Thr Ala Asp Thr Ser Glu Arg Gln Ala Lys Glu Ile Leu Ile Arg Arg
625                 630                 635                 640

Arg His Ser Leu Arg Glu Ser Ile Arg Lys Asp Ser Ser Leu Asn Arg
                645                 650                 655

Glu His Arg Ala Ser Thr Ser Thr Ser Arg Tyr Leu Ser Leu Pro Lys
            660                 665                 670

Asn Thr Lys Leu Pro Glu Lys Leu Gln Lys Arg Arg Thr Ile Ser Ile
        675                 680                 685

Ala Asp Gly Asn Ser Ser Asp Ser Asp Ala Asp Ala Gly Thr Thr Val
    690                 695                 700

Leu Asn Leu Gln Pro Arg Ala Arg Arg Phe Leu Pro Glu Gln Phe Ser
705                 710                 715                 720

Lys Lys Ser Pro Gln Ser Tyr Lys Met Glu Trp Lys Asn Glu Val Asp
                725                 730                 735

Val Asp Ser Gly Arg Asp Met Pro Ser Thr Pro Pro Thr Pro His Ser
            740                 745                 750

Arg Glu Lys Gly Thr Gln Thr Ser Gly Leu Leu Gln Gln Pro Leu Leu
        755                 760                 765

Ser Lys Asp Gln Ser Gly Ser Glu Arg Glu Asp Ser Leu Thr Glu Gly
    770                 775                 780

Ile Pro Pro Lys Pro Pro Pro Arg Leu Val Trp Arg Ala Ser Glu Pro
785                 790                 795                 800

Gly Ser Arg Lys Ala Arg Phe Gly Ser Glu Lys Pro
                805                 810
```

<210> SEQ ID NO 176
<211> LENGTH: 1164

<212> TYPE: PRT
<213> ORGANISM: Human

<400> SEQUENCE: 176

```
Met Pro Thr Met Arg Arg Thr Val Ser Glu Ile Arg Ser Arg Ala Glu
1               5                   10                  15

Gly Tyr Glu Lys Thr Asp Asp Val Ser Glu Lys Thr Ser Leu Ala Asp
            20                  25                  30

Gln Glu Glu Val Arg Thr Ile Phe Ile Asn Gln Pro Gln Leu Thr Lys
        35                  40                  45

Phe Cys Asn Asn His Val Ser Thr Ala Lys Tyr Asn Ile Ile Thr Phe
    50                  55                  60

Leu Pro Arg Phe Leu Tyr Ser Gln Phe Arg Arg Ala Ala Asn Ser Phe
65                  70                  75                  80

Phe Leu Phe Ile Ala Leu Leu Gln Gln Ile Pro Asp Val Ser Pro Thr
                85                  90                  95

Gly Arg Tyr Thr Thr Leu Val Pro Leu Leu Phe Ile Leu Ala Val Ala
            100                 105                 110

Ala Ile Lys Glu Ile Ile Glu Asp Ile Lys Arg His Lys Ala Asp Asn
        115                 120                 125

Ala Val Asn Lys Lys Gln Thr Gln Val Leu Arg Asn Gly Ala Trp Glu
    130                 135                 140

Ile Val His Trp Glu Lys Val Ala Val Gly Glu Ile Val Lys Val Thr
145                 150                 155                 160

Asn Gly Glu His Leu Pro Ala Asp Leu Ile Ser Leu Ser Ser Ser Glu
                165                 170                 175

Pro Gln Ala Met Cys Tyr Ile Glu Thr Ser Asn Leu Asp Gly Glu Thr
            180                 185                 190

Asn Leu Lys Ile Arg Gln Gly Leu Pro Ala Thr Ser Asp Ile Lys Asp
        195                 200                 205

Val Asp Ser Leu Met Arg Ile Ser Gly Arg Ile Glu Cys Glu Ser Pro
    210                 215                 220

Asn Arg His Leu Tyr Asp Phe Val Gly Asn Ile Arg Leu Asp Gly His
225                 230                 235                 240

Gly Thr Val Pro Leu Gly Ala Asp Gln Ile Leu Leu Arg Gly Ala Gln
                245                 250                 255

Leu Arg Asn Thr Gln Trp Val His Gly Ile Val Val Tyr Thr Gly His
            260                 265                 270

Asp Thr Lys Leu Met Gln Asn Ser Thr Ser Pro Pro Leu Lys Leu Ser
        275                 280                 285

Asn Val Glu Arg Ile Thr Asn Val Gln Ile Leu Ile Leu Phe Cys Ile
    290                 295                 300

Leu Ile Ala Met Ser Leu Val Cys Ser Val Gly Ser Ala Ile Trp Asn
305                 310                 315                 320

Arg Arg His Ser Gly Lys Asp Trp Tyr Leu Asn Leu Asn Tyr Gly Gly
                325                 330                 335

Ala Ser Asn Phe Gly Leu Asn Phe Leu Thr Phe Ile Ile Leu Phe Asn
            340                 345                 350

Asn Leu Ile Pro Ile Ser Leu Leu Val Thr Leu Glu Val Val Lys Phe
        355                 360                 365

Thr Gln Ala Tyr Phe Ile Asn Trp Asp Leu Asp Met His Tyr Glu Pro
    370                 375                 380

Thr Asp Thr Ala Ala Met Ala Arg Thr Ser Asn Leu Asn Glu Glu Leu
385                 390                 395                 400
```

-continued

```
Gly Gln Val Lys Tyr Ile Phe Ser Asp Lys Thr Gly Thr Leu Thr Cys
                405                 410                 415

Asn Val Met Gln Phe Lys Lys Cys Thr Ile Ala Gly Val Ala Tyr Gly
            420                 425                 430

His Val Pro Glu Pro Glu Asp Tyr Gly Cys Ser Pro Asp Glu Trp Gln
        435                 440                 445

Asn Ser Gln Phe Gly Asp Glu Lys Thr Phe Ser Asp Ser Ser Leu Leu
    450                 455                 460

Glu Asn Leu Gln Asn Asn His Pro Thr Ala Pro Ile Ile Cys Glu Phe
465                 470                 475                 480

Leu Thr Met Met Ala Val Cys His Thr Ala Val Pro Glu Arg Glu Gly
                485                 490                 495

Asp Lys Ile Ile Tyr Gln Ala Ala Ser Pro Asp Glu Gly Ala Leu Val
            500                 505                 510

Arg Ala Ala Lys Gln Leu Asn Phe Val Phe Thr Gly Arg Thr Pro Asp
        515                 520                 525

Ser Val Ile Ile Asp Ser Leu Gly Gln Glu Glu Arg Tyr Glu Leu Leu
    530                 535                 540

Asn Val Leu Glu Phe Thr Ser Ala Arg Lys Arg Met Ser Val Ile Val
545                 550                 555                 560

Arg Thr Pro Ser Gly Lys Leu Arg Leu Tyr Cys Lys Gly Ala Asp Thr
                565                 570                 575

Val Ile Tyr Asp Arg Leu Ala Glu Thr Ser Lys Tyr Lys Glu Ile Thr
            580                 585                 590

Leu Lys His Leu Glu Gln Phe Ala Thr Glu Gly Leu Arg Thr Leu Cys
        595                 600                 605

Phe Ala Val Ala Glu Ile Ser Glu Ser Asp Phe Gln Glu Trp Arg Ala
    610                 615                 620

Val Tyr Gln Arg Ala Ser Thr Ser Val Gln Asn Arg Leu Leu Lys Leu
625                 630                 635                 640

Glu Glu Ser Tyr Glu Leu Ile Glu Lys Asn Leu Gln Leu Leu Gly Ala
                645                 650                 655

Thr Ala Ile Glu Asp Lys Leu Gln Asp Gln Val Pro Glu Thr Ile Glu
            660                 665                 670

Thr Leu Met Lys Ala Asp Ile Lys Ile Trp Ile Leu Thr Gly Asp Lys
        675                 680                 685

Gln Glu Thr Ala Ile Asn Ile Gly His Ser Cys Lys Leu Leu Lys Lys
    690                 695                 700

Asn Met Gly Met Ile Val Ile Asn Glu Gly Ser Leu Asp Gly Thr Arg
705                 710                 715                 720

Glu Thr Leu Ser Arg His Cys Thr Thr Leu Gly Asp Ala Leu Arg Lys
                725                 730                 735

Glu Asn Asp Phe Ala Leu Ile Ile Asp Gly Lys Thr Leu Lys Tyr Ala
            740                 745                 750

Leu Thr Phe Gly Val Arg Gln Tyr Phe Leu Asp Leu Ala Leu Ser Cys
        755                 760                 765

Lys Ala Val Ile Cys Cys Arg Val Ser Pro Leu Gln Lys Ser Glu Val
    770                 775                 780

Val Glu Met Val Lys Lys Gln Val Lys Val Val Thr Leu Ala Ile Gly
785                 790                 795                 800

Asp Gly Ala Asn Asp Val Ser Met Ile Gln Thr Ala His Val Gly Val
                805                 810                 815
```

```
Gly Ile Ser Gly Asn Glu Gly Leu Gln Ala Ala Asn Ser Ser Asp Tyr
            820                 825                 830

Ser Ile Ala Gln Phe Lys Tyr Leu Lys Asn Leu Leu Met Ile His Gly
        835                 840                 845

Ala Trp Asn Tyr Asn Arg Val Ser Lys Cys Ile Leu Tyr Cys Phe Tyr
    850                 855                 860

Lys Asn Ile Val Leu Tyr Ile Ile Glu Ile Trp Phe Ala Phe Val Asn
865                 870                 875                 880

Gly Phe Ser Gly Gln Ile Leu Phe Glu Arg Trp Cys Ile Gly Leu Tyr
                885                 890                 895

Asn Val Met Phe Thr Ala Met Pro Pro Leu Thr Leu Gly Ile Phe Glu
            900                 905                 910

Arg Ser Cys Arg Lys Glu Asn Met Leu Lys Tyr Pro Glu Leu Tyr Lys
        915                 920                 925

Thr Ser Gln Asn Ala Leu Asp Phe Asn Thr Lys Val Phe Trp Val His
    930                 935                 940

Cys Leu Asn Gly Leu Phe His Ser Val Ile Leu Phe Trp Phe Pro Leu
945                 950                 955                 960

Lys Ala Leu Gln Tyr Gly Thr Ala Phe Gly Asn Gly Lys Thr Ser Asp
                965                 970                 975

Tyr Leu Leu Leu Gly Asn Phe Val Tyr Thr Phe Val Val Ile Thr Val
            980                 985                 990

Cys Leu Lys Ala Gly Leu Glu Thr  Ser Tyr Trp Thr Trp  Phe Ser His
        995                 1000                1005

Ile Ala  Ile Trp Gly Ser Ile  Ala Leu Trp Val Val  Phe Phe Gly
    1010                1015                1020

Ile Tyr  Ser Ser Leu Trp Pro  Ala Ile Pro Met Ala  Pro Asp Met
    1025                1030                1035

Ser Gly  Glu Ala Ala Met Leu  Phe Ser Ser Gly Val  Phe Trp Met
    1040                1045                1050

Gly Leu  Leu Phe Ile Pro Val  Ala Ser Leu Leu Leu  Asp Val Val
    1055                1060                1065

Tyr Lys  Val Ile Lys Arg Thr  Ala Phe Lys Thr Leu  Val Asp Glu
    1070                1075                1080

Val Gln  Glu Leu Glu Ala Lys  Ser Gln Asp Pro Gly  Ala Val Val
    1085                1090                1095

Leu Gly  Lys Ser Leu Thr Glu  Arg Ala Gln Leu Leu  Lys Asn Val
    1100                1105                1110

Phe Lys  Lys Asn His Val Asn  Leu Tyr Arg Ser Glu  Ser Leu Gln
    1115                1120                1125

Gln Asn  Leu Leu His Gly Tyr  Ala Phe Ser Gln Asp  Glu Asn Gly
    1130                1135                1140

Ile Val  Ser Gln Ser Glu Val  Ile Arg Ala Tyr Asp  Thr Thr Lys
    1145                1150                1155

Gln Arg  Pro Asp Glu Trp
    1160


<210> SEQ ID NO 177
<211> LENGTH: 1148
<212> TYPE: PRT
<213> ORGANISM: Mouse

<400> SEQUENCE: 177

Met Ser Arg Ala Thr Ser Val Gly Asp Gln Leu Glu Ala Pro Ala Arg
1               5                   10                  15
```

```
Ile Ile Tyr Leu Asn Gln Ser His Leu Asn Lys Phe Cys Asp Asn Arg
            20                  25                  30

Ile Ser Thr Ala Lys Tyr Ser Val Leu Thr Phe Leu Pro Arg Phe Leu
        35                  40                  45

Tyr Glu Gln Ile Arg Arg Ala Ala Asn Ala Phe Phe Leu Phe Ile Ala
    50                  55                  60

Leu Leu Gln Gln Ile Pro Asp Val Ser Pro Thr Gly Arg Tyr Thr Thr
65                  70                  75                  80

Leu Val Pro Leu Val Ile Ile Leu Thr Ile Ala Gly Ile Lys Glu Ile
                85                  90                  95

Ile Glu Asp Phe Lys Arg His Lys Ala Asp Asn Ala Val Asn Lys Lys
            100                 105                 110

Lys Thr Ile Val Leu Arg Asn Gly Met Trp His Thr Ile Met Trp Lys
        115                 120                 125

Glu Val Ala Val Gly Asp Ile Val Lys Val Leu Asn Gly Gln Tyr Leu
    130                 135                 140

Pro Ala Asp Met Val Leu Phe Ser Ser Ser Glu Pro Gln Gly Met Cys
145                 150                 155                 160

Tyr Val Glu Thr Ala Asn Leu Asp Gly Glu Thr Asn Leu Lys Ile Arg
                165                 170                 175

Gln Gly Leu Ser His Thr Thr Asp Met Gln Thr Arg Asp Val Leu Met
            180                 185                 190

Lys Leu Ser Gly Arg Ile Glu Cys Glu Gly Pro Asn Arg His Leu Tyr
        195                 200                 205

Asp Phe Thr Gly Asn Leu His Leu Asp Gly Lys Ser Ser Val Ala Leu
    210                 215                 220

Gly Pro Asp Gln Ile Leu Leu Arg Gly Thr Gln Leu Arg Asn Thr Gln
225                 230                 235                 240

Trp Val Phe Gly Val Val Val Tyr Thr Gly His Asp Ser Lys Leu Met
                245                 250                 255

Gln Asn Ser Thr Lys Ala Pro Leu Lys Arg Ser Asn Val Glu Lys Val
            260                 265                 270

Thr Asn Val Gln Ile Leu Val Leu Phe Gly Ile Leu Leu Val Met Ala
        275                 280                 285

Leu Val Ser Ser Val Gly Ala Leu Phe Trp Asn Gly Ser His Gly Gly
    290                 295                 300

Lys Ser Trp Tyr Ile Lys Lys Met Asp Thr Asn Ser Asp Asn Phe Gly
305                 310                 315                 320

Tyr Asn Leu Leu Thr Phe Ile Ile Leu Tyr Asn Asn Leu Ile Pro Ile
                325                 330                 335

Ser Leu Leu Val Thr Leu Glu Val Val Lys Tyr Thr Gln Ala Leu Phe
            340                 345                 350

Ile Asn Trp Asp Met Asp Met Tyr Tyr Ile Glu Asn Asp Thr Pro Ala
        355                 360                 365

Met Ala Arg Thr Ser Asn Leu Asn Glu Glu Leu Gly Gln Val Lys Tyr
    370                 375                 380

Leu Phe Ser Asp Lys Thr Gly Thr Leu Thr Cys Asn Ile Met Asn Phe
385                 390                 395                 400

Lys Lys Cys Ser Ile Ala Gly Val Thr Tyr Gly His Phe Pro Glu Leu
                405                 410                 415

Ala Arg Glu Gln Ser Ser Asp Asp Phe Cys Arg Met Thr Ser Cys Thr
            420                 425                 430
```

-continued

```
Asn Asp Ser Cys Asp Phe Asn Asp Pro Arg Leu Leu Lys Asn Ile Glu
        435                 440                 445

Asp Gln His Pro Thr Ala Pro Cys Ile Gln Glu Phe Leu Thr Leu Leu
    450                 455                 460

Ala Val Cys His Thr Val Val Pro Glu Lys Asp Gly Asp Glu Ile Ile
465                 470                 475                 480

Tyr Gln Ala Ser Ser Pro Asp Glu Ala Ala Leu Val Lys Gly Ala Lys
                485                 490                 495

Lys Leu Gly Phe Val Phe Thr Gly Arg Thr Pro Tyr Ser Val Ile Ile
            500                 505                 510

Glu Ala Met Gly Gln Glu Gln Thr Phe Gly Ile Leu Asn Val Leu Glu
        515                 520                 525

Phe Ser Ser Asp Arg Lys Arg Met Ser Val Ile Val Arg Leu Pro Ser
    530                 535                 540

Gly Gln Leu Arg Leu Tyr Cys Lys Gly Ala Asp Asn Val Ile Phe Glu
545                 550                 555                 560

Arg Leu Ser Lys Asp Ser Lys Tyr Met Glu Glu Thr Leu Cys His Leu
                565                 570                 575

Glu Tyr Phe Ala Thr Glu Gly Leu Arg Thr Leu Cys Val Ala Tyr Ala
            580                 585                 590

Asp Leu Ser Glu Asn Glu Tyr Glu Glu Trp Leu Lys Val Tyr Gln Glu
        595                 600                 605

Ala Ser Ile Ile Leu Lys Asp Arg Ala Gln Arg Leu Glu Glu Cys Tyr
    610                 615                 620

Glu Ile Ile Glu Lys Asn Leu Leu Leu Leu Gly Ala Thr Ala Ile Glu
625                 630                 635                 640

Asp Arg Leu Gln Ala Gly Val Pro Glu Thr Ile Ala Thr Leu Leu Lys
                645                 650                 655

Ala Glu Ile Lys Ile Trp Val Leu Thr Gly Asp Lys Gln Glu Thr Ala
            660                 665                 670

Ile Asn Ile Gly Tyr Ser Cys Arg Leu Val Ser Gln Asn Met Ala Leu
        675                 680                 685

Ile Leu Leu Lys Glu Asp Ser Leu Asp Ala Thr Arg Ala Ala Ile Thr
    690                 695                 700

Gln His Cys Thr Asp Leu Gly Asn Leu Leu Gly Lys Glu Asn Asp Val
705                 710                 715                 720

Ala Leu Ile Ile Asp Gly His Thr Leu Lys Tyr Ala Leu Ser Phe Glu
                725                 730                 735

Val Arg Arg Ser Phe Leu Asp Leu Ala Leu Ser Cys Lys Ala Val Ile
            740                 745                 750

Cys Cys Arg Val Ser Pro Leu Gln Lys Ser Glu Ile Val Asp Val Val
        755                 760                 765

Lys Lys Arg Val Lys Ala Ile Thr Leu Ala Ile Gly Asp Gly Ala Asn
    770                 775                 780

Asp Val Gly Met Ile Gln Thr Ala His Val Gly Val Gly Ile Ser Gly
785                 790                 795                 800

Asn Glu Gly Met Gln Ala Thr Asn Asn Ser Asp Tyr Ala Ile Ala Gln
                805                 810                 815

Phe Ser Tyr Leu Glu Lys Leu Leu Leu Val His Gly Ala Trp Ser Tyr
            820                 825                 830

Asn Arg Val Thr Lys Cys Ile Leu Tyr Cys Phe Tyr Lys Asn Val Val
        835                 840                 845

Leu Tyr Ile Ile Glu Leu Trp Phe Ala Phe Val Asn Gly Phe Ser Gly
```

```
    850                 855                 860

Gln Ile Leu Phe Glu Arg Trp Cys Ile Gly Leu Tyr Asn Val Ile Phe
865                 870                 875                 880

Thr Ala Leu Pro Pro Phe Thr Leu Gly Ile Phe Glu Arg Ser Cys Thr
                885                 890                 895

Gln Glu Ser Met Leu Arg Phe Pro Gln Leu Tyr Arg Ile Thr Gln Asn
            900                 905                 910

Ala Glu Gly Phe Asn Thr Lys Val Phe Trp Gly His Cys Ile Asn Ala
        915                 920                 925

Leu Val His Ser Leu Ile Leu Phe Trp Val Pro Met Lys Ala Leu Glu
    930                 935                 940

His Asp Thr Pro Val Thr Ser Gly His Ala Thr Asp Tyr Leu Phe Val
945                 950                 955                 960

Gly Asn Ile Val Tyr Thr Tyr Val Val Val Thr Val Cys Leu Lys Ala
                965                 970                 975

Gly Leu Glu Thr Thr Ala Trp Thr Lys Phe Ser His Leu Ala Val Trp
            980                 985                 990

Gly Ser Met Leu Ile Trp Leu Val  Phe Phe Gly Val Tyr  Ser Thr Ile
        995                 1000                1005

Trp Pro  Thr Ile Pro Ile Ala  Pro Asp Met Lys Gly  Gln Ala Thr
    1010                1015                1020

Met Val  Leu Ser Ser Ala Tyr  Phe Trp Leu Gly Leu  Phe Leu Val
    1025                1030                1035

Pro Thr  Ala Cys Leu Ile Glu  Asp Val Ala Trp Arg  Ala Ala Lys
    1040                1045                1050

His Thr  Cys Lys Lys Thr Leu  Leu Glu Glu Val Gln  Glu Leu Glu
    1055                1060                1065

Thr Lys  Ser Arg Val Met Gly  Lys Ala Met Leu Arg  Asp Ser Asn
    1070                1075                1080

Gly Lys  Arg Met Asn Glu Arg  Asp Arg Leu Ile Lys  Arg Leu Ser
    1085                1090                1095

Arg Lys  Thr Pro Pro Thr Leu  Phe Arg Thr Gly Ser  Ile Gln Gln
    1100                1105                1110

Cys Val  Ser His Gly Tyr Ala  Phe Ser Gln Glu Glu  His Gly Ala
    1115                1120                1125

Val Thr  Gln Glu Glu Ile Val  Arg Ala Tyr Asp Thr  Thr Lys Glu
    1130                1135                1140

Asn Ser  Arg Lys Lys
    1145


<210> SEQ ID NO 178
<211> LENGTH: 839
<212> TYPE: PRT
<213> ORGANISM: Human

<400> SEQUENCE: 178

Met Lys Lys Trp Ser Ser Thr Asp Leu Gly Ala Ala Ala Asp Pro Leu
1               5                   10                  15

Gln Lys Asp Thr Cys Pro Asp Pro Leu Asp Gly Asp Pro Asn Ser Arg
            20                  25                  30

Pro Pro Pro Ala Lys Pro Gln Leu Ser Thr Ala Lys Ser Arg Thr Arg
        35                  40                  45

Leu Phe Gly Lys Gly Asp Ser Glu Glu Ala Phe Pro Val Asp Cys Pro
    50                  55                  60
```

-continued

```
His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
    210                 215                 220

Gly Ala Asp Val Gln Ala Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
    290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
        355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
            420                 425                 430

Arg Ile Phe Tyr Phe Asn Phe Leu Val Tyr Cys Leu Tyr Met Ile Ile
        435                 440                 445

Phe Thr Met Ala Ala Tyr Tyr Arg Pro Val Asp Gly Leu Pro Pro Phe
    450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Phe Arg Gly Ile Gln Tyr Phe
```

-continued

```
                485                 490                 495

Leu Gln Arg Arg Pro Ser Met Lys Thr Leu Phe Val Asp Ser Tyr Ser
            500                 505                 510

Glu Met Leu Phe Phe Leu Gln Ser Leu Phe Met Leu Ala Thr Val Val
        515                 520                 525

Leu Tyr Phe Ser His Leu Lys Glu Tyr Val Ala Ser Met Val Phe Ser
    530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Ile Val Phe Leu Phe Gly Phe Ser
            580                 585                 590

Thr Ala Val Val Thr Leu Ile Glu Asp Gly Lys Asn Asp Ser Leu Pro
        595                 600                 605

Ser Glu Ser Thr Ser His Arg Trp Arg Gly Pro Ala Cys Arg Pro Pro
    610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
                645                 650                 655

Lys Ala Val Phe Ile Ile Leu Leu Leu Ala Tyr Val Ile Leu Thr Tyr
            660                 665                 670

Ile Leu Leu Leu Asn Met Leu Ile Ala Leu Met Gly Glu Thr Val Asn
        675                 680                 685

Lys Ile Ala Gln Glu Ser Lys Asn Ile Trp Lys Leu Gln Arg Ala Ile
    690                 695                 700

Thr Ile Leu Asp Thr Glu Lys Ser Phe Leu Lys Cys Met Arg Lys Ala
705                 710                 715                 720

Phe Arg Ser Gly Lys Leu Leu Gln Val Gly Tyr Thr Pro Asp Gly Lys
                725                 730                 735

Asp Asp Tyr Arg Trp Cys Phe Arg Val Asp Glu Val Asn Trp Thr Thr
            740                 745                 750

Trp Asn Thr Asn Val Gly Ile Ile Asn Glu Asp Pro Gly Asn Cys Glu
        755                 760                 765

Gly Val Lys Arg Thr Leu Ser Phe Ser Leu Arg Ser Ser Arg Val Ser
    770                 775                 780

Gly Arg His Trp Lys Asn Phe Ala Leu Val Pro Leu Leu Arg Glu Ala
785                 790                 795                 800

Ser Ala Arg Asp Arg Gln Ser Ala Gln Pro Glu Glu Val Tyr Leu Arg
                805                 810                 815

Gln Phe Ser Gly Ser Leu Lys Pro Glu Asp Ala Glu Val Phe Lys Ser
            820                 825                 830

Pro Ala Ala Ser Gly Glu Lys
        835
```